(12) United States Patent
Lehmann

(10) Patent No.: US 6,720,174 B1
(45) Date of Patent: Apr. 13, 2004

(54) PHYTASES

(75) Inventor: Martin Lehmann, Princeton, NJ (US)

(73) Assignees: Novozymes A/S, Bagsvaerd (DK); Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/488,265

(22) Filed: Jan. 20, 2000

Related U.S. Application Data

(60) Provisional application No. 60/156,495, filed on Sep. 28, 1999, and provisional application No. 60/117,659, filed on Jan. 28, 1999.

(51) Int. Cl.[7] .............................. C12N 9/16; C12N 9/14; C12Q 1/34; C07K 17/00; C07H 21/04
(52) U.S. Cl. ..................... 435/196; 435/18; 435/195; 530/350; 536/23.2; 426/6.56
(58) Field of Search .................. 435/18, 195, 196; 536/23.2; 530/350

(56) References Cited

FOREIGN PATENT DOCUMENTS

| EP | 0 183 070 | 6/1986 |
|----|-----------|--------|
| EP | 0 183 071 | 6/1986 |
| EP | 0 207 459 | 1/1987 |
| EP | 0 248 227 | 12/1987 |
| EP | 0 263 311 | 4/1988 |
| EP | 0 299 108 | 1/1989 |
| EP | 0 405 370 | 1/1991 |
| EP | 0 420 358 | 4/1991 |
| EP | 0 422 697 | 4/1991 |
| EP | 0 747 483 | 12/1996 |
| EP | 0 897 010 | 2/1999 |
| EP | 0 897 985 | 2/1999 |
| EP | 0 684 313 | 5/1999 |
| WO | WO 97/35016 | 9/1997 |
| WO | WO 97/35017 | 9/1997 |
| WO | WO 98/28409 | 7/1998 |
| WO | WO 99/48380 | 9/1999 |
| WO | WO 99/49022 | 9/1999 |

OTHER PUBLICATIONS

Broun et al. Science 282:1315–1317, 1998.*
Van de Loo et al. Proc. Natl. Acad. Sci. 92:6743–6747, 1995.*
Piddington et al., Gene 133:55–62, 1993, PIR accession No. JN0899.*
Pasamontes et al., Appl. Environ. Microbiol., 63:1696–1700, 1997, SPTREMBL accession No. 000092.*
Goeddel (ED.) et al., Methods in Enzymology, vol. 185, pp. 199–228.
Wu (ED), Methods in Enzymology, vol. 155, pp. 416–433.
Berke et al., Applied and Environmental Microbiology, vol. 64, No. 11, pp. 4423–4427 (Nov. 1998).
Pasamontes et al., Biochimica et Biophysica Acta, vol. 1353, p. 217–223 (1997).
Matthews, Biochemistry, vol. 26, No. 22, pp. 6885–6888 (Nov. 3, 1987).
Gottesman et al., Journal of Bacteriology, vol. 148, No. 1, pp. 265–273 (Oct. 1981).
Punt et al., Gene, vol. 69, pp. 49–57 (1988).
Hartingsveld et al., Gene, vol. 127, pp. 87–94 (1993).
Schindler et al., Gene, vol. 130, pp. 271–275 (1993).
Mac Rae et al., vol. 132, pp. 193–198 (1993).
Boddy et al., Current Genetics, vol. 24, pp. 60–66 (1993).
MacRae et al., Gene, vol. 71, pp. 339–348 (1988).
Piddington et al., Gene, vol. 133, pp. 55–62 (1993).
Graaff et al., Current Genetics, vol. 22, pp. 21–27 (1992).
Matthews, Curr. Opinion in Structural Biology, vol. 1, pp. 17–21 (1991).
Persht et al., Curr. Opinion in Structural Bio., vol. 3, pp. 75–83(1993).
Punt et al., Journal of Biotechnology, vol. 17, pp. 19–34 (1991).
Koutz etal., Yeast, vol. 5, pp. 167–177 (1989).
Hitzeman etal., Nature, vol. 293, No. 29, pp. 717–722 (1981).
Yansura etal., Proc. Natl. Acad. Sci. USA, vol. 81, pp. 439–443 (Jan. 1984).
Stansans etal., Nucleic Acids Research, vol. 17, No. 12, pp. 4441–4455 (1989).
Ledeboer etal., Nucleic Acids Research, vol. 13, No. 9, pp. 3063–3083 (1985).
Devereux etal., Nucleic Acids Res. vol. 12, No. 1, pp. 387–395 (1984).
Vogel etal., Molecular and Cellular Biol., vol. 9, No. 5 pp. 2050–2057.
Janecek, Process Biochem., vol. 28, pp. 435–445 (1993).
Srekrishna etal., J. Basic Microbiol., vol. 28, No. 4, pp. 265–278.
Smith, Ann. Rev. Genet.: vol. 19, pp. 423–462 (1985).
Gellissen etal.; Bio/Technology, vol. 9, pp. 291–295 (Mar. 1991).
Harkki etal., Bio/Technology, vol. 7, (Jun. 1989).
Christensen etal., Bio/Technology, vol. 6, pp. 1419–1422 (1988).
Pen etal., Bio/Technology, vol. 11, pp. 811–814 (Jul. 1993).
Upshall et al., Bio/Technology, vol. 5, pp. 1301–1304 (Dec. 1987).

(List continued on next page.)

Primary Examiner—Rebecca Riuz
Assistant Examiner—Delia Ramirez
(74) Attorney, Agent, or Firm—Elias J. Lambris

(57) ABSTRACT

This invention relates to improved phytases, preferably phytases of an increased thermostability, and a process of producing them. In particular, stabilizing amino acid mutations are introduced into a homologous protein, or the active site of a phytase is replaced in part or in toto. The corresponding DNA sequences and methods of preparing them are also disclosed, as are methods of producing the improved phytases, and the use thereof. Specific variants of *Aspergillus fumigatus* phytase and of consensus phytases are disclosed.

12 Claims, 56 Drawing Sheets

OTHER PUBLICATIONS

Figure 11:
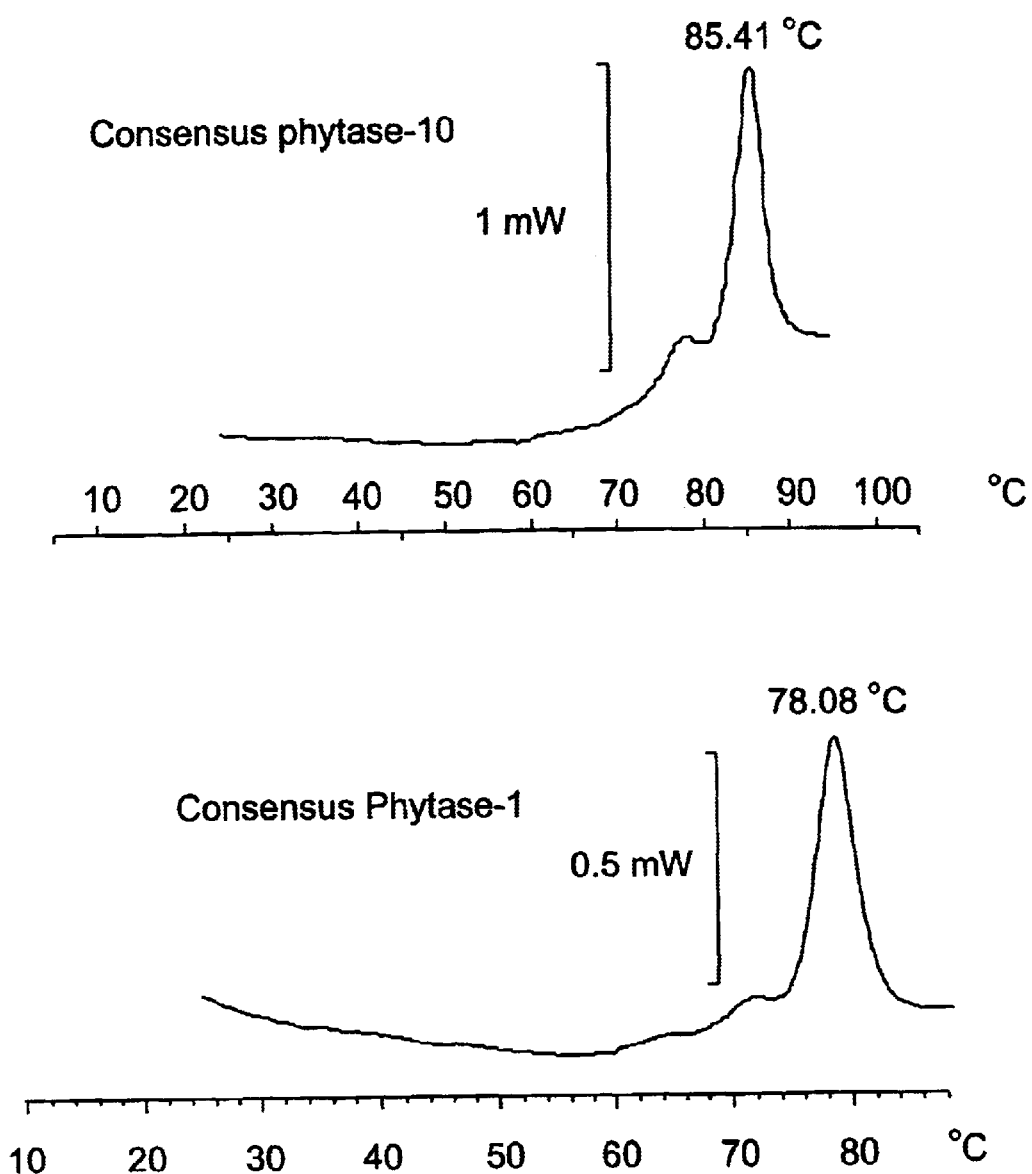

Cullen etal., Bio/Technology, vol. 5, pp. 369–376 (Apr. 1987).

Gwynne etal., Bio/Technology, vol. 5, pp. 713–719 (Jul. 1987).

Goldstein etal., Bio/Technology, vol. 5, pp. 72–79 (Jan. 1987).

Pasamontes etal., Applied and Env. Microbiol., vol. 63, No. 5, pp. 1696–1700 (May 1997).

Alber, Annu. Rev. Biochem., vol. 58, pp. 765–798 (1989).

Mitchell etal., Microbiology, vol. 143, pp. 245–252 (1997).

Villarejo etal., Journal of Bacteriology, vol. 120, No. 1, pp. 466–474 (Oct. 1974).

Needleman etal., J. Mol. Biol., vol. 48, pp. 443–453, (1970).

Stüber etal., Immunological Methods, vol. IV, pp. 121–153 (1990).

Rudolph et al., Proc. Natl. Acad. Sci. USA, vol. 84, pp. 1340–1344 (Mar. 1987).

* cited by examiner

```
                           1                                                              50
A. terreus 9A-1            KhsDCNSVDh GYQCFPELSH kWG1YAPYFS LQDESPFP1D VPEDChITFV
A. terreus cbs             NhsDCTSVDr GYQCFPELSH kWG1YAPYFS LQDESPFP1D VPDDChITFV
A. niger var. awamori      NqsTCDTVDQ GYQCFSETSH LWGQYAPFFS LANESAISPD VPAGCrVTFA
A. niger T213              NqsSCDTVDQ GYQCFSETSH LWGQYAPYFS LANESVISPD VPAGCrVTFA
A. niger NRRL3135          NqsSCDTVDQ GYQCFSETSH LWGQYAPFFS LANESVISPE VPAGCrVTFA
A. fumigatus 13073         GSksCDTVD1 GYQCsPATSH LWGQYSPFFS LEDE1SVSSK LPKDCrITLV
A. fumigatus 32722         GSkSCDTVD1 GYQCsPATSH LWGQYSPFFS LEDE1SVSSK LPKDCrITLV
A. fumigatus 58128         GSkSCDTVD1 GYQCsPATSH LWGQYSPFFS LEDE1SVSSK LPKDCrITLV
A. fumigatus 26906         GSkSCDTVD1 GYQCsPATSH LWGQYSPFFS LEDE1SVSSK LPKDCrITLV
A. fumigatus 32239         GSkACDTVE1 GYQCsPGTSH LWGQYSPFFS LEDE1SVSSD LPKDCrVTFV
E. nidulans                QNHSCNTADG GYQCFPNVSH VWGQYSPYFS IEQESAISeD VPHGCeVTFV
T. thermophilus            DSHSCNTVEG GYQCrPEISH sWGQYSPFFS LADQSEISPD VPQNCkITFV
M. thermophila             ESRPCDTpD1 GFQCgTAISH FWGQYSPYFS VpSE1DaS.. IPDDCeVTFA Consensus                  NSHSCDTVDG GYQCFPEISH LWGQYSPYFS LEDESAISPD VPDDC-VTFV
Consensus phytase          NSHSCDTVDG GYQCFPEISH LWGQYSPYFS LEDESAISPD VPDDCRVTFV 51                                                             100
A. terreus 9A-1            QVLARHGARs PThSKtKAYA AtIAAIQKSA TaFpGKYAPL QSYNYSLDSE
A. terreus cbs             QVLARHGARs PTDSKtKAYA AtIAAIQKNA TaLpGKYAFL KSYNYSMGSE
A. niger var. awamori      QVLSRHGARY PTESKgKkYS ALIEEIQQNV TtFDGKYAFL KTYNYSLGAD
A. niger T213              QVLSRHGARY PTESKgKkYS ALIEEIQQNV TtFDGKYAFL KTYNYSLGAD
A. niger NRRL3135          QVLSRHGARY PTDSKgKkYS ALIEEIQQNA TtFDGKYAFL KTYNYSLGAD
A. fumigatus 13073         QVLSRHGARY PTSSKsKkYK kLVTAIQaNA TdFKGKFAFL KTYNYTLGAD
A. fumigatus 32722         QVLSRHGARY PTSSKsKkYK kLVTAIQaNA TdFKGKFAFL KTYNYTLGAD
A. fumigatus 58128         QVLSRHGARY PTSSKsKkYK kLVTAIQaNA TdFKGKFAFL KTYNYTLGAD
A. fumigatus 26906         QVLSRHGARY PTSSKsKkYK kLVTAIQaNA TdFKGKPAFL KTYNYTLGAD
A. fumigatus 32239         QVLSRHGARY PTASKsKkYK kLVTAIQKNA TeFKGKFAFL ETYNYTLGAD
E. nidulans                QVLSRHGARY PTESKsKAYS GLIEAIQKNA TsFwGQYAFL ESYNYTLGAD
T. thermophilus            QLLSRHGARY PTSSKtE1YS QLISrIQKTA TaYKGyYAFL KDYrYqLGAN
M. thermophila             QVLSRHGARa PT1KRaaSYv DLIDrIHhGA IsYgPgYEFL RTYDYTLGAD Consensus                  QVLSRHGARY PTSSK-KAYS ALIEAIQKNA T-FKGKYAFL KTYNYTLGAD
Consensus phytase          QVLSRHGARY PTSSKSKAYS ALIEAIQKNA TAFKGKYAFL KTYNYTLGAD 101                                                            150
A. terreus 9A-1            ELTPFGrNQL rD1GaQFYeR YNALTRhInP FVRATDASRV hESAEKFVEG
A. terreus cbs             NLTPFGrNQL qD1GaQFYRR YDTLTRhInP FVRAADSSRV hESAEKFVEG
A. niger var. awamori      DLTPFGEQEL VNSGIKFYQR YESLTRNIIP FIRSSGSSRV IASGEKFIEG
A. niger T213              DLTPFGEQEL VNSGIKFYQR YESLTRNIIP FIRSSGSSRV IASGEKFIEG
A. niger NRRL3135          DLTPFGEQEL VNSGIKFYQR YESLTRNIVP FIRSSGSSRV IASGKKFIEG
A. fumigatus 13073         DLTPFGEQQL VNSGIKFYQR YKALARSVVP FIRASGSDRV IASGEKFIEG
A. fumigatus 32722         DLTPFGEQQL VNSGIKFYQR YKALARSVVP FIRASGSDRV IASGEKFIEG
A. fumigatus 58128         DLTPFGEQQL VNSGIKFYQR YKALARSVVP FIRASGSDRV IASGEKFIEG
A. fumigatus 26906         DLTAFGEQQL VNSGIKFYQR YKALARSVVP FIRASGSDRV IASGEKFIEG
A. fumigatus 32239         DLTPFGEQQM VNSGIKFYQK YKALAgSVVP FIRSSGSDRV IASGEKFIEG
E. nidulans                DLTiFGENQM VDSGaKFYRR YKNLARKnTP FIRASGSDRV VASAEKFING
T. thermophilus            DLTPFGENQM IQ1GIKFYnH YKSLARNaVP FVRCSGSDRV IASGr1FIEG
M. thermophila             ELTRtGQQQM VNSGIKFYRR YRALARKsIP FVRTAGqDRV VhSAENFTQG Consensus                  DLTPFGENQM VNSGIKFYRR YKALARK-VP FVRASGSDRV IASAEKFIEG
Consensus phytase          DLTPFGENQM VNSGIKFYRR YKALARKIVP FIRASGSDRV IASAEKFIEG
```

Fig. 1a

```
                          151                                                              200
A. terreus 9A-1           FQTARqDDHh  ANpHQPSPrV  DVaIPEGSAY  NNTLEHS1CT  AFES...STV
A. terreus cbs            FQNARqGDPh  ANpHQPSPrV  DVVIPEGTAY  NNTLEHSICT  AFEA...STV
A. niger var. awamori     FQSTKLkDPr  AqpgQSSPkI  DVVISEASSs  NNTLDPGTCT  VFED...SEL
A. niger T213             FQSTKLkDPr  AqpgQSSPkI  DVVISEASSs  NNTLDPGTCT  VFED...SEL
A. niger NRRL3135         FQSTKLkDPr  AqpgQSSPkI  DVVISEASSs  NNTLDPGTCT  VFED...SEL
A. fumigatus 13073        FQqAKLADPG  A.TNRAAPAI  SVIIPESETF  NNTLDHGVCT  kFEA...SQL
A. fumigatus 32722        FQqAKLADPG  A.TNRAAPAI  SVIIPESETF  NNTLDHGVCT  kFEA...SQL
A. fumigatus 58128        FQqAKLADPG  A.TNRAAPAI  SVIIPESETF  NNTLDHGVCT  kFEA...SQL
A. fumigatus 26906        FQqAKLADPG  A.TNRAAPAI  SVIIPESETF  NNTLDHGVCT  kFEA...SQL
A. fumigatus 32239        FQqANVADPG  A.TNRAAPVI  SVIIPESETY  NNTLDHSVCT  NFEA...SEL
E. nidulans               FRKAQLhDHG  S..gQATPVV  NVIIPEiDGF  NNTLDHSTCV  SFEN...DEr
T. thermophilus           FQSAKV1DPh  SDkHDAPPTI  NVIIeEGPSY  NNTLDtGSCP  VFED...SSg
M. thermophila            FHSA1lADRG  STvRPT1Pyd  mVVIPETAGa  NNTLHNDlCT  AFEEgpySTI Consensus                 FQSAKLADPG  S-PHQASPVI  NVIIPEGSGY  NNTLDHGTCT  AFED---SEL
Consensus phytase         FQSAKLADPG  SQPHQASPVI  DVIIPEGSGY  NNTLDHGTCT  AFED...SEL 201                                                              250
A. terreus 9A-1           GDDAvANFTA  VFAPAIaQRL  EADLPGVqLS  TDDVVnLMAM  CPFETVS1TD
A. terreus cbs            GDAAADNFTA  VFAPAIakRL  EADLPGVqLS  ADDVVnLMAM  CPFETVS1TD
A. niger var. awamori     ADTVEANFTA  TFAPSIRQRL  ENDLSGVTLT  DTEVTyLMDM  CSFDTISEST
A. niger T213             ADTVEANFTA  TFAPSIRQRL  ENDLSGVTLT  DTEVTyLMDM  CSFDTIStST
A. niger NRRL3135         ADTVEANFTA  TFVPSIRQRL  ENDLSGVTLT  DTEVTyLMDM  CSFDTIStST
A. fumigatus 13073        GDEVAANFTA  lFAPDIRARa  EkHLPGVTLT  DEDVVsLMDM  CSFDTVARTS
A. fumigatus 32722        GDEVAANFTA  lFAPDIRARa  EkHLPGVTLT  DEDVVsLMDM  CSFDTVARTS
A. fumigatus 58128        GDEVAANFTA  lFAPDIRARa  EkHLPGVTLT  DEDVVsLMDM  CSFDTVARTS
A. fumigatus 58128        GDEVAANFTA  lFAPDIRARa  EkHLPGVTLT  DEDVVsLMDM  CSFDTVARTS
A. fumigatus 26906        GDEVAANFTA  lFAPDIRARa  KkHLPGVTLT  DEDVVsLMDM  CSFDTVARTS
A. fumigatus 32239        GDEVEANFTA  lFAPAIRARI  EkHLPGVqLT  DDDVVsLMDM  CSFDTVARTA
E. nidulans               ADEiEANFTA  IMGPPIRkRL  ENDLPGIKLT  NENVIyLMDM  CSFDTMARTA
T. thermophilus           GHDAQEKFAk  qFAPAIleKI  KDHLPGVDLA  vSDVpyLMDL  CPFETLARNh
M. thermophila            GDDAQDTY1S  TFAGPItARV  NANLPGANLT  DADTVaLMDL  CPFETVAsSS Consensus                 GDDAEANFTA  TFAPAIRARL  EADLPGVTLT  DEDVV-LMDM  CPFETVARTS
Consensus phytase         GDDVEANFTA  LFAPAIRARL  EADLPGVTLT  DEDVVYLMDM  CPFETVARTS 251                                                              300
A. terreus 9A-1           ........  ...DAhTLSPFC  DLFTAtEWtq  YNYL1SLDKY  YGYGGGNPLG
A. terreus cbs            ........  ...DAhTLSPFC  DLFTAaEWtq  YNYL1SLDKY  YGYGGGNPLG
A. niger var. awamori     ........  ...vDTKLSPFC  DLFTHdEWih  YDYLQSLkKY  YGHGAGNPLG
A. niger T213             ........  ...vDTKLSPFC  DLFTHdEWih  YDYLRSLkKY  YGHGAGNPLG
A. niger NRRL3135         ........  ...vDTKLSPFC  DLFTHdEWin  YDYLQSLkKY  YGHGAGNPLG
A. fumigatus 13073        ........  ...DASQLSPFC  QLFTHnEWkk  YNYLQSLGKY  YGYGAGNPLG
A. fumigatus 32722        ........  ...DASQLSPFC  QLFTHnEWkk  YNYLQSLGKY  YGYGAGNPLG
A. fumigatus 58128        ........  ...DASQLSPFC  QLFTHnEWkk  YNYLQSLGKY  YGYGAGNPLG
A. fumigatus 26906        ........  ...DASQLSPFC  QLFTHnEWkk  YNYLQSLGKY  YGYGAGNPLG
A. fumigatus 32239        ........  ...DASELSPFC  AIFTHnEWkk  YDYLQSLGKY  YGYGAGNPLG
E. nidulans               ........  ...HGTELSPFC  AIFTEkEWlq  YDYLQSLSKY  YGYGAGSPLG
T. thermophilus           ........  ...TDT.LSPFC  ALsTQeEWqa  YDYYQSLGKY  YGnGGGNPLG
M. thermophila            sdpatadagg  gNGrpLSPFC  rLFSEsEWra  YDYLQSVGKW  YGYGPGNPLG Consensus                 ----------  -DATELSPFC  ALFTE-EW--  YDYLQSLGKY  YGYGAGNPLG
Consensus phytase         ..........  .DATELSPFC  ALFTHDEWRQ  YDYLQSLGKY  YGYGAGNPLG
```

Fig. 1b

```
                             301                                                          350
A. terreus 9A-1          PVQGVGWaNE  LMARLTRAPV  HDHTCVNNTL  DASPATFPLN  ATLYADFSHD
A. terreus cbs           PVQGVGWaNE  LIARLTRSPV  HDHTCVNNTL  DANPATFPLN  ATLYADFSHD
A. niger var. awamori    PTQGVGYaNE  LIARLTHSPV  HDDTSSNHTL  DSNPATFPLN  STLYADFSHD
A. niger T213            PTQGVGYaNE  LIARLTHSPV  HDDTSSNHTL  DSNPATFPLN  STLYADFSHD
A. niger NRRL3135        PTQGVGYaNE  LIARLTHSPV  HDDTSSNHTL  DSSPATFPLN  STLYADFSHD
A. fumigatus 13073       PAQGIGFtNE  LIARLTRSPV  QDHTSTNsTL  vSNPATFPLN  ATMYVDFSHD
A. fumigatus 32722       PAQGIGFtNE  LIARLTRSPV  QDHTSTNsTL  vSNPATFPLN  ATMYVDFSHD
A. fumigatus 58128       PAQGIGFtNE  LIARLTRSPV  QDHTSTNsTL  vSNPATFPLN  ATMYVDFSHD
A. fumigatus 26906       PAQGIGFtNE  LIARLTRSPV  QDHTSTNsTL  vSNPATFPLN  ATMYVDFSHD
A. fumigatus 32239       PAQGIGFtNE  LIARLTNSPV  QDHTSTNsTL  DSDPATFPLN  ATIYVDFSHD
E. nidulans              PAQGIGFtNE  LIARLTQSPV  QDNTSTNHTL  DSNPATFPLD  rKLYADFSHD
T. thermophilus          PAQGVGFvNE  LIARMTHSPV  QDYTTVNHTL  DSNPATFPLN  ATLYADFSHD
M. thermophila           PTQGVGFvNE  LLARLAgvPV  RDgTSTNRTL  DGDPrTFPLG  rPLYADFSHD Consensus                PAQGVGF-NE  LIARLTHSPV  QDHTSTNHTL  DSNPATFPLN  ATLYADFSHD
Consensus phytase        PAQGVGFANE  LIARLTRSPV  QDHTSTNHTL  DSNPATFPLN  ATLYADFSHD 351                                                          400
A. terreus 9A-1          SNLVSIFWAL  GLYNGTAPLS  qTSVESVSQT  DGYAAAWTVP  FAARAYVEMM
A. terreus cbs           SNLVSIFWAL  GLYNGTkPLS  qTTVEDITrT  DGYAAAWTVP  FAARAYIEMM
A. niger var. awamori    NGIISILFAL  GLYNGTkPLS  TTTVENITQT  DGFSSAWTVP  FASRlYVEMM
A. niger T213            NGIISILFAL  GLYNGTkPLS  TTTVENITQT  DGFSSAWTVP  FASRlYVEMM
A. niger NRRL3135        NGIISILFAL  GLYNGTkPLS  TTTVENITQT  DGFSSAWTVP  FASRlYVEMM
A. fumigatus 13073       NSMVSIFFAL  GLYNGTEPLS  rTSVESaKEl  DGYSASWVVP  FGARAYFEtM
A. fumigatus 32722       NSMVSIFFAL  GLYNGTGPLS  rTSVESaKEl  DGYSASWVVP  FGARAYFEtM
A. fumigatus 58128       NSMVSIFFAL  GLYNGTEPLS  rTSVESaKEl  DGYSASWVVP  FGARAYFEtM
A. fumigatus 26906       NSMVSIFFAL  GLYNGTEPLS  rTSVESaKEl  DGYSASWVVP  FGARAYFEtM
A. fumigatus 32239       NGMIPIFFAM  GLYNGTEPLS  qTSeESTKES  NGYSASWAVP  FGARAYFEtM
E. nidulans              NSMISIFFAM  GLYNGTQPLS  mDSVESIQEm  DGYAAAWTVP  FGARAYFELM
T. thermophilus          NTMTSIFaAL  GLYNGTAkLS  TTEIKSIEET  DGYSAAWTVP  FGGRAYIEMM
M. thermophila           NDMMGVLgAL  GaYDGVPPLD  KTArrDpEEl  GGYAASWAVP  FAARiYVEKM Consensus                NSMISIFFAL  GLYNGTAPLS  TTSVESIEET  DGYAASWTVP  FGARAYVEMM
Consensus phytase        NSMISIFFAL  GLYNGTAPLS  TTSVESIEET  DGYSASWTVP  FGARAYVEMM 401                                                          450
A. terreus 9A-1          QC........  .....RAEKE  PLVRVLVNDR  VMPLHGCPTD  KLGRCKrDAF
A. terreus cbs           QC........  .....RAEKQ  PLVRVLVNDR  VMPLHGCAVD  NLGRCKrDDF
A. niger var. awamori    QC........  .....QAEQE  PLVRVLVNDR  VVPLHGCPID  aLGRCTrDSF
A. niger T213            QC........  .....QAEQE  PLVRVLVNDR  VVPLHGCPVD  aLGRCTrDSF
A. niger NRRL3135        QC........  .....QAEQE  PLVRVLVNDR  VVPLHGCPVD  aLGRCTrDSF
A. fumigatus 13073       QC........  .....KSEKE  PLVRALINDR  VVPLHGCDVD  KLGRCKLNDF
A. fumigatus 32722       QC........  .....KSEKE  PLVRALINDR  VVPLHGCDVD  KLGRCKLNDF
A. fumigatus 58128       QC........  .....KSEKE  SLVRALINDR  VVPLHGCDVD  KLGRCKLNDF
A. fumigatus 26906       QC........  .....KSEKE  PLVRALINDR  VVPLHGCDVD  KLGRCKLNDF
A. fumigatus 32239       QC........  .....KSEKE  PLVRALINDR  VVPLHGCAVD  KLGRCKLKDF
E. nidulans              QC........  .....E.KKE  PLVRVLVNDR  VVPLHGCAVD  KFGRCTLDDW
T. thermophilus          QC........  .....DDSDE  PVVRVLVNDR  VVPLHGCEVD  SLGRCKrDDF
M. thermophila           RCsggggggg  ggegrQEKDE  eMVRVLVNDR  VMTLkGCGAD  ErGMCTLErF Consensus                QC--------  -----QAEKE  PLVRVLVNDR  VVPLHGCAVD  KLGRCKLDDF
Consensus phytase        QC........  .....QAEKE  PLVRVLVNDR  VVPLHGCAVD  KLGRCKRDDF
```

Fig. 1c

```
                              451               471
A. terreus 9A-1        VAGLSFAQAG GNWADCF--- -
A. terreus cbs         VEGLSFARAG NWAECF---
A. niger var. awamori  VrGLSFARSG GDWAECsA-- -
A. niger T213          VrGLSFARSG GDWAECFA-- -
A. niger NRRL3135      VrGLSFARSG DWAECFA--
A. fumigatus 13073     VKGLSWARSG GNWGECFS-- -
A. fumigatus 32722     VKGLSWARSG GNWGECFS-- -
A. fumigatus 58128     VKGLSWARSG GNWGECFS-- -
A. fumigatus 26906     VKGLSWARSG GNWGECFS-- -
A. fumigatus 32239     VKGLSWARSG NSEQSFS--
E. nidulans            VEGLNFARSG GNWkTCFT1- -
T. thermophilus        VrGLSFARqG GNWEGCYAas e
M. thermophila         IESMAFARGN GKWD1CFA-- -

Consensus              VEGLSFARSG GNWAECFA-- -
Consensus phytase      VEGLSFARSG GNWAECFA.. .
```

Fig. 1d

```
CP-1
    EcoRI  M  G  V  F  V  V  L  L  S  I  A  T  L  F  G  S  T
    TATATGAATTCATGGGCGTGTTCGTCGTGCTACTGTCCATTGCCACCTTGTTCGGTTCCA
  1 ---------+---------+---------+---------+---------+---------+  60
    ATATACTTAAGTACCCGCACAAGCAGCACGATGACAGGTAACGGTGGAACAAGCCAAGGT

S  G  T  A  L  G  P  R  G  N  S  H  S  C  D  T  V  D  G  G
    CATCCGGTACCGCCTTGGGTCCTCGTGGTAATTCTCACTCTTGTGACACTGTTGACGGTG
 61 ---------+---------+---------+---------+---------+---------+ 120
    GTAGGCCATGGCGGAACCCAGGAGCACCATTAAGAGTGAGAACACTGTGACAACTGCCAC
            CP-2
            CP-3
     Y  Q  C  F  P  E  I  S  H  L  W  G  Q  Y  S  P  Y  F  S  L
    GTTACCAATGTTTCCCAGAAATTTCTCACTTGTGGGGTCAATACTCTCCATACTTCTCTT
121 ---------+---------+---------+---------+---------+---------+ 180
    CAATGGTTACAAAGGGTCTTTAAAGAGTGAACACCCCAGTTATGAGAGGTATGAAGAGAA

E  D  E  S  A  I  S  P  D  V  P  D  D  C  R  V  T  F  V  Q
    TGGAAGACGAATCTGCTATTTCTCCAGACGTTCCAGACGACTGTAGAGTTACTTTCGTTC
181 ---------+---------+---------+---------+---------+---------+ 240
    ACCTTCTGCTTAGACGATAAAGAGGTCTGCAAGGTCTGCTGACATCTCAATGAAAGCAAG
              CP-4
                CP-5
     V  L  S  R  H  G  A  R  Y  P  T  S  S  K  S  K  A  Y  S  A
    AAGTTTTGTCTAGACACGGTGCTAGATACCCAACTTCTTCTAAGTCTAAGGCTTACTCTG
241 ---------+---------+---------+---------+---------+---------+ 300
    TTCAAAACAGATCTGTGCCACGATCTATGGGTTGAAGAAGATTCAGATTCCGAATGAGAC

L  I  E  A  I  Q  K  N  A  T  A  F  K  G  K  Y  A  F  L  K
    CTTTGATTGAAGCTATTCAAAAGAACGCTACTGCTTTCAAGGGTAAGTACGCTTTCTTGA
301 ---------+---------+---------+---------+---------+---------+ 360
    GAAACTAACTTCGATAAGTTTTCTTGCGATGACGAAAGTTCCCATTCATGCGAAAGAACT
                            CP-6
                              CP-7
     T  Y  N  Y  T  L  G  A  D  D  L  T  P  F  G  E  N  Q  M  V
    AGACTTACAACTACACTTTGGGTGCTGACGACTTGACTCCATTCGGTGAAAACCAAATGG
361 ---------+---------+---------+---------+---------+---------+ 420
    TCTGAATGTTGATGTGAAACCCACGACTGCTGAACTGAGGTAAGCCACTTTTGGTTTACC

N  S  G  I  K  F  Y  R  R  Y  K  A  L  A  R  K  I  V  P  F
    TTAACTCTGGTATTAAGTTCTACAGAAGATACAAGGCTTTGGCTAGAAAGATTGTTCCAT
421 ---------+---------+---------+---------+---------+---------+ 480
    AATTGAGACCATAATTCAAGATGTCTTCTATGTTCCGAAACCGATCTTTCTAACAAGGTA
                            CP-8
                              CP-9
     I  R  A  S  G  S  D  R  V  I  A  S  A  E  K  F  I  E  G  F
    TCATTAGAGCTTCTGGTTCTGACAGAGTTATTGCTTCTGCTGAAAAGTTCATTGAAGGTT
481 ---------+---------+---------+---------+---------+---------+ 540
    AGTAATCTCGAAGACCAAGACTGTCTCAATAACGAAGACGACTTTTCAAGTAACTTCCAA

Q  S  A  K  L  A  D  P  G  S  Q  P  H  Q  A  S  P  V  I  D
    TCCAATCTGCTAAGTTGGCTGACCCAGGTTCTCAACCACACCAAGCTTCTCCAGTTATTG
541 ---------+---------+---------+---------+---------+---------+ 600
    AGGTTAGACGATTCAACCGACTGGGTCCAAGAGTTGGTGTGGTTCGAAGAGGTCAATAAC
```

Fig. 2a

```
                    CP-10
                         CP-11
        V I I P E G S G Y N N T L D H G T C T A
        ACGTTATTATTCCAGAAGGaTCcGGTTACAACAACACTTTGGACCACGGTACTTGTACTG
    601 ---------+---------+---------+---------+---------+---------+ 660
        TGCAATAATAAGGTCTTCCtAGgCCAATGTTGTTGTGAAACCTGGTGCCATGAACATGAC

F E D S E L G D D V E A N F T A L F A P
        CTTTCGAAGACTCTGAATTGGGTGACGACGTTGAAGCTAACTTCACTGCTTTGTTCGCTC
    661 ---------+---------+---------+---------+---------+---------+ 720
        GAAAGCTTCTGAGACTTAACCCACTGCTGCAACTTCGATTGAAGTGACGAAACAAGCGAG
                                                                CP-12
        A I R A R L E A D L P G V T L T D E D V
        CAGCTATTAGAGCTAGATTGGAAGCTGACTTGCCAGGTGTTACTTTGACTGACGAAGACG
    721 ---------+---------+---------+---------+---------+---------+ 780
        GTCGATAATCTCGATCTAACCTTCGACTGAACGGTCCACAATGAAACTGACTGCTTCTGC

CP-13
        V Y L M D M C P F E T V A R T S D A T E
        TTGTTTACTTGATGGACATGTGTCCATTCGAAACTGTTGCTAGAACTTCTGACGCTACTG
    781 ---------+---------+---------+---------+---------+---------+ 840
        AACAAATGAACTACCTGTACACAGGTAAGCTTTGACAACGATCTTGAAGACTGCGATGAC

L S P F C A L F T H D E W R Q Y D Y L Q
        AATTGTCTCCATTCTGTGCTTTGTTCACTCACGACGAATGGAGACAATACGACTACTTGC
    841 ---------+---------+---------+---------+---------+---------+ 900
        TTAACAGAGGTAAGACACGAAACAAGTGAGTGCTGCTTACCTCTGTTATGCTGATGAACG
              CP-14
           CP-15
        S L G K Y Y G Y G A G N P L G P A Q G V
        AATCTTTGGGTAAGTACTACGGTTACGGTGCTGGTAACCCATTGGGTCCAGCTCAAGGTG
    901 ---------+---------+---------+---------+---------+---------+ 960
        TTAGAAACCCATTCATGATGCCAATGCCACGACCATTGGGTAACCCAGGTCGAGTTCCAC

G F A N E L I A R L T R S P V Q D H T S
        TTGGTTTCGCTAACGAATTGATTGCTAGATTGACTAGATCTCCAGTTCAAGACCACACTT
    961 ---------+---------+---------+---------+---------+---------+ 1020
        AACCAAAGCGATTGCTTAACTAACGATCTAACTGATCTAGAGGTCAAGTTCTGGTGTGAA
                    CP-16
                       CP-17
        T N H T L D S N P A T F P L N A T L Y A
        CTACTAACCACACTTTGGACTCTAACCCAGCTACTTTCCCATTGAACGCTACTTTGTACG
   1021 ---------+---------+---------+---------+---------+---------+ 1080
        GATGATTGGTGTGAAACCTGAGATTGGGTCGATGAAAGGGTAACTTGCGATGAAACATGC

D F S H D N S M I S I F F A L G L Y N G
        CTGACTTCTCTCACGACAACTCTATGATTTCTATTTTCTTCGCTTTGGGTTTGTACAACG
   1081 ---------+---------+---------+---------+---------+---------+ 1140
        GACTGAAGAGAGTGCTGTTGAGATACTAAAGATAAAAGAAGCGAAACCCAAACATGTTGC
                                                CP-18
                                                   CP-19
        T A P L S T T S V E S I E E T D G Y S A
        GTACTGCTCCATTGTCTACTACTTCTGTTGAATCTATTGAAGAAACTGACGGTTACTCTG
   1141 ---------+---------+---------+---------+---------+---------+ 1200
        CATGACGAGGTAACAGATGATGAAGACAACTTAGATAACTTCTTTGACTGCCAATGAGAC
```

Fig. 2b

```
              S  W  T  V  P  F  G  A  R  A  Y  V  E  M  M  Q  C  Q  A  E
        CTTCTTGGACTGTTCCATTCGGTGCTAGAGCTTACGTTGAAATGATGCAATGTCAAGCTG
   1201 ---------+---------+---------+---------+---------+---------+ 1260
        GAAGAACCTGACAAGGTAAGCCACGATCTCGAATGCAACTTTACTACGTTACAGTTCGAC
                                               CP-20
                                                     CP-21
              K  E  P  L  V  R  V  L  V  N  D  R  V  V  P  L  H  G  C  A
        AAAAGGAACCATTGGTTAGAGTTTTGGTTAACGACAGAGTTGTTCCATTGCACGGTTGTG
   1261 ---------+---------+---------+---------+---------+---------+ 1320
        TTTTCCTTGGTAACCAATCTCAAAACCAATTGCTGTCTCAACAAGGTAACGTGCCAACAC

V  D  K  L  G  R  C  K  R  D  D  F  V  E  G  L  S  F  A  R
        CTGTTGACAAGTTGGGTAGATGTAAGAGAGACGACTTCGTTGAAGGTTTGTCTTTCGCTA
   1321 ---------+---------+---------+---------+---------+---------+ 1380
        GACAACTGTTCAACCCATCTACATTCTCTCTGCTGAAGCAACTTCCAAACAGAAAGCGAT
                                                              CP-22
              S  G  G  N  W  A  E  C  F  A  *    Eco RI
        GATCTGGTGGTAACTGGGCTGAATGTTTCGCTTAAGAATTCATATA
   1381 ---------+---------+---------+---------+------ 1426
        CTAGACCACCATTGACCCGACTTACAAAGCGAATTCTTAAGTATAT
```

Fig. 2c

```
                     1                                                           50
P. involutus (phyA1) SvP.KnTAPt  FPIPeseQrn  WSPYSPYFPL  AeYkAPPAGC  QInQVNIIQR
P. involutus (phyA2) SvP.RniAPK  FSIPeseQrn  WSPYSPYFPL  AeYkAPPAGC  EInQVNIIQR
T. pubescens         hiPlRdTSAc  LdVTrDvQqs  WSmYSPYFPa  AtYvAPPASC  QInQVHIIQR
A. pediades          GgvvQaTfvQ  pfFPpQiQds  WAAYTPYYPV  qaYtPPPkDC  KItQVNIIQR
P. lycii             StQfsfvAAQ  LPIPaQntsn  WGPYdPFFPV  EpYaAPPEGC  tVtQVNLIQR Basidio              S-P-R-TAAQ  LPIP-Q-Q--  WSPYSPYFPV  A-Y-APPAGC  QI-QVNIIQR 51                                                          100
P. involutus (phyA1) HGARFPTSGA  TTRIKAGLTK  LQGvqnfTDA  KFNFIkSfkY  dLGnsDLVPF
P. involutus (phyA2) HGARFPTSGA  ATRIKAGLSK  LQSvqnfTDP  KFDFIkSfTY  dLGtsDLVPF
T. pubescens         HGARFPTSGA  AkRIQTAVAK  LKAAsnyTDP  lLAFVtNyTY  sLGqDsLVeL
A. pediades          HGARFPTSGA  GTRIQAAVkK  LQSAktyTDP  RLDFLtNyTY  tLGhDDLVPF
P. lycii             HGARWPTSGA  rSRqvAAVAK  IQmArpfTDP  KYEFLnDfvY  kFGvADLLPF Basidio              HGARFPTSGA  ATRIQAAVAK  LQSA---TDP  KLDFL-N-TY  -LG-DDLVPF 101                                                         150
P. involutus (phyA1) GAaQSfDAGQ  EAFARYSkLV  SkNNLPFIRA  dGSDRVVDSA  TNWTAGFAsA
P. involutus (phyA2) GAaQSfDAGl  EvFARYSkLV  SsDNLPFIRS  dGSDRVVDTA  TNWTAGFAsA
T. pubescens         GAtQSSEAGQ  EAFTRYSsLV  SaDELPFVRA  SGSDRVVATA  nNWTAGFAlA
A. pediades          GAlQSSQAGE  ETFqRYSfLV  SkENLPFVRA  SSSNRVVDSA  TNWTEGFSaA
P. lycii             GAnQShQTGt  DmYTRYStLf  egGDVPFVRA  AGdQRVVDSS  TNWTAGFGdA Basidio              GA-QSSQAGQ  EAFTRYS-LV  S-DNLPFVRA  SGSDRVVDSA  TNWTAGFA-A 151                                                         200
P. involutus (phyA1) ShNTvqPkLn  LILPQtGNDT  LEDNMCPaAG  DSDPQvNaWL  AVafPSITAR
P. involutus (phyA2) SrNAiqPkLd  LILPQtGNDT  LEDNMCPaAG  ESDPQvDaWL  AsafPSVTAQ
T. pubescens         SsNSitPvLs  VIISEaGNDT  LDDNMCPaAG  DSDPQvNqWL  AqFAPPMTAR
A. pediades          ShHvlnPiLf  VILSEslNDT  LDDaMCPnAG  sSDPQtGiWt  SIYGTPIAnR
P. lycii             SgETvlPtLq  VVLqEeGNcT  LcNNMCPnEv  DGDest.tWL  GVFAPnITAR Basidio              S-NT--P-L-  VILSE-GNDT  LDDNMCP-AG  DSDPQ-N-WL  AVFAPPITAR 201                                                         250
P. involutus (phyA1) LNAAAPSvNL  TDtDAfNLvs  LCAFlTVSkE  kkSdFCtLFE  giPGsFeAFa
P. involutus (phyA2) LNAAAPGANL  TDaDAfNLvs  LCPFmTVSkE  qkSdFCtLFE  giPGsFeAFa
T. pubescens         LNAGAPGANL  TDtDTyNLlt  LCPFETVAtE  rrSePCDIYE  elQAE.dAFa
A. pediades          LNqqAPGANI  TAaDvsNLip  LCAFETIvkE  tpSpFCNLF.  .tPEEFaqFe
P. lycii             LNAAAPSANL  SDsDAltLmd  MCPFDTLSsG  naSpFCDLF.  .tAEEYvSYe Basidio              LNAAAPGANL  TD-DA-NL--  LCPFETVS-E  --S-FCDLFE  --PEEF-AF-
```

Fig. 3a

```
                         251                                                               300
P. involutus (phyA1)  YgGDLDKFYG  TGYGQeLGPV  QGVGYVNELI  ARLTnsAVRD  NTQTNRTLDA
P. involutus (phyA2)  YaGDLDKFYG  TGYGQALGPV  QGVGYINELL  ARLTnsAVnD  NTQTNRTLDA
T. pubescens          YnADLDKFYG  TGYGQPLGPV  QGVGYINELI  ARLTaQnVsD  HTQTNsTLDS
A. pediades           YfGDLDKFYG  TGYGQPLGPV  QGVGYINELL  ARLTemPVRD  NTQTNRTLDS
P. lycii              YyyDLDKYYG  TGpGNALGPV  QGVGYVNELL  ARLTgQAVRD  ETQTNRTLDS Basidio               Y-GDLDKFYG  TGYGQPLGPV  QGVGYINELL  ARLT-QAVRD  NTQTNRTLDS 301                                                               350
P. involutus (phyA1)  SPvTFPLNKT  FYADFSHDNl  MVAVFSAMGL  FrQPAPLsTS  vPNPwRTWrT
P. involutus (phyA2)  APdTFPLNKT  MYADFSHDNl  MVAVFSAMGL  FrQSAPLsTS  tPDPNRTWLT
T. pubescens          SPeTFPLNRT  LYADFSHDNQ  MVAIFSAMGL  FNQSAPLDPT  tPDPaRTFLv
A. pediades           SP1TFPLDRS  IYADLSHDNQ  MIAIFSAMGL  FNQSSPLDPS  fPNPKRTWVT
P. lycii              dPaTFPLNRT  FYADFSHDNt  MVPIFAALGL  FNaTA.LDPl  kPDeNRlWVd Basidio               SP-TFPLNRT  FYADFSHDNQ  MVAIFSAMGL  FNQSAPLDPS  -PDPNRTWVT 351                                                               400
P. involutus (phyA1)  SsLVPFSGRM  VVERLsC..f  GT........  ........tkV  RVLVQDqVQP
P. involutus (phyA2)  SsVVPFSARM  aVERLsC..a  GT........  ........tkV  RVLVQDqVQP
T. pubescens          kKIVPFSARM  VVERLdC..g  GA........  ........qsV  RLLVNDAVQP
A. pediades           SRLtPFSARM  VtERLlCqrd  GTgsggpsri  mrngnvqtfV  RILVNDALQP
P. lycii              SKLVPFSGHM  tVEKLaC...  ..........  ....sgkeaV  RVLVNDAVQP Basidio               SKLVPFSARM  VVERL-C---  GT--------  ---------V  RVLVNDAVQP 401                                          441
P. involutus (phyA1)  LEFCGGDrNG  lCTLAkFVES  QtFARsDGaG  DFEKCFATSa  ~
P. involutus (phyA2)  LEFCGGDqDG  lCALDkFVES  QaYARsGGaG  DFEKCLATTv  ~
T. pubescens          LAFCGADtsG  vCTLDAFVES  QaYARNDGEG  DFEKCFAT~~  ~
A. pediades           LKFCGGDmDS  lCTLEAFVES  QkYAREDGQG  DFEKCFD---  ~
P. lycii              LEFCGG.vDG  vCeLsAFVES  QtYARENGQG  DFAKCgfVPs  e Basidio               LEFCGGD-DG  -CTLDAFVES  Q-YAREDGQG  DFEKCFATP-  -
```

Fig. 3b

```
                              1                                                    50
A. terreus 9a1         KhsdCNSVDh  GYQCfPELSH  kWGlYAPYFS  LqDESPFPlD  VPeDCHITFV
A. terreus cbs         NhsdCtSVDr  GYQCfPELSH  kWGlYAPYFS  LqDESPFPlD  VPdDCHITFV
A. niger var. awamori  NqsTCDTVDq  GYQCfSEtSH  LWGQYAPFFS  LANESAISPD  VPaGCRVTFa
A. niger NRRL3135      NqsSCDTVDq  GYQCfSEtSH  LWGQYAPFFS  LANESvISPE  VPaGCRVTFa
A. fumigatus 13073     GSkSCDTVDl  GYQCsPAtSH  LWGQYSPFFS  LEDElSVSSK  LPkDCRITLV
A. fumigatus 32722     GSkSCDTVDl  GYQCsPAtSH  LWGQYSPFFS  LEDElSVSSK  LPkDCRITLV
A. fumigatus 58128     GSkSCDTVDl  GYQCsPAtSH  LWGQYSPFFS  LEDElSVSSK  LPkDCRITLV
A. fumigatus 26906     GSkSCDTVDl  GYQCsPAtSH  LWGQYSPFFS  LEDElSVSSK  LPkDCRITLV
A. fumigatus 32239     GSkACDTVEl  GYQCsPGtSH  LWGQYSPFFS  LEDElSVSSD  LPkDCRVTFV
E. nidulans            QNHSCNTaDG  GYQCfPNVSH  VWGQYSPYFS  IEQESAISeD  VPhGCeVTFV
T. thermophilus        DSHSCNTVEG  GYQCrPEISH  sWGQYSPFFS  LADQSEISPD  VPqNCKITFV
T. lanuginosus         ----------  ----nvDIAR  hWGQYSPFFS  LAEvSEISPA  VPkGCRVeFV
M. thermophila         ESRPCDTpDl  GFQCgTAISH  FWGQYSPYFS  VPsElDaS..  IPdDCeVTFa
Basidio                xSxPxrxtAA  qLPipxQxqx  xWSPYSPYFP  VAxyxA....  pPaGCQIxqV Consensus   NSHSCDTVDG  GYQC-PEISH  LWGQYSPFFS  LADESAISPD  VP-GCRVTFV
                Fcp10  NSHSCDTVDG  GYQCFPEISH  LWGQYSPFFS  LADESAISPD  VPKGCRVTFV 51                                                   100
A. terreus 9a1         QVLARHGARs  PThSKTKaYA  AtIaAIQKSA  TaFpGKYAFL  QSYNYSLDSE
A. terreus cbs         QVLARHGARs  PTdSKTKaYA  AtIaAIQKNA  TaLpGKYAFL  KSYNYSMGSE
A. niger var. awamori  QVLSRHGARY  PTeSKGKKYS  ALIeEIQQNv  TtFDGKYAFL  KTYNYSLGAD
A. niger NRRL3135      QVLSRHGARY  PTdSKGKKYS  ALIeEIQQNA  TtFDGKYAFL  KTYNYSLGAD
A. fumigatus 13073     QVLSRHGARY  PTSSKSKKYk  kLVtAIQaNA  TdFKGKFAFL  KTYNYTLGAD
A. fumigatus 32722     QVLSRHGARY  PTSSKSKKYk  kLVtAIQaNA  TdFKGKFAFL  KTYNYTLGAD
A. fumigatus 58128     QVLSRHGARY  PTSSKSKKYk  kLVtAIQaNA  TdFKGKFAFL  KTYNYTLGAD
A. fumigatus 26906     QVLSRHGARY  PTSSKSKKYk  kLVtAIQaNA  TdFKGKFAFL  KTYNYTLGAD
A. fumigatus 32239     QVLSRHGARY  PTASKSKKYk  kLVtAIQKNA  TeFKGKFAFL  ETYNYTLGAD
E. nidulans            QVLSRHGARY  PTeSKSKaYS  GLIeAIQKNA  TsFwGQYAFL  ESYNYTLGAD
T. thermophilus        QLLSRHGARY  PTSSKTElYS  qLIsrIQKtA  TaYKGyYAFL  KdYrYqLGAN
T. lanuginosus          QVLSRHGARY  PTAhKSEvYA  ELLqrIQDtA  TeFKGDFAFL  RdYaYhLGAD
M. thermophila         QVLSRHGARa  PTlkRAasYv  DLIdrIHhGA  isYgPgYEFL  RTYDYTLGAD
Basidio                NIIqRHGARF  PTSGaAtRiq  AaVakLQsax  xxtDPKLDFL  xnxtYxLGxD Consensus   QVLSRHGARY  PTSSKSKKYS  ALI-AIQKNA  T-FKGKYAFL  KTYNYTLGAD
                Fcp10  QVLSRHGARY  PTSSKSKKYS  ALIEAIQKNA  TAFKGKYAFL  KTYNYTLGAD 101                                                  150
A. terreus 9a1         ELTPFGrNQL  rDlGaQFYeR  YNAL.TRhIn  PFVRATDAsR  VhESAEKFVE
A. terreus cbs         NLTPFGrNQL  qDlGaQFYRR  YDTL.TRhIn  PFVRAADSsR  VhESAEKFVE
A. niger var. awamori  DLTPFGEQEL  VNSGIKFYQR  YESL.TRnII  PFIRSSGSsR  VIASGEKFIE
A. niger NRRL3135      DLTPFGEQEL  VNSGIKFYQR  YESL.TRnIV  PFIRSSGSsR  VIASGKKFIE
A. fumigatus 13073     DLTPFGEQQL  VNSGIKFYQR  YKAL.ARsVV  PFIRASGSDR  VIASGEKFIE
A. fumigatus 32722     DLTPFGEQQL  VNSGIKFYQR  YKAL.ARsVV  PFIRASGSDR  VIASGEKFIE
A. fumigatus 58128     DLTPFGEQQL  VNSGIKFYQR  YKAL.ARsVV  PFIRASGSDR  VIASGEKFIE
A. fumigatus 26906     DLTAFGEQQL  VNSGIKFYQR  YKAL.ARsVV  PFIRASGSDR  VIASGEKFIE
A. fumigatus 32239     DLTPFGEQQM  VNSGIKFYQK  YKAL.AgsVV  PFIRSSGSDR  VIASGEKFIE
E. nidulans            DLTiFGENQM  VDSGaKFYRR  YKnL.ARknt  PFIRASGSDR  VVASAEKFIN
T. thermophilus        DLTPFGENQM  IQlGIKFYnH  YKSL.ARnaV  PFVRCSGSDR  VIASGrlFIE
T. lanuginosus          NLTRFGEEQM  MESGrQFYHR  YREq.AReIV  PFVRAAGSAR  VIASAEfPnr
M. thermophila         ELTRtGQQQM  VNSGIKFYRR  YRAL.ARksI  PFVRTAGgDR  VVhSAENFtQ
Basidio                DLvPFGAxQs  sQAGqEaFtR  YsxLvSxdnL  PFVRASGSDR  VVDSAtNWtA Consensus   DLTPFGEQQM  VNSGIKFYRR  YKAL-AR-IV  PFVRASGSDR  VIASAEKFIE
                Fcp10  DLTPFGEQQM  VNSGIKFYRR  YKAL.ARKIV  PFVRASGSDR  VIASAEKFIE
```

Fig. 4a

```
                              151                                                                                      200
A. terreus 9a1          GFQTARqDDh  hAnphQPSPr   VDVaIPEGsA   YNNTLEHSLC   TAFEs...St
A. terreus cbs          GFQNARqGDP  hAnphQPSPr   VDVVIPEGtA   YNNTLEHSIC   TAFEa...St
A. niger var. awamori   GFQSTKLkDP  rAqpgQSSPk   IDVVISEAsS   sNNTLDpGtC   TvFEd...SE
A. niger NRRL3135       GFQSTKLkDP  rAqpgQSSPk   IDVVISEAsS   sNNTLDpGtC   TvFEd...SE
A. fumigatus 13073      GFQqAKLADP  gAt.nRAAPa   ISVIIPESeT   FNNTLDHGVC   TkFEa...SQ
A. fumigatus 32722      GFQqAKLADP  gAt.nRAAPa   ISVIIPESeT   FNNTLDHGVC   TkFEa...SQ
A. fumigatus 58128      GFQqAKLADP  gAt.nRAAPa   ISVIIPESeT   FNNTLDHGVC   TkFEa...SQ
A. fumigatus 26906      GFQqAKLADP  gAt.nRAAPa   ISVIIPESeT   FNNTLDHGVC   TkFEa...SQ
A. fumigatus 32239      GFQqANVADP  gAt.nRAAPV   ISVIIPESeT   YNNTLDHSVC   TnFEa...SE
E. nidulans             GFRkAQLhDh  g.s.gQATPV   VNVIIPEidG   FNNTLDHStC   vSFEn...dE
T. thermophilus         GFQSAKV1DP  hSdkhDAPPt   INVIIeEGpS   YNNTLDtGsC   PvFEd...Ss
T. lanuginosus          GFQdAKdrDP  rSnkdQAePV   INVIISEEtG   sNNTLDgltC   PAaEe...Ap
M. thermophila          GFHSA1LADR  gStvrPTlPy   dmVVIPETaG   aNNTLHNDLC   TAFEegPySt
Basidio                 GFaxA.....  ..sxntxxPx   LxVILSExg.   .NDTLDDNMC   ......PxAG Consensus      GFQSAKLADP  -A---QASPV   INVIIPEG-G   YNNTLDHGLC   TAFE--P-SE
         Fcp10          GFQSAKLADP  GANPHQASPV   INVIIPEGAG   YNNTLDHGLC   TAFEE...SE 201                                                                                      250
A. terreus 9a1          VGDDavANFT  AVFAPAIaqR   LEAdLPGVQL   StDDVVNLMA   MCPFETVS1T
A. terreus cbs          VGDAaADNFT  AVFAPAIakR   LEAdLPGVQL   SADDVVNLMA   MCPFETVS1T
A. niger var. awamori   LADtVEANFT  AtFAPSIRqR   LEndLSGVtL   TDtEVtyLMD   MCSFDTIStS
A. niger NRRL3135       LADtVEANFT  AtFvPSIRqR   LEndLSGVtL   TDtEVtyLMD   MCSFDTIStS
A. fumigatus 13073      LGDEVAANFT  ALFAPdIRAR   aEkhLPGVtL   TDEDVVSLMD   MCSFDTVArT
A. fumigatus 32722      LGDEVAANFT  ALFAPdIRAR   aEkhLPGVtL   TDEDVVSLMD   MCSFDTVArT
A. fumigatus 58128      LGDEVAANFT  ALFAPdIRAR   aEkhLPGVtL   TDEDVVSLMD   MCSFDTVArT
A. fumigatus 26906      LGDEVAANFT  ALFAPdIRAR   aKkhLPGVtL   TDEDVVSLMD   MCSFDTVArT
A. fumigatus 32239      LGDEVEANFT  ALFAPAIRAR   IEkhLPGVQL   TDDDVVSLMD   MCSFDTVArT
E. nidulans             rADEIEANFT  AIMGPPIrkR   LEndLPGIKL   TNENVIyLMD   MCSFDTMArT
T. thermophilus         gGHDaQEKFA  kqFAPAIIEK   IKDhLPGVDL   AvsDVpyLMD   LCPFETLArn
T. lanuginosus          .DptqpAEFl  qVFGPRVlkK   ItkhMPGVNL   T1EDVplFMD   LCPFDTVGsd
M. thermophila          IGDDaQDtYl  StFAGPItAR   VNAnLPGaNL   TDADtVaLMD   LCPFETVAsS
Basidio                 dSDpqxnxWl  AVFAPPItAR   LNAaaPGaNL   TDxDaxNLxx   LCPFETVS..

Consensus      LGDDVEANFT  AVFAPPIRAR   LEA-LPGVNL   TDEDVVNLMD   MCPFDTVA-T
         Fcp10          LGDDVEANFT  AVFAPPIRAR   LEAHLPGVNL   TDEDVVNLMD   MCPFDTVART 251                                                                                      300
A. terreus 9a1          dD..Aht...  ......LSPF   CDLFTa..tE   WtQYNYL1SL   dKYYGYGGGN
A. terreus cbs          dD..Aht...  ......LSPF   CDLFTa..aE   WtQYNYL1SL   dKYYGYGGGN
A. niger var. awamori   Tv..DTK...  ......LSPF   CDLFTH..dE   WiHYDYLQSL   kKYYGHGAGN
A. niger NRRL3135       Tv..DTK...  ......LSPF   CDLFTH..dE   WiNYDYLQSL   kKYYGHGAGN
A. fumigatus 13073      SD..ASQ...  ......LSPF   CQLFTH..nE   WkKYNYLQSL   gKYYGYGAGN
A. fumigatus 32722      SD..ASQ...  ......LSPF   CQLFTH..nE   WkKYNYLQSL   gKYYGYGAGN
A. fumigatus 58128      SD..ASQ...  ......LSPF   CQLFTH..nE   WkKYNYLQSL   gKYYGYGAGN
A. fumigatus 26906      SD..ASQ...  ......LSPF   CQLFTH..nE   WkKYNYLQSL   gKYYGYGAGN
A. fumigatus 32239      AD..ASE...  ......LSPF   CAIFTH..nE   WkKYDYLQSL   gKYYGYGAGN
E. nidulans             AH..GTE...  ......LSPF   CAIFTE..kE   WlQYDYLQSL   sKYYGYGAGS
T. thermophilus         ht..DT....  ......LSPF   CALsTQ..eE   WqaYDYYQSL   gKYYGnGGGN
T. lanuginosus          PvlfPrQ...  ......LSPF   CHLFTa..dD   WmaYDYYyTL   dKYYSHGGGS
M. thermophila          SsdpATadag  ggngrpLSPF   CrLFSE..sE   WraYDxLQSV   gKWYGYGPGN
Basidio                 ..........  ...xexxSxF   CDLFexxpeE   FxaFxYxgdL   dKFYGtGyGQ Consensus      SD--ATQ---  ------LSPF   CDLFTH---E   W-QYDYLQSL   -KYYGYGAGN
         Fcp10          SD..ATQ...  ......LSPF   CDLFTH..DE   WIQYDYLQSL   GKYYGYGAGN
```

Fig. 4b

```
                         301                                                                    350
A. terreus 9a1           PLGPvQGVGW aNELMARLTR A.PVHDHTCv NNTLDASPAT FPLNATLYAD
A. terreus cbs           PLGPvQGVGW aNELIARLTR S.PVHDHTCv NNTLDANPAT FPLNATLYAD
A. niger var. awamori    PLGPTQGVGY aNELIARLTH S.PVHDDTSS NHTLDSNPAT FPLNSTLYAD
A. niger NRRL3135        PLGPTQGVGY aNELIARLTH S.PVHDDTSS NHTLDSSPAT FPLNSTLYAD
A. fumigatus 13073       PLGPAQGIGF tNELIARLTR S.PVQDHTST NsTLvSNPAT FPLNATMYvD
A. fumigatus 32722       PLGPAQGIGF tNELIARLTR S.PVQDHTST NsTLvSNPAT FPLNATMYvD
A. fumigatus 58128       PLGPAQGIGF tNELIARLTR S.PVQDHTST NsTLvSNPAT FPLNATMYvD
A. fumigatus 26906       PLGPAQGIGF tNELIARLTR S.PVQDHTST NsTLvSNPAT FPLNATMYvD
A. fumigatus 32239       PLGPAQGIGF tNELIARLTN S.PVQDHTST NsTLDSDPAT FPLNATIYvD
E. nidulans              PLGPAQGIGF tNELIARLTQ S.PVQDNTST NHTLDSNPAT FPLDrkLYAD
T. thermophilus          PLGPAQGVGF vNELIARMTH S.PVQDYTTv NHTLDSNPAT FPLNATLYAD
T. lanuginosus              AFGPSRGVGF vNELIARMTg N1PVKDHTTv NHTLDdNPET FPLDAvLYAD
M. thermophila           PLGPTQGVGF vNELLARLA. GvPVRDgTST NRTLDGDPrT FPLGrPLYAD
Basidio                  PLGPvQGVGY iNELLARLTx qa.VRDNTqT NRTLDSSPxT FPLNrTFYAD Consensus     PLGPAQGVGF -NELIARLTH S-PVQDHTST NHTLDSNPAT FPLNATLYAD
                Fcp10    PLGPAQGVGF VNELIARLTH S.PVQDHTST NHTLDSNPAT FPLNATLYAD 351                                                                    400
A. terreus 9a1           FSHDSnLVSI FWALGLYNGT aPLSqTSVE. .SvsQTDGYA AAWTVPFAAR
A. terreus cbs           FSHDSnLVSI FWALGLYNGT kPLSqTTVE. .ditrTDGYA AAWTVPFAAR
A. niger var. awamori    FSHDNGIISI LFALGLYNGT kPLSTTTVE. .NitQTDGFS SAWTVPFASR
A. niger NRRL3135        FSHDNGIISI LFALGLYNGT kPLSTTTVE. .NitQTDGFS SAWTVPFASR
A. fumigatus 13073       FSHDNSMVSI FFALGLYNGT ePLSrTSVE. .SaKElDGYS ASWvVPFGAR
A. fumigatus 32722       FSHDNSMVSI FFALGLYNGT gPLSrTSVE. .SaKElDGYS ASWvVPFGAR
A. fumigatus 58128       FSHDNSMVSI FFALGLYNGT ePLSrTSVE. .SaKElDGYS ASWvVPFGAR
A. fumigatus 26906       FSHDNSMVSI FFALGLYNGT ePLSrTSVE. .SaKElDGYS ASWvVPFGAR
A. fumigatus 32239       FSHDNGMIPI FFAMGLYNGT ePLSqTSeE. .StKESNGYS ASWAVPFGAR
E. nidulans              FSHDNSMISI FFAMGLYNGT qPLSmdSVE. .SiQEmDGYA ASWTVPFGAR
T. thermophilus          FSHDNTMtSI FaALGLYNGT akLSTTeIK. .SiEETDGYS AAWTVPFGGR
T. lanuginosus              FSHDNTMtGI FsAMGLYNGT kPLSTSkIQP pTgAAADGYA ASWTVPFAAR
M. thermophila           FSHDNdMMGV LgALGaYDGv pPLdkTA..R rdpEElGGYA ASWAVPFAAR
Basidio                  FSHDNqMVAI FsAMGLFNqS aPLdPSxpDP nrt.....Wv TSklVPFSAR Consensus     FSHDNTMVSI FFALGLYNGT -PLSTTSVEP -S-EETDGYA ASWTVPFAAR
                Fcp10    FSHDNTMVSI FFALGLYNGT KPLSTTSVE. .SIEETDGYA ASWTVPFAAR 401                                                                    450
A. terreus 9a1           AYVEMMQC.. ra........ .....EKEPL VRVLVNDRVM PLHGCPtDKL
A. terreus cbs           AYIEMMQC.. ra........ .....EKQPL VRVLVNDRVM PLHGCAVDNL
A. niger var. awamori    lYVEMMQC.. Qa........ .....EQBPL VRVLVNDRVV PLHGCPIDaL
A. niger NRRL3135        lYVEMMQC.. Qa........ .....EQBPL VRVLVNDRVV PLHGCPVDaL
A. fumigatus 13073       AYfEtMQC.. Ks........ .....EKEPL VRaLINDRVV PLHGCDVDKL
A. fumigatus 32722       AYfEtMQC.. Ks........ .....EKEPL VRaLINDRVV PLHGCDVDKL
A. fumigatus 58128       AYfEtMQC.. Ks........ .....EKESL VRaLINDRVV PLHGCDVDKL
A. fumigatus 26906       AYfEtMQC.. Ks........ .....EKEPL VRaLINDRVV PLHGCDVDKL
A. fumigatus 32239       AYfEtMQC.. Ks........ .....EKEPL VRaLINDRVV PLHGCAVDKL
E. nidulans              AYfELMQC.. E......... .....KKEPL VRVLVNDRVV PLHGCAVDKF
T. thermophilus          AYIEMMQC.. Dd........ ......sDEPV VRVLVNDRVV PLHGCEVDsL
T. lanuginosus              AYVELLRC.. Etetsseeee EG...EDEPF VRVLVNDRVV PLHGCrVDRW
M. thermophila           iYVEkMRC.. sgggggggggg EGrqeKDBeM VRVLVNDRVM TLkGCGaDEr
Basidio                  mvVErLxCxx xgtxxxxxxx xxxxxxxxxx VRVLVNDaVq PLEfCGgDxd Consensus     AYVEMMQC-- E--------- EG---EKEPL VRVLVNDRVV PLHGCGVDKL
                Fcp10    AYVEMMQC.. EA........ .....EKEPL VRVLVNDRVV PLHGCGVDKL
```

Fig. 4c

```
                          451                    482
A. terreus 9a1         GRCKrDAFVA GLSFAQAG.. GNWADCF--- --
A. terreus cbs         GRCKrDDFVE GLSFARAG.. GNWAECF--- --
A. niger var. awamori  GRCtrDsFVr GLSFARSG.. GDWAECsA-- --
A. niger NRRL3135      GRCtrDsFVr GLSFARSG.. GDWAECFA-- --
A. fumigatus 13073     GRCK1NDFVK GLSWARSG.. GNWGECFS-- --
A. fumigatus 32722     GRCK1NDFVK GLSWARSG.. GNWGECFS-- --
A. fumigatus 58128     GRCK1NDFVK GLSWARSG.. GNWGECFS-- --
A. fumigatus 26906     GRCK1NDFVK GLSWARSG.. GNWGECFS-- --
A. fumigatus 32239     GRCK1KDFVK GLSWARSG.. GNSEQSFS-- --
E. nidulans            GRCtlDDWVE GLNFARSG.. GNWKtCFT1- --
T. thermophilus        GRCKrDDFVr GLSFARqG.. GNWEGCYAas e-
T. lanuginosus          GRCRrDEWIK GLTFARqG.. GHWDrCF--- --
M. thermophila         GmCtlErFIE SMAFARGN.. GKWD1CFA-- --
Basidio                GxCtlDAFVE SqxYAReDgq GDFEKCFAtp xx Consensus GRCK-DDFVE GLSFARSG-- GNWEECFA-- --
                  Fcp10 GRCKRDDFVE GLSFARSG.. GNWEECFA.. ..
```

Fig. 4d

```
       CP-1
     EcoRI  M  G  V  F  V  V  L  L  S  I  A  T  L  F  G  S  T   17
     TATATGAATTCATGGGCGTGTTCGTCGTGCTACTGTCCATTGCCACCTTGTTCGGTTCCA
   1 ---------+---------+---------+---------+---------+---------+  60
     ATATACTTAAGTACCCGCACAAGCAGCACGATGACAGGTAACGGTGGAACAAGCCAAGGT

S  G  T  A  L  G  P  R  G  N  S  H  S  C  D  T  V  D  G  G   37
     CATCCGGTACCGCCTTGGGTCCTCGTGGTAATTCTCACTCTTGTGACACTGTTGACGGTG
  61 ---------+---------+---------+---------+---------+---------+ 120
     GTAGGCCATGGCGGAACCCAGGAGCACCATTAAGAGTGAGAACACTGTGACAACTGCCAC
          CP-2
          CP-3.10
       Y  Q  C  F  P  E  I  S  H  L  W  G  Q  Y  S  P  F  S  L   57
     GTTACCAATGTTTCCCAGAAATTTCTCACTTGTGGGGTCAATACTCTCCATTCTTCTCTT
 121 ---------+---------+---------+---------+---------+---------+ 180
     CAATGGTTACAAAGGGTCTTTAAAGAGTGAACACCCCAGTTATGAGAGGTAAGAAGAGAA

A  D  E  S  A  I  S  P  D  V  P  K  G  C  R  V  T  F  V  Q   77
     TGGCTGACGAATCTGCTATTTCTCCAGACGTTCCAAAGGGTTGTAGAGTTACTTTCGTTC
 181 ---------+---------+---------+---------+---------+---------+ 240
     ACCGACTGCTTAGACGATAAAGAGGTCTGCAAGGTTTCCCGACATCTCAATGAAAGCAAG
            CP-4.10
             CP-5.10
       V  L  S  R  H  G  A  R  Y  P  T  S  S  K  S  K  K  Y  S  A   97
     AAGTTTTGTCTAGACACGGTGCTAGATACCCAACTTCTTCTAAGTCTAAGAAGTACTCTG
 241 ---------+---------+---------+---------+---------+---------+ 300
     TTCAAAACAGATCTGTGCCACGATCTATGGGTTGAAGAAGATTCAGATTCTTCATGAGAC

L  I  E  A  I  Q  K  N  A  T  A  F  K  G  K  Y  A  F  L  K  117
     CTTTGATTGAAGCTATTCAAAAGAACGCTACTGCTTTCAAGGGTAAGTACGCTTTCTTGA
 301 ---------+---------+---------+---------+---------+---------+ 360
     GAAACTAACTTCGATAAGTTTTCTTGCGATGACGAAAGTTCCCATTCATGCGAAAGAACT
                CP-6
                 CP-7.10
       T  Y  N  Y  T  L  G  A  D  D  L  T  P  F  G  E  Q  Q  M  V  137
     AGACTTACAACTACACTTTGGGTGCTGACGACTTGACTCCATTCGGTGAACAACAAATGG
 361 ---------+---------+---------+---------+---------+---------+ 420
     TCTGAATGTTGATGTGAAACCCACGACTGCTGAACTGAGGTAAGCCACTTGTTGTTTACC

N  S  G  I  K  F  Y  R  R  Y  K  A  L  A  R  K  I  V  P  F  157
     TTAACTCTGGTATTAAGTTCTACAGAAGATACAAGGCTTTGGCTAGAAAGATTGTTCCAT
 421 ---------+---------+---------+---------+---------+---------+ 480
     AATTGAGACCATAATTCAAGATGTCTTCTATGTTCCGAAACCGATCTTTCTAACAAGGTA
                                        CP-8.10
                                         CP-9.10
       V  R  A  S  G  S  D  R  V  I  A  S  A  E  K  F  I  E  G  F  177
     TCGTTAGAGCTTCTGGTTCTGACAGAGTTATTGCTTCTGCTGAAAAGTTCATTGAAGGTT
 481 ---------+---------+---------+---------+---------+---------+ 540
     AGCAATCTCGAAGACCAAGACTGTCTCAATAACGAAGACGACTTTTCAAGTAACTTCCAA

Q  S  A  K  L  A  D  P  G  A  N  P  H  Q  A  S  P  V  I  N  197
     TCCAATCTGCTAAGTTGGCTGACCCAGGTGCTAACCCACACCAAGCTTCTCCAGTTATTA
 541 ---------+---------+---------+---------+---------+---------+ 600
     AGGTTAGACGATTCAACCGACTGGGTCCACGATTGGGTGTGGTTCGAAGAGGTCAATAAT
```

Fig. 5a

```
                                        CP-10.10
                                                CP-11.10
         V  I  I  P  E  G  A  G  Y  N  N  T  L  D  H  G  L  C  T  A  217
         ACGTTATTATTCCAGAAGGTGCTGGTTACAACAACACTTTGGACCACGGTTTGTGTACTG
    601  ---------+---------+---------+---------+---------+---------+  660
         TGCAATAATAAGGTCTTCCACGACCAATGTTGTTGTGAAACCTGGTGCCAAACACATGAC

F  E  E  S  E  L  G  D  D  V  E  A  N  F  T  A  V  F  A  P  237
         CTTTCGAAGAATCTGAATTGGGTGACGACGTTGAAGCTAACTTCACTGCTGTTTTCGCTC
    661  ---------+---------+---------+---------+---------+---------+  720
         GAAAGCTTCTTAGACTTAACCCACTGCTGCAACTTCGATTGAAGTGACGACAAAAGCGAG
                                                                CP-12.10
         P  I  R  A  R  L  E  A  H  L  P  G  V  N  L  T  D  E  D  V  257
         CACCTATTAGAGCTAGATTGGAAGCTCACTTGCCAGGTGTTAACTTGACTGACGAAGACG
    721  ---------+---------+---------+---------+---------+---------+  780
         GTGGATAATCTCGATCTAACCTTCGAGTGAACGGTCCACAATTGAACTGACTGCTTCTGC

CP-13.10
         V  N  L  M  D  M  C  P  F  D  T  V  A  R  T  S  D  A  T  Q  277
         TTGTTAACTTGATGGACATGTGTCCATTCGACACTGTTGCTAGAACTTCTGACGCTACTC
    781  ---------+---------+---------+---------+---------+---------+  840
         AACAATTGAACTACCTGTACACAGGTAAGCTGTGACAACGATCTTGAAGACTGCGATGAG

L  S  P  F  C  D  L  F  T  H  D  E  W  I  Q  Y  D  Y  L  Q  297
         AATTGTCTCCATTCTGTGACTTGTTCACTCACGACGAATGGATTCAATACGACTACTTGC
    841  ---------+---------+---------+---------+---------+---------+  900
         TTAACAGAGGTAAGACACTGAACAAGTGAGTGCTGCTTACCTAAGTTATGCTGATGAACG
                    CP-14.10
                        CP-15.10
         S  L  G  K  Y  Y  G  Y  G  A  G  N  P  L  G  P  A  Q  G  V  317
         AATCTTTGGGTAAGTACTACGGTTACGGTGCTGGTAACCCATTGGGTCCAGCTCAAGGTG
    901  ---------+---------+---------+---------+---------+---------+  960
         TTAGAAACCCATTCATGATGCCAATGCCACGACCATTGGGTAACCCAGGTCGAGTTCCAC

G  F  V  N  E  L  I  A  R  L  T  H  S  P  V  Q  D  H  T  S  337
         TTGGTTTCGTTAACGAATTGATTGCTAGATTGACTCACTCTCCAGTTCAAGACCACACTT
    961  ---------+---------+---------+---------+---------+---------+ 1020
         AACCAAAGCAATTGCTTAACTAACGATCTAACTGAGTGAGAGGTCAAGTTCTGGTGTGAA
                   CP-16.10
                       CP-17.10
         T  N  H  T  L  D  S  N  P  A  T  F  P  L  N  A  T  L  Y  A  357
         CTACTAACCACACTTTGGACTCTAACCCAGCTACTTTCCCATTGAACGCTACTTTGTACG
   1021  ---------+---------+---------+---------+---------+---------+ 1080
         GATGATTGGTGTGAAACCTGAGATTGGGTCGATGAAAGGGTAACTTGCGATGAAACATGC

D  F  S  H  D  N  T  M  V  S  I  F  F  A  L  G  L  Y  N  G  377
         CTGACTTCTCTCACGACAACACTATGGTTTCTATTTTCTTCGCTTTGGGTTTGTACAACG
   1081  ---------+---------+---------+---------+---------+---------+ 1140
         GACTGAAGAGAGTGCTGTTGTGATACCAAAGATAAAAGAAGCGAAACCCAAACATGTTGC
                                     CP-18.10
                                         CP-19.10
         T  K  P  L  S  T  T  S  V  E  S  I  E  E  T  D  G  Y  A  A  397
         GTACTAAGCCATTGTCTACTACTTCTGTTGAATCTATTGAAGAAACTGACGGTTACGCTG
   1141  ---------+---------+---------+---------+---------+---------+ 1200
         CATGATTCGGTAACAGATGATGAAGACAACTTAGATAACTTCTTTGACTGCCAATGCGAC
```

Fig. 5b

```
        S  W  T  V  P  F  A  A  R  A  Y  V  E  M  M  Q  C  E  A  E  417
       CTTCTTGGACTGTTCCATTCGCTGCTAGAGCTTACGTTGAAATGATGCAATGTGAAGCTG
1201   ---------+---------+---------+---------+---------+---------+ 1260
       GAAGAACCTGACAAGGTAAGCCACGATCTCGAATGCAACTTTACTACGTTACACTTCGAC
                                     CP-20.10
                                        CP-21.10
        K  E  P  L  V  R  V  L  V  N  D  R  V  V  P  L  H  G  C  G  437
       AAAAGGAACCATTGGTTAGAGTTTTGGTTAACGACAGAGTTGTTCCATTGCACGGTTGTG
1261   ---------+---------+---------+---------+---------+---------+ 1320
       TTTTCCTTGGTAACCAATCTCAAAACCAATTGCTGTCTCAACAAGGTAACGTGCCAACAC

V  D  K  L  G  R  C  K  R  D  D  F  V  E  G  L  S  F  A  R  457
       GTGTTGACAAGTTGGGTAGATGTAAGAGAGACGACTTCGTTGAAGGTTTGTCTTTCGCTA
1321   ---------+---------+---------+---------+---------+---------+ 1380
       CACAACTGTTCAACCCATCTACATTCTCTCTGCTGAAGCAACTTCCAAACAGAAAGCGAT
                                                       CP-22.10
        S  G  G  N  W  E  E  C  F  A  *   Eco RI        467
       GATCTGGTGGTAACTGGGAAGAATGTTTCGCTTAAGAATTCATATA
1381   ---------+---------+---------+---------+------ 1426
       CTAGACCACCATTGACCCTTCTTACAAAGCGAATTCTTAAGTATAT
```

Fig. 5c

```
                              1                                                              50
P. involutus (phyA1)       ----------  -FPipeseqR  nWSPYSPYFP  LAEykA....  pPaGCQInqV
P. involutus (phyA2)       ----------  -FsipeseqR  nWSPYSPYFP  LAEykA....  pPaGCeInqV
T. pubescens               ----------  -LDvtRDVqQ  sWSmYSPYFP  aAtyvA....  pPaSCQInqV
A. pediades                ----------  -pffpPQIqD  sWAaYTPYYP  VqAyTP....  pPKDCKITqV
P. lycii                   ----------  -LPipAQnTs  nWGPYdPFFP  VEpyAA....  pPEGCtVTqV
A. terreus 9a1             KhsdCNSVDh  GYQCfPELSH  kWGlYAPYFS  LqDESPFPlD  VPEDCHITFV
A. terreus cbs             NhsdCtSVDr  GYQCfPELSH  kWGlYAPYFS  LqDESPFPlD  VPDDCHITFV
A. niger var. awamori      NqsTCDTVDq  GYQCfSEtSH  LWGQYAPPFS  LANESAISPD  VPaGCRVTFa
A. niger T213              NqsSCDTVDq  GYQCfSEtSH  LWGQYAPFFS  LANESvISPD  VPaGCRVTFa
A. niger NRRL3135          NqsSCDTVDq  GYQCfSEtSH  LWGQYAPFFS  LANESvISPE  VPaGCRVTFa
A. fumigatus ATCC13073     GSkSCDTVDl  GYQCsPAtSH  LWGQYSPFFS  LEDElSVSSK  LPKDCRITLV
A. fumigatus ATCC32722     GSkSCDTVDl  GYQCsPAtSH  LWGQYSPFFS  LEDElSVSSK  LPKDCRITLV
A. fumigatus ATCC58128     GSkSCDTVDl  GYQCsPAtSH  LWGQYSPFFS  LEDElSVSSK  LPKDCRITLV
A. fumigatus ATCC26906     GSkSCDTVDl  GYQCsPAtSH  LWGQYSPFFS  LEDElSVSSK  LPKDCRITLV
A. fumigatus ATCC32239     GSkACDTVEl  GYQCsPGtSH  LWGQYSPFFS  LEDElSVSSD  LPKDCRVTFV
E. nidulans                QNHSCNTaDg  GYQCfPNVSH  VWGQYSPYFS  IEQESAISeD  VPhGCeVTFV
T. thermophilus            DSHSCNTVEg  GYQCrPEISH  sWGQYSPFFS  LADQSEISPD  VPQNCKITFV
T. lanuginosus             ----------  ----nvDIAR  hWGQYSPFFS  LAEvSEISPA  VPKGCRVeFV
M. thermophila             ESRPCDTpDl  GFQCgTAISH  FWGQYSPYFS  VPsElDaS..  IPDDCeVTFa Consensus Seq. 11          NSHSCDTVD-  GYQC-PEISH  LWGQYSPFFS  LADESAISPD  VPKGCRVTFV 51                                                             100
P. involutus (phyA1)       NIIqRHGARF  PTSGaTtRik  AgLtKLQgvq  nftDAKFnFI  KSFKYdLGns
P. involutus (phyA2)       NIIqRHGARF  PTSGaAtRik  AgLsKLQsvq  nftDPKFDFI  KSFtYdLGTs
T. pubescens               HIIqRHGARF  PTSGaAKRiq  TaVAKLKaaS  nytDPlLAFV  tnYtYSLGqD
A. pediades                NIIqRHGARF  PTSGaGtRiq  AaVKKLQsak  TytDPRLDFL  tnYtYTLGhD
P. lycii                   NLIqRHGARW  PTSGarsRqv  AaVAKIQmar  PftDPKYEFL  NdFvYkFGvA
A. terreus 9a1             QVLARHGARs  PThSKTKaYA  AtIAaIQKSA  TaFpGKYAFL  QSYNYSLDSE
A. terreus cbs             QVLARHGARs  PTdSKTKaYA  AtIAaIQKNA  TaLpGKYAFL  KSYNYSMGSE
A. niger var. awamori      QVLSRHGARY  PTeSKGKKYS  ALIEeIQQNv  TtFDGKYAFL  KTYNYSLGAD
A. niger T213              QVLSRHGARY  PTeSKGKKYS  ALIEeIQQNv  TtFDGKYAFL  KTYNYSLGAD
A. niger NRRL3135          QVLSRHGARY  PTdSKGKKYS  ALIEeIQQNA  TtFDGKYAFL  KTYNYSLGAD
A. fumigatus ATCC13073     QVLSRHGARY  PTSSKSKKYk  kLVtaIQaNA  TdFKGKFAFL  KTYNYTLGAD
A. fumigatus ATCC32722     QVLSRHGARY  PTSSKSKKYk  kLVtaIQaNA  TdFKGKFAFL  KTYNYTLGAD
A. fumigatus ATCC58128     QVLSRHGARY  PTSSKSKKYk  kLVtaIQaNA  TdFKGKFAFL  KTYNYTLGAD
A. fumigatus ATCC26906     QVLSRHGARY  PTSSKSKKYk  kLVtaIQaNA  TdFKGKFAFL  KTYNYTLGAD
A. fumigatus ATCC32239     QVLSRHGARY  PTASKSKKYk  kLVtaIQKNA  TeFKGKFAFL  ETYNYTLGAD
E. nidulans                QVLSRHGARY  PTeSKSKaYS  GLIEaIQKNA  TsFwGQYAFL  ESYNYTLGAD
T. thermophilus            QLLSRHGARY  PTSSKTElYS  qLIsRIQKtA  TaYKGyYAFL  KdYrYqLGAN
T. lanuginosus              QVLSRHGARY  PTAhKSEvYA  ELLQRIQDtA  TeFKGDFAFL  RdYaYhLGAD
M. thermophila             QVLSRHGARa  PTlkRAasYv  DLIDRIHhGA  isYgPgYEFL  RTYDYTLGAD Consensus Seq. 11          QVLSRHGARY  PTSSKSKKYS  ALIERIQKNA  T-FKGKYAFL  KTYNYTLGAD
```

Fig. 6a

```
                            101                                                    150
P. involutus (phyA1)    DLvPFGAaQs  fDAGqEaFaR  YskLvSKNnL  PFIRAdGSDR  VVDSAtNWtA
P. involutus (phyA2)    DLvPFGAaQs  fDAGLEvFaR  YskLvSsDnL  PFIRSdGSDR  VVDTAtNWtA
T. pubescens            sLveLGAtQs  sEAGqEaFtR  YsSLvSaDeL  PFVRASGSDR· VVATANNWtA
A. pediades             DLvPFGAlQs  sQAGeEtFQR  YsfLvSKEnL  PFVRASSSNR  VVDSAtNWtE
P. lycii                DLlPFGANQs  hQTGtDMYtR  YsTLfEgGdV  PFVRAAGdQR  VVDSStNWtA
A. terreus 9a1          ELTPFGrNQL  rDlGaQPYeR  YNAL.TRHIn  PFVRATDAsR  VhESAEKFVE
A. terreus cbs          NLTPFGrNQL  qDlGaQFYRR  YDTL.TRHIn  PFVRAADSsR  VhESAEKFVE
A. niger var. awamori   DLTPFGEQEL  VNSGIKFYQR  YESL.TRNII  PFIRSSGSsR  VIASGEKFIE
A. niger T213           DLTPFGEQEL  VNSGIKFYQR  YESL.TRNII  PFIRSSGSsR  VIASGEKFIE
A. niger NRRL3135       DLTPFGEQEL  VNSGIKFYQR  YESL.TRNIV  PFIRSSGSsR  VIASGKKFIE
A. fumigatus ATCC13073  DLTPFGEQQL  VNSGIKFYQR  YKAL.ARSVV  PPIRASGSDR  VIASGEKFIE
A. fumigatus ATCC32722  DLTPFGEQQL  VNSGIKFYQR  YKAL.ARSVV  PFIRASGSDR  VIASGEKFIE
A. fumigatus ATCC58128  DLTPFGEQQL  VNSGIKFYQR  YKAL.ARSVV  PFIRASGSDR  VIASGEKFIE
A. fumigatus ATCC26906  DLTAFGEQQL  VNSGIKFYQR  YKAL.ARSVV  PFIRASGSDR  VIASGEKFIE
A. fumigatus ATCC32239  DLTPFGEQQM  VNSGIKFYQK  YKAL.AgSVV  PPIRSSGSDR  VIASGEKFIE
E. nidulans             DLTiFGENQM  VDSGaKFYRR  YKnL.ARKnt  PFIRASGSDR  VVASAEKFIN
T. thermophilus         DLTPFGENQM  IQlGIKFYnH  YKSL.ARNaV  PFVRCSGSDR  VIASGrlFIE
T. lanuginosus             NLTRFGEEQM  MESGrQFYHR  YREq.AREIV  PFVRAAGSAR  VIASAEfFnr
M. thermophila          ELTRtGQQQM  VNSGIKFYRR  YRAL.ARKsI  PFVRTAGqDR  VVhSAENFtQ Consensus Seq. 11       DLTPFGENQM  VNSGIKFYRR  YKAL-ARNIV  PFVRASGSDR  VIASAEKFIE 151                                                    200
P. involutus (phyA1)    GFaSA.....  ..shNtvqPk  LNLILPQ..T  gNDTLEDNMC  PAaGD.....
P. involutus (phyA2)    GFaSA.....  ..srNaiqPk  LDLILPQ..T  gNDTLEDNMC  PAaGE.....
T. pubescens            GFalA.....  ..ssNsiTPV  LSVIISE..A  gNDTLDDNMC  PAaGD.....
A. pediades             GFsAA.....  ..shHvlNPI  LfVILSE...S LNDTLDDAMC  PnaGs.....
P. lycii                GFgdA.....  ..sgEtvlPt  LQVVLQE...E gNcTLcNNMC  PnevD.....
A. terreus 9a1          GFQTARqDDh  hAnpHQPSPr  VDVaIPEGSA  YNNTLEHSLC  TAFEs...ST
A. terreus cbs          GFQNARqGDP  hAnpHQPSPr  VDVVIPEGTA  YNNTLEHSIC  TAFEA...ST
A. niger var. awamori   GFQSTKLkDP  rAqpgQSSPk  IDVVISEASS  sNNTLDpGtC  TvFED...Se
A. niger T213           GFQSTKLkDP  rAqpgQSSPk  IDVVISEASS  sNNTLDpGtC  TvFED...Se
A. niger NRRL3135       GFQSTKLkDP  rAqpgQSSPk  IDVVISEASS  sNNTLDpGtC  TvFED...Se
A. fumigatus ATCC13073  GFQqAKLADP  gAt.NRAAPa  ISVIIPESeT  FNNTLDHGVC  TkFEA...Sq
A. fumigatus ATCC32722  GFQqAKLADP  gAt.NRAAPa  ISVIIPESeT  FNNTLDHGVC  TkFEA...Sq
A. fumigatus ATCC58128  GFQqAKLADP  gAt.NRAAPa  ISVIIPESeT  FNNTLDHGVC  TkFEA...Sq
A. fumigatus ATCC26906  GFQqAKLADP  gAt.NRAAPa  ISVIIPESeT  FNNTLDHGVC  TkFEA...Sq
A. fumigatus ATCC32239  GFQqANVADP  gAt.NRAAPV  ISVIIPESeT  YNNTLDHSVC  TnFEA...Se
E. nidulans             GFRkAQLhDh  g.s.gQATPV  VNVIIPEidG  FNNTLDHStC  vSFEN...de
T. thermophilus         GFQSAKV1DP  hSdkHDAPPt  INVIIeEGPS  YNNTLDtGsC  PvFED...SS
T. lanuginosus             GFQdAKdrDP  rSnkDQAePV  INVIISEETG  sNNTLDgltC  PAaEE...AP
M. thermophila          GFHSAlLADR  gStvRPTlPy  dmVVIPETAG  aNNTLHNDLC  TAFEEgpyST Consensus Seq. 11       GFQSAKLADP  -A--HQASPV  INVIIPEGSG  YNNTLDHGLC  TAFED---ST
```

Fig. 6b

```
                              201                                                        250
P. involutus (phyA1)          .SDpqvnaWl  AVafPSItAR  LNAaaPSVNL  TDtDafNLVs  LCAFlTVSK.
P. involutus (phyA2)          .SDpqvDaWl  AsafPSVtAQ  LNAaaPGaNL  TDADafNLVs  LCPFmTVSK.
T. pubescens                  .SDpqvnQWl  AqFAPPMtAR  LNAgaPGaNL  TDtDtyNLLt  LCPFETVAt.
A. pediades                   .SDpqtGiWT  SIYGTPIanR  LNqqaPGaNI  TAADVsNLIp  LCAFETIvK.
P. lycii                      .GDESt.tWl  GVFAPnItAR  LNAaaPSaNL  SDsDaLtLMD  MCPFDTLSs.
A. terreus 9al                VGDDAvANFT  AVFAPAIaqR  LEAdLPGVQL  StDDVVNLMA  MCPFETVS1T
A. terreus cbs                VGDAAADNFT  AVFAPAIakR  LEAdLPGVQL  SADDVVNLMA  MCPFETVS1T
A. niger var. awamori         LADtvEANFT  AtFAPSIRqR  LEndLSGVtL  TDtEVtyLMD  MCSFDTIStS
A. niger T213                 LADtvEANFT  AtFAPSIRqR  LEndLSGVtL  TDtEVtyLMD  MCSFDTIStS
A. niger NRRL3135             LADtvEANFT  AtFvPSIRqR  LEndLSGVtL  TDtEVtyLMD  MCSFDTIStS
A. fumigatus ATCC13073        LGDEvAANFT  ALFAPdIRAR  aEkhLPGVtL  TDEDVVSLMD  MCSFDTVART
A. fumigatus ATCC32722        LGDEvAANFT  ALFAPdIRAR  aEkhLPGVtL  TDEDVVSLMD  MCSFDTVART
A. fumigatus ATCC58128        LGDEvAANFT  ALFAPdIRAR  aEkhLPGVtL  TDEDVVSLMD  MCSFDTVART
A. fumigatus ATCC26906        LGDEvAANFT  ALFAPdIRAR  aKkhLPGVtL  TDEDVVSLMD  MCSFDTVART
A. fumigatus ATCC32239        LGDEvEANFT  ALFAPAIRAR  IEkhLPGVQL  TDDDVVSLMD  MCSFDTVART
E. nidulans                   rADEiEANFT  AIMGPPIRkR  LEndLPGIKL  TNENVIyLMD  MCSFDTMART
T. thermophilus               gGHDAQEKFA  kqFAPAIlEK  IKDhLPGVDL  AvsDVpyLMD  LCPFETLARn
T. lanuginosus                .DptqpAEFl  qVFGPRVlkK  ItkhMPGVNL  TlEDVplFMD  LCPFDTVGsd
M. thermophila                IGDDAQDtYl  StFAGPItAR  VNAnLPGaNL  TDADtVaLMD  LCPFETVAsS Consensus Seq. 11             LGDDAEANFT  AVFAPPIRAR  LEA-LPGVNL  TDEDVVNLMD  MCPFDTVART 251                                                        300
P. involutus (phyA1)          ..........  ....ekkSdF  CtLFegiPGs  FeaFAYggdL  dKFYGtGyGQ
P. involutus (phyA2)          ..........  ....eqkSdF  CtLFegiPGs  FeaFAYagdL  dKFYGtGyGQ
T. pubescens                  ..........  ....errSeF  CDIYeelqAE  .daFAYnadL  dKFYGtGyGQ
A. pediades                   ..........  ....etpSPF  CNLF..TPEE  FaQFEYFgdL  dKFYGtGyGQ
P. lycii                      ..........  ....gnaSPF  CDLF..TAEE  YvsYEYYydL  dKYYGtGPGN
A. terreus 9al                dD..Aht...  ......LSPF  CDLF..TAtE  WtQYNYLlSL  dKYYGYGGGN
A. terreus cbs                dD..Aht...  ......LSPF  CDLF..TAAE  WtQYNYLlSL  dKYYGYGGGN
A. niger var. awamori         Tv..DTK...  ......LSPF  CDLF..ThDE  WiHYDYLQSL  kKYYGHGAGN
A. niger T213                 Tv..DTK...  ......LSPF  CDLF..ThDE  WiHYDYLRSL  kKYYGHGAGN
A. niger NRRL3135             Tv..DTK...  ......LSPF  CDLF..ThDE  WiNYDYLQSL  kKYYGHGAGN
A. fumigatus ATCC13073        SD..ASQ...  ......LSPF  CQLF..ThNE  WkKYNYLQSL  gKYYGYGAGN
A. fumigatus ATCC32722        SD..ASQ...  ......LSPF  CQLF..ThNE  WkKYNYLQSL  gKYYGYGAGN
A. fumigatus ATCC58128        SD..ASQ...  ......LSPF  CQLF..ThNE  WkKYNYLQSL  gKYYGYGAGN
A. fumigatus ATCC26906        SD..ASQ...  ......LSPF  CQLF..ThNE  WkKYNYLQSL  gKYYGYGAGN
A. fumigatus ATCC32239        AD..ASE...  ......LSPF  CAIF..ThNE  WkKYDYLQSL  gKYYGYGAGN
E. nidulans                   AH..GTE...  ......LSPF  CAIF..TEKE  WlQYDYLQSL  sKYYGYGAGS
T. thermophilus               ht..DT....  ......LSPF  CALs..TqEE  WqaYDYYQSL  gKYYGnGGGN
T. lanuginosus                PvlfPrQ...  ......LSPF  CHLF..TADD  WmaYDYYyTL  dKYYSHGGGS
M. thermophila                SsdpATadag  ggngrpLSPF  CrLF..SEsE  WraYDYLQSV  gKWYGYGPGN Consensus Seq. 11             SD--ATQ---  ------LSPF  CDLF--TADE  W-QYDYLQSL  -KYYGYGAGN
```

Fig. 6c

```
                          301                                                      350
P. involutus (phyA1)      eLGPvQGVGY  vNELIARLTN  S.AVRDNTqT  NRTLDASPvT  FPLNkTFYAD
P. involutus (phyA2)      ALGPvQGVGY  iNELLARLTN  S.AVNDNTqT  NRTLDAaPDT  FPLNkTMYAD
T. pubescens              PLGPvQGVGY  iNELIARLTa  q.nVsDHTqT  NsTLDSSPET  FPLNrTLYAD
A. pediades               PLGPvQGVGY  iNELLARLTE  m.PVRDNTqT  NRTLDSSP1T  FPLDrSIYAD
P. lycii                  ALGPvQGVGY  vNELLARLTg  q.AVRDETqT  NRTLDSDPAT  FPLNrTFYAD
A. terreus 9a1            PLGPvQGVGW  aNELMARLTR  A.PVHDHTCv  NNTLDASPAT  FPLNATLYAD
A. terreus cbs            PLGPvQGVGW  aNELIARLTR  S.PVHDHTCv  NNTLDANPAT  FPLNATLYAD
A. niger var. awamori     PLGPTQGVGY  aNELIARLTH  S.PVHDDTSS  NHTLDSNPAT  FPLNSTLYAD
A. niger T213             PLGPTQGVGY  aNELIARLTH  S.PVHDDTSS  NHTLDSNPAT  FPLNSTLYAD
A. niger NRRL3135         PLGPTQGVGY  aNELIARLTH  S.PVHDDTSS  NHTLDSSPAT  FPLNSTLYAD
A. fumigatus ATCC13073    PLGPAQGIGF  tNELIARLTR  S.PVQDHTST  NsTLvSNPAT  FPLNATMYvD
A. fumigatus ATCC32722    PLGPAQGIGF  tNELIARLTR  S.PVQDHTST  NsTLvSNPAT  FPLNATMYvD
A. fumigatus ATCC58128    PLGPAQGIGF  tNELIARLTR  S.PVQDHTST  NsTLvSNPAT  FPLNATMYvD
A. fumigatus ATCC26906    PLGPAQGIGF  tNELIARLTR  S.PVQDHTST  NsTLvSNPAT  FPLNATMYvD
A. fumigatus ATCC32239    PLGPAQGIGF  tNELIARLTN  S.PVQDHTST  NsTLDSDPAT  FPLDrkLYAD
E. nidulans               PLGPAQGIGF  tNELIARLTQ  S.PVQDNTST  NHTLDSNPAT  FPLNATLYAD
T. thermophilus           PLGPAQGVGF  vNELIARMTH  S.PVQDYTTv  NHTLDSNPAT  FPLNATLYAD
T. lanuginosus             AFGPSRGVGF  vNELIARMTg  N1PVKDHTTv  NHTLDdNPET  FPLDAvLYAD
M. thermophila            PLGPTQGVGF  vNELLARLA.  GvPVRDgTST  NRTLDGDPrT  FPLGrPLYAD Consensus Seq. 11         PLGPAQGVGF  -NELIARLTH  S-PVQDHTST  NHTLDSNPAT  FPLNATLYAD 351                                                      400
P. involutus (phyA1)      FSHDN1MVAV  FsAMGLFrqP  aPLSTSvpNP  wrt.....Wr  TSS1VPFSGR
P. involutus (phyA2)      FSHDN1MVAV  FsAMGLFrqS  aPLSTSTpDP  nrt.....W1  TSSvVPFSAR
T. pubescens              FSHDNqMVAI  FsAMGLFNqS  aPLdPTTpDP  art.....F1  vkkiVPFSAR
A. pediades               LSHDNqMIAI  FsAMGLFNqS  sPLdPSfpNP  krt.....Wv  TSR1tPFSAR
P. lycii                  FSHDNTMVPI  FaALGLFNAT  a.LdP1kpDe  nrl.....Wv  DSk1VPFSGH
A. terreus 9a1            FSHDSnLVSI  FWALGLYNGT  aPLSqTSVES  Vs..QTDGYA  AAWTVPFAAR
A. terreus cbs            FSHDSnLVSI  FWALGLYNGT  KPLSqTTVEd  It..rTDGYA  AAWTVPFAAR
A. niger var. awamori     FSHDNGIISI  LFALGLYNGT  KPLSTTTVEN  It..QTDGFS  SAWTVPFASR
A. niger T213             FSHDNGIISI  LFALGLYNGT  KPLSTTTVEN  It..QTDGFS  SAWTVPFASR
A. niger NRRL3135         FSHDNGIISI  LFALGLYNGT  KPLSTTTVEN  It..QTDGFS  SAWTVPFASR
A. fumigatus ATCC13073    FSHDNSMVSI  FFALGLYNGT  EPLSrTSVES  ak..E1DGYS  ASWvVPFGAR
A. fumigatus ATCC32722    FSHDNSMVSI  FFALGLYNGT  gPLSrTSVES  ak..E1DGYS  ASWvVPFGAR
A. fumigatus ATCC58128    FSHDNSMVSI  FFALGLYNGT  EPLSrTSVES  ak..E1DGYS  ASWvVPFGAR
A. fumigatus ATCC26906    FSHDNSMVSI  FFALGLYNGT  EPLSrTSVES  ak..E1DGYS  ASWvVPFGAR
A. fumigatus ATCC32239    FSHDNGMIPI  FPAMGLYNGT  EPLSqTSeES  tk..ESNGYS  ASWAVPFGAR
E. nidulans               FSHDNSMISI  FFAMGLYNGT  QPLSmdSVES  Iq..EmDGYA  ASWTVPFGAR
T. thermophilus           FSHDNTMtSI  FaALGLYNGT  akLSTTeIKS  Ie..ETDGYS  AAWTVPFGGR
T. lanuginosus             FSHDNTMtGI  FsAMGLYNGT  KPLSTSkIQP  ptgaAADGYA  ASWTVPFAAR
M. thermophila            FSHDNdMMGV  LgALGaYDGv  pPLdkTArrd  ..peE1GGYA  ASWAVPFAAR Consensus Seq. 11         FSHDNTMVSI  FFALGLYNGT  KPLSTTSVES  I---ETDGYA  ASWTVPFAAR
```

Fig. 6d

```
                              401                                           450
P. involutus (phyA1)    mvVErLsC.. fGt....... .......Tk VRVLVQDQVq PLEfCGgDRn
P. involutus (phyA2)    maVErLsC.. AGt....... .......Tk VRVLVQDQVq PLEfCGgDQd
T. pubescens            mvVErLDC.. GGa....... .......Qs VRLLVNDaVq PLafCGaDts
A. pediades             mvtErLlCQr DGtGsGGpsr imrNgnvQTF VRILVNDaLq PLkfCGgDmd
P. lycii                mtVEkLaC.. .......... .....sgKea VRVLVNDaVq PLEfCGg.vd
A. terreus 9a1          AYVEMMQCrA .......... ..EK...EPL VRVLVNDRVM PLHGCPtDKL
A. terreus cbs          AYIEMMQCrA .......... ..EK...QPL VRVLVNDRVM PLHGCAVDNL
A. niger var. awamori   lYVEMMQCQA .......... ..EQ...EPL VRVLVNDRVV PLHGCPIDaL
A. niger T213           lYVEMMQCQA .......... ..EQ...EPL VRVLVNDRVV PLHGCPIDaL
A. niger NRRL3135       lYVEMMQCQA .......... ..EQ...EPL VRVLVNDRVV PLHGCPVDaL
A. fumigatus ATCC13073  AYfEtMQCKS .......... ..EK...EPL VRaLINDRVV PLHGCDVDKL
A. fumigatus ATCC32722  AYfEtMQCKS .......... ..EK...EPL VRaLINDRVV PLHGCDVDKL
A. fumigatus ATCC58128  AYfEtMQCKS .......... ..EK...ESL VRaLINDRVV PLHGCDVDKL
A. fumigatus ATCC26906  AYfEtMQCKS .......... ..EK...EPL VRaLINDRVV PLHGCDVDKL
A. fumigatus ATCC32239  AYfEtMQCKS .......... ..EK...EPL VRaLINDRVV PLHGCAVDKL
E. nidulans             AYfELMQCE. .......... ..KK...EPL VRVLVNDRVV PLHGCAVDKF
T. thermophilus         AYIEMMQCDD .......... ..sD...EPV VRVLVNDRVV PLHGCEVDsL
T. lanuginosus           AYVELLRCET ETsSeEEeEG ..ED...EPF VRVLVNDRVV PLHGCrVDRW
M. thermophila          iYVEkMRCsG GGgGgGGgEG ..rQekdEeM VRVLVNDRVM TLkGCGaDEr Consensus Seq. 11       AYVEMMQCEA GG-G-GG-EG --EK---EPL VRVLVNDRVV PLHGCGVDKL 451                       482
P. involutus (phyA1)    GlCtLAKFVE SqTPARSDga GDFEKCPAts a~
P. involutus (phyA2)    GlCaLDKFVE SqAYARSGga GDFEKCLAtt v~
T. pubescens            GvCtLDAFVE SqAYARNDge GDFEKCFAt~ ~~
A. pediades             SlCtLEAFVE SqkYAReDgq GDFEKCFD~~ ~~
P. lycii                GvCELsAFVE SqTYAReNgq GDFAKCgfvp se
A. terreus 9a1          GRCKrDAFVA GLSFAQAG.. GNWADCF~~~ ~~
A. terreus cbs          GRCKrDDFVE GLSFARAG.. GNWAECF~~~ ~~
A. niger var. awamori   GRCtrDsFVr GLSFARSG.. GDWAECsA~~ ~~
A. niger T213           GRCtrDsFVr GLSFARSG.. GDWAECFA~~ ~~
A. niger NRRL3135       GRCtrDsFVr GLSFARSG.. GDWAECFA~~ ~~
A. fumigatus ATCC13073  GRCKLNDFVK GLSWARSG.. GNWGECFS~~ ~~
A. fumigatus ATCC32722  GRCKLNDFVK GLSWARSG.. GNWGECFS~~ ~~
A. fumigatus ATCC58128  GRCKLNDFVK GLSWARSG.. GNWGECFS~~ ~~
A. fumigatus ATCC26906  GRCKLNDFVK GLSWARSG.. GNWGECFS~~ ~~
A. fumigatus ATCC32239  GRCKLKDFVK GLSWARSG.. GNSEQSFS~~ ~~
E. nidulans             GRCtLDDWVE GLNFARSG.. GNWktCFTl~ ~~
T. thermophilus         GRCKrDDFVr GLSFARqG.. GNWEGCYAas e~
T. lanuginosus           GRCRrDEWIK GLTFArqG.. GHWDrCF~~~ ~~
M. thermophila          GmCtLErFIE SMAFARGN.. GKWD1CFA~~ ~~

Consensus Seq. 11       GRCKLDDFVE GLSFARSG-- GNWAECFA-- --
```

Fig. 6e

```
      M   G   V   F   V   V   L   L   S   I   A   T   L   F   G   S   T   S   G   T         20
      ATGGGCGTGTTCGTCGTGCTACTGTCCATTGCCACCTTGTTCGGTTCCACATCCGGTACC
  1   ---------+---------+---------+---------+---------+---------+        60
      TACCCGCACAAGCAGCACGATGACAGGTAACGGTGGAACAAGCCAAGGTGTAGGCCATGG

A   L   G   P   R   G   N   S   H   S   C   D   T   V   D   G   G   Y   Q   C         40
      GCCTTGGGTCCTCGTGGTAATTCTCACTCTTGTGACACTGTTGACGGTGGTTACCAATGT
 61   ---------+---------+---------+---------+---------+---------+       120
      CGGAACCCAGGAGCACCATTAAGAGTGAGAACACTGTGACAACTGCCACCAATGGTTACA

F   P   E   I   S   H   L   W   G   T   Y   S   P   Y   F   S   L   A   D   E         60
      TTCCCAGAAATTTCTCACTTGTGGGGTACCTACTCTCCATACTTCTCTTTGGCAGACGAA
121   ---------+---------+---------+---------+---------+---------+       180
      AAGGGTCTTTAAAGAGTGAACACCCCATGGATGAGAGGTATGAAGAGAAACCGTCTGCTT

S   A   I   S   P   D   V   P   D   D   C   R   V   T   F   V   Q   V   L   S         80
      TCTGCTATTTCTCCAGACGTTCCAGACGACTGTAGAGTTACTTTCGTTCAAGTTTTGTCT
187   ---------+---------+---------+---------+---------+---------+       240
      AGACGATAAAGAGGTCTGCAAGGTCTGCTGACATCTCAATGAAAGCAAGTTCAAAACAGA

R   H   G   A   R   Y   P   T   S   S   A   S   K   A   Y   S   A   L   I   E        100
      AGACACGGTGCTAGATACCCAACTTCTTCTGCGTCTAAGGCTTACTCTGCTTTGATTGAA
241   ---------+---------+---------+---------+---------+---------+       300
      TCTGTGCCACGATCTATGGGTTGAAGAAGACGCAGATTCCGAATGAGACGAAACTAACTT

A   I   Q   K   N   A   T   A   F   K   G   K   Y   A   F   L   K   T   Y   N        120
      GCTATTCAAAAGAACGCTACTGCTTTCAAGGGTAAGTACGCTTTCTTGAAGACTTACAAC
301   ---------+---------+---------+---------+---------+---------+       360
      CGATAAGTTTTCTTGCGATGACGAAAGTTCCCATTCATGCGAAAGAACTTCTGAATGTTG

Y   T   L   G   A   D   D   L   T   P   F   G   E   N   Q   M   V   N   S   G        140
      TACACTTTGGGTGCTGACGACTTGACTCCATTCGGTGAAAACCAAATGGTTAACTCTGGT
361   ---------+---------+---------+---------+---------+---------+       420
      ATGTGAAACCCACGACTGCTGAACTGAGGTAAGCCACTTTTGGTTTACCAATTGAGACCA

I   K   F   Y   R   R   Y   K   A   L   A   R   K   I   V   P   F   I   R   A        160
      ATTAAGTTCTACAGAAGATACAAGGCTTTGGCTAGAAAGATTGTTCCATTCATTAGAGCT
421   ---------+---------+---------+---------+---------+---------+       480
      TAATTCAAGATGTCTTCTATGTTCCGAAACCGATCTTTCTAACAAGGTAAGTAATCTCGA

S   G   S   D   R   V   I   A   S   A   E   K   F   I   E   G   F   Q   S   A        180
      TCTGGTTCTGACAGAGTTATTGCTTCTGCTGAAAAGTTCATTGAAGGTTTCCAATCTGCT
481   ---------+---------+---------+---------+---------+---------+       540
      AGACCAAGACTGTCTCAATAACGAAGACGACTTTTCAAGTAACTTCCAAAGGTTAGACGA

K   L   A   D   P   G   S   Q   P   H   Q   A   S   P   V   I   N   V   I   I        200
      AAGTTGGCTGACCCAGGTTCTCAACCACACCAAGCTTCTCCAGTTATTAACGTGATCATT
541   ---------+---------+---------+---------+---------+---------+       600
      TTCAACCGACTGGGTCCAAGAGTTGGTGTGGTTCGAAGAGGTCAATAATTGCACTAGTAA

P   E   G   S   G   Y   N   N   T   L   D   H   G   T   C   T   A   F   E   D        220
      CCAGAAGGATCCGGTTACAACAACACTTTGGACCACGGTACTTGTACTGCTTTCGAAGAC
601   ---------+---------+---------+---------+---------+---------+       660
      GGTCTTCCTAGGCCAATGTTGTTGTGAAACCTGGTGCCATGAACATGACGAAAGCTTCTG
```

Fig. 7a

```
               S  E  L  G  D  D  V  E  A  N  F  T  A  L  F  A  P  A  I  R      240
            TCTGAATTAGGTGACGACGTTGAAGCTAACTTCACTGCTTTGTTCGCTCCAGCTATTAGA
    661     ---------+---------+---------+---------+---------+---------+      720
            AGACTTAATCCACTGCTGCAACTTCGATTGAAGTGACGAAACAAGCGAGGTCGATAATCT

A  R  L  E  A  D  L  P  G  V  T  L  T  D  E  D  V  V  Y  L      260
            GCTAGATTGGAAGCTGACTTGCCAGGTGTTACTTTGACTGACGAAGACGTTGTTTACTTG
    721     ---------+---------+---------+---------+---------+---------+      780
            CGATCTAACCTTCGACTGAACGGTCCACAATGAAACTGACTGCTTCTGCAACAAATGAAC

M  D  M  C  P  F  D  T  V  A  R  T  S  D  A  T  E  L  S  P      280
            ATGGACATGTGTCCATTCGACACTGTCGCTAGAACTTCTGACGCTACTGAATTGTCTCCA
    781     ---------+---------+---------+---------+---------+---------+      840
            TACCTGTACACAGGTAAGCTGTGACAGCGATCTTGAAGACTGCGATGACTTAACAGAGGT

F  C  A  L  F  T  H  D  E  W  I  Q  Y  D  Y  L  Q  S  L  G      300
            TTCTGTGCTTTGTTCACTCACGACGAATGGATCCAATACGACTACTTGCAAAGCTTGGGT
    841     ---------+---------+---------+---------+---------+---------+      900
            AAGACACGAAACAAGTGAGTGCTGCTTACCTAGGTTATGCTGATGAACGTTTCGAACCCA

K  Y  Y  G  Y  G  A  G  N  P  L  G  P  A  Q  G  V  G  F  A      320
            AAGTACTACGGTTACGGTGCTGGTAACCCATTGGGTCCAGCTCAAGGTGTTGGTTTCGCT
    901     ---------+---------+---------+---------+---------+---------+      960
            TTCATGATGCCAATGCCACGACCATTGGGTAACCCAGGTCGAGTTCCACAACCAAAGCGA

N  E  L  I  A  R  L  T  H  S  P  V  Q  D  H  T  S  T  N  H      340
            AACGAATTGATTGCTAGATTGACTCACTCTCCAGTTCAAGACCACACTTCTACTAACCAC
    961     ---------+---------+---------+---------+---------+---------+     1020
            TTGCTTAACTAACGATCTAACTGAGTGAGAGGTCAAGTTCTGGTGTGAAGATGATTGGTG

T  L  D  S  N  P  A  T  F  P  L  N  A  T  L  Y  A  D  F  S      360
            ACTTTGGACTCTAACCCAGCTACTTTCCCATTGAACGCTACTTTGTACGCTGACTTCTCT
   1021     ---------+---------+---------+---------+---------+---------+     1080
            TGAAACCTGAGATTGGGTCGATGAAAGGGTAACTTGCGATGAAACATGCGACTGAAGAGA

H  D  N  T  M  I  S  I  F  F  A  L  G  L  Y  N  G  T  K  P      380
            CACGACAACACTATGATATCTATTTTCTTCGCTTTGGGTTTGTACAACGGTACCAAGCCA
   1081     ---------+---------+---------+---------+---------+---------+     1140
            GTGCTGTTGTGATACTATAGATAAAAGAAGCGAAACCCAAACATGTTGCCATGGTTCGGT

L  S  T  T  S  V  E  S  I  E  E  T  D  G  Y  S  A  S  W  T      400
            TTGTCTACTACTTCTGTTGAATCTATTGAAGAAACTGACGGTTACTCTGCTTCTTGGACT
   1141     ---------+---------+---------+---------+---------+---------+     1200
            AACAGATGATGAAGACAACTTAGATAACTTCTTTGACTGCCAATGAGACGAAGAACCTGA

V  P  F  A  A  R  A  Y  V  E  M  M  Q  C  Q  A  E  K  E  P      420
            GTTCCATTCGCTGCTAGAGCTTACGTTGAAATGATGCAATGTCAAGCTGAAAAGGAACCA
   1201     ---------+---------+---------+---------+---------+---------+     1260
            CAAGGTAAGCGACGATCTCGAATGCAACTTTACTACGTTACAGTTCGACTTTTCCTTGGT

L  V  R  V  L  V  N  D  R  V  V  P  L  H  G  C  A  V  D  K      440
            TTGGTTAGAGTTTTGGTTAACGACAGAGTTGTTCCATTGCACGGTTGTGCTGTTGACAAG
   1261     ---------+---------+---------+---------+---------+---------+     1320
            AACCAATCTCAAAACCAATTGCTGTCTCAACAAGGTAACGTGCCAACACGACAACTGTTC
```

Fig. 7b

```
           L  G  R  C  K  R  D  D  F  V  E  G  L  S  F  A  R  S  G  G      460
        TTGGGTAGATGTAAGAGAGACGACTTCGTTGAAGGTTTGTCTTTCGCTAGATCTGGTGGT
 1321   ---------+---------+---------+---------+---------+---------+  1380
        AACCCATCTACATTCTCTCTGCTGAAGCAACTTCCAAACAGAAAGCGATCTAGACCACCA

N  W  A  E  C  F  A  *     467
        AACTGGGCTGAATGTTTCGCTTAA
 1381   ---------+---------+----  1410
        TTGACCCGACTTACAAAGCGAATT
```

Fig. 7c

```
        M   G   V   F   V   V   L   L   S   I   A   T   L   F   G   S   T   S   G   T     20
      ATGGGCGTGTTCGTCGTGCTACTGTCCATTGCCACCTTGTTCGGTTCCACATCCGGTACC
  1   ---------+---------+---------+---------+---------+---------+    60
      TACCCGCACAAGCAGCACGATGACAGGTAACGGTGGAACAAGCCAAGGTGTAGGCCATGG

A   L   G   P   R   G   N   S   H   S   C   D   T   V   D   G   G   Y   Q   C     40
      GCCTTGGGTCCTCGTGGTAACTCTCACTCTTGTGACACTGTTGACGGTGGTTACCAATGT
 61   ---------+---------+---------+---------+---------+---------+   120
      CGGAACCCAGGAGCACCATTGAGAGTGAGAACACTGTGACAACTGCCACCAATGGTTACA

F   P   E   I   S   H   L   W   G   T   Y   S   P   F   F   S   L   A   D   E     60
      TTCCCAGAAATTTCTCACTTGTGGGGTACATACTCTCCATTCTTCTCTTTGGCTGACGAA
121   ---------+---------+---------+---------+---------+---------+   180
      AAGGGTCTTTAAAGAGTGAACACCCCATGTATGAGAGGTAAGAAGAGAAACCGACTGCTT

S   A   I   S   P   D   V   P   K   G   C   R   V   T   F   V   Q   V   L   S     80
      TCTGCTATTTCTCCAGACGTTCCAAAGGGTTGTAGAGTTACTTTCGTTCAAGTTTTGTCT
181   ---------+---------+---------+---------+---------+---------+   240
      AGACGATAAAGAGGTCTGCAAGGTTTCCCAACATCTCAATGAAAGCAAGTTCAAAACAGA

R   H   G   A   R   Y   P   T   S   S   A   S   K   A   Y   S   A   L   I   E    100
      AGACACGGTGCTAGATACCCAACTTCTTCTGCGTCTAAGGCGTACTCTGCTTTGATTGAA
241   ---------+---------+---------+---------+---------+---------+   300
      TCTGTGCCACGATCTATGGGTTGAAGAAGACGCAGATTCCGCATGAGACGAAACTAACTT

A   I   Q   K   N   A   T   A   F   K   G   K   Y   A   F   L   K   T   Y   N    120
      GCTATTCAAAAGAACGCTACTGCTTTCAAGGGTAAGTACGCTTTCTTGAAGACTTACAAC
301   ---------+---------+---------+---------+---------+---------+   360
      CGATAAGTTTTCTTGCGATGACGAAAGTTCCCATTCATGCGAAAGAACTTCTGAATGTTG

Y   T   L   G   A   D   D   L   T   P   F   G   E   Q   Q   M   V   N   S   G    140
      TACACTTTGGGTGCTGACGACTTGACTCCATTCGGTGAACAACAAATGGTTAACTCTGGT
361   ---------+---------+---------+---------+---------+---------+   420
      ATGTGAAACCCACGACTGCTGAACTGAGGTAAGCCACTTGTTGTTTACCAATTGAGACCA

I   K   F   Y   R   R   Y   K   A   L   A   R   K   I   V   P   F   I   R   A    160
      ATTAAGTTCTACAGAAGATACAAGGCTTTGGCTAGAAAGATTGTTCCATTCATTAGAGCT
421   ---------+---------+---------+---------+---------+---------+   480
      TAATTCAAGATGTCTTCTATGTTCCGAAACCGATCTTTCTAACAAGGTAAGTAATCTCGA

S   G   S   D   R   V   I   A   S   A   E   K   F   I   E   G   F   Q   S   A    180
      TCTGGTTCTGACAGAGTTATTGCTTCTGCTGAAAAGTTCATTGAAGGTTTCCAATCTGCT
481   ---------+---------+---------+---------+---------+---------+   540
      AGACCAAGACTGTCTCAATAACGAAGACGACTTTTCAAGTAACTTCCAAAGGTTAGACGA

K   L   A   D   P   G   A   N   P   H   Q   A   S   P   V   I   N   V   I   I    200
      AAGTTGGCTGACCCAGGTGCTAACCCACACCAAGCTTCTCCAGTTATTAACGTTATTATT
541   ---------+---------+---------+---------+---------+---------+   600
      TTCAACCGACTGGGTCCACGATTGGGTGTGGTTCGAAGAGGTCAATAATTGCAATAATAA

P   E   G   A   G   Y   N   N   T   L   D   H   G   L   C   T   A   F   E   E    220
      CCAGAAGGTGCTGGTTACAACAACACTTTGGACCACGGTTTGTGTACTGCTTTCGAAGAA
601   ---------+---------+---------+---------+---------+---------+   660
      GGTCTTCCACGACCAATGTTGTTGTGAAACCTGGTGCCAAACACATGACGAAAGCTTCTT
```

Fig. 8a

```
        S  E  L  G  D  D  V  E  A  N  F  T  A  V  F  A  P  P  I  R    240
        TCTGAATTGGGTGACGACGTTGAAGCTAACTTCACTGCTGTTTTCGCTCCACCAATTAGA
    661 ---------+---------+---------+---------+---------+---------+  720
        AGACTTAACCCACTGCTGCAACTTCGATTGAAGTGACGACAAAAGCGAGGTGGTTAATCT

A  R  L  E  A  H  L  P  G  V  N  L  T  D  E  D  V  V  N  L    260
        GCTAGATTGGAAGCTCACTTGCCAGGTGTTAACTTGACTGACGAAGACGTTGTTAACTTG
    721 ---------+---------+---------+---------+---------+---------+  780
        CGATCTAACCTTCGAGTGAACGGTCCACAATTGAACTGACTGCTTCTGCAACAATTGAAC

M  D  M  C  P  F  D  T  V  A  R  T  S  D  A  T  Q  L  S  P    280
        ATGGACATGTGTCCATTCGACACTGTTGCTAGAACTTCTGACGCTACTCAATTGTCTCCA
    781 ---------+---------+---------+---------+---------+---------+  840
        TACCTGTACACAGGTAAGCTGTGACAACGATCTTGAAGACTGCGATGAGTTAACAGAGGT

F  C  D  L  F  T  H  D  E  W  I  Q  Y  D  Y  L  Q  S  L  G    300
        TTCTGTGACTTGTTCACTCACGACGAATGGATTCAATACGACTACTTGCAATCTTTGGGT
    841 ---------+---------+---------+---------+---------+---------+  900
        AAGACACTGAACAAGTGAGTGCTGCTTACCTAAGTTATGCTGATGAACGTTAGAAACCCA

K  Y  Y  G  Y  G  A  G  N  P  L  G  P  A  Q  G  V  G  F  V    320
        AAGTACTACGGTTACGGTGCTGGTAACCCATTGGGTCCAGCTCAAGGTGTTGGTTTCGTT
    901 ---------+---------+---------+---------+---------+---------+  960
        TTCATGATGCCAATGCCACGACCATTGGGTAACCCAGGTCGAGTTCCACAACCAAAGCAA

N  E  L  I  A  R  L  T  H  S  P  V  Q  D  H  T  S  T  N  H    340
        AACGAATTGATTGCTAGATTGACTCACTCTCCAGTTCAAGACCACACTTCTACTAACCAC
    961 ---------+---------+---------+---------+---------+---------+ 1020
        TTGCTTAACTAACGATCTAACTGAGTGAGAGGTCAAGTTCTGGTGTGAAGATGATTGGTG

T  L  D  S  N  P  A  T  F  P  L  N  A  T  L  Y  A  D  F  S    360
        ACTTTGGACTCTAACCCAGCTACTTTCCCATTGAACGCTACTTTGTACGCTGACTTCTCT
   1021 ---------+---------+---------+---------+---------+---------+ 1080
        TGAAACCTGAGATTGGGTCGATGAAAGGGTAACTTGCGATGAAACATGCGACTGAAGAGA

H  D  N  T  M  V  S  I  F  F  A  L  G  L  Y  N  G  T  K  P    380
        CACGACAACACTATGGTTTCTATTTTCTTCGCTTTGGGTTTGTACAACGGTACTAAGCCA
   1081 ---------+---------+---------+---------+---------+---------+ 1140
        GTGCTGTTGTGATACCAAAGATAAAAGAAGCGAAACCCAAACATGTTGCCATGATTCGGT

L  S  T  T  S  V  E  S  I  E  E  T  D  G  Y  S  A  S  W  T    400
        TTGTCTACTACTTCTGTTGAATCTATTGAAGAAACTGACGGTTACTCTGCTTCTTGGACT
   1141 ---------+---------+---------+---------+---------+---------+ 1200
        AACAGATGATGAAGACAACTTAGATAACTTCTTTGACTGCCAATGAGACGAAGAACCTGA

V  P  F  A  A  R  A  Y  V  E  M  M  Q  C  E  A  E  K  E  P    420
        GTTCCATTCGCTGCTAGAGCTTACGTTGAAATGATGCAATGTGAAGCTGAAAAGGAACCA
   1201 ---------+---------+---------+---------+---------+---------+ 1260
        CAAGGTAAGCGACGATCTCGAATGCAACTTTACTACGTTACACTTCGACTTTTCCTTGGT

L  V  R  V  L  V  N  D  R  V  V  P  L  H  G  C  G  V  D  K    440
        TTGGTTAGAGTTTTGGTTAACGACAGAGTTGTTCCATTGCACGGTTGTGGTGTTGACAAG
   1261 ---------+---------+---------+---------+---------+---------+ 1320
        AACCAATCTCAAAACCAATTGCTGTCTCAACAAGGTAACGTGCCAACACCACAACTGTTC
```

Fig. 8b

```
            L   G   R   C   K   R   D   D   F   V   E   G   L   S   F   A   R   S   G   G      460
         TTGGGTAGATGTAAGAGAGACGACTTCGTTGAAGGTTTGTCTTTCGCTAGATCTGGTGGT
1321     ---------+---------+---------+---------+---------+---------+ 1380
         AACCCATCTACATTCTCTCTGCTGAAGCAACTTCCAAACAGAAAGCGATCTAGACCACCA

N   W   E   E   C   F   A   *      467
         AACTGGGAAGAATGTTTCGCTTAA
1381     ---------+---------+---- 1404
         TTGACCCTTCTTACAAAGCGAATT
```

Fig. 8c

```
          M  G  V  F  V  V  L  L  S  I  A  T  L  F  G  S  T  S  G  T    20
         ATGGGGGTTTTCGTCGTTCTATTATCTATCGCGACTCTGTTCGGCAGCACATCGGGCACT
   1     ---------+---------+---------+---------+---------+---------+    60
         TACCCCCAAAAGCAGCAAGATAATAGATAGCGCTGAGACAAGCCGTCGTGTAGCCCGTGA

A  L  G  P  R  G  N  H  S  K  S  C  D  T  V  D  L  G  Y  Q    40
         GCGCTGGGCCCCCGTGGAAATCACTCCAAGTCCTGCGATACGGTAGACCTAGGGTACCAG
  61     ---------+---------+---------+---------+---------+---------+   120
         CGCGACCCGGGGGCACCTTTAGTGAGGTTCAGGACGCTATGCCATCTGGATCCCATGGTC

C  S  P  A  T  S  H  L  W  G  T  Y  S  P  Y  F  S  L  E  D    60
         TGCTCCCCTGCGACTTCTCATCTATGGGGCACGTACTCGCCATaCTTTTCGCTCGAGGAC
 121     ---------+---------+---------+---------+---------+---------+   180
         ACGAGGGGACGCTGAAGAGTAGATACCCCGtgCATGAGCGGTAtGAAAAGCGAGCTCCTG

E  L  S  V  S  S  K  L  P  K  D  C  R  I  T  L  V  Q  V  L    80
         GAGCTGTCCGTGTCGAGTAAGCTTCCCAAGGATTGCCGGATCACCTTGGTACAGGTGCTA
 181     ---------+---------+---------+---------+---------+---------+   240
         CTCGACAGGCACAGCTCATTCGAAGGGTTCCTAACGGCCTAGTGGAACCATGTCCACGAT

S  R  H  G  A  R  Y  P  T  S  S  K  S  K  K  Y  K  K  L  I   100
         TCGCGCCATGGAGCGCGGTACCCAACCAGCTCCAAGAGCAAAAAGTATAAGAAGCTTaTt
 241     ---------+---------+---------+---------+---------+---------+   300
         AGCGCGGTACCTCGCGCCATGGGTTGGTCGAGGTTCTCGTTTTTCATATTCTTCGAAtAa

T  A  I  Q  A  N  A  T  D  F  K  G  K  Y  A  F  L  K  T  Y   120
         ACGGCGATCCAGGCCAATGCCACCGACTTCAAGGGCAAGTaCGCCTTTTTGAAGACGTAC
 301     ---------+---------+---------+---------+---------+---------+   360
         TGCCGCTAGGTCCGGTTACGGTGGCTGAAGTTCCCGTTCAtgCGGAAAAACTTCTGCATG

N  Y  T  L  G  A  D  D  L  T  P  F  G  E  Q  Q  L  V  N  S   140
         AACTATACTCTGGGTGCGGATGACCTCACTCCCTTTGGGGAGCAGCAGCTGGTGAACTCG
 361     ---------+---------+---------+---------+---------+---------+   420
         TTGATATGAGACCCACGCCTACTGGAGTGAGGGAAACCCCTCGTCGTCGACCACTTGAGC

G  I  K  F  Y  Q  R  Y  K  A  L  A  R  S  V  V  P  F  I  R   160
         GGCATCAAGTTCTACCAGAGGTACAAGGCTCTGGCGCGCAGTGTGGTGCCGTTTATTCGC
 421     ---------+---------+---------+---------+---------+---------+   480
         CCGTAGTTCAAGATGGTCTCCATGTTCCGAGACCGCGCGTCACACCACGGCAAATAAGCG

A  S  G  S  D  R  V  I  A  S  G  E  K  F  I  E  G  F  Q  Q   180
         GCCTCAGGCTCGGACCGGGTTATTGCTTCGGGAGAGAAGTTCATCGAGGGGTTCCAGCAG
 481     ---------+---------+---------+---------+---------+---------+   540
         CGGAGTCCGAGCCTGGCCCAATAACGAAGCCCTCTCTTCAAGTAGCTCCCCAAGGTCGTC

A  K  L  A  D  P  G  A  T  N  R  A  A  P  A  I  S  V  I  I   200
         GCGAAGCTGGCTGATCCTGGCGCGACGAACCGCGCCGCTCCGGCGATTAGTGTGATTATT
 541     ---------+---------+---------+---------+---------+---------+   600
         CGCTTCGACCGACTAGGACCGCGCTGCTTGGCGCGGCGAGGCCGCTAATCACACTAATAA

P  E  S  E  T  F  N  N  T  L  D  H  G  V  C  T  K  F  E  A   220
         CCGGAGAGCGAGACGTTCAACAATACGCTGGACCACGGTGTGTGCACGAAGTTTGAGGCG
 601     ---------+---------+---------+---------+---------+---------+   660
         GGCCTCTCGCTCTGCAAGTTGTTATGCGACCTGGTGCCACACACGTGCTTCAAACTCCGC
```

Fig. 9a

```
          S  Q  L  G  D  E  V  A  A  N  F  T  A  L  F  A  P  D  I  R    240
         AGTCAGCTGGGAGATGAGGTTGCGGCCAATTTCACTGCGCTCTTTGCACCCGACATCCGA
   661   ---------+---------+---------+---------+---------+---------+    720
         TCAGTCGACCCTCTACTCCAACGCCGGTTAAAGTGACGCGAGAAACGTGGGCTGTAGGCT

A  R  L  E  K  H  L  P  G  V  T  L  T  D  E  D  V  V  S  L    260
         GCTCGCctCGAGAAGCATCTTCCTGGCGTGACGCTGACAGACGAGGACGTTGTCAGTCTA
   721   ---------+---------+---------+---------+---------+---------+    780
         CGAGCGgaGCTCTTCGTAGAAGGACCGCACTGCGACTGTCTGCTCCTGCAACAGTCAGAT

M  D  M  C  P  F  D  T  V  A  R  T  S  D  A  S  Q  L  S  P    280
         ATGGACATGTGTcCGTTTGATACGGTAGCGCGCACCAGCGACGCAAGTCAGCTGTCACCG
   781   ---------+---------+---------+---------+---------+---------+    840
         TACCTGTACACAgGCAAACTATGCCATCGCGCGTGGTCGCTGCGTTCAGTCGACAGTGGC

F  C  Q  L  F  T  H  N  E  W  K  K  Y  D  Y  L  Q  S  L  G    300
         TTCTGTCAACTCTTCACTCACAATGAGTGGAAGAAGTACgACTACCTTCAGTCCTTGGGC
   841   ---------+---------+---------+---------+---------+---------+    900
         AAGACAGTTGAGAAGTGAGTGTTACTCACCTTCTTCATGcTGATGGAAGTCAGGAACCCG

K  Y  Y  G  Y  G  A  G  N  P  L  G  P  A  Q  G  I  G  F  T    320
         AAGTACTACGGCTACGGCGCAGGCAACCCTCTGGGACCGGCTCAGGGGATAGGGTTCACC
   901   ---------+---------+---------+---------+---------+---------+    960
         TTCATGATGCCGATGCCGCGTCCGTTGGGAGACCCTGGCCGAGTCCCCTATCCCAAGTGG

N  E  L  I  A  R  L  T  R  S  P  V  Q  D  H  T  S  T  N  S    340
         AACGAGCTGATTGCCCGGTTGACgCGTTCGCCAGTGCAGGACCACACCAGCACTAACTCG
   961   ---------+---------+---------+---------+---------+---------+   1020
         TTGCTCGACTAACGGGCCAACTGcGCAAGCGGTCACGTCCTGGTGTGGTCGTGATTGAGC

T  L  V  S  N  P  A  T  F  P  L  N  A  T  M  Y  V  D  F  S    360
         ACTCTAGTCTCCAACCCGGCCACCTTCCCGTTGAACGCTACCATGTACGTCGACTTTTCA
  1021   ---------+---------+---------+---------+---------+---------+   1080
         TGAGATCAGAGGTTGGGCCGGTGGAAGGGCAACTTGCGATGGTACATGCAGCTGAAAAGT

H  D  N  S  M  V  S  I  F  F  A  L  G  L  Y  N  G  T  E  P    380
         CACGACAACAGCATGGTTTCCATCTTCTTTGCATTGGGCCTGTACAACGGCACTGAACCC
  1081   ---------+---------+---------+---------+---------+---------+   1140
         GTGCTGTTGTCGTACCAAAGGTAGAAGAAACGTAACCCGGACATGTTGCCGTGACTTGGG

L  S  R  T  S  V  E  S  A  K  E  L  D  G  Y  S  A  S  W  V    400
         TTGTCCCGGACCTCGGTGGAAAGCGCCAAGGAATTGGATGGGTATTCTGCATCCTGGGTG
  1141   ---------+---------+---------+---------+---------+---------+   1200
         AACAGGGCCTGGAGCCACCTTTCGCGGTTCCTTAACCTACCCATAAGACGTAGGACCCAC

V  P  F  G  A  R  A  Y  F  E  T  M  Q  C  K  S  E  K  E  P    420
         GTGCCTTTCGGCGCGCGAGCCTACTTCGAGACGATGCAATGCAAGTCGGAAAAGGAGCCT
  1201   ---------+---------+---------+---------+---------+---------+   1260
         CACGGAAAGCCGCGCGCTCGGATGAAGCTCTGCTACGTTACGTTCAGCCTTTTCCTCGGA

L  V  R  A  L  I  N  D  R  V  V  P  L  H  G  C  D  V  D  K    440
         CTTGTTCGCGCTTTGATTAATGACCGGGTTGTGCCACTGCATGGCTGCGATGTGGACAAG
  1261   ---------+---------+---------+---------+---------+---------+   1320
         GAACAAGCGCGAAACTAATTACTGGCCCAACACGGTGACGTACCGACGCTACACCTGTTC
```

Fig. 9b

```
       L   G   R   C   K   L   N   D   F   V   K   G   L   S   W   A   R   S   G   G      460
       CTGGGGCGATGCAAGCTGAATGACTTTGTCAAGGGATTGAGTTGGGCCAGATCTGGGGGC
1321   ---------+---------+---------+---------+---------+---------+  1380
       GACCCCGCTACGTTCGACTTACTGAAACAGTTCCCTAACTCAACCCGGTCTAGACCCCCG

N   W   G   E   C   F   S   *      467
       AACTGGGGAGAGTGCTTTAGTTGA
1381   ---------+---------+----  1404
       TTGACCCCTCTCACGAAATCAACT
```

Fig. 9c

```
                                    CP-1
      EcoRI    M  G  V  F  V  V  L  L  S  I  A  T  L  F  G  S  T
      TATATGAATTCATGGGCGTGTTCGTCGTGCTACTGTCCATTGCCACCTTGTTCGGTTCCA
  1   ---------+---------+---------+---------+---------+---------+  60
      ATATACTTAAGTACCCGCACAAGCAGCACGATGACAGGTAACGGTGGAACAAGCCAAGGT

S  G  T  A  L  G  P  R  G  N  S  H  S  C  D  T  V  D  G  G
      CATCCGGTACCGCCTTGGGTCCTCGTGGTAATTCTCACTCTTGTGACACTGTTGACGGTG
 61   ---------+---------+---------+---------+---------+---------+ 120
      GTAGGCCATGGCGGAACCCAGGAGCACCATTAAGAGTGAGAACACTGTGACAACTGCCAC
                    CP-2
              CP-3
       Y  Q  C  F  P  E  I  S  H  L  W  G  Q  Y  S  P  Y  F  S  L
      GTTACCAATGTTTCCCAGAAATTTCTCACTTGTGGGGTCAATACTCTCCATACTTCTCTT
121   ---------+---------+---------+---------+---------+---------+ 180
      CAATGGTTACAAAGGGTCTTTAAAGAGTGAACACCCCAGTTATGAGAGGTATGAAGAGAA

E  D  E  S  A  I  S  P  D  V  P  D  D  C  R  V  T  F  V  Q
      TGGAAGACGAATCTGCTATTTCTCCAGACGTTCCAGACGACTGTAGAGTTACTTTCGTTC
181   ---------+---------+---------+---------+---------+---------+ 240
      ACCTTCTGCTTAGACGATAAAGAGGTCTGCAAGGTCTGCTGACATCTCAATGAAAGCAAG
                  CP-4.7
                    CP-5.7
       V  L  S  R  H  G  A  R  Y  P  T  D  S  K  G  K  K  Y  S  A
      AAGTTTTGTCTAGACACGGTGCTAGATACCCAACTgacTCTAAGggtAAGaagTACTCTG
241   ---------+---------+---------+---------+---------+---------+ 300
      TTCAAAACAGATCTGTGCCACGATCTATGGGTTGACtgaGATTCccaTTCttcATGAGAC L  I  E  A  I  Q  K  N  A  T  A  F  K  G  K  Y  A  F  L  K
      CTTTGATTGAAGCTATTCAAAAGAACGCTACTGCTTTCAAGGGTAAGTACGCTTTCTTGA
301   ---------+---------+---------+---------+---------+---------+ 360
      GAAACTAACTTCGATAAGTTTTCTTGCGATGACGAAAGTTCCCATTCATGCGAAAGAACT
                              CP-6
                                CP-7
       T  Y  N  Y  T  L  G  A  D  D  L  T  P  F  G  E  N  Q  M  V
      AGACTTACAACTACACTTTGGGTGCTGACGACTTGACTCCATTCGGTGAAAACCAAATGG
361   ---------+---------+---------+---------+---------+---------+ 420
      TCTGAATGTTGATGTGAAACCCACGACTGCTGAACTGAGGTAAGCCACTTTTGGTTTACC N  S  G  I  K  F  Y  R  R  Y  K  A  L  A  R  K  I  V  P  F
      TTAACTCTGGTATTAAGTTCTACAGAAGATACAAGGCTTTGGCTAGAAAGATTGTTCCAT
421   ---------+---------+---------+---------+---------+---------+ 480
      AATTGAGACCATAATTCAAGATGTCTTCTATGTTCCGAAACCGATCTTTCTAACAAGGTA
                                                     CP-8.7
                                                       CP-9
       I  R  A  S  G  S  S  R  V  I  A  S  A  E  K  F  I  E  G  F
      TCATTAGAGCTTCTGGTTCTtctAGAGTTATTGCTTCTGCTGAAAAGTTCATTGAAGGTT
481   ---------+---------+---------+---------+---------+---------+ 540
      AGTAATCTCGAAGACCAAGAagaTCTCAATAACGAAGACGACTTTTCAAGTAACTTCCAA Q  S  A  K  L  A  D  P  G  S  Q  P  H  Q  A  S  P  V  I  D
      TCCAATCTGCTAAGTTGGCTGACCCAGGTTCTCAACCACACCAAGCTTCTCCAGTTATTG
541   ---------+---------+---------+---------+---------+---------+ 600
      AGGTTAGACGATTCAACCGACTGGGTCCAAGAGTTGGTGTGGTTCGAAGAGGTCAATAAC
```

Fig. 10a

```
                                         CP-10.7
                                                 CP-11.7
        V  I  I  S  E  A  S  S  Y  N  N  T  L  D  P  G  T  C  T  A
       ACGTTATTATTtctGAcgctTCTtctTACAACAACACTTTGGACccaGGTACTTGTACTG
 601   ---------+---------+---------+---------+---------+---------+  660
       TGCAATAATAAagaCTgcgaAGGagaATGTTGTTGTGAAACCTGggtCCATGAACATGAC F  E  D  S  E  L  A  D  T  V  E  A  N  F  T  A  L  F  A  P
       CTTTCGAAGACTCTGAATTGgctGACactGTTGAAGCTAACTTCACTGCTTTGTTCGCTC
 661   ---------+---------+---------+---------+---------+---------+  720
       GAAAGCTTCTGAGACTTAACcgaCTGtgaCAACTTCGATTGAAGTGACGAAACAAGCGAG
                                                            CP-12.7

A  I  R  A  R  L  E  A  D  L  P  G  V  T  L  T  D  T  E  V
       CAGCTATTAGAGCTAGATTGGAAGCTGACTTGCCAGGTGTTACTTTGACTGACactgaaG
 721   ---------+---------+---------+---------+---------+---------+  780
       GTCGATAATCTCGATCTAACCTTCGACTGAACGGTCCACAATGAAACTGACTGtgacttC CP-13.7
        T  Y  L  M  D  M  C  S  F  E  T  V  A  R  T  S  D  A  T  E
       TTactTACTTGATGGACATGTGTtctTTCGAAACTGTTGCTAGAACTTCTGACGCTACTG
 781   ---------+---------+---------+---------+---------+---------+  840
       AAtgaATGAACTACCTGTACACAagaAAGCTTTGACAACGATCTTGAAGACTGCGATGAC L  S  P  F  C  A  L  F  T  H  D  E  W  R  H  Y  D  Y  L  Q
       AATTGTCTCCATTCTGTGCTTTGTTCACTCACGACGAATGGAGAcaTACGACTACTTGC
 841   ---------+---------+---------+---------+---------+---------+  900
       TTAACAGAGGTAAGACACGAAACAAGTGAGTGCTGCTTACCTCTgtgATGCTGATGAACG
              CP-14.7
                CP-15.7
        S  L  K  K  Y  Y  G  H  G  A  G  N  P  L  G  P  T  Q  G  V
       AATCTTTGaagAAGTACTACGGTcacGGTGCTGGTAACCCATTGGGTCCAactCAAGGTG
 901   ---------+---------+---------+---------+---------+---------+  960
       TTAGAAACttcTTCATGATGCCAgtgCCACGACCATTGGGTAACCCAGGTtgaGTTCCAC G  F  A  N  E  L  I  A  R  L  T  R  S  P  V  Q  D  H  T  S
       TTGGTTTCGCTAACGAATTGATTGCTAGATTGACTAGATCTCCAGTTCAAGACCACACTT
 961   ---------+---------+---------+---------+---------+---------+  1020
       AACCAAAGCGATTGCTTAACTAACGATCTAACTGATCTAGAGGTCAAGTTCTGGTGTGAA
                  CP-16
                      CP-17.7
        T  N  H  T  L  D  S  N  P  A  T  F  P  L  N  A  T  L  Y  A
       CTACTAACCACACTTTGGACTCTAACCCAGCTACTTTCCCATTGAACGCTACTTTGTACG
1021   ---------+---------+---------+---------+---------+---------+ 1080
       GATGATTGGTGTGAAACCTGAGATTGGGTCGATGAAAGGGTAACTTGCGATGAAACATGC D  F  S  H  D  N  G  I  I  S  I  F  F  A  L  G  Y  N  G
       CTGACTTCTCTCACGACAACggtattATTTCTATTTTCTTCGCTTTGGGTTTGTACAACG
1081   ---------+---------+---------+---------+---------+---------+ 1140
       GACTGAAGAGAGTGCTGTTGccataaTAAAGATAAAAGAAGCGAAACCCAAACATGTTGC
                                                        CP-18.7
                                                           CP-19.7
        T  A  P  L  S  T  T  S  V  E  S  I  E  E  T  D  G  Y  S  S
       GTACTGCTCCATTGTCTACTACTTCTGTTGAATCTATTGAAGAAACTGACGGTTACTCTt
1141   ---------+---------+---------+---------+---------+---------+ 1200
       CATGACGAGGTAACAGATGATGAAGACAACTTAGATAACTTCTTTGACTGCCAATGAGAa
```

Fig. 10b

```
            A  W  T  V  P  F  A  S  R  A  Y  V  E  M  M  Q  C  Q  A  E
        ctgctTGGACTGTTCCATTCgcttctAGAGCTTACGTTGAAATGATGCAATGTCAAGCTG
1201    ---------+---------+---------+---------+---------+---------+  1260
        gacgaACCTGACAAGGTAAGcgaagaTCTCGAATGCAACTTTACTACGTTACAGTTCGAC
                                      CP-20
                                            CP-21
           K  E  P  L  V  R  V  L  V  N  D  R  V  V  P  L  H  G  C  A
        AAAAGGAACCATTGGTTAGAGTTTTGGTTAACGACAGAGTTGTTCCATTGCACGGTTGTG
1261    ---------+---------+---------+---------+---------+---------+  1320
        TTTTCCTTGGTAACCAATCTCAAAACCAATTGCTGTCTCAACAAGGTAACGTGCCAACAC V  D  K  L  G  R  C  K  R  D  D  F  V  E  G  L  S  F  A  R
        CTGTTGACAAGTTGGGTAGATGTAAGAGAGACGACTTCGTTGAAGGTTTGTCTTTCGCTA
1321    ---------+---------+---------+---------+---------+---------+  1380
        GACAACTGTTCAACCCATCTACATTCTCTCTGCTGAAGCAACTTCCAAACAGAAAGCGAT
                                                          CP-22
           S  G  G  N  W  A  E  C  F  A  *   Eco RI
        GATCTGGTGGTAACTGGGCTGAATGTTTCGCTTAAGAATTCATATA
1381    ---------+---------+---------+---------+------  1426
        CTAGACCACCATTGACCCGACTTACAAAGCGAATTCTTAAGTATAT
```

Fig. 10c

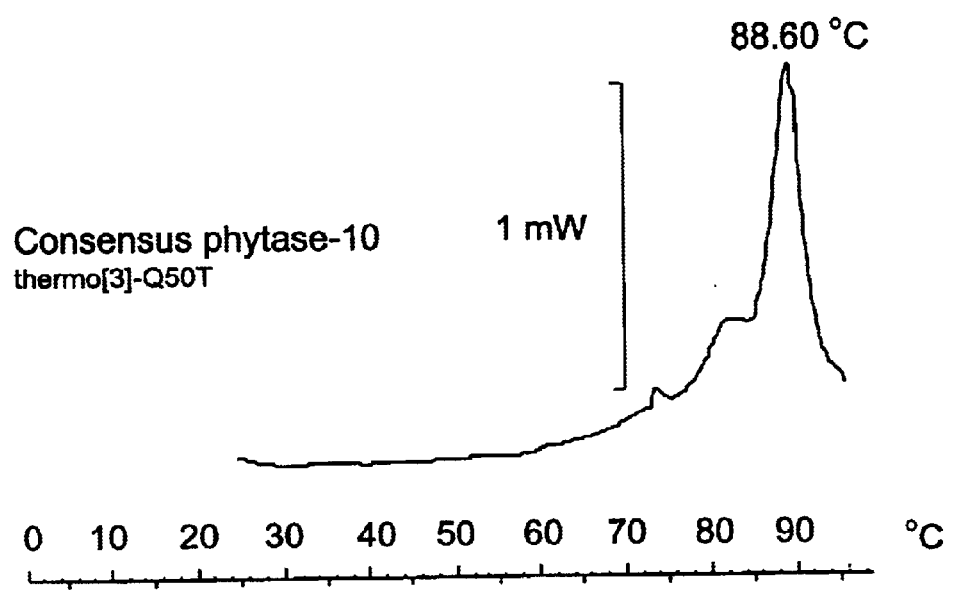
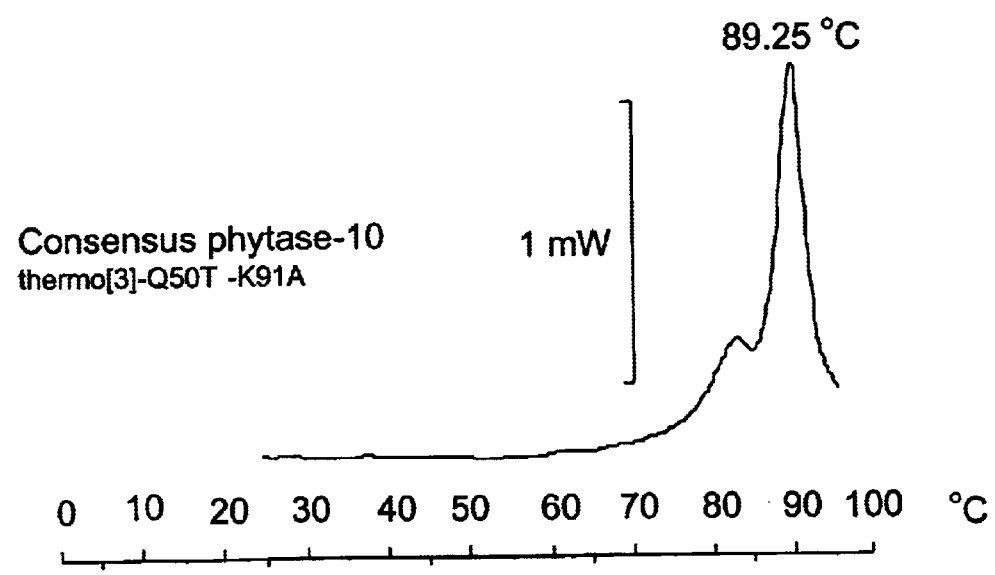
Fig. 12

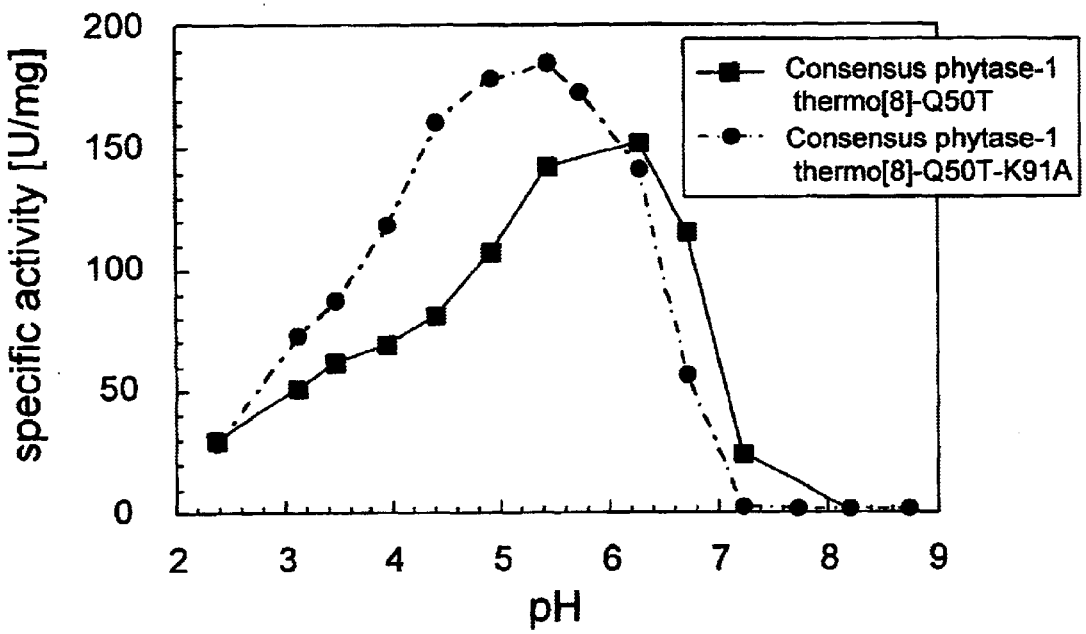
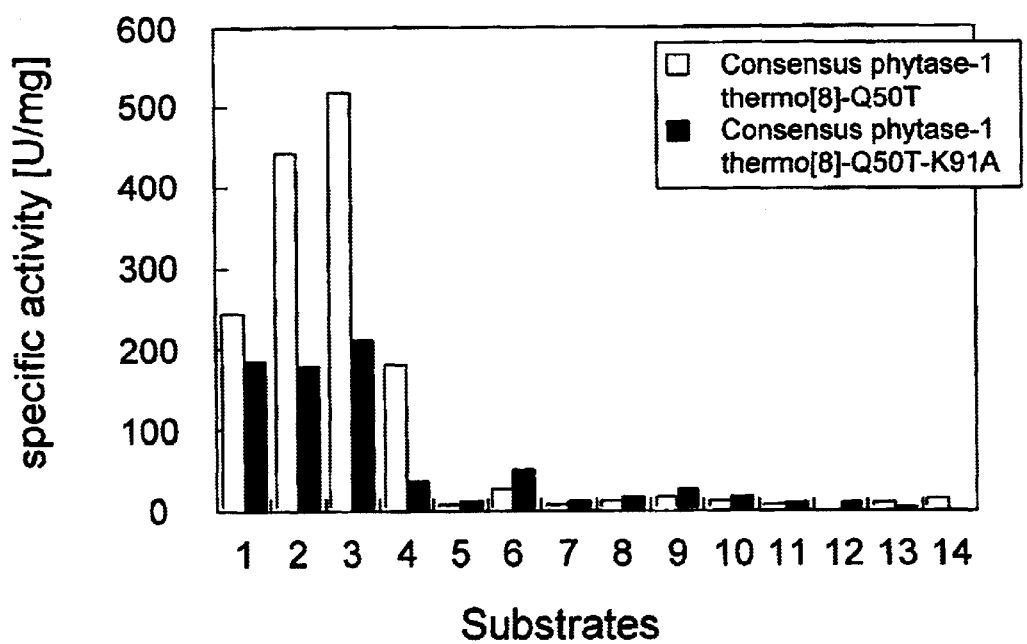
Fig. 15

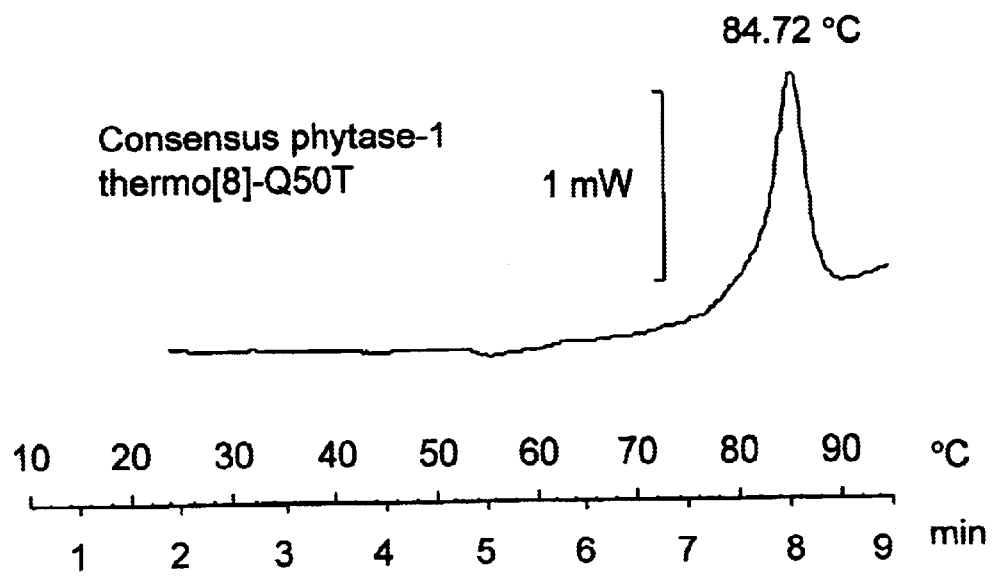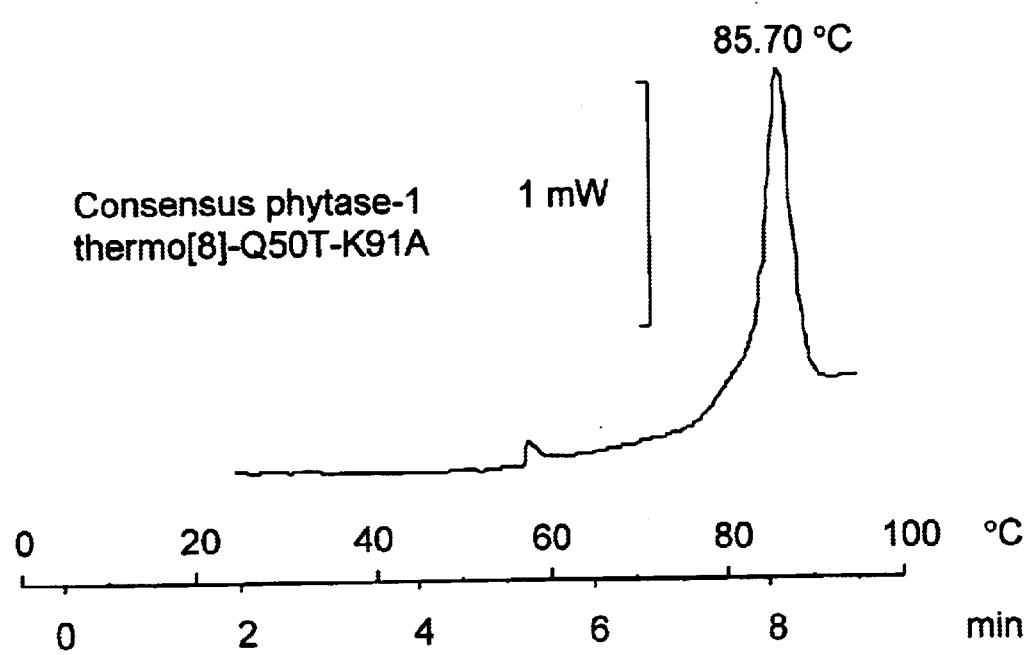
Fig. 16

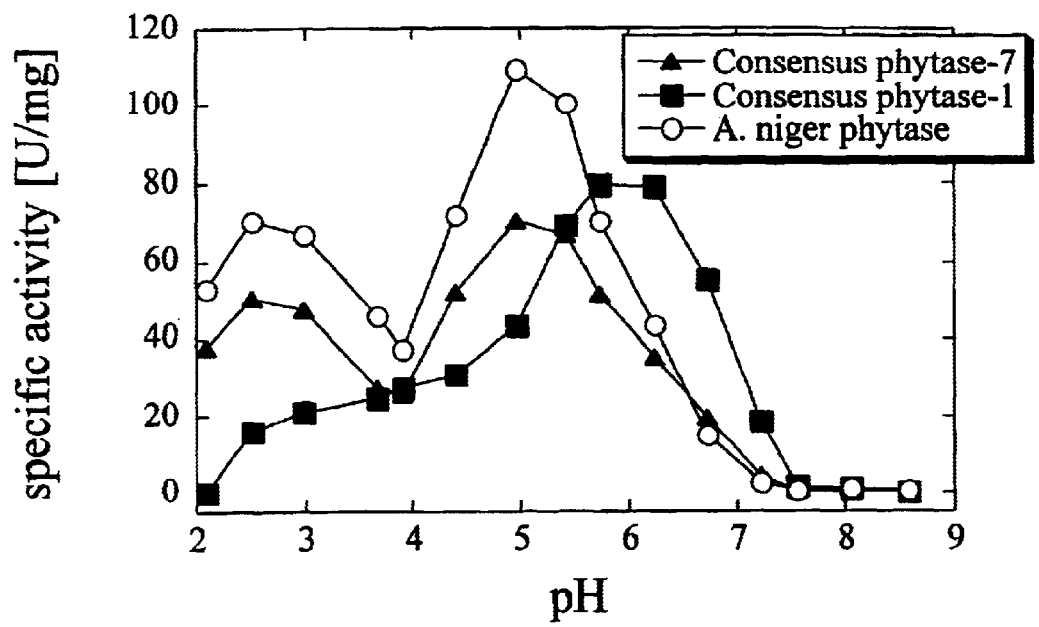
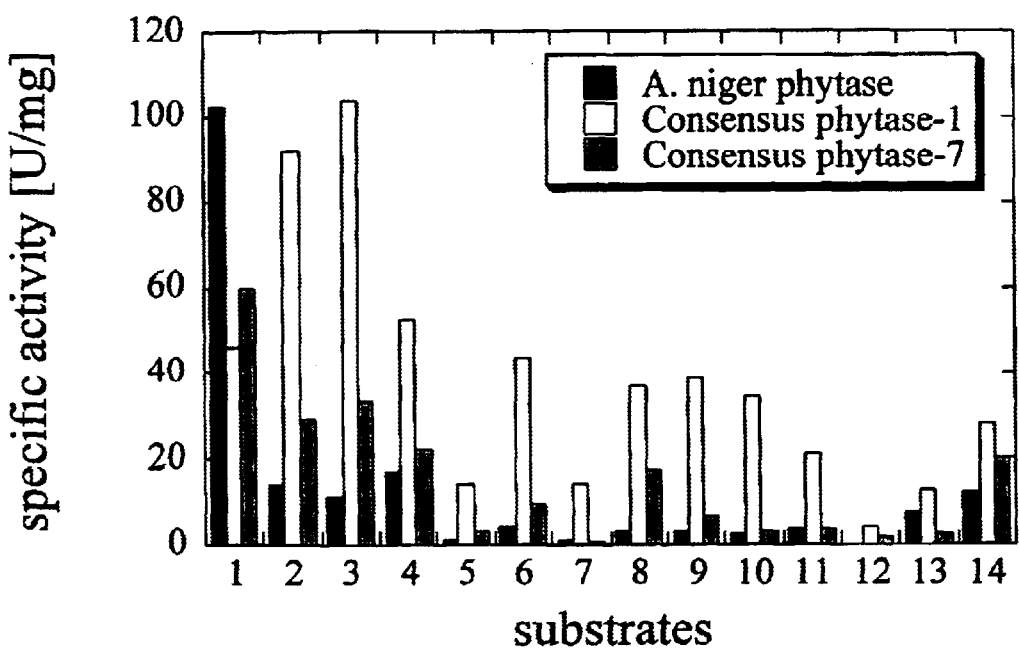
Fig. 18

```
1    MGVFVVLLSI ATLFGSTSGT ALGPRGNSHS CDTVDGGYQC FPEISSNWSP

51   YSPYFSLADE SAISPDVPKG CRVTFVQVLQ RHGARFPTSG AATRISALIE

101  AIQKNATAFK GKYAFLKTYN YTLGADDLVP FGANQSSQAG IKFYRRYKAL

151  ARKIVPFIRA SGSDRVIDSA TNWIEGFQSA KLADPGANPH QASPVINVII

201  PEGAGYNNTL DHGLCTAFEE SELGDDVEAN FTAVFAPPIR ARLEAHLPGV

251  NLTDEDVVNL MDMCPFDTVA RTSDATELSP FCDLFTHDEW IQYDYLGDLD

301  KYYGTGAGNP LGPAQGVGFV NELIARLTHS PVQDHTSTNH TLDSNPATFP

351  LNATLYADFS HDNTMVAIFF ALGLYNGTKP LSTTSVESIE ETDGYSASWL

401  VPFSARMYVE MMQCEAEKEP LVRVLVNDRV VPLHGCGVDK LGRCKRDDFV

451  EGLSFARSGG NWEECFA
```

Fig. 21

```
    ATGGGCGTGTTCGTCGTGCTACTGTCCATTGCCACCTTGTTCGGTTCCACATCCGGTACC
  1 ---------+---------+---------+---------+---------+---------+  60
    TACCCGCACAAGCAGCACGATGACAGGTAACGGTGGAACAAGCCAAGGTGTAGGCCATGG

M  G  V  F  V  V  L  L  S  I  A  T  L  F  G  S  T  S  G  T   -

GCCTTGGGTCCTCGTGGTAATTCTCACTCTTGTGACACTGTTGACGGTGGTTACCAATGT
 61 ---------+---------+---------+---------+---------+---------+ 120
    CGGAACCCAGGAGCACCATTAAGAGTGAGAACACTGTGACAACTGCCACCAATGGTTACA

A  L  G  P  R  G  N  S  H  S  C  D  T  V  D  G  G  Y  Q  C   -

TTCCCAGAAATTTCTCACTTGTGGGGTACCTACTCTCCATACTTCTCTTTGGCAGACGAA
121 ---------+---------+---------+---------+---------+---------+ 180
    AAGGGTCTTTAAAGAGTGAACACCCCATGGATGAGAGGTATGAAGAGAAACCGTCTGCTT

F  P  E  I  S  H  L  W  G  T  Y  S  P  Y  F  S  L  A  D  E   -

TCTGCTATTTCTCCAGACGTCCCAAAGGACTGTAGAGTTACTTTCGTTCAAGTTTTGTCT
181 ---------+---------+---------+---------+---------+---------+ 240
    AGACGATAAAGAGGTCTGCAGGGTTTCCTGACATCTCAATGAAAGCAAGTTCAAAACAGA

S  A  I  S  P  D  V  P  K  D  C  R  V  T  F  V  Q  V  L  S   -

AGACACGGTGCTAGATACCCAACTTCTTCTAAGTCTAAGGCTTACTCTGCTTTGATTGAA
241 ---------+---------+---------+---------+---------+---------+ 300
    TCTGTGCCACGATCTATGGGTTGAAGAAGATTCAGATTCCGAATGAGACGAAACTAACTT

R  H  G  A  R  Y  P  T  S  S  K  S  K  A  Y  S  A  L  I  E   -

GCTATTCAAAAGAACGCTACTGCTTTCAAGGGTAAGTACGCTTTCTTGAAGACTTACAAC
301 ---------+---------+---------+---------+---------+---------+ 360
    CGATAAGTTTTCTTGCGATGACGAAAGTTCCCATTCATGCGAAAGAACTTCTGAATGTTG

A  I  Q  K  N  A  T  A  F  K  G  K  Y  A  F  L  K  T  Y  N   -

TACACTTTGGGTGCTGACGACTTGACTCCATTCGGTGAAAACCAAATGGTTAACTCTGGT
361 ---------+---------+---------+---------+---------+---------+ 420
    ATGTGAAACCCACGACTGCTGAACTGAGGTAAGCCACTTTTGGTTTACCAATTGAGACCA

Y  T  L  G  A  D  D  L  T  P  F  G  E  N  Q  M  V  N  S  G   -

ATTAAGTTCTACAGAAGATACAAGGCTTTGGCTAGAAAGATTGTTCCATTCATTAGAGCT
421 ---------+---------+---------+---------+---------+---------+ 480
    TAATTCAAGATGTCTTCTATGTTCCGAAACCGATCTTTCTAACAAGGTAAGTAATCTCGA

I  K  F  Y  R  R  Y  K  A  L  A  R  K  I  V  P  F  I  R  A   -

TCTGGTTCTGACAGAGTTATTGCTTCTGCTGAAAAGTTCATTGAAGGTTTCCAATCTGCT
481 ---------+---------+---------+---------+---------+---------+ 540
    AGACCAAGACTGTCTCAATAACGAAGACGACTTTTCAAGTAACTTCCAAAGGTTAGACGA

S  G  S  D  R  V  I  A  S  A  E  K  F  I  E  G  F  Q  S  A   -
```

Fig. 22a

```
                 AAGTTGGCTGACCCAGGTTCTCAACCACACCAAGCTTCTCCAGTTATTAACGTGATCATT
541              ---------+---------+---------+---------+---------+---------+ 600
                 TTCAACCGACTGGGTCCAAGAGTTGGTGTGGTTCGAAGAGGTCAATAATTGCACTAGTAA

K  L  A  D  P  G  S  Q  P  H  Q  A  S  P  V  I  N  V  I  I  -

CCAGAAGGATCCGGTTACAACAACACTTTGGACCATGGTCTTTGTACTGCTTTCGAAGAC
601              ---------+---------+---------+---------+---------+---------+ 660
                 GGTCTTCCTAGGCCAATGTTGTTGTGAAACCTGGTACCAGAAACATGACGAAAGCTTCTG

P  E  G  S  G  Y  N  N  T  L  D  H  G  L  C  T  A  F  E  D  -

TCTACCCTAGGTGACGACGTTGAAGCTAACTTCACTGCTTTGTTCGCTCCAGCTATTAGA
661              ---------+---------+---------+---------+---------+---------+ 720
                 AGATGGGATCCACTGCTGCAACTTCGATTGAAGTGACGAAACAAGCGAGGTCGATAATCT

S  T  L  G  D  D  V  E  A  N  F  T  A  L  F  A  P  A  I  R  -

GCTAGATTGGAAGCTGACTTGCCAGGTGTTACTTTGACTGACGAAGACGTTGTTTACTTG
721              ---------+---------+---------+---------+---------+---------+ 780
                 CGATCTAACCTTCGACTGAACGGTCCACAATGAAACTGACTGCTTCTGCAACAAATGAAC

A  R  L  E  A  D  L  P  G  V  T  L  T  D  E  D  V  V  Y  L  -

ATGGACATGTGTCCATTCGACACTGTCGCTAGAACTTCTGACGCTACTGAATTGTCTCCA
781              ---------+---------+---------+---------+---------+---------+ 840
                 TACCTGTACACAGGTAAGCTGTGACAGCGATCTTGAAGACTGCGATGACTTAACAGAGGT

M  D  M  C  P  F  D  T  V  A  R  T  S  D  A  T  E  L  S  P  -

TTCTGTGCTTTGTTCACTCACGACGAATGGATCCAATACGACTACTTGCAAAGCTTGGGT
841              ---------+---------+---------+---------+---------+---------+ 900
                 AAGACACGAAACAAGTGAGTGCTGCTTACCTAGGTTATGCTGATGAACGTTTCGAACCCA

F  C  A  L  F  T  H  D  E  W  I  Q  Y  D  Y  L  Q  S  L  G  -

AAGTACTACGGTTACGGTGCTGGTAACCCATTGGGTCCAGCTCAAGGTGTTGGTTTCGCT
901              ---------+---------+---------+---------+---------+---------+ 960
                 TTCATGATGCCAATGCCACGACCATTGGGTAACCCAGGTCGAGTTCCACAACCAAAGCGA

K  Y  Y  G  Y  G  A  G  N  P  L  G  P  A  Q  G  V  G  F  A  -

AACGAATTGATTGCTAGATTGACTCACTCTCCAGTTCAAGACCACACTTCTACTAACCAC
961              ---------+---------+---------+---------+---------+---------+ 1020
                 TTGCTTAACTAACGATCTAACTGAGTGAGAGGTCAAGTTCTGGTGTGAAGATGATTGGTG

N  E  L  I  A  R  L  T  H  S  P  V  Q  D  H  T  S  T  N  H  -

ACTTTGGACTCTAACCCAGCTACTTTCCCATTGAACGCTACTTTGTACGCTGACTTCTCT
1021             ---------+---------+---------+---------+---------+---------+ 1080
                 TGAAACCTGAGATTGGGTCGATGAAAGGGTAACTTGCGATGAAACATGCGACTGAAGAGA

T  L  D  S  N  P  A  T  F  P  L  N  A  T  L  Y  A  D  F  S  -
```

Fig. 22b

```
      CACGACAACACTATGATATCTATTTTCTTCGCTTTGGGTTTGTACAACGGTACCAAGCCA
1081  ------------+---------+---------+---------+---------+---------+ 1140
      GTGCTGTTGTGATACTATAGATAAAAGAAGCGAAACCCAAACATGTTGCCATGGTTCGGT

H  D  N  T  M  I  S  I  F  F  A  L  G  L  Y  N  G  T  K  P   -

TTGTCTACTACTTCTGTTGAATCTATTGAAGAAACTGACGGTTACTCTGCTTCTTGGACT
1141  ------------+---------+---------+---------+---------+---------+ 1200
      AACAGATGATGAAGACAACTTAGATAACTTCTTTGACTGCCAATGAGACGAAGAACCTGA

L  S  T  T  S  V  E  S  I  E  E  T  D  G  Y  S  A  S  W  T   -

GTTCCATTCGCTGCTAGAGCTTACGTTGAAATGATGCAATGTCAAGCTGAAAAGGAACCA
1201  ------------+---------+---------+---------+---------+---------+ 1260
      CAAGGTAAGCGACGATCTCGAATGCAACTTTACTACGTTACAGTTCGACTTTTCCTTGGT

V  P  F  A  A  R  A  Y  V  E  M  M  Q  C  Q  A  E  K  E  P   -

TTGGTTAGAGTTTTGGTTAACGACAGAGTTGTTCCATTGCACGGTTGTGCTGTTGACAAG
1261  ------------+---------+---------+---------+---------+---------+ 1320
      AACCAATCTCAAAACCAATTGCTGTCTCAACAAGGTAACGTGCCAACACGACAACTGTTC

L  V  R  V  L  V  N  D  R  V  V  P  L  H  G  C  A  V  D  K   -

TTGGGTAGATGTAAGAGAGACGACTTCGTTGAAGGTTTGTCTTTCGCTAGATCTGGTGGT
1321  ------------+---------+---------+---------+---------+---------+ 1380
      AACCCATCTACATTCTCTCTGCTGAAGCAACTTCCAAACAGAAAGCGATCTAGACCACCA

L  G  R  C  K  R  D  D  F  V  E  G  L  S  F  A  R  S  G  G   -

AACTGGGCTGAATGTTTCGCTTAA
1381  ------------+---------+---- 1404
      TTGACCCGACTTACAAAGCGAATT

N  W  A  E  C  F  A  *
```

Fig. 22c

```
    ATGGGCGTGTTCGTCGTGCTACTGTCCATTGCCACCTTGTTCGGTTCCACATCCGGTACC
  1 ---------+---------+---------+---------+---------+---------+  60
    TACCCGCACAAGCAGCACGATGACAGGTAACGGTGGAACAAGCCAAGGTGTAGGCCATGG

M  G  V  F  V  V  L  L  S  I  A  T  L  F  G  S  T  S  G  T   -

GCCTTGGGTCCTCGTGGTAATTCTCACTCTTGTGACACTGTTGACGGTGGTTACCAATGT
 61 ---------+---------+---------+---------+---------+---------+ 120
    CGGAACCCAGGAGCACCATTAAGAGTGAGAACACTGTGACAACTGCCACCAATGGTTACA

A  L  G  P  R  G  N  S  H  S  C  D  T  V  D  G  G  Y  Q  C   -

TTCCCAGAAATTTCTCACTTGTGGGGTACCTACTCTCCATACTTCTCTTTGGCAGACGAA
121 ---------+---------+---------+---------+---------+---------+ 180
    AAGGGTCTTTAAAGAGTGAACACCCCATGGATGAGAGGTATGAAGAGAAACCGTCTGCTT

F  P  E  I  S  H  L  W  G  T  Y  S  P  Y  F  S  L  A  D  E   -

TCTGCTATTTCTCCAGACGTCCCAAAGGACTGTAGAGTTACTTTCGTTCAAGTTTTGTCT
181 ---------+---------+---------+---------+---------+---------+ 240
    AGACGATAAAGAGGTCTGCAGGGTTTCCTGACATCTCAATGAAAGCAAGTTCAAAACAGA

S  A  I  S  P  D  V  P  K  D  C  R  V  T  F  V  Q  V  L  S   -

AGACACGGTGCTAGATACCCAACTTCTTCTGCGTCTAAGGCTTACTCTGCTTTGATTGAA
241 ---------+---------+---------+---------+---------+---------+ 300
    TCTGTGCCACGATCTATGGGTTGAAGAAGACGCAGATTCCGAATGAGACGAAACTAACTT

R  H  G  A  R  Y  P  T  S  S  A  S  K  A  Y  S  A  L  I  E   -

GCTATTCAAAAGAACGCTACTGCTTTCAAGGGTAAGTACGCTTTCTTGAAGACTTACAAC
301 ---------+---------+---------+---------+---------+---------+ 360
    CGATAAGTTTTCTTGCGATGACGAAAGTTCCCATTCATGCGAAAGAACTTCTGAATGTTG

A  I  Q  K  N  A  T  A  F  K  G  K  Y  A  F  L  K  T  Y  N   -

TACACTTTGGGTGCTGACGACTTGACTCCATTCGGTGAAAACCAAATGGTTAACTCTGGT
361 ---------+---------+---------+---------+---------+---------+ 420
    ATGTGAAACCCACGACTGCTGAACTGAGGTAAGCCACTTTTGGTTTACCAATTGAGACCA

Y  T  L  G  A  D  D  L  T  P  F  G  E  N  Q  M  V  N  S  G   -

ATTAAGTTCTACAGAAGATACAAGGCTTTGGCTAGAAAGATTGTTCCATTCATTAGAGCT
421 ---------+---------+---------+---------+---------+---------+ 480
    TAATTCAAGATGTCTTCTATGTTCCGAAACCGATCTTTCTAACAAGGTAAGTAATCTCGA

I  K  F  Y  R  R  Y  K  A  L  A  R  K  I  V  P  F  I  R  A   -

TCTGGTTCTGACAGAGTTATTGCTTCTGCTGAAAAGTTCATTGAAGGTTTCCAATCTGCT
481 ---------+---------+---------+---------+---------+---------+ 540
    AGACCAAGACTGTCTCAATAACGAAGACGACTTTTCAAGTAACTTCCAAAGGTTAGACGA

S  G  S  D  R  V  I  A  S  A  E  K  F  I  E  G  F  Q  S  A   -
```

Fig. 23a

```
       AAGTTGGCTGACCCAGGTTCTCAACCACACCAAGCTTCTCCAGTTATTAACGTGATCATT
541    ---------+---------+---------+---------+---------+---------+ 600
       TTCAACCGACTGGGTCCAAGAGTTGGTGTGGTTCGAAGAGGTCAATAATTGCACTAGTAA

K  L  A  D  P  G  S  Q  P  H  Q  A  S  P  V  I  N  V  I  I  -

CCAGAAGGATCCGGTTACAACAACACTTTGGACCATGGTCTTTGTACTGCTTTCGAAGAC
601    ---------+---------+---------+---------+---------+---------+ 660
       GGTCTTCCTAGGCCAATGTTGTTGTGAAACCTGGTACCAGAAACATGACGAAAGCTTCTG

P  E  G  S  G  Y  N  N  T  L  D  H  G  L  C  T  A  F  E  D  -

TCTACCCTAGGTGACGACGTTGAAGCTAACTTCACTGCTTTGTTCGCTCCAGCTATTAGA
661    ---------+---------+---------+---------+---------+---------+ 720
       AGATGGGATCCACTGCTGCAACTTCGATTGAAGTGACGAAACAAGCGAGGTCGATAATCT

S  T  L  G  D  D  V  E  A  N  F  T  A  L  F  A  P  A  I  R  -

GCTAGATTGGAAGCTGACTTGCCAGGTGTTACTTTGACTGACGAAGACGTTGTTTACTTG
721    ---------+---------+---------+---------+---------+---------+ 780
       CGATCTAACCTTCGACTGAACGGTCCACAATGAAACTGACTGCTTCTGCAACAAATGAAC

A  R  L  E  A  D  L  P  G  V  T  L  T  D  E  D  V  V  Y  L  -

ATGGACATGTGTCCATTCGACACTGTCGCTAGAACTTCTGACGCTACTGAATTGTCTCCA
781    ---------+---------+---------+---------+---------+---------+ 840
       TACCTGTACACAGGTAAGCTGTGACAGCGATCTTGAAGACTGCGATGACTTAACAGAGGT

M  D  M  C  P  F  D  T  V  A  R  T  S  D  A  T  E  L  S  P  -

TTCTGTGCTTTGTTCACTCACGACGAATGGATCCAATACGACTACTTGCAAAGCTTGGGT
841    ---------+---------+---------+---------+---------+---------+ 900
       AAGACACGAAACAAGTGAGTGCTGCTTACCTAGGTTATGCTGATGAACGTTTCGAACCCA

F  C  A  L  F  T  H  D  E  W  I  Q  Y  D  Y  L  Q  S  L  G  -

AAGTACTACGGTTACGGTGCTGGTAACCCATTGGGTCCAGCTCAAGGTGTTGGTTTCGCT
901    ---------+---------+---------+---------+---------+---------+ 960
       TTCATGATGCCAATGCCACGACCATTGGGTAACCCAGGTCGAGTTCCACAACCAAAGCGA

K  Y  Y  G  Y  G  A  G  N  P  L  G  P  A  Q  G  V  G  F  A  -

AACGAATTGATTGCTAGATTGACTCACTCTCCAGTTCAAGACCACACTTCTACTAACCAC
961    ---------+---------+---------+---------+---------+---------+ 1020
       TTGCTTAACTAACGATCTAACTGAGTGAGAGGTCAAGTTCTGGTGTGAAGATGATTGGTG

N  E  L  I  A  R  L  T  H  S  P  V  Q  D  H  T  S  T  N  H  -

ACTTTGGACTCTAACCCAGCTACTTTCCCATTGAACGCTACTTTGTACGCTGACTTCTCT
1021   ---------+---------+---------+---------+---------+---------+ 1080
       TGAAACCTGAGATTGGGTCGATGAAAGGGTAACTTGCGATGAAACATGCGACTGAAGAGA

T  L  D  S  N  P  A  T  F  P  L  N  A  T  L  Y  A  D  F  S  -
```

Fig. 23b

```
          CACGACAACACTATGATATCTATTTTCTTCGCTTTGGGTTTGTACAACGGTACCAAGCCA
1081      ---------+---------+---------+---------+---------+---------+  1140
          GTGCTGTTGTGATACTATAGATAAAAGAAGCGAAACCCAAACATGTTGCCATGGTTCGGT

H  D  N  T  M  I  S  I  F  F  A  L  G  L  Y  N  G  T  K  P    -

TTGTCTACTACTTCTGTTGAATCTATTGAAGAAACTGACGGTTACTCTGCTTCTTGGACT
1141      ---------+---------+---------+---------+---------+---------+  1200
          AACAGATGATGAAGACAACTTAGATAACTTCTTTGACTGCCAATGAGACGAAGAACCTGA

L  S  T  T  S  V  E  S  I  E  E  T  D  G  Y  S  A  S  W  T    -

GTTCCATTCGCTGCTAGAGCTTACGTTGAAATGATGCAATGTCAAGCTGAAAAGGAACCA
1201      ---------+---------+---------+---------+---------+---------+  1260
          CAAGGTAAGCGACGATCTCGAATGCAACTTTACTACGTTACAGTTCGACTTTTCCTTGGT

V  P  F  A  A  R  A  Y  V  E  M  M  Q  C  Q  A  E  K  E  P    -

TTGGTTAGAGTTTTGGTTAACGACAGAGTTGTTCCATTGCACGGTTGTGCTGTTGACAAG
1261      ---------+---------+---------+---------+---------+---------+  1320
          AACCAATCTCAAAACCAATTGCTGTCTCAACAAGGTAACGTGCCAACACGACAACTGTTC

L  V  R  V  L  V  N  D  R  V  V  P  L  H  G  C  A  V  D  K    -

TTGGGTAGATGTAAGAGAGACGACTTCGTTGAAGGTTTGTCTTTCGCTAGATCTGGTGGT
1321      ---------+---------+---------+---------+---------+---------+  1380
          AACCCATCTACATTCTCTCTGCTGAAGCAACTTCCAAACAGAAAGCGATCTAGACCACCA

L  G  R  C  K  R  D  D  F  V  E  G  L  S  F  A  R  S  G  G    -

AACTGGGCTGAATGTTTCGCTTAA
1381      ---------+---------+---- 1404
          TTGACCCGACTTACAAAGCGAATT

N  W  A  E  C  F  A  *
```

Fig. 23c

```
    ATGGGCGTGTTCGTCGTGCTACTGTCCATTGCCACCTTGTTCGGTTCCACATCCGGTACC
  1 ------------------+---------+---------+---------+---------+---------+  60
    TACCCGCACAAGCAGCACGATGACAGGTAACGGTGGAACAAGCCAAGGTGTAGGCCATGG

M   G   V   F   V   V   L   L   S   I   A   T   L   F   G   S   T   S   G   T   -

GCCTTGGGTCCTCGTGGTAATTCTCACTCTTGTGACACTGTTGACGGTGGTTACCAATGT
 61 ---------+---------+---------+---------+---------+---------+ 120
    CGGAACCCAGGAGCACCATTAAGAGTGAGAACACTGTGACAACTGCCACCAATGGTTACA

A   L   G   P   R   G   N   S   H   S   C   D   T   V   D   G   G   Y   Q   C   -

TTCCCAGAAATTTCTCACTTGTGGGGTACATACTCTCCATTCTTCTCTTTGGCTGACGAA
121 ---------+---------+---------+---------+---------+---------+ 180
    AAGGGTCTTTAAAGAGTGAACACCCCATGTATGAGAGGTAAGAAGAGAAACCGACTGCTT

F   P   E   I   S   H   L   W   G   T   Y   S   P   F   F   S   L   A   D   E   -

TCTGCTATTTCTCCAGACGTTCCAAAGGGTTGTAGAGTTACTTTCGTTCAAGTTTTGTCT
181 ---------+---------+---------+---------+---------+---------+ 240
    AGACGATAAAGAGGTCTGCAAGGTTTCCCAACATCTCAATGAAAGCAAGTTCAAAACAGA

S   A   I   S   P   D   V   P   K   G   C   R   V   T   F   V   Q   V   L   S   -

AGACACGGTGCTAGATACCCAACTTCTTCTAAGTCTAAGGCTTACTCTGCTTTGATTGAA
241 ---------+---------+---------+---------+---------+---------+ 300
    TCTGTGCCACGATCTATGGGTTGAAGAAGATTCAGATTCCGAATGAGACGAAACTAACTT

R   H   G   A   R   Y   P   T   S   S   K   S   K   A   Y   S   A   L   I   E   -

GCTATTCAAAAGAACGCTACTGCTTTCAAGGGTAAGTACGCTTTCTTGAAGACTTACAAT
301 ---------+---------+---------+---------+---------+---------+ 360
    CGATAAGTTTTCTTGCGATGACGAAAGTTCCCATTCATGCGAAAGAACTTCTGAATGTTA

A   I   Q   K   N   A   T   A   F   K   G   K   Y   A   F   L   K   T   Y   N   -

TACACTTTGGGTGCTGACGACTTGACTCCATTCGGTGAACAACAAATGGTTAACTCTGGT
361 ---------+---------+---------+---------+---------+---------+ 420
    ATGTGAAACCCACGACTGCTGAACTGAGGTAAGCCACTTGTTGTTTACCAATTGAGACCA

Y   T   L   G   A   D   D   L   T   P   F   G   E   Q   Q   M   V   N   S   G   -

ATTAAGTTCTACAGAAGATACAAGGCTTTGGCTAGAAAGATTGTTCCATTCATTAGAGCT
421 ---------+---------+---------+---------+---------+---------+ 480
    TAATTCAAGATGTCTTCTATGTTCCGAAACCGATCTTTCTAACAAGGTAAGTAATCTCGA

I   K   F   Y   R   R   Y   K   A   L   A   R   K   I   V   P   F   I   R   A   -

TCTGGTTCTGACAGAGTTATTGCTTCTGCCGAAAAGTTCATTGAAGGTTTCCAATCTGCT
481 ---------+---------+---------+---------+---------+---------+ 540
    AGACCAAGACTGTCTCAATAACGAAGACGGCTTTTCAAGTAACTTCCAAAGGTTAGACGA

S   G   S   D   R   V   I   A   S   A   E   K   F   I   E   G   F   Q   S   A   -
```

Fig. 24a

```
              AAGTTGGCTGACCCAGGTGCTAACCCACACCAAGCTTCTCCAGTTATTAACGTTATTATT
     541      ---------+---------+---------+---------+---------+---------+  600
              TTCAACCGACTGGGTCCACGATTGGGTGTGGTTCGAAGAGGTCAATAATTGCAATAATAA

K  L  A  D  P  G  A  N  P  H  Q  A  S  P  V  I  N  V  I  I  -

CCAGAAGGTGCTGGTTACAACAACACTTTGGACCACGGTTTGTGTACTGCTTTCGAAGAA
     601      ---------+---------+---------+---------+---------+---------+  660
              GGTCTTCCACGACCAATGTTGTTGTGAAACCTGGTGCCAAACACATGACGAAAGCTTCTT

P  E  G  A  G  Y  N  N  T  L  D  H  G  L  C  T  A  F  E  E  -

TCTACCCTAGGTGACGACGTTGAAGCTAACTTCACTGCTGTTTTCGCTCCACCAATTAGA
     661      ---------+---------+---------+---------+---------+---------+  720
              AGATGGGATCCACTGCTGCAACTTCGATTGAAGTGACGACAAAAGCGAGGTGGTTAATCT

S  T  L  G  D  D  V  E  A  N  F  T  A  V  F  A  P  P  I  R  -

GCTAGATTGGAAGCTCACTTGCCAGGTGTTAACTTGACTGACGAAGACGTTGTTAACTTG
     721      ---------+---------+---------+---------+---------+---------+  780
              CGATCTAACCTTCGAGTGAACGGTCCACAATTGAACTGACTGCTTCTGCAACAATTGAAC

A  R  L  E  A  H  L  P  G  V  N  L  T  D  E  D  V  V  N  L  -

ATGGACATGTGTCCATTCGACACTGTTGCTAGAACTTCTGACGCTACTCAATTGTCTCCA
     781      ---------+---------+---------+---------+---------+---------+  840
              TACCTGTACACAGGTAAGCTGTGACAACGATCTTGAAGACTGCGATGAGTTAACAGAGGT

M  D  M  C  P  F  D  T  V  A  R  T  S  D  A  T  Q  L  S  P  -

TTCTGTGACTTGTTCACTCACGACGAATGGATTCAATACGACTACTTGCAATCTTTGGGT
     841      ---------+---------+---------+---------+---------+---------+  900
              AAGACACTGAACAAGTGAGTGCTGCTTACCTAAGTTATGCTGATGAACGTTAGAAACCCA

F  C  D  L  F  T  H  D  E  W  I  Q  Y  D  Y  L  Q  S  L  G  -

AAGTACTACGGTTACGGTGCTGGTAACCCATTGGGTCCAGCTCAAGGTGTTGGTTTCGTT
     901      ---------+---------+---------+---------+---------+---------+  960
              TTCATGATGCCAATGCCACGACCATTGGGTAACCCAGGTCGAGTTCCACAACCAAAGCAA

K  Y  Y  G  Y  G  A  G  N  P  L  G  P  A  Q  G  V  G  F  V  -

AACGAATTGATTGCTAGATTGACTCACTCTCCAGTTCAAGACCACACTTCTACTAACCAC
     961      ---------+---------+---------+---------+---------+---------+ 1020
              TTGCTTAACTAACGATCTAACTGAGTGAGAGGTCAAGTTCTGGTGTGAAGATGATTGGTG

N  E  L  I  A  R  L  T  H  S  P  V  Q  D  H  T  S  T  N  H  -

ACTTTGGACTCTAACCCAGCTACTTTCCCATTGAACGCTACTTTGTACGCTGACTTCTCT
    1021      ---------+---------+---------+---------+---------+---------+ 1080
              TGAAACCTGAGATTGGGTCGATGAAAGGGTAACTTGCGATGAAACATGCGACTGAAGAGA

T  L  D  S  N  P  A  T  F  P  L  N  A  T  L  Y  A  D  F  S  -
```

Fig. 24b

```
      CACGACAACACTATGGTTTCTATTTTCTTCGCTTTGGGTTTGTACAACGGTACTAAGCCA
1081  ------------+---------+---------+---------+---------+---------+ 1140
      GTGCTGTTGTGATACCAAAGATAAAAGAAGCGAAACCCAAACATGTTGCCATGATTCGGT

H  D  N  T  M  V  S  I  F  F  A  L  G  L  Y  N  G  T  K  P   -

TTGTCTACTACTTCTGTTGAATCTATTGAAGAAACTGACGGTTACTCTGCTTCTTGGACT
1141  ------------+---------+---------+---------+---------+---------+ 1200
      AACAGATGATGAAGACAACTTAGATAACTTCTTTGACTGCCAATGAGACGAAGAACCTGA

L  S  T  T  S  V  E  S  I  E  E  T  D  G  Y  S  A  S  W  T   -

GTTCCATTCGCTGCTAGAGCTTACGTTGAAATGATGCAATGTGAAGCTGAAAAGGAACCA
1201  ------------+---------+---------+---------+---------+---------+ 1260
      CAAGGTAAGCGACGATCTCGAATGCAACTTTACTACGTTACACTTCGACTTTTCCTTGGT

V  P  F  A  A  R  A  Y  V  E  M  M  Q  C  E  A  E  K  E  P   -

TTGGTTAGAGTTTTGGTTAACGACAGAGTTGTTCCATTGCACGGTTGTGCTGTTGACAAG
1261  ------------+---------+---------+---------+---------+---------+ 1320
      AACCAATCTCAAAACCAATTGCTGTCTCAACAAGGTAACGTGCCAACACGACAACTGTTC

L  V  R  V  L  V  N  D  R  V  V  P  L  H  G  C  A  V  D  K   -

TTGGGTAGATGTAAGAGAGACGACTTCGTTGAAGGTTTGTCTTTCGCTAGATCTGGTGGT
1321  ------------+---------+---------+---------+---------+---------+ 1380
      AACCCATCTACATTCTCTCTGCTGAAGCAACTTCCAAACAGAAAGCGATCTAGACCACCA

L  G  R  C  K  R  D  D  F  V  E  G  L  S  F  A  R  S  G  G   -

AACTGGGAAGAATGTTTCGCTTAA
1381  ------------+---------+---- 1404
      TTGACCCTTCTTACAAAGCGAATT

N  W  E  E  C  F  A  *
```

Fig. 24c

```
      ATGGGCGTGTTCGTCGTGCTACTGTCCATTGCCACCTTGTTCGGTTCCACATCCGGTACC
   1  ------------+---------+---------+---------+---------+---------+  60
      TACCCGCACAAGCAGCACGATGACAGGTAACGGTGGAACAAGCCAAGGTGTAGGCCATGG

M  G  V  F  V  V  L  L  S  I  A  T  L  F  G  S  T  S  G  T   -

GCCTTGGGTCCTCGTGGTAATTCTCACTCTTGTGACACTGTTGACGGTGGTTACCAATGT
  61  ------------+---------+---------+---------+---------+---------+ 120
      CGGAACCCAGGAGCACCATTAAGAGTGAGAACACTGTGACAACTGCCACCAATGGTTACA

A  L  G  P  R  G  N  S  H  S  C  D  T  V  D  G  G  Y  Q  C   -

TTCCCAGAAATTTCTCACTTGTGGGGTACATACTCTCCATTCTTCTCTTTGGCTGACGAA
 121  ------------+---------+---------+---------+---------+---------+ 180
      AAGGGTCTTTAAAGAGTGAACACCCCATGTATGAGAGGTAAGAAGAGAAACCGACTGCTT

F  P  E  I  S  H  L  W  G  T  Y  S  P  F  F  S  L  A  D  E   -

TCTGCTATTTCTCCAGACGTTCCAAAGGGTTGTAGAGTTACTTTCGTTCAAGTTTTGTCT
 181  ------------+---------+---------+---------+---------+---------+ 240
      AGACGATAAAGAGGTCTGCAAGGTTTCCCAACATCTCAATGAAAGCAAGTTCAAAACAGA

S  A  I  S  P  D  V  P  K  G  C  R  V  T  F  V  Q  V  L  S   -

AGACACGGTGCTAGATACCCAACTTCTTCTGCGTCTAAGGCTTACTCTGCTTTGATTGAA
 241  ------------+---------+---------+---------+---------+---------+ 300
      TCTGTGCCACGATCTATGGGTTGAAGAAGACGCAGATTCCGAATGAGACGAAACTAACTT

R  H  G  A  R  Y  P  T  S  S  A  S  K  A  Y  S  A  L  I  E   -

GCTATTCAAAAGAACGCTACTGCTTTCAAGGGTAAGTACGCTTTCTTGAAGACTTACAAT
 301  ------------+---------+---------+---------+---------+---------+ 360
      CGATAAGTTTTCTTGCGATGACGAAAGTTCCCATTCATGCGAAAGAACTTCTGAATGTTA

A  I  Q  K  N  A  T  A  F  K  G  K  Y  A  F  L  K  T  Y  N   -

TACACTTTGGGTGCTGACGACTTGACTCCATTCGGTGAACAACAAATGGTTAACTCTGGT
 361  ------------+---------+---------+---------+---------+---------+ 420
      ATGTGAAACCCACGACTGCTGAACTGAGGTAAGCCACTTGTTGTTTACCAATTGAGACCA

Y  T  L  G  A  D  D  L  T  P  F  G  E  Q  Q  M  V  N  S  G   -

ATTAAGTTCTACAGAAGATACAAGGCTTTGGCTAGAAAGATTGTTCCATTCATTAGAGCT
 421  ------------+---------+---------+---------+---------+---------+ 480
      TAATTCAAGATGTCTTCTATGTTCCGAAACCGATCTTTCTAACAAGGTAAGTAATCTCGA

I  K  F  Y  R  R  Y  K  A  L  A  R  K  I  V  P  F  I  R  A   -

TCTGGTTCTGACAGAGTTATTGCTTCTGCCGAAAAGTTCATTGAAGGTTTCCAATCTGCT
 481  ------------+---------+---------+---------+---------+---------+ 540
      AGACCAAGACTGTCTCAATAACGAAGACGGCTTTTCAAGTAACTTCCAAAGGTTAGACGA

S  G  S  D  R  V  I  A  S  A  E  K  F  I  E  G  F  Q  S  A   -
```

Fig. 25a

```
                 AAGTTGGCTGACCCAGGTGCTAACCCACACCAAGCTTCTCCAGTTATTAACGTTATTATT
541              ------------+---------+---------+---------+---------+---------+ 600
                 TTCAACCGACTGGGTCCACGATTGGGTGTGGTTCGAAGAGGTCAATAATTGCAATAATAA

K  L  A  D  P  G  A  N  P  H  Q  A  S  P  V  I  N  V  I  I  -

CCAGAAGGTGCTGGTTACAACAACACTTTGGACCACGGTTTGTGTACTGCTTTCGAAGAA
601              ------------+---------+---------+---------+---------+---------+ 660
                 GGTCTTCCACGACCAATGTTGTTGTGAAACCTGGTGCCAAACACATGACGAAAGCTTCTT

P  E  G  A  G  Y  N  N  T  L  D  H  G  L  C  T  A  F  E  E  -

TCTACCCTAGGTGACGACGTTGAAGCTAACTTCACTGCTGTTTTCGCTCCACCAATTAGA
661              ------------+---------+---------+---------+---------+---------+ 720
                 AGATGGGATCCACTGCTGCAACTTCGATTGAAGTGACGACAAAAGCGAGGTGGTTAATCT

S  T  L  G  D  D  V  E  A  N  F  T  A  V  F  A  P  P  I  R  -

GCTAGATTGGAAGCTCACTTGCCAGGTGTTAACTTGACTGACGAAGACGTTGTTAACTTG
721              ------------+---------+---------+---------+---------+---------+ 780
                 CGATCTAACCTTCGAGTGAACGGTCCACAATTGAACTGACTGCTTCTGCAACAATTGAAC

A  R  L  E  A  H  L  P  G  V  N  L  T  D  E  D  V  V  N  L  -

ATGGACATGTGTCCATTCGACACTGTTGCTAGAACTTCTGACGCTACTCAATTGTCTCCA
781              ------------+---------+---------+---------+---------+---------+ 840
                 TACCTGTACACAGGTAAGCTGTGACAACGATCTTGAAGACTGCGATGAGTTAACAGAGGT

M  D  M  C  P  F  D  T  V  A  R  T  S  D  A  T  Q  L  S  P  -

TTCTGTGACTTGTTCACTCACGACGAATGGATTCAATACGACTACTTGCAATCTTTGGGT
841              ------------+---------+---------+---------+---------+---------+ 900
                 AAGACACTGAACAAGTGAGTGCTGCTTACCTAAGTTATGCTGATGAACGTTAGAAACCCA

F  C  D  L  F  T  H  D  E  W  I  Q  Y  D  Y  L  Q  S  L  G  -

AAGTACTACGGTTACGGTGCTGGTAACCCATTGGGTCCAGCTCAAGGTGTTGGTTTCGTT
901              ------------+---------+---------+---------+---------+---------+ 960
                 TTCATGATGCCAATGCCACGACCATTGGGTAACCCAGGTCGAGTTCCACAACCAAAGCAA

K  Y  Y  G  Y  G  A  G  N  P  L  G  P  A  Q  G  V  G  F  V  -

AACGAATTGATTGCTAGATTGACTCACTCTCCAGTTCAAGACCACACTTCTACTAACCAC
961              ------------+---------+---------+---------+---------+---------+ 1020
                 TTGCTTAACTAACGATCTAACTGAGTGAGAGGTCAAGTTCTGGTGTGAAGATGATTGGTG

N  E  L  I  A  R  L  T  H  S  P  V  Q  D  H  T  S  T  N  H  -

ACTTTGGACTCTAACCCAGCTACTTTCCCATTGAACGCTACTTTGTACGCTGACTTCTCT
1021             ------------+---------+---------+---------+---------+---------+ 1080
                 TGAAACCTGAGATTGGGTCGATGAAAGGGTAACTTGCGATGAAACATGCGACTGAAGAGA

T  L  D  S  N  P  A  T  F  P  L  N  A  T  L  Y  A  D  F  S  -
```

Fig. 25b

```
       CACGACAACACTATGGTTTCTATTTTCTTCGCTTTGGGTTTGTACAACGGTACTAAGCCA
1081   ---------+---------+---------+---------+---------+---------+ 1140
       GTGCTGTTGTGATACCAAAGATAAAAGAAGCGAAACCCAAACATGTTGCCATGATTCGGT

H  D  N  T  M  V  S  I  F  F  A  L  G  L  Y  N  G  T  K  P  -

TTGTCTACTACTTCTGTTGAATCTATTGAAGAAACTGACGGTTACTCTGCTTCTTGGACT
1141   ---------+---------+---------+---------+---------+---------+ 1200
       AACAGATGATGAAGACAACTTAGATAACTTCTTTGACTGCCAATGAGACGAAGAACCTGA

L  S  T  T  S  V  E  S  I  E  E  T  D  G  Y  S  A  S  W  T  -

GTTCCATTCGCTGCTAGAGCTTACGTTGAAATGATGCAATGTGAAGCTGAAAAGGAACCA
1201   ---------+---------+---------+---------+---------+---------+ 1260
       CAAGGTAAGCGACGATCTCGAATGCAACTTTACTACGTTACACTTCGACTTTTCCTTGGT

V  P  F  A  A  R  A  Y  V  E  M  M  Q  C  E  A  E  K  E  P  -

TTGGTTAGAGTTTTGGTTAACGACAGAGTTGTTCCATTGCACGGTTGTGCTGTTGACAAG
1261   ---------+---------+---------+---------+---------+---------+ 1320
       AACCAATCTCAAAACCAATTGCTGTCTCAACAAGGTAACGTGCCAACACGACAACTGTTC

L  V  R  V  L  V  N  D  R  V  V  P  L  H  G  C  A  V  D  K  -

TTGGGTAGATGTAAGAGAGACGACTTCGTTGAAGGTTTGTCTTTCGCTAGATCTGGTGGT
1321   ---------+---------+---------+---------+---------+---------+ 1380
       AACCCATCTACATTCTCTCTGCTGAAGCAACTTCCAAACAGAAAGCGATCTAGACCACCA

L  G  R  C  K  R  D  D  F  V  E  G  L  S  F  A  R  S  G  G  -

AACTGGGAAGAATGTTTCGCTTAA
1381   ---------+---------+---- 1404
       TTGACCCTTCTTACAAAGCGAATT

N  W  E  E  C  F  A  *
```

Fig. 25c

PHYTASES

This application claims benefit of provisional U.S. Application No. 60/117,659 filed on Jan. 28, 1999 and Ser. No. 60/156,495 filed on Sep. 28, 1999.

Phytases are enzymes that hydrolyze phytate (myo-inositol hexakisphosphate) to myo-inositol and inorganic phosphate. They are known to be valuable feed additives.

The present invention relates to improved phytases, viz. phytases of amended characteristics, e.g. amended activity characteristics, reference being made to e.g. the phytase(s) it has been derived from, or to known phytases. Amended activity characteristics means amended in at least one phytase activity related respect, such as (non-exclusive list): pH stability, temperature stability, pH profile, temperature profile, specific activity (in particular in relation to pH and temperature), substrate specificity, substrate cleavage pattern, substrate binding, position specificity, the velocity and level of release of phosphate from corn, reaction rate, phytate degradation rate), end level of released phosphate reached.

Examples of amended activity characteristics are amended specific activity (e.g. increased, e.g. increased at a pH of 3, 4, 5, or 6); amended pH or temperature profile; and/or amended (e.g. increased) thermostability, e.g. of an increased melting temperature as measured using Differential Scanning Calorimetry (DSC).

The present invention also relates to a process for the preparation of a modified protein, wherein in a first step a consensus sequence is determined from a number of highly homologous sequences according to steps a), b) and c) below:

a) at least three, preferably at least four amino acid sequences are aligned by any standard alignment program known in the art;

b) at every position of the amino acid sequence alignment, the amino acids are evaluated for their evolutionary similarity and a consensus residue is chosen by any standard program known in the art, whereby the minimal requirements for calculation of a consensus residue are set in such a way that the program is already able to determine a consensus residue if a given residue occurs in only two of the aligned sequences. However, if there is a subgroup of sequences among the compared amino acid sequences that shows a much higher degree of similarity with each other than with the remaining sequences of the alignment, the subgroup may be represented in the calculation only with its consensus sequence determined in the same way as outlined in EP 897985, or alternatively, to each sequence of the subgroup, a vote weight of 1 divided by the number of sequences in the subgroup will be assigned;

c) in case no consensus amino acid at a defined position is identified by the program, any of the amino acids, preferably the most frequently occurring amino acid at this position is selected.

In a second aspect of the invention, a homologous sequence is compared with the consensus sequence, and one or more non-consensus residues in this homologous sequence are replaced by the corresponding consensus residues.

Preferably, only such amino acid residues are replaced in the homologous amino acid sequence where a consensus residue can clearly be defined by the program under moderately stringent conditions whereas at all positions of the alignment where no preferred consensus amino acid can be determined under moderately stringent conditions, the amino acids of the homologous protein remain unchanged.

In a third aspect of the invention, the active center of the protein of interest is determined, comprising all amino acid residues that are involved in forming the active center, both in the consensus sequence, and in the sequence of a homologous protein; subsequently, some or all of the divergent amino acid residues of the homologous protein are inserted in the backbone of the consensus sequence.

In one embodiment of this process, the program used for the comparison of amino acids at a defined position regarding their evolutionary similarity is the program "PRETTY".

The active center of the protein can be determined by using an analysis of the three-dimensional structure of the protein.

An example of a homologous protein is an enzyme family, an example of a defined protein family is the family of phytases, e.g. of fungal origin.

For example, the amino acid sequence of the phytase can be changed by the introduction of at least one mutation or substitution chosen from

| | |
|---|---|
| E58A | F54Y |
| D69K | I73V |
| D197N | K94A |
| T214L | R101A |
| E222T | N153K |
| E267D | V158I |
| R291I | A203G |
| R329H | S205G |
| S364T | V217A |
| A379K | A227V |
| G404A | V234L |
| | P238A |
| | Q277E |
| | A287H |
| | A292Q |
| | V366I |
| | A396S |
| | E415Q |
| | G437A |
| | R451E |

For interpreting these abbreviations, as an example, the mutation E58A is to be interpreted as follows: When subtracting 26 from the number, you get the position or residue number in the consensus phytase sequence or another phytase sequence aligned as shown in FIG. 1 (corresponding to the addition of a 26 amino acid signal sequence to the sequences shown in FIG. 1). For example, in E58A, number 58 means position number 32 (58−26=32). And the letter before the number, i.e. E, represents the amino acid in the phytase to be modified which is replaced by the amino acid behind the number, i.e. A.

The above-mentioned amino acid replacements, alone and/or in combination, have a positive effect on the protein stability.

The following sub-groups of mutations are also interesting (i.e. phytases comprising at least one mutation selected from either one of the groups of):

E58A, D69K, D197N, T214L, E222T, E267D, R291I, R329H, S364T, A379K, G404A;

F54Y, I73V, K94A, R101A, N153K, V158I, A203G, S205G, V217A, A227V, V234L, P238A, Q277E, A287H, A292Q, V366I, A396S, E415Q, G437A, R451E;

E58A, D69K, D197N, F54Y, I73V, K94A;

T214L, E222T, E267DR101A, N153K, V158I;

R291I, R329H, S364TA203G, S205G, V217A;
A379K, G404AA227V, V234L, P238A, Q277E;
A287H, A292Q, V366I, A396S, E415Q, G437A, R451E;
T214L, E222T, S364T, V158I, A203G, G404A, A227V, P238A, A396S, G437A, R451E.

Examples of host cells are plant cells, animal cells, and microbial cells, e.g. prokaryotic or eukaryotic cells, such as bacterial, fungal or yeast cells. An example of a fungal host is a strain of the genus Aspergillus, and examples of yeast hosts are strains of Saccharomyces, and strains of Hansenula.

The invention also relates to a modified protein obtainable or obtained by any of the processes described above.

The invention also relates to a variant or mutein of a phytase such as (but not limited to) the consensus phytase-1, wherein, in the amino acid sequence in FIG. 2, at least one of the following replacements have been effected: Q50L, Q50T, Q50G, Q50T-Y51N, Q50L-Y51N or Q50T-K91A.

In the third aspect mentioned above, a consensus sequence is determined from homologous sequences as described above; in a second step the active center of the protein comprising all amino acid residues that are involved in forming the active center is determined in the consensus sequence and in the sequence of a single homologous protein as well. The single homologous protein may have preferred properties like high specific activity or different pH dependency of enzymatic activity. In a third step some or all amino acid residues that are involved in forming the active center of the homologous protein are inserted into the backbone of the consensus sequence. The result thereof is a chimeric protein having the active center derived from a single protein and the backbone of the consensus sequence.

The active center of the protein can be determined e.g. by using any analysis of the three-dimensional structure of the protein, e.g. by homology modelling on the basis of a known 3D-structure of a known protein.

The present invention also provides consensus proteins obtainable or obtained by such processes, in particular proteins comprising at least one of the amino acid sequences shown in FIGS. 2–6, 10 or 21, or variants or muteins thereof. Examples of such variants are shown in FIGS. 7–9.

Such variants or muteins can be defined and prepared on the basis of the teachings given in European Patent Application number 0897010, e.g. Q50L, Q50T, Q50G, Q50L-Y51N, or Q50T-Y51N.

These mutations are defined as above, or, alternatively, by reference to FIG. 2. When referring to FIG. 2, no subtraction of the 26 amino acid signal peptide is required (e.g. in "Q50L," at position 50 of the amino acid sequence of FIG. 2, the amino acid Q has been replaced by amino acid L).

A food, feed, or pharmaceutical composition comprising the phytases of the invention is another aspect of the invention.

In this context, and relating to the process of the invention, "at least three, preferably at least four amino acid sequences of such defined protein family" means that three, four, five, six to twelve, twenty, fifty, or even more sequences can be used for the alignment and the comparison to create the amino acid sequence of the consensus protein. "Sequences of a defined protein family" means that such sequences fold into a three-dimensional structure, wherein the alpha-helices, the beta-sheets and beta-turns are at the same position so that such structures are, as called by the man skilled in the art, largely superimposable. Furthermore these sequences characterize proteins that show the same type of biological activity, e.g. a defined enzyme class, e.g. the phytases. The three-dimensional structure of one such protein is sufficient to allow the modelling of the structure of the other homologous proteins of such a family. An example, how this can be done, is given in Example 1. "Evolutionary similarity" in the context of the present invention refers to a scheme which classifies amino acids regarding their structural similarity which allows that one amino acid can be replaced by another amino acid with a minimal influence on the overall structure, as this is done e.g. by programs, like "PRETTY", known in the art. The phrase "the degree of similarity provided by such a program . . . is set to less stringent number" means in the context of the present invention that values for the parameters which determine the degree of similarity in the program used in the practice of the present invention are chosen in a way to allow the program to define a consensus amino acid for a maximum of positions of the whole amino acid sequence, e.g. in case of the program PRETTY a value of 2 or 3 for the THRESHOLD and a value of 2 for the PLURALITY can be chosen. Furthermore, "a vote weight of one divided by the number of such sequences" means in the context of the present invention that the sequences which define a group of sequences with a higher degree of similarity as the other sequences used for the determination of the consensus sequence only contribute to such determination with a factor which is equal to one divided by the number of all sequences of this group.

As mentioned before, should the program not allow to select the consensus amino acid, the most frequent amino acid is selected; should the latter be impossible the man skilled in the art will select an amino acid from all the sequences used for the comparison which is known in the art for its property to improve the thermostability in proteins as discussed e.g. by Janecek, S. (1993), Process Biochem. 28, 435–445; Fersht, A. R. & Serrano, L. (1993), Curr. Opin. Struct. Biol. 3, 75–83; Alber, T. (1989), Annu. Rev. Biochem. 58, 765–798; Matthews, B. W. (1987), Biochemistry 26, 6885–6888; or Matthews, B. W. (1991), Curr. Opin. Struct. Biol. 1, 17–21.

The stability of an enzyme is relevant for many industrial applications. Therefore, a lot of attempts, more or less successful, have been made to improve the stability, preferably the thermostability of enzymes by rational or random approaches.

Here we present an alternative way to improve the thermostability of a protein.

The invention provides a process for the preparation of a consensus protein comprising a process to calculate an amino acid residue for nearly all positions of a so-called consensus protein and to synthesize a complete gene from this sequence that can be expressed in a pro- or eukaryotic expression system.

DNA sequences of the present invention can be constructed starting from genomic or cDNA sequences encoding the proteins, e.g. phytases, of interest. For example, they can be constructed by methods of in vitro mutagenesis [see e.g. Sambrook et al., Molecular Cloning, Cold Spring Harbor Laboratory Press, New York]. A widely used strategy for "site-directed mutagenesis", as originally outlined by Hurchinson and Edgell [J. Virol. 8, 181 (1971)], involves the annealing of a synthetic oligonucleotide carrying the desired nucleotide substitution to a target region of a single-stranded DNA sequence wherein the mutation should be introduced [for review see Smith, Annu. Rev. Genet. 19, 423 (1985), and for improved methods, see references 2–6 in Stanssen et al., Nucl. Acids Res., 17, 4441–4454 (1989). Another possibility of mutating a given DNA sequence is the mutagenesis by using the polymerase chain reaction (PCR). DNA as starting material can be isolated by methods known in the art and described e.g. in Sambrook et al. (Molecular Cloning) from the respective strains.

For strain information, see e.g. EP 684313 or any depository authority indicated below. *Aspergillus niger* [ATCC 9142], *Myceliophthora thermophila* [ATCC 481021, *Talaromyces thermophilus* (ATCC 20186] and *Aspergillus fumigatus* [ATCC 34625] have been redeposited according to the conditions of the Budapest Treaty at the American Type Culture Cell Collection under the following accession numbers: ATCC 74337, ATCC 74340, ATCC 74338 and ATCC 74339, respectively. It is, however, understood that DNA encoding a consensus protein in accordance with the present invention can also be prepared in a synthetic manner as described, e.g. in EP 747483 or EP 897985, or in the examples, by methods known in the art.

For sequence information, see e.g. EP 684313, or sequence data bases, for example like Genbank (Intelligenetics, California, USA), European Bioinformatics Institute (Hinston Hall, Cambridge, GB), NBRF (Georgetown University, Medical Centre, Washington D.C., USA) and Vecbase (University of Wisconsin, Biotechnology Centre, Madison, Wis., USA).

The process of the present invention can e.g. be used to improve the thermostability of the enzyme phytase.

Once complete DNA sequences of the present invention have been obtained they can be integrated into vectors by methods known in the art and described e.g. in Sambrook et al. (s.a.) to overexpress the encoded polypeptide in appropriate host systems. However, a man skilled in the art knows that also the DNA sequences themselves can be used to transform the suitable host systems of the invention to get overexpression of the encoded polypeptide. Appropriate host systems are for example fungi, like Aspergilli, e.g. *Aspergillus niger* [ATCC 9142] or *Aspergillus ficuum* [NRRL 3135] or like Trichoderma, e.g. *Trichoderma reesei*; or yeasts, like Saccharomyces, e.g. *Saccharomyces cerevisiae* or Pichia, like *Pichia pastoris*, or *Hansenula polymorpha*, e.g. *H. polymorpha* (DSM5215); or plants, as described, e.g. by Pen et al., Bio/Technology 11, 811–814 (1994). A man skilled in the art knows that such microorganisms are available from depository authorities, e.g. the American Type Culture Collection (ATCC), the Centraalbureau voor Schimmelcultures (CBS) or the Deutsche Sammlung für Mikroorganismen und Zellkulturen GmbH (DSM) or any other depository authority as listed in the Journal "Industrial Property" (1991) 1, pages 29–401. Bacteria which can be used are e.g. *E. coli*; Bacilli as, e.g., *Bacillus subtilis*; or Streptomyces, e.g. *Streptomyces lividans* (see e.g. Anne and Mallaert in FEMS Microbiol. Lett. 114, 121 (1993). Preferred *E. coli* strains, which can be used are *E. coli* K12 strains e.g. M15 [described as DZ 291 by Villarejo et al. in J. Bacteriol. 120, 466–474 (1974)], HB 101 [ATCC No. 33694] or *E. coli* SG13009 [Gottesman et al., J. Bacteriol. 148, 265–273 (1981)].

Vectors which can be used for expression in fungi are known in the art and described e.g. in BP 420358, or by Cullen et al. [Bio/Technology 5, 369–376 (1987)], Ward [Molecular Industrial Mycology, Systems and Applications for Filamentous Fungi, Marcel Dekker, New York (1991)], Upshall et al. [Bio/Technology 5, 1301–1304 (1987)], Gwynne et al. [Bio/Technology 5, 71–79 (1987)], or Punt et al. [J. Biotechnol. 17, 19–34 (1991)]; and for yeasts by Sreekrishna et al. [J. Basic Microbiol. 28, 265–278 (1988), Biochemistry 28, 4117–4125 (1989)], Hitzemann et al. [Nature 293, 717–722 (1981)] or in EP 183070, EP 183071, EP 248227, or EP 263311. Suitable vectors which can be used for expression in *E. coli* are mentioned, e.g. by Sambrook et al. [s.a.], Fiers et al. [Procd. 8th Int. Biotechnology Symposium", Soc. Franc. de Microbiol., Paris (Durand et al., eds.), pp. 680–697 (1988)], Bujard et al. [Meth. Enzymol. 155, 416–433 (1987)], or Stüber et al. [Immunological Methods, eds. Lefkovits and Pernis, Academic Press, Inc., Vol. IV, 121–152 (1990)]. Vectors that can be used for expression in Bacilli are known in the art and described, e.g. in EP 207459, EP 405370, Proc. Natl. Acad. Sci. USA 81, 439 (1984) or Yansura and Henner, Meth. Enzymol. 185, 199–228 (1990). Vectors which can be used for the expression in *H. Polymorpha* are known in the art and described, e.g. in Gellissen et al., Biotechnology 9, 291–295 (1991).

Either such vectors already carry regulatory elements, e.g. promotors, or the DNA sequences of the present invention can be engineered to contain such elements. Suitable promotor elements which can be used are known in the art and are, e.g. for *Trichoderma reesei* the cbh1- [Haarki et al., Biotechnology 7, 596–600 (1989)] or the pki1-promotor [Schindler et al., Gene 130, 271–275 (1993)]; for *Aspergillus oryzae* the amy-promotor [Christensen et al., Abstr. 19th Lunteren Lectures on Molecular Genetics F23 (1987), Christensen et al., Biotechnology 6, 1419–1422 (1988), Tada et al., Mol. Gen. Genet. 229, 301 (1991)]; and for *Aspergillus niger* the glaA- [Cullen et al., Bio/Technology 5, 369–376 (1987), Gwynne et al., Bio/Technology 5, 713–719 (1987), Ward in Molecular Industrial Mycology, Systems and Applications for Filamentous Fungi, Marcel Dekker, New York, 83–106 (1991)], alcA- [Gwynne et al., Bio/Technology 5, 718–719 (1987)], suc1- [Boddy et al., Curr. Genet. 24, 60–66 (1993)], aphA- [MacRae et al., Gene 71, 339–348 (1988), MacRae et al., Gene 132, 193–198 (1993)], tpiA- [McKnight et al., Cell 46, 143–147 (1986), Upshall et al., Bio/Technology 5, 1301–1304 (1987)], gpdA- [Punt et al., Gene 69, 49–57 (1988), Punt et al., J. Biotechnol. 17, 19–37 (1991)] and the pkiA-promotor [de Graaff et al., Curr. Genet. 22, 21–27 (1992)]. Suitable promotor elements that can be used for expression in yeast are known in the art and are, e.g. the pho5-promotor [Vogel et al., Mol. Cell. Biol., 2050–2057 (1989); Rudolf and Hinnen, Proc. Natl. Acad. Sci. 84, 1340–1344 (1987)] or the gap-promotor for expression in *Saccharomyces cerevisiae*; the aox1-promotor [Koutz et al., Yeast 5, 167–177 (1989); Sreekrishna et al., J. Basic Microbiol. 28, 265–278 (1988)] for *Pichia pastoris*; or the FMD promoter [Hollenberg et al., EPA No. 02991081 or MOX-promotor [Ledeboer et al., Nucl. Acids Res. 13, 3063–3082 (1985)] for *H. polymorpha*.

Accordingly vectors comprising DNA sequences of the present invention, preferably for the expression of said DNA sequences in bacteria or a fungal or a yeast host and such transformed bacteria or fungal or yeast hosts are also a part of the invention.

The invention also provides a system that allows for high expression of proteins, in particular of the phytases of the invention, such as recombinant Hansenula strains. To achieve that, the codons of the DNA sequence of such a protein may be selected on the basis of a codon frequency table of the organism used for expression, e.g. of yeast as in the present case (see e.g. in Example 1). Optionally, the codons for the signal sequence may be selected in a manner as described for the specific case in Example 1; that means that a codon frequency table is prepared on the basis of the codons used in the DNA sequences which encode the amino acid sequences of the given protein family. Then the codons for the design of the DNA sequence of the signal sequence are selected from a codon frequency table of the host cell used for expression whereby always codons of comparable frequency in both tables are used.

Once such DNA sequences have been expressed in an appropriate host cell in a suitable medium, the encoded protein can be isolated either from the medium in the case the protein is secreted into the medium or from the host organism in case such protein is present intracellularly by methods known in the art of protein purification or described in case of a phytase, e.g. in EP 420358. Accordingly, a process for the preparation of a polypeptide of the present invention wherein transformed bacteria or a host cell as described above are cultured under suitable culture conditions, and the polypeptide is recovered therefrom and a polypeptide when produced by such a process; or a polypeptide encoded by a DNA sequence of the present invention, are also a part of the present invention.

Once obtained, the polypeptides of the present invention can be characterized regarding their properties that make them useful in agriculture by any assay known in the art.

In general, the polypeptides of the present invention can be used without being limited to a specific field of application, e.g. in case of phytases for the conversion of inositol polyphosphates, like phytate, to inositol and inorganic phosphate.

Furthermore, the polypeptides of the present invention can be used in a process for the preparation of a pharmaceutical composition or compound food or feeds wherein the components of such a composition are mixed with at least one polypeptide of the present invention. Accordingly, compound food or feeds or pharmaceutical compositions comprising at least one polypeptide of the present invention are also a part of the present invention. A man skilled in the art is familiar with their process of preparation. Such pharmaceutical compositions or compound foods or feeds can further comprise additives or components generally used for such purpose and known in the state of the art.

The present invention also provides a process for the reduction of levels of phytate in animal manure wherein an animal is fed such a feed composition in an amount effective in converting phytate contained in the feedstuff to lower inositol phosphates and/or inositol, and inorganic phosphate.

In the present context, a phytase is an enzyme or polypeptide that has phytase activity. A phytase can be e.g. a myo-inositol hexakisphosphate phosphohydrolase, such as (myo-inositol hexakisphosphate 3-phosphohydrolase, EC 3.1.3.8) and (myo-inositol hexakisphosphate 6-phosphohydrolase, EC 3.1.3.26).

In one embodiment, the phytase is purified, viz. at least 85%, preferably at least 86, 87, 88, 89, 90, 91, 92, 93, 94, 95, 96, 97, 98, 99% pure, as evaluated by SDS-PAGE. The phytase may be isolated. Phytase activity can be determined using any phytase assay known in the art, e.g. the assay described herein (see Example 9). The assay temperature may be the optimum temperature of the actual phytase, and the assay pH may be the optimum pH of the actual phytase.

The assay temperature may e.g. be selected within the range of 20–90° C., or 30–80° C., or 35–75° C., for instance temperatures of 37° C., 50° C., 60° C., or 70° C.

The assay pH may e.g. be selected within the range of pH 2–9, or 3–8, or 3–6, for instance assay pH values of 3, 4, 5, 6, or 7 may be chosen.

Amino acid sequence homology (or polypeptide or amino acid homology) is determined as the degree of identity between two sequences. This may suitably be determined by means of computer programs known in the art such as GAP provided in the GCG program package [Program Manual for the Wisconsin Package, Genetics Computer Group, 575 Science Drive, Madison, Wisconsin 53711, USA], see also Needleman, S. B. and Wunsch, C. D., (1970), J. Mol. Biol., 48, 443–453). In release 9.1, for comparing polypeptide sequences, the Length Weight is set to 0, and the Gap Weight is set to 3.0.

The degree of identity or homology between two DNA (nucleic acid) sequences may be determined by means of computer programs known in the art such as GAP provided in the GCG program package [Program Manual for the Wisconsin Package, Genetics Computer Group, 575 Science Drive, Madison, Wis. 53711, USA), see also Needleman, S. B. and Wunsch, C. D., (1970), J. Mol. Biol., 48, 443–453). In release 9.1, GAP is used with the following settings for DNA sequence comparison: GAP creation penalty of 50 and GAP extension penalty of 3.

Suitable experimental conditions for determining whether a given DNA or RNA sequence hybridizes to a specified nucleotide or oligonucleotide probe involves presoaking of the filter containing the DNA or RNA fragments to examine for hybridization in 5×SSC (Sodium chloride/Sodium citrate; (J. Sambrook, E. F. Fritsch, and T. Maniatis, 1989, Molecular Cloning, A Laboratory Manual, 2nd edition, Cold Spring Harbor, New York) for 10 min, and prehybridization of the filter in a solution of 5×SSC, 5×Denhardt's solution, 0.5% SDS and 100 $\mu$g/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), $^{32}$P-dCTP-labeled (specific activity <1×10$^9$ cpm/$\mu$g) probe for 12 hours at approximately 45° C.

The filter is then washed twice for 30 minutes in 2×SSC, 0.5% SDS at at least 55° C. (low stringency), at at least 60° C. (medium stringency), at at least 65° C. (medium/high stringency), at at least 70° C. (high stringency), or at at least 75° C. (very high stringency).

Molecules to which the oligonucleotide probe hybridizes under these conditions can be detected using an x-ray film.

Phytases of amended thermostability, or thermostable phytases, are one aspect of the present invention. A "thermostable" phytase is a phytase that has a Tm (melting temperature)—as measured on purified phytase protein by Differential Scanning Calorimetry (DSC)—of at least 65° C. For the DSC, a constant heating rate may be used, e.g. of 10° C./min. In alternative embodiments, the Tm is at least 66, 67, 68, 69, 70, 71, 72, 73, 74 or 75° C. Or, the Tm is equal to or lower than 150° C., or equal to or lower than 145, 140, 135, 130, 125, 120, 115 or 110° C. Accordingly, examples of intervals of Tm are: 65–150° C., 66–150° C.,—(etc.)— 75–150° C.; 65–145° C., 66–145° C., —(etc.)—75–145° C.; 65–140° C.,—(etc.)—75–140° C.;—(etc.)—65–110° C., 66–110° C.,—(etc.)—75–110° C.

Particular ranges for Tm are the following: between 65 and 110° C.; between 70 and 110° C.; between 70 and 100° C.; between 75 and 95° C., or between 80 and 90° C.

In Examples 9 and 10 below, the measurement of Tm by DSC is described, and the Tm's of a number of phytases are shown.

The optimum temperatures are also indicated, since—as an alternative mean—a thermostable phytase can be defined as a phytase having a temperature-optimum of at least 60° C. Preferably, the optimum temperature is determined on the substrate phytate or phytic acid at pH 5.0 or 5.5. Example 9 describes an example of a phytase assay, including a definition of units.

In alternative embodiments, the optimum temperature is at least 61, 62, 63, 64, 65, 66, 67, 68, 69 or 70° C. In a particular embodiment, the optimum temperature is equal to or lower than 140° C., or equal to or lower than 135, 130, 125, 120, 115, 110, 105 or 100° C. Accordingly, examples of intervals of optimum temperature are: 60–140° C., 61–140° C.,—(etc.)—70–140° C.; 60–135° C., 61–135° C.,—(etc.)—70–135° C.; 60–130° C.,—(etc.)—70–130° C.;—(etc.)—60–100° C., 61–100° C.,—(etc.)—70–100° C.

Before describing the present invention in more detail a short explanation of the Figures enclosed is given below.

FIG. 1: Design of the consensus phytase-1 sequence. The following sequences were used for the alignment: phyA from *Aspergillus terreus* 9A-1 [Mitchell, D. B., Vogel, K., Weimann, S. J., Pasamontes, L. & van Loon, A. P. G. M. (1997) The phytase subfamily of histidine acid phosphatases: isolation of genes for two novel phytases from the fungi *Aspergillus terreus* and *Myceliophthora thermophila*, Microbiology 143, 245–252); from amino acid (aa) 27; SEQ ID NO: 1]; phyA from *A. terreus* cbs116.46 [EP 897985]. A heat resistant phytase of *Aspergillus fumigatus* with superior performance in animal experiments. Phytase optimization and natural variability. In: The Biochemistry of phytate and phytases (eds. Rasmussen, S. K; Raboy, V.; DalbØge, H. and Loewus, F.; Kluwer Academic Publishers); from aa 27; SEQ ID NO: 2; phyA from *Aspergillus niger* var. awamori (Piddington et al (1993) Gene 133, 55–62; from aa 27; SEQ ID NO: 3); phyA from *A. niger* T213 (EP 897985); from aa 27; SEQ ID NO: 4); phyA from *A. niger* strain NRRL3135 [van Hartingsveldt, W., van Zeijl, C. M. F., Harteveld, G. M., Gouka, R. J., Suykerbuyk, M. E. G., Luiten, R. G. M., van Paridon, P. A., Selten, G. C. M., Veenstra, A. E., van Gorcom, R. F. M., & van den Hondel, C. A. M. J. J. (1993) Cloning, characterization and overexpression of the phytase-encoding gene (phyA) of *Aspergillus niger*. Gene 127, 87–94; from aa 27; SEQ ID NO: 5]; phyA from *Aspergillus fumigatus* ATCC 13073 (Pasamontes, L., Haiker, M., Wyss, M., Tessier, M. & van Loon, A. P. G. M. (1997) Cloning, purification and characterization of a heat stable phytase from the fungus *Aspergillus fumigatus*, Appl. Environ. Microbiol. 63, 1696–1700; from aa 25; SEQ ID NO: 6]; phyA from *A. fumigatus* ATCC 32722 (EP 897985); from aa 27; SEQ ID NO: 7); phyA from *A. fumigatus* ATCC 58128 (EP 897985); from aa 27; SEQ ID NO: 8); phyA from *A. fumigatus* ATCC 26906 (EP 897985); from aa 27; SEQ ID NO: 9); phyA from *A. fumigatus* ATCC 32239 (EP 897985); from aa 30; SEQ ID NO: 10; phyA from *Emericella nidulans* [Pasamontes, L., Haiker, M., Henriquez-Huecas, M., Mitchell, D. B. & van Loon, A. P. G. M. (1997a). Cloning of the phytases from *Emericelia nidulans* and the thermophilic fungus *Talaromyces thermophilus*. Biochim. Biophys. Acta 1353, 217–223; from aa 25; SEQ ID NO: 11]; phyA from *Talaromyces thermophilus* (Pasamontes et al., 1997a; from aa 24; SEQ ID NO: 12); and phyA from *Mycelioph-thora thermophila* (Mitchell et al., 1997; from aa 19; SEQ ID NO: 13). The alignment was calculated using the program PILEUP. The location of the gaps was refined by hand. Capitalized amino acid residues in the alignment at a given position belong to the amino acid coalition that establish the consensus residue. In bold, beneath the calculated consensus sequence (SEQ ID NO: 98), the amino acid sequence of the finally constructed consensus phytase (Fcp) is shown (SEQ ID NO: 14). The gaps in the calculated consensus sequence were filled by hand according to principals stated in Example 1.

FIG. 2: DNA sequence (SEQ ID NO: 15) of the consensus phytase-1 gene (fcp) and of the primers used for the gene construction. The calculated amino acid sequence (FIG. 1, SEQ ID NO: 14) was converted into a DNA sequence using the program BACKTRANSLATE [Devereux, J., Haeberli, P. & Smithies, O. (1984) A comprehensive set of sequence analysis programs for the VAX. Nucl. Acids Res. 12, 387–395], and the codon frequency table of highly expressed yeast genes (GCG program package, 9.0). The signal peptide of the phytase from *A. terreus* cbs 116.46 was fused to the N-terminus. The amino acid sequence shown in FIG. 2 is SEQ ID NO: 16. The bold bases represent the sequences of the oligonucleotides used to generate the gene. The names of the respective oligonucleotides are alternately noted above or below the sequence. The underlined bases represent the start and stop codon of the gene. The bases written in italics represent the two introduced Eco RI sites.

FIG. 3: Alignment and consensus sequence of five Basidiomycete phytases. The letters represent the amino acid residues in the one-letter code. The amino acid sequences of the phytases from *Paxillus involutus*, phyA1 (from aa 21; SEQ ID NO: 17; and phyA2 (from aa 21, WO 98/28409; SEQ ID NO: 18); *Trametes pubescens* (from aa 24, WO 98/28409; SEQ ID NO: 19); *Agrocybe pediades* (from aa 19, WO 98/28409; SEQ ID NO: 20); and *Peniophora lycii* (from aa 21, WO 98/28409; SEQ ID NO: 21), starting with the amino acid residues mentioned in parentheses, were used for the alignment and the calculation of the corresponding consensus sequence called "Basidio" (Example 2; SEQ ID NO: 22). The alignment was performed with the program PILEPUP. The location of the gaps was refined by hand. The consensus sequence was calculated by the program PRETTY. While a vote weight of 0.5 was assigned to the two *P. involutus* phytases, all other genes were used with a vote weight of 1.0 for the consensus sequence calculation. At positions where the program was not able to determine a consensus residue, the Basidio sequence contains a dash. Capitalized amino acid residues in the alignment at a given position represent the amino acid coalition that established the consensus residue.

FIG. 4: Design of consensus phytase-10 amino acid sequence. By adding the sequence of *Thermomyces lanuginosus* phytase [Berka, R. M., Rey, M. W., Brown, K. M., Byun, T. & Klotz, A. V. (1998) Molecular characterization and expression of a phytase gene from the thermophilic fungus *Thermomyces lanuginosus*. Appl. Environ. Microbiol. 64, 4423–4427; SEQ ID NO: 23] and the consensus sequence of the phytases from five Basidiomycetes (SEQ ID NO: 22) to the alignment of FIG. 1, an improved consensus sequence was calculated by the program PRETTY. Additionally, the amino acid sequence of *A. niger* T213 was omitted, and a vote weight of 0.5 was assigned to the remaining two *A. niger* phytase sequences. For further information see Example 2.

FIG. 5: DNA and amino acid sequence of consensus phytase-10 (SEQ ID NO: 25, and SEQ ID NO: 26, respectively). The amino acid sequence of the mature consensus phytase-10 is shown in SEQ ID NO:24. The sequence of the oligonucleotides that were used to assemble the gene are in bold letters. The names of the respective oligonucleotides and the amino acids that differ relative to consensus phytase-1 are underlined. The fcp10 gene was assembled from the following oligonucleotides: CP-1, CP-2, CP-3.10, CP-4.10, CP-5.10, CP-6, CP-7.10, CP-8.10, CP-9.10, CP-10.10, CP-11.10, CP-12.10, CP-13.10, CP-14.10, CP-15.10, CP-16.10, CP-17.10, CP18.10, CP-19.10, CP-20.10, CP-21.10, and CP-22.10. The newly synthesized oligonucleotides are additionally marked by the number 10. The phytase contains the following 32 exchanges relative to consensus phytase-1. Y54F, E58A, D69K, D70G, A94K, N134Q, I158V, S187A, Q188N, D197N, S204A, T214L, D220E, L234V, A238P, D246H, T251N, Y259N, E267D, A283D, R291I, A320V, R329H, S364T, I366V, A379K, S396A, G404A, Q415E, A437G, The underlined mutations revealed a stabilizing effect on consensus phytase-1 when tested as single mutations in consensus phytase-1.

FIG. 6: Alignment for the design of consensus phytase-11 (SEQ ID NO: 27). In contrast to the design of consensus phytase-10, for the design of the amino acid sequence of consensus phytase-11, all Basidiomycete phytases were used as independent sequences using an assigned vote weight of 0.2 for each Basidiomycete sequence. Additionally, the amino acid sequence of A. niger T213 was again used in this alignment.

FIG. 7: DNA and amino acid sequence of consensus phytase-1-thermo[8]-Q50T-K91A (SEQ ID NO: 28, and SEQ ID NO: 29, respectively). The amino acid sequence is written above the corresponding DNA sequence using the one-letter code. The replaced amino acid residues (relative to consensus phytase-1) are underlined. The stop codon of the gene is marked by a star FIG. 8: DNA and amino acid sequence of consensus phytase-10-thermo[3]-Q50T-K91A (SEQ ID NO: 30, and SEQ ID NO: 31, respectively). The amino acid sequence is written above the corresponding DNA sequence using the one-letter code. The replaced amino acid residues (relative to consensus phytase-10) are underlined. The stop codon of the gene is marked by a star (*).

FIG. 9: DNA and amino acid sequence of A. fumigatus ATCC 13073 phytase alpha-mutant Q51T (SEQ ID NO: 32, and SEQ ID NO: 33, respectively). The amino acid sequence is written above the corresponding DNA sequence using the one-letter code. The replaced amino acid residues (relative to A. fumigatus ATCC 13073 phytase) are underlined. The stop codon of the gene is marked by a star (*).

FIG. 10: DNA and amino acid sequence of consensus phytase-7 (SEQ ID NO: 34, and SEQ ID NO: 35, respectively). The amino acids are written above the corresponding DNA sequence using the one-letter code. The sequence of the oligonucleotides used to assemble the gene are in bold letters. Oligonucleotides and amino acids that were exchanged (relative to consensus phytase-1) are underlined and the corresponding triplets are written in small case letters. The fcp7 gene was assembled from the following oligonucleotides: CP-1, CP-2, CP-3, CP-4.7, CP-5.7, CP-6, CP-7, CP-8.7, CP-9, CP-10.7, CP-11.7, CP-12.7, CP-13.7, CP-14.7, CP-15.7, CP-16, CP-17.7, CP-18.7, CP-19.7, CP-20, CP-21, and CP-22. The newly synthesized oligonucleotides are additionally marked by the number 7. Consensus phytase-7 contains the following 24 exchanges in comparison to the original consensus phytase-1: S89D, S92G, A94K, D164S, P201S, G203A, G205S, H212P, G224A, D226T, E255T, D256E, V258T, P265S, Q292H, G300K, Y305H, A314T, S364G, M365I, A397S, S398A, G404A, and A405S.

FIG. 11: Differential scanning calorimetry (DSC) of consensus phytase-1 and consensus phytase-10. The protein samples were concentrated to about 50–60 mg/ml and extensively dialyzed against 10 mM sodium acetate, pH 5.0. A constant heating rate of 10° C./min was applied up to 95° C. DSC of consensus phytase-10 (upper graph) yielded a melting temperature of 85.4° C., which is 7.3° C. higher than the melting point of consensus phytase-1 (78.1° C., lower graph).

FIG. 12: Differential scanning calorimetry (DSC) of consensus phytase-10-thermo[3]-Q50T and consensus phytase-10-thermo[3]-Q50T-K91A. The protein samples were concentrated to ca. 50–60 mg/ml and extensively dialyzed against 10 mM sodium acetate, pH 5.0. A constant heating rate of 10° C./min was applied up to 95° C. DSC of consensus phytase-10-thermo[3]-Q50T (upper graph) yielded a melting temperature of 88.6° C., while the melting temperature of consensus phytase-10-thermo-Q50T-K91A was determined to be 89.3° C.

Figure 13:
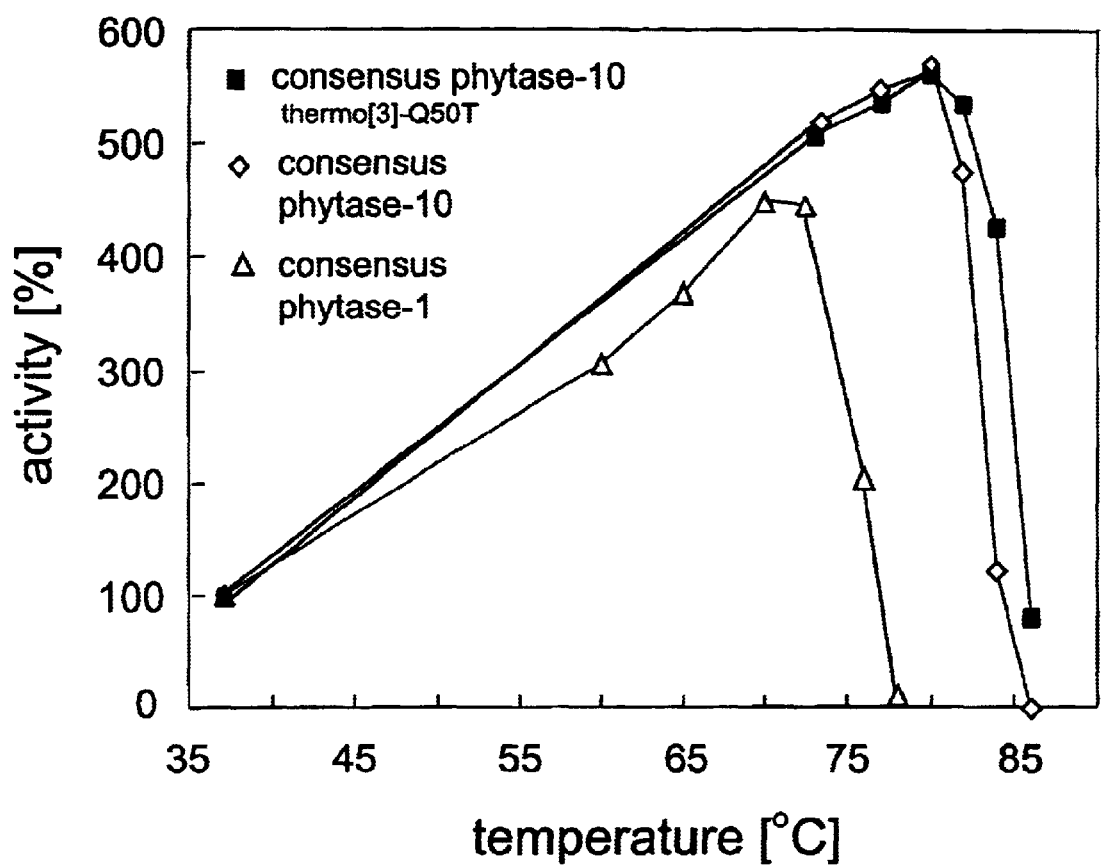

FIG. 13: Comparison of the temperature optimum between consensus phytase-1, consensus phytase-10 and consensus phytase-10-thermo[3]-Q50T. For the determination of the temperature optimum, the phytase standard assay of Example 9 was performed at a series of temperatures between 37 and 86° C. The diluted supernatant of transformed S. cerevisiae strains was used for the determination. The other components of the supernatant had no influence on the determination of the temperature optimum: Λ, consensus phytase-1; ◇, consensus phytase-10; ■, consensus phytase 10-thermo[3]-Q50T.

Figure 14:
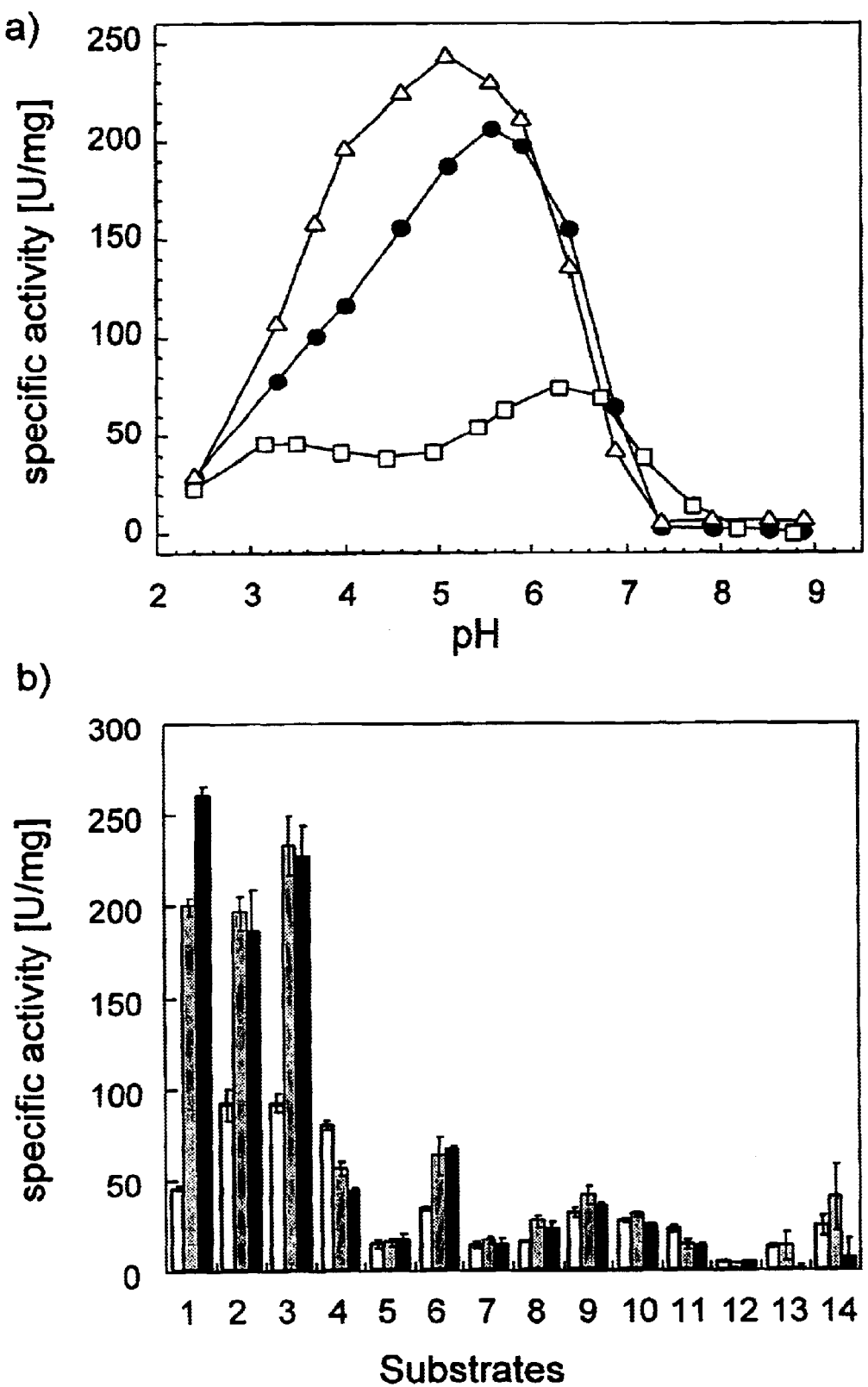

FIG. 14: pH-dependent activity profile and substrate specificity of consensus phytase-10 and its variants thermo[3]-Q50T and thermo[3]-Q50T-K91A. The phytase activity was determined using the standard assay in appropriate buffers (see Example 9) at different pH-values. Graph a) shows the pH-dependent activity profile of consensus phytase-10 (□), consensus phytase-10-thermo[3]-Q50T (•), and consensus phytase-10-thermo[3]-Q50T-K91A (Λ). Graph b) shows the corresponding substrate specificity tested by replacement of phytate in the standard assay by the indicated compounds; open bars, consensus phytase-10; grey bars, consensus phytase-10-thermo[3]-Q50T; dark bars, consensus phytase-10-thermo[3]-Q50T-K91A). The numbers correspond to the following substrates: 1, phytate; 2, p-nitrophenyl phosphate; 3, phenyl phosphate; 4, fructose-1,6-bisphosphate; 5, fructose-6-phosphate; 6, glucose-6-phosphate; 7, ribose-5-phosphate; 8, DL-glycerol-3-phosphate; 9, glycerol-2-phosphate; 10, 3-phosphoglycerate; 11, phosphoenolpyruvate; 12, AMP; 13, ADP; 14, ATP.

FIG. 15: pH-dependent activity profile and substrate specificity of consensus phytase-1-thermo[8]-Q50T and of consensus phytase-1-thermo[8]-Q50T-K91A. The phytase activity was determined using the standard assay in appropriate buffers (see Example 9) at different pH-values. Graph a) shows the pH-dependent activity profile of the Q50T- (■) and the Q50T-K91A-variant (•). Graph b) shows the corresponding substrate specificities tested by replacement of phytate in the standard assay by the indicated compounds (open bars, consensus phytase-1-thermo[8]-Q50T; filled bars, consensus phytase-1-thermo[8]-Q50T-K91A). The substrates are listed in the legend of FIG. 14.

FIG. 16: Differential scanning calorimetry (DSC) of consensus phytase-1-thermo[8]-Q50T and consensus phytase-1-thermo[8]-Q50T-K91A. The protein samples were concentrated to ca. 50–60 mg/ml and extensively dialyzed against 10 mM sodium acetate, pH 5.0. A constant heating rate of 10° C./min was applied up to 95° C. DSC of consensus phytase-1-thermo[8]-Q50T (upper graph) showed a melting temperature of 84.7° C., while the melting point of consensus phytase-1-thermo[8]-Q50T-K91A was found at 85.7° C.

Figure 17:
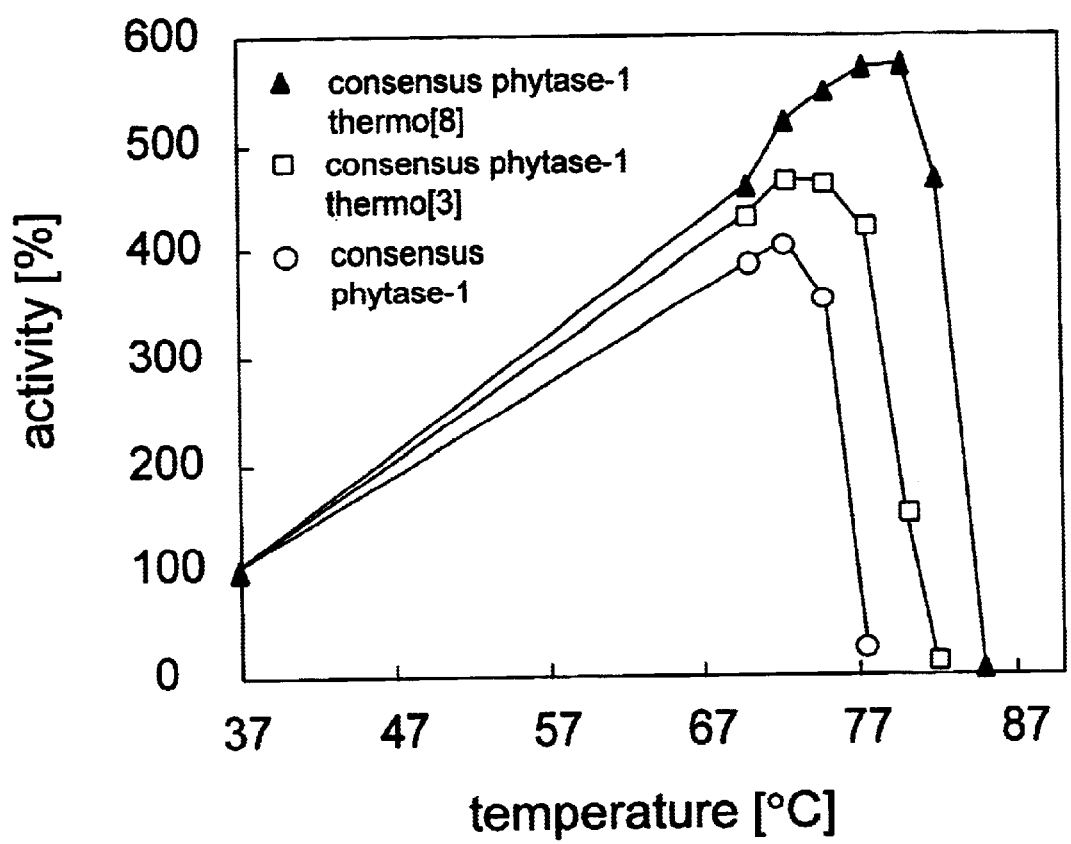

FIG. 17: Comparison of the temperature optimum between consensus phytase-1, consensus phytase-1-thermo[3] and consensus phytase-1-thermo[8]). For the determination of the temperature optimum, the phytase standard assay was performed at a series of temperatures between 37 and 86° C. Protein purified from the supernatant of transformed S. cerevisiae strains was used for the determination. O, consensus phytase-1; □, consensus phytase-1-thermo[3]; ▲, consensus phytase 1-thermo[8].

FIG. 18: Comparison of the pH-dependent activity profile and substrate specificity between consensus phytase-1, consensus phytase-7, and the phytase from *A. niger* NRRL 3135. The phytase activity was determined using the standard assay in appropriate buffers (see Example 9) at different pH-values. Graph a) shows the pH-dependent activity profile of consensus phytase-1 (■), the phytase from *A. niger* NRRL 3135 (O), and of consensus phytase-7 (▲). Graph b) shows the corresponding substrate specificities tested by replacement of phytate in the standard assay by the indicated compounds (black bars, *A. niger* NRRL 3135 phytase; open bars, consensus phytase-1; dashed bars, consensus phytase-7). The substrates are listed in the legend of FIG. 14.

Figure 19:
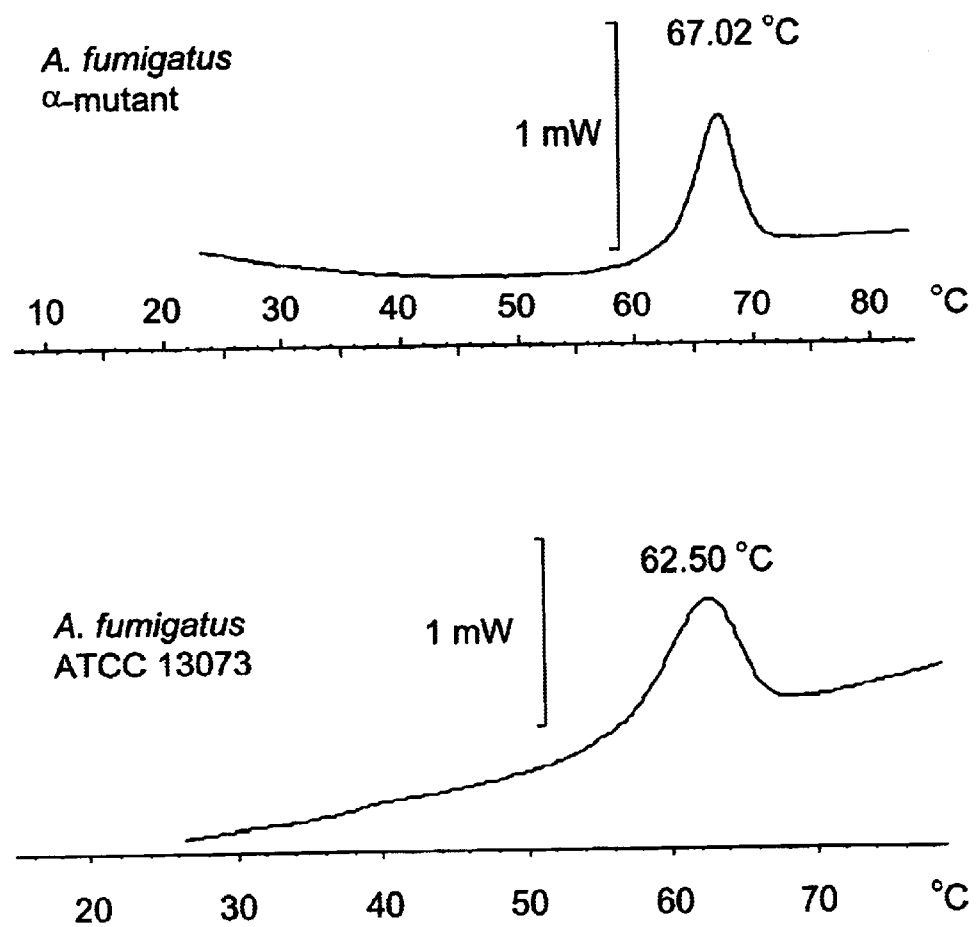

FIG. 19: Differential scanning calorimetry (DSC) of the phytase from *A. fumigatus* ATCC 13073 and of its stabilized alpha-mutant, which contains the following amino acid exchanges: F55Y, V100I, F114Y, A243L, S265P, and N294D.

The protein samples were concentrated to ca. 50–60 mg/ml and extensively dialyzed against 10 mM sodium acetate, pH 5.0. A constant heating rate of 1° C./min was applied up to 95° C. DSC of *A. fumigatus* 13073 phytase (lower graph) revealed a melting temperature of 62.5° C., while the melting point of the alpha-mutant was found at 67.0° C.

Figure 20:
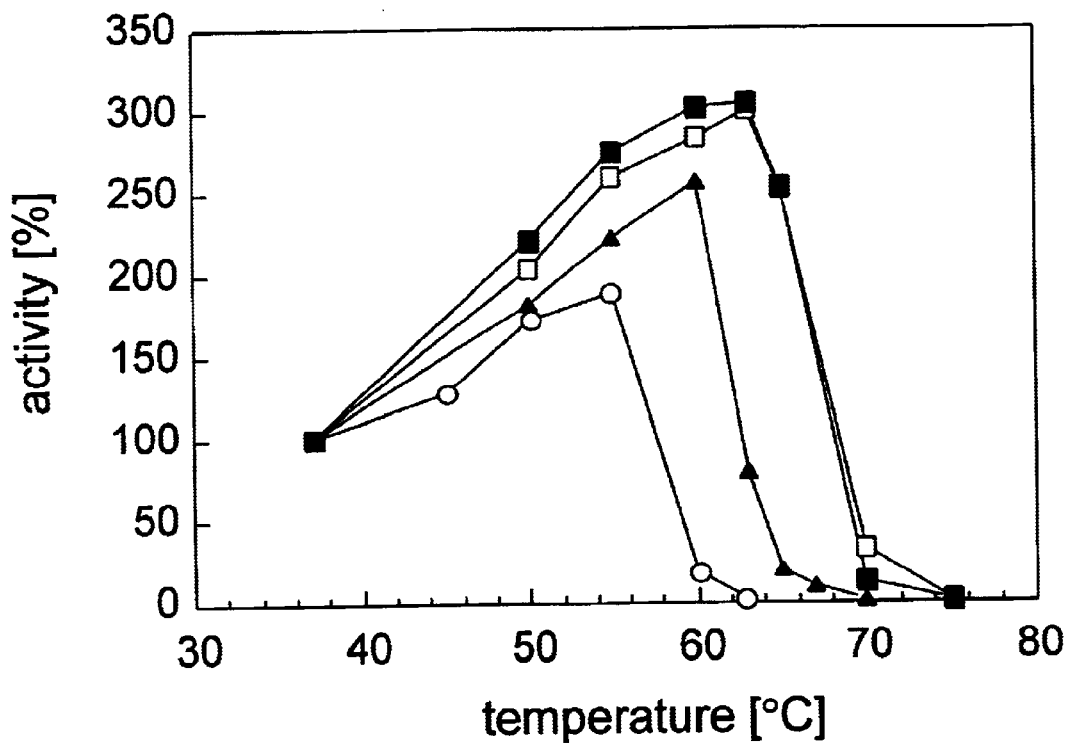

FIG. 20: Comparison of the temperature optima of *A. fumigatus* 13073 wild-type phytase, its alpha-mutant, and a further stabilized alpha-mutant (E59A-S154N-R329H-S364T-G404A). For the determination of the temperature optimum, the phytase standard assay was performed at a series of temperatures between 37 and 75° C. The diluted supernatant of transformed *S. cerevisiae* strains was used for the determination. The other components of the supernatant had no influence on the determination of the temperature optimum. O, *A. fumigatus* ATCC 13073 phytase; ▲, *A. fumigatus* ATCC 13073 alpha-mutant; ▲, *A. fumigatus* ATCC 13073 alpha-mutant- (E59A-S154N-R329H-S364T-G404A) -Q27T; ■, *A. fumigatus* ATCC 13073 alpha-mutant-(E59A-S154N-R329H-S364T-G404A)-Q51T-K2A. Q51T and K92A correspond to consensus phytase-1 substitutions Q50T and K91A, respectively.

FIG. 21: Amino acid sequence of consensus phytase-12 (consphy12; SEQ ID NO: 36) which contains a number of active site residues transferred from the "basidio" consensus sequence to consensus phytase-10-thermo[3]-Q50T-K91A (underlined).

FIG. 22: DNA and amino acid sequence of consensus phytase-3-thermo[11]-Q50T (SEQ ID NOS:90–91).

FIG. 23: DNA and amino acid sequence of consensus phytase-3-thermo[11]-Q50T-K91A (SEQ ID NOS:92–93).

FIG. 24: DNA and amino acid sequence of consensus phytase-10-thermo[5]-Q50T (SEQ ID NOS:94–95).

FIG. 25: DNA and amino acid sequence of consensus phytase-10-thermo[5]-Q50T-K91A (SEQ ID NOS:96–97).

The phytase-producing microorganism strains mentioned herein, viz. *Paxillus involutus* CBS 100231; *Peniophora lycii* CBS 686.96; *Agrocybe pediades* CBS 900.96; and *Trametes pubescens* CBS 100232; were isolated from natural samples originating from, respectively, Denmark; Denmark; Denmark; and Sweden (the Uppsala collection. The samples were collected in November 1992; October 1993; June 1995; and in November 1995, respectively.

EXAMPLE 1

Consensus Phytase-1

The amino acid sequence of consensus phytase-1 (fungal consensus phytase, fcp) was designed and calculated as described in Examples 1 and 2 of EP 897985. Table 1 below shows the origin and vote weight of the phytase amino acid sequences used for the design of consensus phytase-1. The consensus phytase-1 sequence was furthermore converted into a DNA sequence as described in Example 3 of EP 897985, and the consensus phytase-1 gene was constructed and cloned as described in Example 4 of EP 897985.

Table 1
Origin and Vote Weight of the Phytase Amino Acid Sequences phyA from *Aspergillus terreus* 9A-1, aa 27, vote weight 0.5 (Mitchell et al., 1997)

phyA from *Aspergillus terreus* cbs116.46, aa 27, vote weight 0.5 (EP 897985)

phyA from *Aspergillus niger* var. awamori, aa 27, vote weight 0.33 [Piddington, C. S., Houston, C. S., Paloheimo, M., Cantrell, M., Miettinen-Oinonen, A., Nevalainen, H., & Rambosek, J. (1993) The cloning and sequencing of the genes encoding phytase (phy) and pH 2.5-optimum acid phosphatase (aph) from *Aspergillus niger* var. awamori. Gene 133, 55–62].

phyA from *Aspergillus niger* T213 (EP 897985), aa 27, vote weight 0.33 phyA from *Aspergillus niger* strain NRRL3135, aa 27, vote weight 0.33 (van Hartingsveldt et al., 1993)

phyA from *Aspergillus fumigatus* ATCC 13073, aa 26, vote weight 0.2 (Pasamontes et al., 1997)

phyA from *Aspergillus fumigatus* ATCC 32722, aa 26, vote weight 0.2 (EP 897985)

phyA from *Aspergillus fumigatus* ATCC 58128, aa 26, vote weight 0.2 (EP 897985)

phyA from *Aspergillus fumigatus* ATCC 26906, aa 26, vote weight 0.2 (EP 897985)

phyA from *Aspergillus fumigatus* ATCC 32239, aa 30, vote weight 0.2 (EP 897985)

phyA from *Emericella nidulans*, aa 25, vote weight 1.0 (Pasamontes et al., 1997a)

phyA from *Talaromyces thermophilus* ATCC 20186, aa 24, vote weight 1.0 (Pasamontes et al., 1997a)

phyA from *Myceliophthora thermophila*, aa 19, vote weight 1.0 (Mitchell et al., 1997)

EXAMPLE 2

Design of an Improved Consensus Phytase (Consensus Phytase-10) Amino Acid Sequence The alignments used for the design of consensus phytase-10 were calculated using the program PILEUP from the GCG Sequence Analysis Package Release 9.0 (Devereux et al., 1984) with the standard parameters (gap creation penalty 12, gap extension penalty 4). The location of the gaps was refined using a text editor.

The following sequences were used for the alignment of the Basiodiomycete phytases starting with the amino acid (aa) mentioned in Table 2:

Table 2
Origin and Vote Weight of Five Basidiomycete Phytases Used for the Calculation of the Corresponding Consensus Amino Acid Sequence (basidio)

phyA1 from *Paxillus involutus* CBS No. 100231, aa 21, vote weight 0.5 (WO 98/28409)

phyA2 from *Paxillus involutus* CBS No. 100231, aa 21, vote weight 0.5 (WO 98/28409)

phyA from *Trametes pubescens* CBS No. 100232, aa 24, vote weight 1.0 (WO 98/28409)

phyA from *Agrocybe pediades* CBS No. 900.96, aa 19, vote weight 1.0 (WO 98/28409)

phyA from *Peniophora lycii* CBS No. 686.96, aa 21, vote weight is 1.0 (WO 98/28409)

The alignment is shown in FIG. 3.

In Table 3 the genes that were used for the final alignment are listed. The first amino acid (aa) of the sequence that is used in the alignment is mentioned behind the organism's designation.

Table 3
Origin and Vote Weight of the Phytase Sequences Used for the Design of Consensus Phytase-10 phyA from *Aspergillus terreus* 9A-1, aa 27, vote weight 0.5 (Mitchell et al., 1997).

phyA from *Aspergillus terreus* cbs116.46, aa 27, vote weight 0.5 (EP 897985)

phyA from *Aspergillus niger* var. awamori, aa 27, vote weight 0.5 (Piddington et al., 1993)

phyA from *Aspergillus niger* strain NRRL3135, aa 27, vote weight 0.5 (van Hartingsveldt et al., 1993)

phyA from *Aspergillus fumigatus* ATCC 13073, aa 26, vote weight 0.2 (Pasamontes et al., 1997)

phyA from *Aspergillus fumigatus* ATCC 32722, aa 26, vote weight 0.2 (EP 897985)

phyA from *Aspergillus fumigatus* ATCC 58128, aa 26, vote weight 0.2 (EP 897985)

phyA from *Aspergillus fumigatus* ATCC 26906, aa 26, vote weight 0.2 (EP 897985)

phyA from *Aspergillus fumigatus* ATCC 32239, aa 30, vote weight 0.2 (EP 897985)

phyA from *Emericella nidulans*, aa 25, vote weight 1.0 (Pasamontes et al., 1997a)

phyA from *Talaromyces thermophilus* ATCC 20186, aa 24, vote weight 1.0 (Pasamontes et al., 1997a)

phyA from *Myceliophthora thermophila*, aa 19, vote weight 1.0 (Mitchell et al., 1997)

phyA from *Thermomyces lanuginosus*, aa 36, vote weight 1.0 (Berka et al., 1998)

Consensus sequence of five Basidiomycete phytases, vote weight 1.0 (Basidio, FIG. 3)

The corresponding alignment is shown in FIG. 4.

Calculation of the Amino Acid Sequence of Consensus Phytase-10

To improve the alignment, we added the original consensus sequence of five phytases from four different Basidiomycetes (called Basidio; still containing the undefined sequence positions; see FIG. 3), nearly all phytase sequences used for the calculation of the original consensus phytase sequences and one new phytase sequence from the Ascomycete *Thermomyces lanuginosus* to a larger alignment.

We set plurality on 2.0 and threshold on 3. The used vote weights are listed in Table 3. The alignment and the corresponding consensus sequence are presented in FIG. 4. The new consensus phytase sequence has 32 different amino acids in comparison to the original consensus phytase-1. Positions for which the program PRETTY was not able to calculate a consensus amino acid residue were filled according to rules mentioned in Example 1. None of the residues suggested by the program was replaced.

Furthermore, in another calculation, we included all Basidiomycete phytases as single amino acid sequences but assigning a vote weight of 0.2 in the calculation. The corresponding alignment is shown in FIG. 6. The calculated consensus amino acid sequence (consensus phytase-11) has the following differences to the sequence of consensus phytase-10. Letter X means that the program was not able to calculate a consensus amino acid; the amino acid in parenthesis corresponds to the amino acid finally included into consensus phytase-10.

D35X (first letter for consensus phytase-10, last letter for consensus phytase-11), X(K)69K, X(E)100E, A101R, Q134N, X(K)153N, X(H)190H, X(A)204S, X(E)220D, E222T, V227A, X(R)271R, H287A, X(D)288D, X(K)379K, X(I)389I, E390X, X(E)415E, X(A)416A, X(R)446L, E463A. The numbering is as in FIG. 5.

We also checked single amino acid replacements suggested by the improved consensus sequences 10 and 11 on their influence on the stability of the original consensus phytase-1. The approach is described in example 3.

Conversion of the Consensus Phytase-10 Amino Acid Sequence Into a DNA Sequence

The first 26 amino acid residues of *A. terreus* cbs116.46 phytase were used as signal peptide and fused to the N-terminus of consensus phytase-10. The used procedure is further described in Example 1.

The resulting sequence of the fcp10 gene is shown in FIG. 5.

Construction and Cloning of the Consensus Phytase-10 Gene (fcp10)

The calculated DNA sequence of fcp10 was divided into oligonucleotides of 85 bp, alternately using the sequence of the sense and the anti-sense strand. Every oligonucleotide overlaps 20 bp with the previous and the following oligonucleotide of the opposite strand. The location of all primers, purchased from Microsynth, Balgach (Switzerland) and obtained in a PAGE-purified form, is indicated in FIG. 5.

PCR-Reactions

In three PCR reactions, the synthesized oligonucleotides were composed to the entire gene. For the PCR, the High Fidelity Kit from Boehringer Mannheim (Boehringer Mannheim, Mannheim, Germany) and the thermo cycler "The Protokol™" from AMS Biotechnology (Europe) Ltd. (Lugano, Switzerland) were used. The following oligonucleotides were used in a concentration of 0.2 pMol/ml.

| | |
|---|---|
| Mix 1.10: | CP-1, CP-2, CP-3.10, CP-4.10, CP-5.10, CP-6, CP-7.10, CP-8.10, CP-9.10, CP-10.10 |
| Mix 2.10: | CP-9.10, CP-11.10, CP-12.10, CP-13.10, CP-14.10, CP-15.10, CP-16.10, CP-17.10, CP-18.10, CP-19.10, CP-20.10, CP-21.10, CP-22.10 |

The newly synthesized oligonucleotides are marked by the number 10. Consensus phytase-10 contains the following 32 exchanges, which are underlined in FIG. 5, in comparison to the original consensus phytase-1: Y54F, E58A, D69K, D70G, A94K, N134Q, I158V, S187A, Q188N, D197N, S204A, T214L, D220E, L234V, A238P, D246H, T251N, Y259N, E267D, E277Q, A283D, R291I, A320V, R329H, S364T, I366V, A379K, S396A, G404A, Q415E, A437G, A463E.

Four short PCR primers were used for the assembling of the oligonucleotides:

| CP-a: | Eco RI |  |
|---|---|---|
|  | 5'-TATATGAATTCATGGGCGTGTTCGTC-3' | (SEQ ID NO: 37) |
| CP-b: |  |  |
|  | 5'-TGAAAAGTTCATTGAAGGTTTC-3' | (SEQ ID NO: 38) |
| CP-c.10: |  |  |
|  | 5'-TCTTCGAAAGCAGTACACAAAC-3' | (SEQ ID NO: 39) |
| CP-e: | Eco RI |  |
|  | 5'-TATATGAATTCTTAAGCGAAAC-3' | (SEQ ID NO: 40) |

PCR reaction a:

10 µl Mix 1.10 (2.0 pmol of each oligonucleotide)
2 µl nucleotides (10 mM of each nucleotide)
2 µl primer CP-a (10 pmol/ml)
2 µl primer CP-c.10 (10 pmol/ml)
10,0 µl PCR buffer
0.75 µl polymerase mixture (2.6 U)
73.25 µl H₂O PCR reaction b:

10 µl Mix 2.10 (2.0 pmol of each oligonucleotide)
2 µl nucleotides (10 mM each nucleotide)
2 µl primer CP-b (10 pmol/ml)
2 µl primer CP-e (10 pmol/ml)
10,0 µl PCR buffer
0.75 µl polymerase mixture (2.6 U)
73.25 µl H₂O Reaction conditions for PCR reactions a and b:

| step 1 | 2 min - 45° C. |
|---|---|
| step 2 | 30 sec - 72° C. |
| step 3 | 30 sec - 94° C. |
| step 4 | 30 sec - 52° C. |
| step 5 | 1 min - 72° C. |

Steps 3 to 5 were repeated 40-times.

The PCR products (670 and 905 bp) were purified by agarose gel electrophoresis (0.9% agarose), followed by gel extraction (QIAEX II Gel Extraction Kit, Qiagen, Hilden, Germany). The purified DNA fragments were used for the PCR reaction c.

PCR reaction c:

6 µl PCR product of reaction a ≈50 ng)
6 µl PCR product of reaction b ≈50 ng)
2 µl primer CP-a (10 pmol/ml)
2 µl primer CP-e (10 pmol/ml)
10,0 µl PCR buffer
0.75 µl polymerase mixture (2.6 U)
73.25 µl H₂O Reaction conditions for PCR reaction c:

| step 1 | 2 min - 94° C. |
|---|---|
| step 2 | 30 sec - 94° C. |
| step 3 | 30 sec - 55° C. |
| step 4 | 1 min - 72° C. |

Steps 2 to 4 were repeated 31-times.

The resulting PCR product (1.4 kb) was purified as mentioned above, digested with EcoRI, and ligated in an EcoRI-digested and dephosphorylated pBsk(−)-vector (Stratagene, La Jolla, Calif., USA). 1 µl of the ligation mixture was used to transform *E. coli* XL-1 competent cells (Stratagene, La Jolla, Calif., USA). All standard procedures were carried out as described by Sambrook et al. (1987). The DNA sequence of the constructed gene (fcp10) was checked by sequencing as known in the art.

EXAMPLE 3

Increasing the Thermostability of Consensus Phytase-1 by Introduction of Single Mutations Suggested by the Amino Acid Sequences of Consensus Phytase-10 and Consensus phytase-11

In order to increase the thermostability of homologous genes, it is also possible to test the stability effect of each differing amino acid residue between the protein of interest and the calculated consensus sequence and to combine all stabilizing mutations into the protein of interest. We used the consensus phytase-1 as protein of interest and tested the effect on the protein stability of 34 amino acid residues that differ relative to consensus phytase-10 and/or -11 by single site-directed mutagenesis.

To construct muteins for expression in *A. niger*, *S. cerevisiae*, or *H. polymorpha*, the corresponding expression plasmid containing the consensus phytase-1 gene was used as template for site-directed mutagenesis (see Examples 6–8). Mutations were introduced using the "quick exchange™ site-directed mutagenesis kit" from Stratagene (La Jolla, Calif., USA) following the manufacturer's protocol and using the corresponding primers. All mutations made and the corresponding primers are summarized in Table 4. Plasmids harboring the desired mutation were identified by DNA sequence analysis as known in the art.

TABLE 4

Primers used for site-directed mutagenesis of consensus phytase-1 Exchanged bases are highlighted in bold. The introduction of a restriction site is marked above the sequence. When a restriction site is written in parenthesis, the mentioned site was destroyed by introduction of the mutation.

| mutation | Primer set | | |
|---|---|---|---|
|  | Kpn I | | |
| Q50T | 5' | -CACTTGTGGGTACCTACTCTCCATACTTCTC-3' | (SEQ ID NO: 41) |
|  | 5' | -GAGAAGTATGGAGAGTAGGTACCCCACAAGTG-3' |  |
| Y54F | 5' | -GGTCAATACTCTCCATTCTTCTCTTTGGAAG-3' | (SEQ ID NO: 42) |
|  | 5' | -CTTCCAAAGAGAAGAATGGAGAGTATTGACC-3' |  |
| E58A | 5' | -CATACTTCTCTTTGGCAGACGAATCTGC-3' | (SEQ ID NO: 43) |
|  | 5' | -GCAGATTCGTCTGCCAAAGAGAAGTATG-3' |  |

TABLE 4-continued

Primers used for site-directed mutagenesis of consensus phytase-1
Exchanged bases are highlighted in bold. The introduction of a
restriction site is marked above the sequence. When a
restriction site is written in parenthesis, the mentioned site
was destroyed by introduction of the mutation.

| mutation | Primer set | |
|---|---|---|
| D69K | Aat II<br>5'-CTCCAGACGTCCCAAAGGACTGTAGAGTTAC-3'<br>5'-GTAACTCTACAGTCCTTTGGGACGTCTGGAG-3' | (SEQ ID NO: 44) |
| D70G | Aat II<br>5'-CTCCAGACGTCCCAGACGGCTGTAGAGTTAC-3'<br>5'-GTAACTCTACAGCCGTCTGGGACGTCTGGAG-3' | (SEQ ID NO: 45) |
| K91A | 5'-GATACCCAACTTCTTCTGCGTCTAAGGCTTACTCTG-3'<br>5'-CAGAGTAAGCCTTAGACGCAGAAGAAGTTGGGTATC-3' | (SEQ ID NO: 46) |
| A94K | Sca I<br>5'-CTTCTAAGTCTAAGAAGTACTCTGCTTTG-3'<br>5'-CAAAGCAGAGTACTTCTTAGACTTAGAAG-3' | (SEQ ID NQ: 47) |
| A101R | 5'-GCTTACTCTGCTTTGATTGAACGGATTCAAAAGAACGCTAC-3'<br>5'-GTAGCGTTCTTTTGAATCCGTTCAATCAAAGCAGAGTAAGC-3' | (SEQ ID NO: 48) |
| N134Q | 5'-CCATTCGGTGAACAGCAAATGGTTAACTC-3'<br>5'-GAGTTAACCATTTGCTGTTCACCGAATGG-3' | (SEQ ID NO: 49) |
| K153N | Nru I<br>5'-GATACAAGGCTCTCGCGAGAAACATTGTTC-3'<br>5'-GGAACAATGTTTCTCGCGAGAGCCTTGTATC-3' | (SEQ ID NO: 50) |
| I158V | Bss HI<br>5'-GATTGTTCCATTCGTGCGCGCTTCTGGTTC-3'<br>5'-GAACCAGAAGCGCGCACGAATGGAACAATC-3' | (SEQ ID NO: 51) |
| S187A | Apa I<br>5'-GGCTGACCCAGGGGCCCAACCACACCAAGC-3'<br>5'-GCTTGGTGTGGTTGGGCCCCTGGGTCAGCC-3' | (SEQ ID NO: 53) |
| D197N | Bcl I<br>5'-CTCCAGTTATTAACGTGATCATTCCAGAAGG-3'<br>5'-CCTTCTGGAATGATCACGTTAATAACTGGAG-3' | (SEQ ID NO: 52) |
| T214L | Nco I<br>5'-CACTTTGGACCATGGTCTTTGTACTGCTTTCG-3'<br>5'-CGAAAGCAGTACAAAGACCATGGTCCAAAGTG-3' | (SEQ ID NO: 54) |
| E222T | Avr II<br>5'-GCTTTCGAAGACTCTACCCTAGGTGACGACGTTG-3'<br>5'-CAACGTCGTCACCTAGGGTAGAGTCTTCGAAAGC-3' | (SEQ ID NO: 55) |
| V227A | 5'-GGTGACGACGCTGAAGCTAACTTCAC-3'<br>5'-GTGAAGTTAGCTTCAGCGTCGTCACC-3' | (SEQ ID NO: 56) |
| L234V | Sac II<br>5'-CTAACTTCACCGCGGTGTTCGCTCCAG-3'<br>5'-CTGGAGCGAACACCGCGGTGAAGTTAG-3' | (SEQ ID NO: 57) |
| A238P | 5'-GCTTTGTTCGCTCCACCTATTAGAGCTAGATTGG-3'<br>5'-CCAATCTAGCTCTAATAGGTGGAGCGAACAAAGC-3' | (SEQ ID NO: 58) |
| T251N | Hpa I<br>5'-GCCAGGTGTTAACTTGACTGACGAAG-3'<br>5'-TTCGTCAGTCAAGTTAACACCTGGC-3' | (SEQ ID NO: 59) |
| Y259N | Aat II<br>5'-GACGAAGACGTCGTTAACTTGATGGAC-3'<br>5'-GTCCATCAAGTTAACGACGTCTTCGTC-3' | (SEQ ID NO: 60) |
| E267D | Asp I<br>5'-GTCCATTCGACACTGTCGCTAGAACTTC-3'<br>5'-GAAGTTCTAGCGACAGTGTCGAATGGAC-3' | (SEQ ID NO: 61) |
| E277Q | 5'-CTGACGCTACTCAGCTGTCTCCATTC-3'<br>5'-GAATGGAGACAGCTGAGTAGCGTCAG-3' | (SEQ ID NO: 62) |
| A283D | 5'-GTCTCCATTCTGTGATTTGTTCACTCAC-3'<br>5'-GTGAGTGAACAAATCACAGAATGGAGAC-3' | (SEQ ID NO: 63) |
| H287A | Ksp I<br>5'-GCTTTGTTCACCGCGGACGAATGGAG-3'<br>5'-CTCCATTCGTCCGCGGTGAACAAAGC-3' | (SEQ ID NO: 64) |
| R291I | Bam HI<br>5'-CACGACGAATGGATCCAATACGACTAC-3'<br>5'-GTAGTCGTATTGGATCCATTCGTCGTG-3' | (SEQ ID NO: 65) |
| Q292A | Bsi WI<br>5'-GACGAATGGAGAGCGTACGACTACTTG-3'<br>5'-CAAGTAGTCGTACGCTCTCCATTCGTC-3' | (SEQ ID NO: 66) |
| A320V | Hpa I<br>5'-GGTGTTGGTTTCGTTAACGAATTGATTGC-3'<br>5'-GCAATCAATTCGTTAACGAAACCAACACC-3' | (SEQ ID NO: 67) |
| R329H | (Bgl II)<br>5'-GCTAGATTGACTCACTCTCCAGTTCAAG-3' | (SEQ ID NO: 68) |

TABLE 4-continued

Primers used for site-directed mutagenesis of consensus phytase-1 Exchanged bases are highlighted in bold. The introduction of a restriction site is marked above the sequence. When a restriction site is written in parenthesis, the mentioned site was destroyed by introduction of the mutation.

| mutation | Primer set | |
|---|---|---|
| | 5'-CTTGAACTGGAGAGTGAGTCAATCTAGC-3' <br> Eco RV | |
| S364T | 5'-CTCACGACAACACTATGATATCTATTTTCTTC-3' <br> 5'-GAAGAAAATAGATATCATAGTGTTGTCGTGAG-3' <br> Nco I | (SEQ ID NO: 69) |
| I366V | 5'-CGACAACTCCATGGTTTCTATTTTCTTCGC-3' <br> 5'-GCGAAGAAAATAGAAACCATGGAGTTGTCG-3' <br> Kpn I | (SEQ ID NO: 70) |
| A379K | 5'-GTACAACGGTACCAAGCCATTGTCTAC-3' <br> 5'-GTAGACAATGGCTTGGTACCGTTGTAC-3' | (SEQ ID NO: 71) |
| S396A | 5'-CTGACGGTTACGCTGCTTCTTGGAC-3' <br> 5'-GTCCAAGAAGCAGCGTAACCGTCAG-3' | (SEQ ID NO: 72) |
| G404A | 5'-CTGTTCCATTCGCTGCTAGAGCTTAC-3' <br> 5'-GTAAGCTCTAGCAGCGAATGGAACAG-3' | (SEQ ID NO: 73) |
| Q415E | 5'-GATGCAATGTGAAGCTGAAAAGGAACC-3' <br> 5'-GGTTCCTTTTCAGCTTCACATTGCATC-3' <br> Sal I | (SEQ ID NO: 74) |
| A437G | 5'-CACGGTTGTGGTGTCGACAAGTTGGG-3' <br> 5'-CCCAACTTGTCGACACCACAACCGTG-3' <br> Mun I | (SEQ ID NO: 75) |
| A463E | 5'-GATCTGGTGGCAATTGGGAGGAATGTTTCG-3' <br> 5'-CGAAACATTCCTCCCAATTGCCACCAGATC-3' | (SEQ ID NO: 76) |
| and, accordingly, for other mutations. | | |

The temperature optimum of the purified phytases, expressed in *Saccharomyces cerevisiae* (Example 7), was determined as outlined in Example 9. Table 5 shows the effect of each mutation introduced on the stability of consensus phytase-1.

Table 5
Stability Effect of the Individual Amino Acid Replacements in Consensus Phytase-1
+ or − means a positive, respectively, negative effect on the protein stability up to 1° C., ++ and −− means a positive, respectively, negative effect on the protein stability between 1 and 3° C.; the numbers 10 or 11 in parentheses indicate the consensus phytase sequence that suggested the amino acid replacement.

TABLE 5

Stability effect of the individual amino acid replacements in consensus phytase-1
+ or − means a positive, respectively, negative effect on the protein stability up to 1° C., ++ and −− means a positive, respectively, negative effect on the protein stability between 1 and 3° C.; the numbers 10 or 11 in parentheses indicate the consensus phytase sequence that suggested the amino acid replacement.

| stabilizing | | neutral | | destabilizing | |
|---|---|---|---|---|---|
| mutation | effect | mutation | effect | mutation | effect |
| E58A (10) | + | D69A | ± | Y54F (10) | − |
| D69K (11) | + | D70G (10) | ± | V73I | − |
| D197N (10) | + | N134Q (10) | ± | A94K (10) | − |
| T214L (10) | ++ | G186H | ± | A101R (11) | − |
| E222T (11) | ++ | S187A (10) | ± | K153N (11) | − |
| E267D (10) | + | T214V | ± | I158V (10) | −− |
| R291I | + | T251N (10) | ± | G203A | −− |
| R329H (10) | + | Y259N (10) | ± | G205S | − |
| S364T (10) | ++ | A283D (10) | ± | A217V | − |
| A379K (11) | + | A320V (10) | ± | V227A (11) | −− |
| G404A (10) | ++ | K445T | ± | L234V (10) | − |
| | | | | A238P (10) | −− |
| | | | | E277Q (10) | − |
| | | | | H287A (11) | − |
| | | | | Q292A | − |
| | | | | I366V (10) | − |
| | | | | S396A (10) | −− |
| | | | | Q415E (11) | − |
| | | | | A437G (10) | −− |
| | | | | E451R | −− |
| | | A463E (10) | ± | | |

We combined eight positive mutations (E58A, D197N, E267D, R291I, R329H, S364T, A379K, G404A) in consensus phytase-1 thermo[8], using the primers and the technique mentioned above in this example. Furthermore, the mutations Q50T and/or K91A were introduced which mainly influence the catalytic characteristics of phytase (see patent applications EP 897010 and EP 897985, as well as Example 9). The DNA and amino acid sequence of the resulting phytase (consensus phytase-1-thermo[8]-Q50T-K91A) are shown in FIG. 7. In this way, the temperature optimum and the melting point of the consensus phytase were increased by 7° C. (FIGS. 15, 16, 17).

In a further consensus protein, we combined eleven positive mutations (ES8A, D69K, D197N, T214L, E222T, E267D, R291I, R329H, S364T, A379K, G404A) in consensus phytase-1 thermo[11]. Furthermore, the mutations Q50T and/or K91A were introduced. In this way, the melting temperature was increased by another 3–4° C. when compared to consensus phytase-1 thermo[8].

Using the results of Table 5, we further improved the thermostability of consensus phytase-10 by the back mutations K94A, V158I, and A396S, the reverse of which (A94K, I158V, and S396A) revealed a strong negative influence on the stability of consensus phytase-1. The resulting protein was called consensus phytase-10-thermo[3]. SEQ ID NO: 26 plus the three mutations K94A, V158I, and A396S. Furthermore, we introduced the mutations Q50T and K91A that mainly influence the catalytic characteristics of consensus phytase (see patent applications EP 897010 and EP 897985, as well as Example 9 and FIGS. 14 and 15). The resulting DNA and amino acid sequence are shown in FIG. 8. The optimized phytase showed a 4° C. higher temperature optimum and melting point than consensus phytase-10 (FIGS. 12 and 13). Furthermore, the phytase has also a strongly increased specific activity with phytate as substrate of 250 U/mg at pH 5.5 (FIG. 14).

In a still further consensus protein, two additional mutations were introduced into consensus phytase-10 thermo[3] (E222T, G437A) which yielded consensus phytase-10 thermo[5]. Furthermore, the mutations Q50T and/or K91A were introduced. In this way, the melting temperature was increased by another 1–2° C. when compared to consensus phytase-10 thermo[3].

EXAMPLE 4

Stabilization of the Phytase of *A. fumigatus* ATCC 13073 by Replacement of Amino Acid Residues With the Corresponding Consensus Phytase-1 and/ or Consensus Phytase-10 Residues At six amino acid sequence positions where *A. fumigatus* 13073 phytase is the only or nearly the only phytase in the alignment of FIG. 1 that does not contain the corresponding consensus phytase amino acid residue, the non-consensus amino acid residue was replaced by the consensus one. The following amino acids were substituted in *A. fumigatus* 13073 phytase, containing additionally the Q51(24)T substitution (influencing the catalytic properties and corresponding to the Q50T substitution in the consensus phytases) and the signal sequence of *A. terreus* cbs116.46 phytase (see European Patent Application No. 0897010, and FIG. 9): F55(28)Y, V100(73)I, F114(87)Y, A243(220)L, S265(242)P, N294(282)D. The numbers in parentheses refer to the numbering in FIG. 1.

In a second round, four of the seven stabilizing amino acid exchanges (E58A, R329H, S364T, G404A) identified in consensus phytase-10 and tested as single mutations in consensus phytase-1 (Table 5) were additionally introduced into the *A. fumigatus* alpha-mutant. Furthermore, the amino acid replacement S154N, shown to reduce the protease susceptibility of the phytase, was introduced.

The mutations were introduced as described in Example 3 (see Table 6) and expressed as described in Examples 6 to 8. The resulting *A. fumigatus* 13073 phytase variants were called alpha-mutant (i.e. the *A. fumigatus* ATCC 13073 phytase with the substitutions Q24T, F28Y, V73I, F87Y, A220L, S242P, N282D) and "optimized" alpha-mutant (i.e. the *A. fumigatus* alpha-mutant having the additional substitutions E59A-S154N-R329H-S364T-G404A). K92A is an additional preferred mutation.

The temperature optimum (60° C., FIG. 20) and the melting temperature (67.0° C., FIG. 19) of the *A. fumigatus* 13073 alpha-mutant phytase were increased by 5–7° C. in comparison to the values of the wild-type phytase (temperature optimum: 55° C., Tm: 60° C.). The five additional amino acid replacements further increased the temperature optimum by 3° C. (FIG. 20).

TABLE 6

Mutagenesis primers for the stabilization of A. fumigatus ATCC 13073 phytase

| Mutation | Primer | |
|---|---|---|
| F55Y | 5'-CACGTACTCGCCATACTTTTCGCTCGAG-3' | (SEQ ID NO: 77) |
| | 5'-CTCGAGCGAAAAGTATGGCGAGTACGTG-3' (Xho I) | |
| E58A | 5'-CCATACTTTTCGCTCGCGGACGAGCTGTCCGTG-3' | (SEQ ID NO: 78) |
| | 5'-CACGGACAGCTCGTCCGCGAGCGAAAAGTAGG-3' | |
| V100I | 5'-GTATAAGAAGCTTATTACGGCGATCCAGGCC-3' | (SEQ ID NO: 79) |
| | 5'-GGCCTGGATCGCCGTAATAAGCTTCTTATAC-3' | |
| F114Y | 5'-CTTCAAGGGCAAGTACGCCTTTTTGAAGACG-3' | (SEQ ID NO: 80) |
| | 5'-CGTCTTCAAAAAGGCGTACTTGCCCTTGAAG-3' | |
| A243L | 5'-CATCCGAGCTCGCCCTCGAGAAGCATCTTC-3' | (SEQ ID NO: 81) |
| | 5'-GAAGATGCTTCTCGAGGGCGAGCTCGGATG-3' | |
| S265P | 5'-CTAATGGA TGTGTCCGTTTGATACGGTAG-3' | (SEQ ID NO: 82) |
| | 5'-CTACCGTATCAAACGGACACATGTCCATTAG-3' | |
| N294D | 5'-GTGGAAGAAGTACGACTACCTTCAGTC-3' | (SEQ ID NO: 83) |
| | 5'-GACTGAAGGTAGTCGTACTTCTTCCAC-3' (Mlu I) | |
| R329H | 5'-GCCCGGTTGACGCATTCGCCAGTGCAGG-3' | (SEQ ID NO: 84) |
| | 5'-CCTGCACTGGCGAATGCGTCAACCGGGC-3' Nco I | |
| S364T | 5'-CACACGACAACACCATGGTTTCCATCTTC-3' | (SEQ ID NO: 85) |
| | 5'-GAAGATGGAAACCATGGTGTTGTCGTGTG-3' (Bss HI) | |
| G404A | 5'-GTGGTGCCTTTCGCCGCGCGAGCCTACTTC-3' | (SEQ ID NO: 86) |
| | 5'-GAAGTAGGCTCGCGCGGCGAAAGGCACCAC-3' | |

EXAMPLE 5

Introduction of the Active Site Amino Acid Residues of A. niger NRRL 3135 Phytase Into Consensus Phytase-1

We used the crystal structure of *Aspergillus niger* NRRL 3135 phytase to define all active site amino acid residues (see Example 1, and EP 897010). Using the alignment of FIG. 1, we replaced the following active site residues and additionally the non-identical adjacent ones of consensus phytase-1 by those of *A. niger* phytase:

S89D, S92G, A94K, D164S, P201S, G203A, G205S, H212P, G224A, D226T, E255T, D256E, V258T, P265S, Q292H, G300K, Y305H, A314T, S364G, M365I, A397S, S398A, G404A, and A405S.

The new consensus phytase-7 protein sequence was back-translated into a DNA sequence (FIG. 10) as described in Example 1. The corresponding gene (fcp7) was generated as described in Example 1 using the following oligonucleotide mixes:

| | |
|---|---|
| Mix 1.7: | CP-1, CP-2, CP-3, CP-4.7, CP-5.7, CP-6, CP-7, CP-8.7, CP-9, CP-10.7 |
| Mix 2.7: | CP-9, CP-10.7, CP-11.7, CP-12.7, CP-13.7, CP-14.7, CP-15.7, CP-16, CP-17.7, CP-18.7, CP-19.7, CP-20, CP-21, CP-22. |

The DNA sequences of the oligonucleotides are indicated in FIG. 10. The newly synthesized oligonucleotides are additionally marked by the number 7. After assembling of the oligonucleotides using the same PCR primers as mentioned in Example 1, the gene was cloned into an expression vector as described in Examples 6–8.

The pH-profile of the enzyme determined after expression in *H. polymorpha* and purification was very similar to that of *A. niger* phytase (see FIG. 18).

EXAMPLE 6

Expression of the Consensus Phytase genes in Hansenula polymorpha

The phytase expression vectors used to transform *H. polymorpha* RB11 [Gellissen, G., Hollenberg, C. P., Janowicz, Z. A. (1994) Gene expression in methylotrophic yeasts, in Smith, A. (ed.) Gene expression in recombinant microorganisms. Dekker, New York, pp. 395–4391 were constructed by inserting the Eco RI fragment of pBsk-fcp or variants thereof into the multiple cloning site of the *H. polymorpha* expression vector pFPMT121, which is based on an ura3 selection marker from *S. cerevisiae*, a formate dehydrogenase (FMD) promoter element and a methanol oxidase (MO) terminator element from *H. polymorpha*. The 5' end of the fcp gene is fused to the FMD promoter, the 3' end to the MOX terminator (Gellissen et al., Appl. Microbiol. Biotechnol. 46, 46–54, 1996; EP 299108). The resulting expression vectors are designated pFPMTfcp, pFPMTfcp10, and pFPMTfcp7.

The constructed plasmids were propagated in *E. coli*. Plasmid DNA was purified using standard state of the art procedures. The expression plasmids were transformed into the *H. polymorpha* strain RB11 deficient in orotidine-5'-phosphate decarboxylase (ura3) using the procedure for preparation of competent cells and for transformation of yeast as described in Gellissen et al. (1996). Each transformation mixture was plated on YNB medium (0.14% w/v Difco YNB and 0.5% ammonium sulfate) containing 2% glucose and 1.8% agar, and incubated at 37° C. After 4 to 5 days individual transformant colonies were picked and grown in the liquid medium described above for 2 days at 37° C. Subsequently, an aliquot of this culture was used to inoculate fresh vials with YNB-medium containing 2% glucose. After seven further passages in selective medium, the expression vector had integrated into the yeast genome in multimeric form. Subsequently, mitotically stable transformants were obtained by two additional cultivation steps in 3 ml non-selective liquid medium (YPD, 2% glucose, 10 g/l yeast extract, and 20 g/l peptone). In order to obtain genetically homogeneous recombinant strains, an aliquot from the last stabilization culture was plated on a selective plate. Single colonies were isolated for analysis of phytase expression in YNB containing 2% glycerol instead of glucose to derepress the FMD promoter. Purification of the consensus phytases was done as described in Example 7.

EXAMPLE 7

Expression of the Consensus Phytase Genes in Saccharomyces cerevisiae and Purification of the Phytase From the Culture Supernatant The consensus phytase genes were isolated from the corresponding Bluescript-plasmid (pBsk-fcp, pBSK-fcp10, pBsk-fcp7) and ligated into the Eco RI sites of the expression cassette of the *Saccharomyces cerevisiae* expression vector pYES2 (Invitrogen, San Diego, Calif., USA) or subcloned between the shortened GAPPL (glyceraldhyde-3-phosphate dehydrogenase) promoter and the pho5 terminator as described by Janes et al., Curr. Genet. 18, 97–103. The correct orientation of the gene was checked by PCR. Transformation of *S. cerevisiae* strains, e.g. INVSc1 (Invitrogen, San Diego, Calif., USA), was done according to Hinnen et al., Proc. Natl. Acad. Sci. USA 75, 1929–1933 (1978). Single colonies harboring the phytase gene under the control of the GAPFL promoter were picked and cultivated in 5 ml selection medium [SD-uracil; Sherman, J. P., Finck, G. R. & Hicks, J. B. (1986) Laboratory course manual for methods in yeast genetics. Cold Spring Harbor University] at 30° C. under vigorous shaking (250 rpm) for one day. The preculture was then added to 500 ml YPD medium (Sherman et al., 1986) and grown under the same conditions. Induction of the gall promoter was done according to the manufacturer's instructions. After four days of incubation, the cell broth was centrifuged (7000 rpm, GS3 rotor, 15 min, 5° C.) to remove the cells, and the supernatant was concentrated by way of ultrafiltration in Amicon 8400 cells (PM30 membranes; Grace AG, Wallizeller, Switzerland) and ultrafree-15 centrifugal filter devices (Biomax-30K, Millipore, Bedford, Mass., USA). The concentrate (10 ml) was desalted on a 40 ml Sephadex G25 Superfine column (Pharmacia Biotech, Freiburg, Germany), with 10 mM sodium acetate, pH 5.0, serving as elution buffer. The desalted sample was brought to 2 M $(NH_4)_2SO_4$ and directly loaded onto a 1 ml Butyl Sepharose 4 Fast Flow hydrophobic interaction chromatography column (Pharmacia Biotech, Feiburg, Germany) which was eluted with a linear gradient from 2 M to 0 M $(NH_4)_2SO_4$ in 10 mM sodium acetate, pH 5.0. Phytase was eluted in the breakthrough, concentrated and loaded on a 120 ml Sephacryl S-300 gel permeation chromatography column (Pharmacia Biotech, Freiburg, Germany). Consensus phytases −1, −7 and −10 eluted as a homogeneous symmetrical peak and were shown by SDS-PAGE to be approx. 95% pure.

EXAMPLE 8

Expression of the Consensus Phytase Genes in Aspergillus niger

The Bluescript-plasmids pBsk-fcp, pBsk-fcp10, and pBsk-fcp7 were used as template for the introduction of a Bsp HI-site upstream of the start codon of the genes and an Eco RV-site downstream of the stop codon. The Expand™ High Fidelity PCR Kit (Boehringer Mannheim, Mannheim, Germany) was used with the following primers:

Primer Asp-1:

Bsp HI 5'-TATATCATGAGCGTGTTCGTCGTGC TACTGTTC-3' (SEQ ID NO: 87)

Primer Asp-2 used for cloning of fcp and fcp7:

Eco RV 3'-ACCCGACTTACAAAGCGAATTCTA TAGATATAT-5' (SEQ ID NO: 88)

Primer Asp-3 used for cloning of fcp10:

Eco RV 3'-ACCCTTCTTACAAAGCGAATTCTAT AGATATAT-5' (SEQ ID NO: 89)

The reaction was performed as described by the supplier. The PCR-amplified fcp-genes had a new Bsp HI site at the start codon, introduced by primer Asp-1, which resulted in a replacement of the second amino acid residue glycine by serine. Subsequently, the DNA-fragment was digested with Bsp HI and Eco RV and ligated into the Nco I site downstream of the glucoamylase promoter of *Aspergillus niger* (glaA) and the Eco RV site upstream of the *Aspergillus nidulans* tryptophan C terminator (trpc) (Mullaney et al., 1985). After this cloning step, the genes were sequenced to detect possible errors introduced by PCR. The resulting expression plasmids, which basically correspond to the pGLAC vector as described in Example 9 of EP 684313, contained the orotidine-5'-phosphate decarboxylase gene (pyr4) of *Neurospora crassa* as a selection marker. Transformation of *Aspergillus niger* and expression of the consensus phytase genes was done as described in EP 684313. The consensus phytases were purified as described in Example 7.

EXAMPLE 9

Determination of Phytase Activity and of the pH and Temperature Optima

This example relates i.a. to the determination of phytase activity and of the temperature optimum. Various phytases have been tested.

The phytase of *Aspergillus niger* NRRL 3135 was prepared as described in EP 420358 and by van Hartingsveldt et al. (Gene 127, 87–94, 1993).

The phytases of *Aspergillus fumigatus* ATCC 13073, *Aspergillus terreus* 9A-1, *Aspergillus terreus* cbs116.46, *Americella nidulans, Myceliophthora thermophila*, and *Talaromyces thermophilus* were prepared as described in EP-0897985 and in the references therein.

The remaining phytases tested were prepared as described herein.

Consensus phytase-1-thermo[8] designates a variant of consensus phytase-1, which further comprises the eight mutations which are underlined in the legend to FIG. 5. Consensus phytase-1 is shown in FIG. 1 (SEQ ID NO: 14) without signal peptide, and in FIG. 2 (SEQ ID NO: 16) with the signal peptide.

Phytase activity was determined basically as described by Mitchell et al. (1997). The activity was measured in an assay mixture containing 0.5% phytic acid ($\approx$5 mM) in 200 mM sodium acetate, pH 5.0. After 15 min of incubation at 37° C., the reaction was stopped by addition of an equal volume of 15% trichloroacetic acid. The liberated inorganic phosphate was quantified by mixing 100 µl of the assay mixture with 900 µl $H_2O$ and 1 ml of 0.6 M $H_2SO_4$, 2% ascorbic acid and 0.5% ammonium molybdate. Standard solutions of potassium phosphate were used as reference. One unit of enzyme activity was defined as the amount of enzyme that releases 1 µmol phosphate per minute at 37° C. The protein concentration was determined using the enzyme extinction coefficient at 280 nm calculated according to Pace et al. (Pace N. C., Vajdos, F., Fee, L., Grimsley, G. & Gray, T. (1995) How to measure and predict the molar absorption coefficient of a protein. Prot. Sci. 4, 2411–2423]: 1 absorption unit (1 OD) at 280 nm corresponds to 1.101 mg/ml of consensus phytase-1, 1.068 mg/ml of consensus phytase-7, and 1.039 mg/ml of consensus phytase-10.

In case of pH-optimum curves, the purified enzymes were diluted in 10 mM sodium acetate, pH 5.0. Incubations were started by mixing aliquots of the diluted protein with an equal volume of 1% phytic acid ($\approx$10 mM) in a series of different buffers: 0.4 M glycine/HCl, pH 2.5; 0.4 M acetate/NaOH, pH 3.0, 3.5, 4.0, 4.5, 5.0, 5.5; 0.4 M imidazole/HCl, pH 6.0, 6.5; 0.4 M Tris/HCl pH 7.0, 7.5, 8.0, 8.5, 9.0. Control experiments showed that pH was only slightly affected by the mixing step.

Incubations were performed for 15 min at 37° C. as described above.

For determination of the substrate specificities of the phytases, phytic acid in the assay mixture was replaced by 5 mM concentrations of the respective phosphate compounds. Besides, the activity tests were performed as described above.

For determination of the temperature optimum, enzyme (100 µl) and substrate solution (100 µl) were pre-incubated for 5 min at the given temperature. The reaction was started by addition of the substrate solution to the enzyme. After 15 min of incubation, the reaction was stopped with trichloroacetic acid, and the amount of phosphate released was determined, The pH-optimum of consensus phytase-1 was around pH 6.0–6.5 (70 U/mg). Introduction of the Q50T mutation shifted the pH-optimum to pH 6.0 (130 U/mg). Introduction of the K91A mutation further shifted the pH optimum into the more acidic pH-range. Comparable effects of the Q50T and K91A mutations were also observed for consensus phytase-10 and for further stabilized consensus phytase variants (FIGS. 14 and 15).

Consensus phytase-7, which was constructed to transfer the catalytic characteristics of *A. niger* NRRL 3135 phytase to consensus phytase-1, had a pH-profile very similar to that of *A. niger* NRRL 3135 phytase (see FIG. 18). The substrate specificity also resembled more that of *A. niger* NRRL 3135 phytase than that of consensus phytase-1.

The temperature optimum of consensus phytase-1 (71° C.) was 16–26° C. higher than the temperature optima of the wild-type phytases (45–55° C., Table 7) that were used to calculate the consensus sequence. The improved consensus phytase-10 showed a further increase of its temperature optimum to 80° C. (FIG. 13).

The temperature optimum of consensus phytase-1-thermo [8] was found to be in the same range (78° C.) when using the supernatant of an overproducing *S. cerevisiae* strain. The highest temperature optimum reached of 82° C. was determined for consensus phytase-10-thermo[3]-Q50T-K91A.

Table 7

Temperature Optima and Tm-values of Consensus Phytase and of the Phytases from *A. fumigatus, A. niger, E. nidulans*, and *M. thermophila*

The determination of the temperature optimum was performed as described in Example 9. The Tm-values were determined by differential scanning calorimetry as described in Example 10.

| Phytase | Optimum temperature (° C.) | Tm (° C.) |
|---|---|---|
| Aspergillus niger NRRL 3135 | 55 | 63.3 |
| Aspergillus fumigatus ATCC 13073 | 55 | 62.5 |
| Aspergillus terreus 9A-1 | 49 | 57.5 |
| Aspergillus terreus cbs116.46 | 45 | 58.5 |
| Emericella nidulans | 45 | 55.7 |
| Myceliophthora thermophila | 55 | — |
| Talaromyces thermophilus | 45 | — |
| Consensus-phytase-10-thermo [5]-Q50T-K91A | — | 90.4 |
| Consensus-phytase-10-thermo [3]-Q50T-K91A | 82 | 89.3 |
| Consensus-phytase-10-thermo [3]-Q50T | 82 | 88.6 |
| Consensus-phytase-10 | 80 | 85.4 |
| Consensus phytase-1-thermo [11]-Q50T-K91A | — | 88.0 |
| Consensus phytase-1-thermo [11]-Q50T | — | 88.5 |
| Consensus-phytase-1-thermo [8]-Q50T-K91A | — | 85.7 |
| Consensus-phytase-1-thermo [8]-Q50T | 78 | 84.7 |
| Consensus-phytase-1-thermo [8] | 81 | — |
| Consensus-phytase-1-thermo [3] | 75 | — |
| Consensus-phytase-1-Q50T | — | 78.9 |
| Consensus-phytase-1 | 71 | 78.1 |
| Aspergillus fumigatus α-mutant Q51T | 60 | 67.0 |
| Aspergillus fumigatus α-mutant, plus mutations E59A, S154N, R329H, S364T, G404A | 63 | — |
| Aspergillus fumigatus "optimized" alpha-mutant, plus mutation K92A | 63 | — |

EXAMPLE 10

Determination of the Melting Temperature by Differential Scanning Calorimetry (DSC)

In order to determine the unfolding temperature of the phytases, differential scanning calorimetry was applied as described by Brugger et al., 1997 [Brugger, R., Mascarello, F., Augem, S., van Loon, A. P. G. M. & Wyss, M. (1997). Thermal denaturation of phytases and pH 2.5 acid phosphatase studied by differential scanning calorimetry. In The Biochemistry of phytate and phytase (eds. Rasmussen, S. K.; Raboy, V.; DalbØge, H. and Loewus, F.; Kluwer Academic Publishers, Dordrecht, the Netherlands]. Solutions of 50–60 mg/ml of homogeneous phytase were used for the tests. A constant heating rate of 10° C./min was applied up to 90–95° C.

The determined melting points confirm the results obtained for the temperature optima (Table 7). The most stable consensus phytase designed so far is consensus phytase-10-thermo[3]-Q50T-K91A showing a melting temperature under the chosen conditions of 89.3° C. This is 26.0 to 33.6° C. higher than the melting temperature of the wild-type phytases used.

EXAMPLE 11

Transfer of Basidiomycete Phytase Active Site Into Consensus Phytase-10-thermo[3]-Q50T-K91A As described previously (Example 5), mutations derived from the basidiomycete phytase active sites were introduced into consensus phytase-10. The following five constructs a) to e) were prepared:

a) The construct called consensus phytase-12, and it comprises a selected number of active site residues of the basidio consensus sequence. Its amino acid sequence is shown in FIG. 21 (the first 26 amino acids form the signal peptide; positions differing from consensus phytase-10-thermo[3]-Q50T-K91A are underlined);

b) a cluster of mutations (Cluster II) was transferred to the consensus phytase-1 and -10 sequences, viz.: S80Q, Y86F, S90G, K91A, S92A, K93T, A94R, Y95I;

c) in a similar way, another cluster of mutations (Cluster III) was transferred, viz.: T129V, E133A, Q134N, M136S, V137S, N138Q, S139A;

d) in a similar way, a further cluster of mutations (Cluster IV) was transferred, viz.: A168D, E171T, K172N, F173W;

e) and finally, a further cluster of mutations (Cluster V) was transferred, viz.: Q297G, S298D, G300D, Y305T.

These constructs were expressed as described in Examples 6 to 8.

EXAMPLE 12

Phytase Alignment Using GAP

The phytases described herein—i.e. the amino acid sequences as well as the corresponding DNA sequences—were aligned against each other. Also some other phytases were correspondingly aligned, viz. the following:
the consensus phytase-1 described in EP 897985;
the phytase derived from Aspergillus niger (ficuum) NRRL 3135 (A. niger NRRL3135) described in EP 420358;
the phytases derived from Aspergillus fumigatus ATCC 13073 (A. fumigatus 13073); Aspergillus fumigatus ATCC 32239 (A. fumigatus 32239); Aspergillus terreus cbs116.46 (A.terreus cbs); Emericella nidulans (E. nidulans); and Talaromyces thermophilus (T. thermophilus)—all described in EP 897010;
the phytases derived from Myceliophthora thermophila (M. thermophila); and Aspergillus terreus 9-A1 (A. terreus 9-A1)—both described in EP 684313;
the phytase derived from Thermomyces lanuginosus (T. lanuginosus) described in WO 9735017 (PCT/US97/04559);
the phytases derived from Agrocybe pediades (A. pediades), Paxillus involutus 1 and 2 (P. involutus phyA1 and phyA2); and Trametes pubescens (T. pubescens)—all described in WO 98/28409; and
the phytase derived from Peniophora lycii (P. lycii) described in WO 98/28408.

For the alignments, the program GAP was used with the settings as described above.

For polypeptide comparisons, the signal peptides were included with the exception of comparisons with consensus phytase-11.

The results of the amino acid sequence comparisons are shown in Table 8 below. The first number in each cell is the amino acid similarity, the second number is the amino acid identity.

For DNA sequence comparisons, the signal sequence was always included. The results are shown in Table 9 below.

This invention comprises e.g. the following embodiments (A) to (J) that are described below.

In these embodiments, when determining % identity or % similarity at the amino acid level for another phytase, its amino acid sequence is aligned with the reference sequence (e.g. in embodiment (A) the consensus phytase-10 amino acid sequence), using an alignment program such as GAP referred to above. Percentage identity, as well as percentage similarity, is calculated by the program. The amino acid sequence of the other phytase may or may not include the signal peptide.

When determining % identity on the DNA level for another phytase-encoding DNA, this DNA sequence is aligned with the reference sequence [e.g. in embodiment (A) nucleotides 12–1412 of SEQ ID NO: 25 (the DNA sequence of consensus phytase-10 (Fcp10) as shown in FIG. 5], using an alignment program such as GAP referred to above. Percentage identity is calculated by the program. The DNA sequence encoding the other phytase can be a genomic DNA sequence including introns, or it can be a cDNA sequence. It may or may not include the signal peptide-encoding part.

When determining hybridization, the probe to be used is the specified DNA sequence [e.g. in embodiment (A) nucleotides 12–1412 of SEQ ID NO: 25 (the DNA sequence of consensus phytase-10 (Fcp10) as shown in FIG. 5)]. The DNA sequence encoding the other phytase can be a genomic DNA sample which contains a phytase-encoding DNA-sequence; a purified genomic DNA sequence (purified with respect to the phytase-encoding DNA sequence); or it can be a phytase-encoding cDNA sequence, preferably purified or amplified, e.g. PCR-amplified. The phytase-encoding DNA, whatever type, may or may not include the signal peptide-encoding part. Suitable hybridization conditions are referred to above.

The term "DNA sequence" includes such fragments or parts of the herein exemplified DNA sequences, as long as they are capable of encoding an active enzyme (e.g. phytase).

The term "amino acid sequence" includes such fragments or parts of the herein exemplified amino acid sequences, as long as they are enzymatically active (e.g. displaying phytase activity).

(A) Phytases and Corresponding DNA Sequences Related to Consensus Phytase-10 (CP10, Fcp 10)

A phytase that comprises an amino acid sequence which is at least 93.80%; or at least 94, 94.5, 95, 95.5, 96, 96.5, 97, 97.5, 98, 98.5, 99, 99.5% identical to the sequence of amino acids 1–467 of consensus phytase-10 (Fcp10) as shown in FIG. 5.

A phytase that comprises an amino acid sequence which is at least 95.09%; or at least 95.5, 96, 96.5, 97, 97.5, 98, 98.5, 99, 99.5% similar to the sequence of amino acids 1–467 of consensus phytase-10.

A phytase which is encoded by a DNA sequence which is at least 95.88%; or at least 96, 96.5, 97, 97.5, 98, 98.5, 99, 99.5% identical to nucleotides 12–1412 of the DNA sequence of consensus phytase-10 (Fcp10) as shown in FIG. 5.

A DNA sequence which encodes a phytase and which (i) is at least 95.88%; or at least 96, 96.5, 97, 97.5, 98, 98.5, 99, 99.5% identical; or (ii) hybridizes under low, or medium, medium/high, high, or very high stringency conditions to nucleotides 12–1412 of the DNA sequence of consensus phytase-10 (Fcp10) as shown in FIG. 5. A suitable negative control is DNA encoding consensus phytase-1. A suitable positive control is DNA encoding any of CP10, CP10-thermo[3]-Q50T, K91A, CP1-thermo[8], CP1-thermo[8] Q50T, K91A.

A DNA sequence which encodes a phytase comprising an amino acid sequence which is at least 93.80%; or at least 94, 94.5, 95, 95.5, 96, 96.5, 97, 97.5, 98, 98.5, 99, 99.5% identical to the sequence of amino acids 1–467 of consensus phytase-10 (Fcp10) as shown in FIG. 5.

(B) Phytases and Corresponding DNA Sequences Related to Consensus Phytase-10-thermo[3]-Q50T-K91A A phytase which comprises an amino acid sequence which is at least 93.37%; or at least 93.5, 94, 94.5, 95, 95.5, 96, 96.5, 97, 97.5, 98, 98.5, 99, 99.5% identical to the sequence of amino acids 1–467 of consensus phytase-10-thermo[3]-Q50T-K91A as shown in FIG. 8.

A phytase which comprises an amino acid sequence which is at least 94.66%; or at least 95.0, 95.5, 96, 96.5, 97, 97.5, 98, 98.5, 99, 99.5% similar to the sequence of amino acids 1–467 of consensus phytase-10-thermo[3]-Q50T-K91A as shown in FIG. 8.

A phytase which is encoded by a DNA sequence which is at least 95.88%; or at least 96, 96.5, 97, 97.5, 98, 98.5, 99, 99.5% identical to nucleotides 12–1412 of the DNA sequence of consensus phytase-10-thermo[3]-Q50T-K91A as shown in FIG. 8.

A DNA sequence which encodes a phytase and which (i) is at least 95.88%; or at least 96, 96.5, 97, 97.5, 98, 98.5, 99, 99.5% identical; or (ii) hybridizes under low, or medium, medium/high, high, or very high stringency conditions to nucleotides 12–1412 of the DNA sequence of consensus phytase-10-thermo[3]-Q50T-K91A as shown in FIG. 8. A suitable negative control is DNA encoding consensus phytase-1. A suitable positive control is DNA encoding any of CP10, CP10-thermo[3]-Q50T-K91A, CP1-thermo[8], or CP1-thermo[8]-Q50T-K91A.

A DNA sequence which encodes a phytase comprising an amino acid sequence which is at least 93.37%; or at least 93.5, 94, 94.5, 95, 95.5, 96, 96.5, 97, 97.5, 98, 98.5, 99, 99.5% identical to the sequence of amino acids 1–467 of consensus phytase-10-thermo[3]-Q50T-K91A as shown in FIG. 8.

(C) Phytases and Corresponding DNA Sequences Related to Consensus Phytase-1-thermo[8]

A phytase which comprises an amino acid sequence which is at least 98.30%; or at least 98.5, 99, 99.5% identical to the sequence of amino acids 1–467 of consensus phytase-1-thermo[8] (as shown in FIG. 7; backmutations T50Q and A91K to be added).

A phytase which comprises an amino acid sequence which is at least 98.51%; or at least 99, 99.5% similar to the sequence of amino acids 1–467 of consensus phytase-1-thermo[8] (as shown in FIG. 7; backmutations T50Q and A91K to be added).

A phytase which is encoded by a DNA sequence which is at least 98.73%; or at least 99, 99.5% identical to nucleotides 1–1407 of the DNA sequence of consensus phytase-1-thermo[8] (as shown in FIG. 7; backmutations T50Q and A91K to be added).

A DNA sequence which encodes a phytase and which (i) is at least 98.73%; or at least 99, 99.5% identical; or (ii) hybridizes under low, or medium, medium/high, high, or very high stringency conditions to nucleotides 1–1407 of the DNA sequence of consensus phytase-1-thermo[8] (as shown in FIG. 7; backmutations T50Q and A91K to be added). A suitable negative control is DNA encoding consensus phytase-1. A suitable positive control is DNA encoding any of CP1-thermo[8], CP1-thermo[8]-Q50T-K91A.

A DNA sequence which encodes a phytase comprising an amino acid sequence which is at least 98.30%; or at least 98.5, 99, 99.5% identical to the sequence of amino acids 1–467 of consensus phytase-1-thermo[8] (as shown in FIG. 7; backmutations T50Q and A91K to be added).

(D) Phytases and Corresponding DNA Sequences Related to Consensus Phytase-1-thermo[8]

A phytase which comprises an amino acid sequence which is at least 97.87%; or at least 98, 98.5, 99, 99.5% identical to the sequence of amino acids 1–467 of consensus phytase-1-thermo[8]-Q50T-K91A as shown in FIG. 7.

A phytase which comprises an amino acid sequence which is at least 98.08%; or at least 98.5, 99, 99.5% similar to the sequence of amino acids 1–467 of consensus phytase-1-thermo[8]-Q50T-K91A as shown in FIG. 7.

A phytase which is encoded by a DNA sequence which is at least 98.37%; or at least 98.5, 99, 99.5% identical to nucleotides 1–1407 of the DNA sequence of consensus phytase-1-thermo[8]-Q50T-K91A as shown in FIG. 7.

A DNA sequence which encodes a phytase and which (i) is at least 98.37%; or at least 98.5, 99, 99.5% identical; or (ii) hybridizes under low, or medium, medium/high, high, or very high stringency conditions to nucleotides 1–1407 of the DNA sequence of consensus phytase-1-thermo[8]-Q50T-K91A as shown in FIG. 7. A suitable negative control is DNA encoding consensus phytase-1. A suitable positive control is DNA encoding any of CP1-thermo[8], CP1-thermo[8]-Q50T-K91A.

A DNA sequence which encodes a phytase comprising an amino acid sequence which is at least 97.87%; or at least 98, 98.5, 99, 99.5% identical to the sequence of amino acids 1–467 of consensus phytase 1-thermo[8]-Q50T-K91A as shown in FIG. 7.

(E) Phytases and Corresponding DNA Sequences Related to Consensus Phytase-1

A phytase that comprises an amino acid sequence which is at least 90.71%; or at least 91, 91.5, 92, 92.5, 93, 93.5, 94, 94.5, 95, 95.5, 96, 96.5, 97, 97.5, 98, 98.5, 99, 99.5% identical to the sequence of amino acids 1–482 of consensus phytase-11 as shown in FIG. 6.

A phytase that comprises an amino acid sequence which is at least 92.07%; or at least 92.5, 93, 93.5, 94, 94.5, 95, 95.5, 96, 96.5, 97, 97.5, 98, 98.5, 99, 99.5% similar to the sequence of amino acids 1–482 of consensus phytase-11 as shown in FIG. 6.

A DNA sequence that encodes a phytase comprising an amino acid sequence which is at least 90.71%; or at least 91. 91.5, 92, 92.5, 93, 93.5, 94, 94.5, 95, 95.5, 96, 96.5, 97, 97.5, 98, 98.5, 99, 99.5% identical to the sequence of amino acids 1–482 of consensus phytase-11 as shown in FIG. 6.

(F) Phytases and Corresponding DNA Sequences Related to A. fumigatus Alpha-mutant A phytase that comprises an amino acid sequence which is at least 97.17%; or at least 97.5, 98, 98.5, 99, 99.5% identical to the sequence of amino acids 1–467 of A. fumigatus alpha-mutant (phytase) as shown in FIG. 9.

A phytase that comprises an amino acid sequence that is at least 97.82%; or at least 98, 98.5, 99, 99.5% similar to the sequence of amino acids 1–467 of A. fumigatus alpha-mutant (phytase) as shown in FIG. 9.

A phytase which is encoded by a DNA sequence which is at least 96.13%; or at least 96.5, 97, 97.5, 98, 98.5, 99, 99.5% identical to nucleotides 1–1401 of the DNA sequence of A. fumigatus ATCC 13073 alpha-mutant (phytase) as shown in FIG. 9.

A DNA sequence which encodes a phytase comprising an amino acid sequence which is at least 97.17%; or at least 97.5, 98, 98.5, 99, 99.5% identical to the sequence of amino acids 1–467 of A. fumigatus ATCC 13073 alpha-mutant (phytase) as shown in FIG. 9.

A DNA sequence which encodes a phytase and which (i) is at least 96.13%; or 96.5, 97, 97.5, 98, 98.5, 99, 99.5% identical; or (ii) hybridizes under low, or medium, medium/high, high, or very high stringency conditions to nucleotides 1–1401 of the DNA sequence of A. fumigatus ATCC 13073 alpha-mutant (phytase) shown in FIG. 9. A suitable negative control is DNA encoding A. fumigatus 13073 phytase. A suitable positive control is DNA encoding any one of the A. fumigatus ATCC 13073 alpha mutant phytase or the optimised alpha-mutant.

(G) Phytases and Corresponding DNA Sequences Related to the Optimized A. fumigatus Alpha-mutant A phytase that comprises an amino acid sequence that is at least 96.08%; or at least 96.5, 97, 97.5, 98, 98.5, 99, 99.5% identical to the sequence of the phytase of the optimized A. fumigatus alpha-mutant.

A phytase that comprises an amino acid sequence that is at least 96.74%; or at least 97, 97.5, 98, 98.5, 99, 99.5% similar to the sequence of the phytase of the optimized A. fumigatus alpha-mutant.

A phytase which is encoded by a DNA sequence which is at least 95.63%; or at least 96, 96.5, 97, 97.5, 98, 98.5, 99, 99.5% identical to nucleotides 1–1401 of the DNA sequence encoding the optimized A. fumigatus alpha-mutant phytase.

A DNA sequence that encodes a phytase comprising an amino acid sequence that is at least 96.08%; or at least 96.5, 97, 97.5, 98, 98.5, 99, 99.5% identical to the optimized A. fumigatus alpha-mutant phytase.

A DNA sequence which encodes a phytase and which (i) is at least 95.63%; or at least 96, 96.5, 97, 97.5, 98, 98.5, 99, 99.5% identical; or (ii) hybridizes under low, or medium, medium/high, high, very high stringency conditions to nucleotides 1–1401 of the DNA sequence encoding the optimized A. fumigatus alpha-mutant phytase.

A suitable negative control is DNA encoding A. fumigatus ATCC 13073 phytase. A suitable positive control is DNA encoding any one of the A. fumigatus ATCC 13073 alpha mutant phytase of the optimised alpha-mutant.

(H) Phytases and Corresponding DNA Sequences Related to Consensus Phytase-7

A phytase that comprises an amino acid sequence which is is at least 94.87%; or at least 95, 95.5, 96, 96.5, 97, 97.5, 98, 98.5, 99, 99.5% identical to the sequence of amino acids 1–467 of consensus phytase-7 as shown in FIG. 10.

A phytase that comprises an amino acid sequence which is at least 95.30%; or at least 95.5, 96, 96.5, 97, 97.5, 98, 98.5, 99, 99.5% similar to the sequence of amino acids 1–467 of consensus phytase-7 as shown in FIG. 10.

A phytase which is encoded by a DNA sequence which is at least 96.38%; or 96.5, 97, 97.5, 98, 98.5, 99, 99.5% identical to nucleotides 12–1412 of the DNA sequence of consensus phytase-7 shown in FIG. 10.

A DNA sequence which encodes a phytase and which (i) is at least 96.38%; or at least 96.5, 97, 97.5, 98, 98.5, 99, 99.5% identical; or (ii) hybridizes under low, or medium, medium/high, high, or very high stringency conditions to nucleotides 12–1412 of the DNA sequence of consensus phytase-7 as shown in FIG. 10.

A DNA sequence which encodes a phytase comprising an amino acid sequence which is at least 94.87%; or at least 95, 95.5, 96, 96.5, 97, 97.5, 98, 98.5, 99, 99.5 identical to the sequence of amino acids 1–467 of consensus phytase-7 as shown in FIG. 10.

(I) Phytases Related to Basidio Consensus Phytase

A phytase which comprises an amino acid sequence which is at least 76.23%; or at least 77, 78, 79, 80, 81, 82, 83, 84, 85, 86, 87, 88, 89, 90, 91, 92, 93, 94, 94.5, 95, 95.5, 96, 96.5, 97, 97.5, 98, 98.5, 99, 99.5% identical to the combined sequence of (i) amino acids 1–441 of basidio consensus phytase shown in FIG. 3, and (ii) amino acids 1–26 shown in FIG. 5 (the sequence of (ii) to be added at the N-terminus of the sequence of (i)).

A phytase that comprises an amino acid sequence which is at least 79.50%; or at least 80, 81, 82, 83, 84, 85, 86, 87, 88, 89, 90, 91, 92, 93, 94, 95, 95.5, 96, 96.5, 97, 97.5, 98, 98.5, 99, 99.5% similar to the sequence of amino acids 1–441 of basidio consensus phytase as shown in FIG. 3.

(J) Phytases Related to Consensus Phytase-12

A phytase which comprises an amino acid sequence which is at least 70, 75, 76, 77, 78, 79, 80, 81, 82, 83, 84, 85, 86, 87, 88, 89, 90, 91, 92, 93, 94, 95, 95.5, 96, 96.5, 97, 97.5, 98, 98.5, 99, 99.5% identical to the sequence of amino acids 1–467 of consensus phytase-12 as shown in FIG. 21.

A phytase which comprises an amino acid sequence which is at least 75, 76, 77, 78, 79, 80, 81, 82, 83, 84, 85, 86, 87, 88, 89, 90, 91, 92, 93, 94, 95, 95.5, 96, 96.5, 97, 97.5, 98, 98.5, 99, 99.5% similar to the sequence of amino acids 1–467 of consensus phytase-12 as shown in FIG. 21.

TABLE 8

Comparison of phytase amino acid sequences

| Phytase | CP10 | CP10 thermo[3]-Q50T-K91A | CP1-thermo[8] | CP1-Thermo[8] Q50T-K91A | CP11 | CP7 | Basidio | A. fumigatus alpha-mutant | A. fumigatus alpha-mutant (opt.) |
|---|---|---|---|---|---|---|---|---|---|
| Consensus phytase-1 | 95.08/93.79 | 94.65/93.36 | 98.50/98.29 | 98.07/97.86 | 92.06/90.70 | 95.29/94.86 | 69.42/62.16 | 85.59/82.58 | 84.73/81.72 |
| A. niger NRRL3135 | 79.48/76.46 | 79.05/76.03 | 80.35/77.75 | 79.91/77.32 | 79.27/76.31 | 84.02/81.64 | 67.19/59.32 | 74.07/70.11 | 74.95/70.99 |
| A. terreus 9-A1 | 76.04/72.11 | 75.82/71.90 | 76.47/72.33 | 76.51/71.84 | 76.51/73.02 | 75.76/71.18 | 65.39/58.02 | 69.67/64.84 | 69.45/64.84 |
| A. terreus cbs | 79.04/75.11 | 78.82/74.89 | 79.48/75.76 | 79.26/75.55 | 77.19/73.27 | 79.17/75.00 | 66.92/59.65 | 72.59/67.76 | 72.37/67.76 |
| E. nidulans | 78.70/74.35 | 78.26/73.91 | 79.78/75.87 | 79.35/75.44 | 80.56/76.62 | 76.96/73.04 | 67.20/58.13 | 72.39/67.83 | 72.11/67.54 |
| A. fumigatus 13073 | 82.93/80.31 | 82.50/76.87 | 82.31/79.04 | 81.88/78.60 | 81.36/78.64 | 80.13/76.20 | 63.54/57.91 | 97.82/97.16 | 96.73/96.07 |
| A. fumigatus 32239 | 81.30/77.39 | 80.87/76.96 | 81.09/77.61 | 80.65/77.17 | 79.95/76.08 | 79.13/75.22 | 63.61/54.97 | 90.22/86.52 | 89.57/85.87 |
| T. thermophilus | 77.83/73.84 | 77.38/73.39 | 78.67/74.89 | 78.22/74.44 | 78.47/74.76 | 76.51/73.15 | 61.54/54.36 | 72.01/66.82 | 72.69/67.49 |
| N. thermophila | 69.16/62.81 | 69.48/63.33 | 69.27/62.84 | 69.59/63.36 | 69.65/63.06 | 68.82/62.13 | 65.56/57.91 | 66.21/58.45 | 66.44/58.68 |
| T. lanuginosus | 73.52/66.70 | 73.06/66.44 | 71.92/64.61 | 71.46/64.16 | 74.21/68.86 | 69.50/62.62 | 67.20/57.41 | 68.91/61.02 | 69.61/61.72 |
| P. lycil | 64.92/59.10 | 64.91/59.37 | 64.46/58.09 | 64.46/58.36 | 65.03/59.84 | 63.13/56.50 | 77.75/73.07 | 64.08/57.11 | 62.47/55.91 |
| A. pediades | 64.51/51.81 | 64.86/51.94 | 62.98/51.41 | 63.33/51.54 | 64.50/52.30 | 63.05/51.15 | 78.92/74.71 | 61.64/52.38 | 62.13/53.07 |
| P. involutus 1 | 66.67/58.07 | 66.67/58.33 | 64.84/56.51 | 64.84/56.77 | 63.30/54.52 | 65.33/56.53 | 79.49/76.22 | 59.59/51.81 | 59.95/52.20 |
| P. involutus 2 | 65.54/55.70 | 65.30/55.53 | 66.85/56.87 | 66.58/56.68 | 66.30/56.35 | 64.27/54.13 | 78.09/74.59 | 61.26/52.62 | 61.04/52.47 |
| T. pubescens | 65.46/57.22 | 65.72/57.47 | 62.89/55.67 | 63.14/55.93 | 65.03/57.65 | 63.28/56.51 | 78.34/75.12 | 64.08/57.11 | 62.30/55.24 |
| CP10 | — | 99.57/99.57 | 99.57/99.57 | 96.57/95.50 | 96.15/95.08 | 95.02/94.56 | 91.01/89.29 | 70.22/62.28 | 85.13/82.76 | 85.99/83.62 |
| CP10t[3] Q50TK91A | 99.57/99.57 | — | 96.15/95.08 | 96.57/95.50 | 94.56/94.10 | 90.58/88.87 | 70.47/62.28 | 85.13/82.76 | 85.99/83.62 |
| CP1thermo[8] | 96.57/95.50 | 96.15/95.08 | — | 99.57/99.57 | 93.42/92.29 | 94.43/93.79 | 68.40/60.74 | 84.52/81.94 | 85.38/82.80 |
| CP1t[8]Q50TK91A | 96.15/95.08 | 96.57/95.50 | 99.57/99.57 | — | 92.97/91.84 | 94.00/93.36 | 68.64/60.74 | 84.52/81.94 | 85.38/82.80 |
| CP11 | 95.02/94.56 | 94.56/94.10 | 93.42/92.29 | 92.97/91.84 | — | 88.44/86.62 | 68.27/59.73 | 82.23/79.73 | 83.37/80.87 |
| CP7 | 91.01/89.29 | 90.58/88.87 | 94.43/93.79 | 94.00/93.36 | 88.44/86.62 | — | 69.80/62.69 | 81.94/78.71 | 81.72/78.50 |
| Basidio | 70.22/62.28 | 70.47/62.28 | 68.40/60.74 | 68.64/60.74 | 68.27/59.73 | 69.80/62.69 | — | 65.97/60.52 | 66.41/60.68 |
| A. fumigatus alpha-mut. | 85.13/82.76 | 85.13/82.76 | 84.52/81.94 | 84.52/81.94 | 82.23/79.73 | 81.94/78.71 | 65.97/60.52 | — | 98.93/98.93 |
| A. fum alpha-mut-opt. | 85.99/83.62 | 85.99/83.62 | 85.38/82.80 | 85.38/82.80 | 83.37/80.87 | 81.72/78.50 | 66.43/60.68 | 98.93/98.93 | — |

TABLE 9

Comparison of phytase encoding DNA sequences

| Phytase | CP10 | CP10-thermo[3]-Q50T-K91A | CP1-thermo[8] | CP1-thermo[8]-Q50T-K91A | CP7 | Basidio | A. fumigatus alpha-mutant | A. fumigatus alpha-mutant (opt.) |
|---|---|---|---|---|---|---|---|---|
| Consensus phytase-1 | 95.87 | 95.87 | 98.72 | 98.36 | 96.37 | 65.46 | 66.88 | 66.88 |
| A. niger NRRL3135 | 65.10 | 64.82 | 66.10 | 65.74 | 67.52 | 50.68 | 65.88 | 66.17 |
| A. terreus 9-A1 | 61.74 | 61.53 | 62.17 | 62.03 | 60.53 | 49.40 | 66.24 | 66.31 |
| A. terreus cbs | 62.52 | 62.30 | 63.02 | 62.88 | 61.45 | 49.74 | 68.17 | 68.24 |
| E. nidulans | 65.08 | 64.94 | 65.30 | 65.01 | 64.22 | 49.92 | 64.90 | 65.44 |
| A. fumigatus 13073 | 65.66 | 65.38 | 64.19 | 64.08 | 63.65 | 48.27 | 96.12 | 95.62 |
| T. thermophilus | 62.52 | 62.50 | 62.53 | 62.66 | 62.00 | 52.19 | 61.77 | 61.92 |
| M. thermophila | 55.51 | 55.15 | 55.36 | 55.22 | 53.91 | 48.44 | 58.17 | 58.24 |
| T. lanuginosus | 57.56 | 57.20 | 56.76 | 56.47 | 62.00 | 44.66 | 59.71 | 60.07 |
| P. lycil | 45.76 | 46.51 | 45.14 | 55.21 | 55.46 | 58.50 | 48.91 | 49.44 |
| A. pediades | 49.89 | 49.89 | 49.89 | 50.11 | 45.54 | 61.66 | 47.49 | 47.56 |
| P. involutus 1 | 48.32 | 49.03 | 47.81 | 47.96 | 49.59 | 59.80 | 49.96 | 50.19 |
| P. involutus 2 | 48.24 | 49.00 | 48.08 | 48.63 | 47.94 | 60.16 | 47.56 | 47.63 |
| T. pubescens | 47.00 | 47.17 | 46.46 | 47.62 | 46.83 | 60.37 | 49.89 | 49.96 |

TABLE 9-continued

Comparison of phytase encoding DNA sequences

| Phytase | CP10 | CP10-thermo[3]-Q50T-K91A | CP1-thermo[8] | CP1-thermo[8]-Q50T-K91A | CP7 | Basidio | A. fumigatus alpha-mutant | A. fumigatus alpha-mutant (opt.) |
|---|---|---|---|---|---|---|---|---|
| CP10 | — | 99.43 | 96.40 | 96.05 | 93.73 | 66.40 | 67.81 | 68.24 |
| CP10t[3]Q50TK91A | 99.43 | — | 96.37 | 96.58 | 93.45 | 66.29 | 67.81 | 68.24 |
| CP1thermo[8] | 96.40 | 96.37 | — | 99.65 | 95.30 | 65.40 | 66.74 | 67.17 |
| CP1t[8]Q50TK91A | 96.05 | 96.58 | 99.65 | — | 94.94 | 65.47 | 66.74 | 67.17 |
| CP7 | 93.73 | 93.45 | 95.30 | 94.94 | — | 64.56 | 65.88 | 65.88 |
| Basidio | 66.40 | 66.29 | 65.40 | 65.47 | 64.56 | — | 50.41 | 50.49 |
| A. fumigatus alpha-mut. | 67.81 | 67.81 | 66.74 | 66.74 | 65.88 | 50.41 | — | 99.50 |
| A. fum alpha-mut-opt. | 68.24 | 68.24 | 67.17 | 67.17 | 65.88 | 50.49 | 99.50 | — |

What is claimed is:

1. A phytase comprising an amino acid sequence which is at least 93.80% identical to the sequence of amino acid residues 1–467 of SEQ ID NO: 26, wherein the % identity is determined by GAP provided in the GCG program package using a length weight of 0 and a gap weight of 3.

2. A phytase that is encoded by a DNA sequence that is at least 95.88% identical to nucleotides 12–1412 of the DNA sequence of SEQ ID NO: 25, wherein the % identity is determined by GAP provided in the GCG program package using a gap creation penalty of 50 and a gap extension penalty of 3.

3. A phytase that comprises:
   (a) the amino acid sequence of SEQ ID NO: 26 or amino acid residues 1–441 of SEQ ID NO: 26; or
   (b) the amino acid sequence encoded by nucleotides 12–1412 or 90–1412 of SEQ ID NO: 25.

4. A phytase comprising:
   (a) the amino acid sequence of SEQ ID NO: 31,
   (b) the amino acid sequence of SEQ ID NO: 31 in which the amino acid residue at position 24 is glutamine,
   (c) the amino add sequence of SEQ ID NO: 31 in which the amino add residue at position 65 is lysine,
   (d) the amino acid sequence of SEQ ID NO: 31 in which the amino acid residue at position 24 is glutamine and the amino acid residue at position 65 is lysine,
   (e) the amino add sequence of residues 1–441 of any of (a)–(d), or
   (f) the amino acid sequence encoded by nucleotides 1–1401 or 79–1401 of SEQ ID NO: 30.

5. A phytase comprising:
   (a) the amino acid sequence of SEQ ID NO: 29,
   (b) the amino acid sequence of SEQ ID NO: 29 in which the amino add residue at position 24 is glutamine,
   (c) the amino acid sequence of SEQ ID NO: 29 in which the amino acid residue at position 65 is lysine,
   (d) the amino acid sequence of SEQ ID NO: 29 in which the amino acid residue at position 24 is glutamine and the amino acid residue at position 65 is lysine,
   (e) the amino add sequence of residues 1–441 of any of (a)–(d), or
   (f) the amino acid sequence encoded by nucleotides 1–1401 or 79–1401 of SEQ ID NO: 28.

6. A phytase comprising the amino acid sequence of SEQ ID NO: 27.

7. A food or feed composition comprising the phytase of claim 1.

8. A food or feed composition comprising the phytase of claim 2.

9. A food or feed composition comprising the phytase of claim 3.

10. A food or feed composition comprising the phytase of claim 4.

11. A food or feed composition comprising the phytase of claim 5.

12. A food or feed composition comprising the phytase of claim 6.

* * * * *

SEQUENCE LISTING

<160> NUMBER OF SEQ ID NOS: 98

<210> SEQ ID NO 1
<211> LENGTH: 440
<212> TYPE: PRT
<213> ORGANISM: Aspergillus terreus 9A-1

<400> SEQUENCE: 1

```
Lys His Ser Asp Cys Asn Ser Val Asp His Gly Tyr Gln Cys Phe Pro
1               5                   10                  15

Glu Leu Ser His Lys Trp Gly Leu Tyr Ala Pro Tyr Phe Ser Leu Gln
            20                  25                  30

Asp Glu Ser Pro Phe Pro Leu Asp Val Pro Glu Asp Cys His Ile Thr
        35                  40                  45

Phe Val Gln Val Leu Ala Arg His Gly Ala Arg Ser Pro Thr His Ser
    50                  55                  60

Lys Thr Lys Ala Tyr Ala Ala Thr Ile Ala Ala Ile Gln Lys Ser Ala
65                  70                  75                  80

Thr Ala Phe Pro Gly Lys Tyr Ala Phe Leu Gln Ser Tyr Asn Tyr Ser
                85                  90                  95

Leu Asp Ser Glu Glu Leu Thr Pro Phe Gly Arg Asn Gln Leu Arg Asp
            100                 105                 110

Leu Gly Ala Gln Phe Tyr Glu Arg Tyr Asn Ala Leu Thr Arg His Ile
        115                 120                 125

Asn Pro Phe Val Arg Ala Thr Asp Ala Ser Arg Val His Glu Ser Ala
    130                 135                 140

Glu Lys Phe Val Glu Gly Phe Gln Thr Ala Arg Gln Asp Asp His His
145                 150                 155                 160

Ala Asn Pro His Gln Pro Ser Pro Arg Val Asp Val Ala Ile Pro Glu
                165                 170                 175

Gly Ser Ala Tyr Asn Asn Thr Leu Glu His Ser Leu Cys Thr Ala Phe
            180                 185                 190

Glu Ser Ser Thr Val Gly Asp Asp Ala Val Ala Asn Phe Thr Ala Val
        195                 200                 205

Phe Ala Pro Ala Ile Ala Gln Arg Leu Glu Ala Asp Leu Pro Gly Val
    210                 215                 220

Gln Leu Ser Thr Asp Asp Val Val Asn Leu Met Ala Met Cys Pro Phe
225                 230                 235                 240
```

```
Glu Thr Val Ser Leu Thr Asp Asp Ala His Thr Leu Ser Pro Phe Cys
            245                 250                 255

Asp Leu Phe Thr Ala Thr Glu Trp Thr Gln Tyr Asn Tyr Leu Leu Ser
            260                 265                 270

Leu Asp Lys Tyr Tyr Gly Tyr Gly Gly Asn Pro Leu Gly Pro Val
            275                 280                 285

Gln Gly Val Gly Trp Ala Asn Glu Leu Met Ala Arg Leu Thr Arg Ala
            290                 295                 300

Pro Val His Asp His Thr Cys Val Asn Thr Leu Asp Ala Ser Pro
305                 310                 315                 320

Ala Thr Phe Pro Leu Asn Ala Thr Leu Tyr Ala Asp Phe Ser His Asp
            325                 330                 335

Ser Asn Leu Val Ser Ile Phe Trp Ala Leu Gly Leu Tyr Asn Gly Thr
            340                 345                 350

Ala Pro Leu Ser Gln Thr Ser Val Glu Ser Val Ser Gln Thr Asp Gly
            355                 360                 365

Tyr Ala Ala Trp Thr Val Pro Phe Ala Ala Arg Ala Tyr Val Glu
            370                 375                 380

Met Met Gln Cys Arg Ala Glu Lys Glu Pro Leu Val Arg Val Leu Val
385                 390                 395                 400

Asn Asp Arg Val Met Pro Leu His Gly Cys Pro Thr Asp Lys Leu Gly
            405                 410                 415

Arg Cys Lys Arg Asp Ala Phe Val Ala Gly Leu Ser Phe Ala Gln Ala
            420                 425                 430

Gly Gly Asn Trp Ala Asp Cys Phe
            435                 440

<210> SEQ ID NO 2
<211> LENGTH: 440
<212> TYPE: PRT
<213> ORGANISM: Aspergillus terreus cbs

<400> SEQUENCE: 2

Asn His Ser Asp Cys Thr Ser Val Asp Arg Gly Tyr Gln Cys Phe Pro
1               5                   10                  15

Glu Leu Ser His Lys Trp Gly Leu Tyr Ala Pro Tyr Phe Ser Leu Gln
            20                  25                  30

Asp Glu Ser Pro Phe Pro Leu Asp Val Pro Asp Cys His Ile Thr
            35                  40                  45

Phe Val Gln Val Leu Ala Arg His Gly Ala Arg Ser Pro Thr Asp Ser
    50                  55                  60

Lys Thr Lys Ala Tyr Ala Ala Thr Ile Ala Ala Ile Gln Lys Asn Ala
65                  70                  75                  80

Thr Ala Leu Pro Gly Lys Tyr Ala Phe Leu Lys Ser Tyr Asn Tyr Ser
            85                  90                  95

Met Gly Ser Glu Asn Leu Thr Pro Phe Gly Arg Asn Gln Leu Gln Asp
            100                 105                 110

Leu Gly Ala Gln Phe Tyr Arg Arg Tyr Asp Thr Leu Thr Arg His Ile
            115                 120                 125

Asn Pro Phe Val Arg Ala Ala Asp Ser Ser Arg Val His Glu Ser Ala
            130                 135                 140

Glu Lys Phe Val Glu Gly Phe Gln Asn Ala Arg Gln Gly Asp Pro His
145                 150                 155                 160

Ala Asn Pro His Gln Pro Ser Pro Arg Val Asp Val Val Ile Pro Glu
```

-continued

```
                            165                 170                 175
Gly Thr Ala Tyr Asn Asn Thr Leu Glu His Ser Ile Cys Thr Ala Phe
                180                 185                 190

Glu Ala Ser Thr Val Gly Asp Ala Ala Asp Asn Phe Thr Ala Val
            195                 200                 205

Phe Ala Pro Ala Ile Ala Lys Arg Leu Glu Ala Asp Leu Pro Gly Val
        210                 215                 220

Gln Leu Ser Ala Asp Val Val Asn Leu Met Ala Met Cys Pro Phe
225                 230                 235                 240

Glu Thr Val Ser Leu Thr Asp Asp Ala His Thr Leu Ser Pro Phe Cys
                245                 250                 255

Asp Leu Phe Thr Ala Ala Glu Trp Thr Gln Tyr Asn Tyr Leu Leu Ser
            260                 265                 270

Leu Asp Lys Tyr Tyr Gly Tyr Gly Gly Asn Pro Leu Gly Pro Val
        275                 280                 285

Gln Gly Val Gly Trp Ala Asn Glu Leu Ile Ala Arg Leu Thr Arg Ser
290                 295                 300

Pro Val His Asp His Thr Cys Val Asn Asn Thr Leu Asp Ala Asn Pro
305                 310                 315                 320

Ala Thr Phe Pro Leu Asn Ala Thr Leu Tyr Ala Asp Phe Ser His Asp
                325                 330                 335

Ser Asn Leu Val Ser Ile Phe Trp Ala Leu Gly Leu Tyr Asn Gly Thr
            340                 345                 350

Lys Pro Leu Ser Gln Thr Thr Val Glu Asp Ile Thr Arg Thr Asp Gly
        355                 360                 365

Tyr Ala Ala Trp Thr Val Pro Phe Ala Ala Arg Ala Tyr Ile Glu
        370                 375                 380

Met Met Gln Cys Arg Ala Glu Lys Gln Pro Leu Val Arg Val Leu Val
385                 390                 395                 400

Asn Asp Arg Val Met Pro Leu His Gly Cys Ala Val Asp Asn Leu Gly
                405                 410                 415

Arg Cys Lys Arg Asp Asp Phe Val Glu Gly Leu Ser Phe Ala Arg Ala
            420                 425                 430

Gly Gly Asn Trp Ala Glu Cys Phe
        435                 440
```

<210> SEQ ID NO 3
<211> LENGTH: 441
<212> TYPE: PRT
<213> ORGANISM: Asergillus niger var. awamori

<400> SEQUENCE: 3

```
Asn Gln Ser Thr Cys Asp Thr Val Asp Gln Gly Tyr Gln Cys Phe Ser
1               5                   10                  15

Glu Thr Ser His Leu Trp Gly Gln Tyr Ala Pro Phe Ser Leu Ala
                20                  25                  30

Asn Glu Ser Ala Ile Ser Pro Asp Val Pro Ala Gly Cys Arg Val Thr
            35                  40                  45

Phe Ala Gln Val Leu Ser Arg His Gly Ala Arg Tyr Pro Thr Glu Ser
        50                  55                  60

Lys Gly Lys Lys Tyr Ser Ala Leu Ile Glu Glu Ile Gln Gln Asn Val
65                  70                  75                  80

Thr Thr Phe Asp Gly Lys Tyr Ala Phe Leu Lys Thr Tyr Asn Tyr Ser
                85                  90                  95
```

```
Leu Gly Ala Asp Asp Leu Thr Pro Phe Gly Glu Gln Glu Leu Val Asn
            100                 105                 110
Ser Gly Ile Lys Phe Tyr Gln Arg Tyr Glu Ser Leu Thr Arg Asn Ile
        115                 120                 125
Ile Pro Phe Ile Arg Ser Ser Gly Ser Ser Arg Val Ile Ala Ser Gly
    130                 135                 140
Glu Lys Phe Ile Glu Gly Phe Gln Ser Thr Lys Leu Lys Asp Pro Arg
145                 150                 155                 160
Ala Gln Pro Gly Gln Ser Ser Pro Lys Ile Asp Val Ile Ser Glu
                165                 170                 175
Ala Ser Ser Asn Asn Thr Leu Asp Pro Gly Thr Cys Thr Val Phe
            180                 185                 190
Glu Asp Ser Glu Leu Ala Asp Thr Val Glu Ala Asn Phe Thr Ala Thr
        195                 200                 205
Phe Ala Pro Ser Ile Arg Gln Arg Leu Glu Asn Asp Leu Ser Gly Val
    210                 215                 220
Thr Leu Thr Asp Thr Glu Val Thr Tyr Leu Met Asp Met Cys Ser Phe
225                 230                 235                 240
Asp Thr Ile Ser Thr Ser Thr Val Asp Thr Lys Leu Ser Pro Phe Cys
                245                 250                 255
Asp Leu Phe Thr His Asp Glu Trp Ile His Tyr Asp Tyr Leu Gln Ser
            260                 265                 270
Leu Lys Lys Tyr Tyr Gly His Gly Ala Gly Asn Pro Leu Gly Pro Thr
        275                 280                 285
Gln Gly Val Gly Tyr Ala Asn Glu Leu Ile Ala Arg Leu Thr His Ser
    290                 295                 300
Pro Val His Asp Asp Thr Ser Ser Asn His Thr Leu Asp Ser Asn Pro
305                 310                 315                 320
Ala Thr Phe Pro Leu Asn Ser Thr Leu Tyr Ala Asp Phe Ser His Asp
                325                 330                 335
Asn Gly Ile Ile Ser Ile Leu Phe Ala Leu Gly Leu Tyr Asn Gly Thr
            340                 345                 350
Lys Pro Leu Ser Thr Thr Thr Val Glu Asn Ile Thr Gln Thr Asp Gly
        355                 360                 365
Phe Ser Ser Ala Trp Thr Val Pro Phe Ala Ser Arg Leu Tyr Val Glu
    370                 375                 380
Met Met Gln Cys Gln Ala Glu Gln Glu Pro Leu Val Arg Val Leu Val
385                 390                 395                 400
Asn Asp Arg Val Val Pro Leu His Gly Cys Pro Ile Asp Ala Leu Gly
                405                 410                 415
Arg Cys Thr Arg Asp Ser Phe Val Arg Gly Leu Ser Phe Ala Arg Ser
            420                 425                 430
Gly Gly Asp Trp Ala Glu Cys Ser Ala
        435                 440

<210> SEQ ID NO 4
<211> LENGTH: 441
<212> TYPE: PRT
<213> ORGANISM: Aspergillus niger T213

<400> SEQUENCE: 4

Asn Gln Ser Ser Cys Asp Thr Val Asp Gln Gly Tyr Gln Cys Phe Ser
1               5                   10                  15
Glu Thr Ser His Leu Trp Gly Gln Tyr Ala Pro Phe Phe Ser Leu Ala
            20                  25                  30
```

-continued

```
Asn Glu Ser Val Ile Ser Pro Asp Val Pro Ala Gly Cys Arg Val Thr
         35                  40                  45

Phe Ala Gln Val Leu Ser Arg His Gly Ala Arg Tyr Pro Thr Glu Ser
 50                  55                  60

Lys Gly Lys Lys Tyr Ser Ala Leu Ile Glu Glu Ile Gln Gln Asn Val
 65                  70                  75                  80

Thr Thr Phe Asp Gly Lys Tyr Ala Phe Leu Lys Thr Tyr Asn Tyr Ser
                 85                  90                  95

Leu Gly Ala Asp Asp Leu Thr Pro Phe Gly Glu Gln Glu Leu Val Asn
                100                 105                 110

Ser Gly Ile Lys Phe Tyr Gln Arg Tyr Glu Ser Leu Thr Arg Asn Ile
                115                 120                 125

Ile Pro Phe Ile Arg Ser Ser Gly Ser Ser Arg Val Ile Ala Ser Gly
130                 135                 140

Glu Lys Phe Ile Glu Gly Phe Gln Ser Thr Lys Leu Lys Asp Pro Arg
145                 150                 155                 160

Ala Gln Pro Gly Gln Ser Ser Pro Lys Ile Asp Val Val Ile Ser Glu
                165                 170                 175

Ala Ser Ser Asn Asn Thr Leu Asp Pro Gly Thr Cys Thr Val Phe
                180                 185                 190

Glu Asp Ser Glu Leu Ala Asp Thr Val Glu Ala Asn Phe Thr Ala Thr
                195                 200                 205

Phe Ala Pro Ser Ile Arg Gln Arg Leu Glu Asn Asp Leu Ser Gly Val
                210                 215                 220

Thr Leu Thr Asp Thr Glu Val Thr Tyr Leu Met Asp Met Cys Ser Phe
225                 230                 235                 240

Asp Thr Ile Ser Thr Ser Thr Val Asp Thr Lys Leu Ser Pro Phe Cys
                245                 250                 255

Asp Leu Phe Thr His Asp Glu Trp Ile His Tyr Asp Tyr Leu Arg Ser
                260                 265                 270

Leu Lys Lys Tyr Tyr Gly His Gly Ala Gly Asn Pro Leu Gly Pro Thr
                275                 280                 285

Gln Gly Val Gly Tyr Ala Asn Glu Leu Ile Ala Arg Leu Thr His Ser
                290                 295                 300

Pro Val His Asp Asp Thr Ser Ser Asn His Thr Leu Asp Ser Asn Pro
305                 310                 315                 320

Ala Thr Phe Pro Leu Asn Ser Thr Leu Tyr Ala Asp Phe Ser His Asp
                325                 330                 335

Asn Gly Ile Ile Ser Ile Leu Phe Ala Leu Gly Leu Tyr Asn Gly Thr
                340                 345                 350

Lys Pro Leu Ser Thr Thr Thr Val Glu Asn Ile Thr Gln Thr Asp Gly
                355                 360                 365

Phe Ser Ser Ala Trp Thr Val Pro Phe Ala Ser Arg Leu Tyr Val Glu
                370                 375                 380

Met Met Gln Cys Gln Ala Glu Gln Pro Leu Val Arg Val Leu Val
385                 390                 395                 400

Asn Asp Arg Val Val Pro Leu His Gly Cys Pro Ile Asp Ala Leu Gly
                405                 410                 415

Arg Cys Thr Arg Asp Ser Phe Val Arg Gly Leu Ser Phe Ala Arg Ser
                420                 425                 430

Gly Gly Asp Trp Ala Glu Cys Phe Ala
                435                 440
```

```
<210> SEQ ID NO 5
<211> LENGTH: 441
<212> TYPE: PRT
<213> ORGANISM: Aspergillus niger NRRL3135

<400> SEQUENCE: 5

Asn Gln Ser Ser Cys Asp Thr Val Asp Gln Gly Tyr Gln Cys Phe Ser
  1               5                  10                  15

Glu Thr Ser His Leu Trp Gly Gln Tyr Ala Pro Phe Phe Ser Leu Ala
             20                  25                  30

Asn Glu Ser Val Ile Ser Pro Glu Val Pro Ala Gly Cys Arg Val Thr
         35                  40                  45

Phe Ala Gln Val Leu Ser Arg His Gly Ala Arg Tyr Pro Thr Asp Ser
     50                  55                  60

Lys Gly Lys Lys Tyr Ser Ala Leu Ile Glu Glu Ile Gln Gln Asn Ala
 65                  70                  75                  80

Thr Thr Phe Asp Gly Lys Tyr Ala Phe Leu Lys Thr Tyr Asn Tyr Ser
                 85                  90                  95

Leu Gly Ala Asp Asp Leu Thr Pro Phe Gly Glu Gln Glu Leu Val Asn
            100                 105                 110

Ser Gly Ile Lys Phe Tyr Gln Arg Tyr Glu Ser Leu Thr Arg Asn Ile
        115                 120                 125

Val Pro Phe Ile Arg Ser Ser Gly Ser Ser Arg Val Ile Ala Ser Gly
    130                 135                 140

Lys Lys Phe Ile Glu Gly Phe Gln Ser Thr Lys Leu Lys Asp Pro Arg
145                 150                 155                 160

Ala Gln Pro Gly Gln Ser Ser Pro Lys Ile Asp Val Val Ile Ser Glu
                165                 170                 175

Ala Ser Ser Ser Asn Asn Thr Leu Asp Pro Gly Thr Cys Thr Val Phe
            180                 185                 190

Glu Asp Ser Glu Leu Ala Asp Thr Val Glu Ala Asn Phe Thr Ala Thr
        195                 200                 205

Phe Val Pro Ser Ile Arg Gln Arg Leu Glu Asn Asp Leu Ser Gly Val
    210                 215                 220

Thr Leu Thr Asp Thr Glu Val Thr Tyr Leu Met Asp Met Cys Ser Phe
225                 230                 235                 240

Asp Thr Ile Ser Thr Ser Thr Val Asp Thr Lys Leu Ser Pro Phe Cys
                245                 250                 255

Asp Leu Phe Thr His Asp Glu Trp Ile Asn Tyr Asp Tyr Leu Gln Ser
            260                 265                 270

Leu Lys Lys Tyr Tyr Gly His Gly Ala Gly Asn Pro Leu Gly Pro Thr
        275                 280                 285

Gln Gly Val Gly Tyr Ala Asn Glu Leu Ile Ala Arg Leu Thr His Ser
    290                 295                 300

Pro Val His Asp Asp Thr Ser Ser Asn His Thr Leu Asp Ser Ser Pro
305                 310                 315                 320

Ala Thr Phe Pro Leu Asn Ser Thr Leu Tyr Ala Asp Phe Ser His Asp
                325                 330                 335

Asn Gly Ile Ile Ser Ile Leu Phe Ala Leu Gly Leu Tyr Asn Gly Thr
            340                 345                 350

Lys Pro Leu Ser Thr Thr Thr Val Glu Asn Ile Thr Gln Thr Asp Gly
        355                 360                 365

Phe Ser Ser Ala Trp Thr Val Pro Phe Ala Ser Arg Leu Tyr Val Glu
    370                 375                 380
```

```
Met Met Gln Cys Gln Ala Glu Gln Glu Pro Leu Val Arg Val Leu Val
385                 390                 395                 400

Asn Asp Arg Val Val Pro Leu His Gly Cys Pro Val Asp Ala Leu Gly
            405                 410                 415

Arg Cys Thr Arg Asp Ser Phe Val Arg Gly Leu Ser Phe Ala Arg Ser
            420                 425                 430

Gly Gly Asp Trp Ala Glu Cys Phe Ala
        435                 440

<210> SEQ ID NO 6
<211> LENGTH: 440
<212> TYPE: PRT
<213> ORGANISM: Aspergillus fumigatus 13073

<400> SEQUENCE: 6

Gly Ser Lys Ser Cys Asp Thr Val Asp Leu Gly Tyr Gln Cys Ser Pro
1               5                   10                  15

Ala Thr Ser His Leu Trp Gly Gln Tyr Ser Pro Phe Phe Ser Leu Glu
            20                  25                  30

Asp Glu Leu Ser Val Ser Ser Lys Leu Pro Lys Asp Cys Arg Ile Thr
        35                  40                  45

Leu Val Gln Val Leu Ser Arg His Gly Ala Arg Tyr Pro Thr Ser Ser
    50                  55                  60

Lys Ser Lys Lys Tyr Lys Lys Leu Val Thr Ala Ile Gln Ala Asn Ala
65                  70                  75                  80

Thr Asp Phe Lys Gly Lys Phe Ala Phe Leu Lys Thr Tyr Asn Tyr Thr
                85                  90                  95

Leu Gly Ala Asp Asp Leu Thr Pro Phe Gly Glu Gln Leu Val Asn
            100                 105                 110

Ser Gly Ile Lys Phe Tyr Gln Arg Tyr Lys Ala Leu Ala Arg Ser Val
            115                 120                 125

Val Pro Phe Ile Arg Ala Ser Gly Ser Asp Arg Val Ile Ala Ser Gly
    130                 135                 140

Glu Lys Phe Ile Glu Gly Phe Gln Gln Ala Lys Leu Ala Asp Pro Gly
145                 150                 155                 160

Ala Thr Asn Arg Ala Ala Pro Ala Ile Ser Val Ile Pro Glu Ser
            165                 170                 175

Glu Thr Phe Asn Asn Thr Leu Asp His Gly Val Cys Thr Lys Phe Glu
            180                 185                 190

Ala Ser Gln Leu Gly Asp Glu Val Ala Ala Asn Phe Thr Ala Leu Phe
        195                 200                 205

Ala Pro Asp Ile Arg Ala Arg Ala Glu Lys His Leu Pro Gly Val Thr
    210                 215                 220

Leu Thr Asp Glu Asp Val Val Ser Leu Met Asp Met Cys Ser Phe Asp
225                 230                 235                 240

Thr Val Ala Arg Thr Ser Asp Ala Ser Gln Leu Ser Pro Phe Cys Gln
                245                 250                 255

Leu Phe Thr His Asn Glu Trp Lys Lys Tyr Asn Tyr Leu Gln Ser Leu
            260                 265                 270

Gly Lys Tyr Tyr Gly Tyr Gly Ala Gly Asn Pro Leu Gly Pro Ala Gln
        275                 280                 285

Gly Ile Gly Phe Thr Asn Glu Leu Ile Ala Arg Leu Thr Arg Ser Pro
    290                 295                 300

Val Gln Asp His Thr Ser Thr Asn Ser Thr Leu Val Ser Asn Pro Ala
```

```
                305                 310                 315                 320
Thr Phe Pro Leu Asn Ala Thr Met Tyr Val Asp Phe Ser His Asp Asn
                325                 330                 335

Ser Met Val Ser Ile Phe Phe Ala Leu Gly Leu Tyr Asn Gly Thr Glu
            340                 345                 350

Pro Leu Ser Arg Thr Ser Val Glu Ser Ala Lys Glu Leu Asp Gly Tyr
            355                 360                 365

Ser Ala Ser Trp Val Val Pro Phe Gly Ala Arg Ala Tyr Phe Glu Thr
        370                 375                 380

Met Gln Cys Lys Ser Glu Lys Glu Pro Leu Val Arg Ala Leu Ile Asn
385                 390                 395                 400

Asp Arg Val Val Pro Leu His Gly Cys Asp Val Asp Lys Leu Gly Arg
                405                 410                 415

Cys Lys Leu Asn Asp Phe Val Lys Gly Leu Ser Trp Ala Arg Ser Gly
                420                 425                 430

Gly Asn Trp Gly Glu Cys Phe Ser
            435                 440

<210> SEQ ID NO 7
<211> LENGTH: 440
<212> TYPE: PRT
<213> ORGANISM: Aspergillus fumigatus 32722

<400> SEQUENCE: 7

Gly Ser Lys Ser Cys Asp Thr Val Asp Leu Gly Tyr Gln Cys Ser Pro
1               5                   10                  15

Ala Thr Ser His Leu Trp Gly Gln Tyr Ser Pro Phe Phe Ser Leu Glu
            20                  25                  30

Asp Glu Leu Ser Val Ser Ser Lys Leu Pro Lys Asp Cys Arg Ile Thr
        35                  40                  45

Leu Val Gln Val Leu Ser Arg His Gly Ala Arg Tyr Pro Thr Ser Ser
    50                  55                  60

Lys Ser Lys Lys Tyr Lys Lys Leu Val Thr Ala Ile Gln Ala Asn Ala
65                  70                  75                  80

Thr Asp Phe Lys Gly Lys Phe Ala Phe Leu Lys Thr Tyr Asn Tyr Thr
                85                  90                  95

Leu Gly Ala Asp Asp Leu Thr Pro Phe Gly Glu Gln Gln Leu Val Asn
            100                 105                 110

Ser Gly Ile Lys Phe Tyr Gln Arg Tyr Lys Ala Leu Ala Arg Ser Val
        115                 120                 125

Val Pro Phe Ile Arg Ala Ser Gly Ser Asp Arg Val Ile Ala Ser Gly
    130                 135                 140

Glu Lys Phe Ile Glu Gly Phe Gln Gln Ala Lys Leu Ala Asp Pro Gly
145                 150                 155                 160

Ala Thr Asn Arg Ala Ala Pro Ala Ile Ser Val Ile Ile Pro Glu Ser
                165                 170                 175

Glu Thr Phe Asn Asn Thr Leu Asp His Gly Val Cys Thr Lys Phe Glu
            180                 185                 190

Ala Ser Gln Leu Gly Asp Glu Val Ala Ala Asn Phe Thr Ala Leu Phe
        195                 200                 205

Ala Pro Asp Ile Arg Ala Arg Ala Glu Lys His Leu Pro Gly Val Thr
    210                 215                 220

Leu Thr Asp Glu Asp Val Val Ser Leu Met Asp Met Cys Ser Phe Asp
225                 230                 235                 240
```

```
Thr Val Ala Arg Thr Ser Asp Ala Ser Gln Leu Ser Pro Phe Cys Gln
            245                 250                 255

Leu Phe Thr His Asn Glu Trp Lys Lys Tyr Asn Tyr Leu Gln Ser Leu
            260                 265                 270

Gly Lys Tyr Tyr Gly Tyr Gly Ala Gly Asn Pro Leu Gly Pro Ala Gln
            275                 280                 285

Gly Ile Gly Phe Thr Asn Glu Leu Ile Ala Arg Leu Thr Arg Ser Pro
            290                 295                 300

Val Gln Asp His Thr Ser Thr Asn Ser Thr Leu Val Ser Asn Pro Ala
305                 310                 315                 320

Thr Phe Pro Leu Asn Ala Thr Met Tyr Val Asp Phe Ser His Asp Asn
            325                 330                 335

Ser Met Val Ser Ile Phe Phe Ala Leu Gly Leu Tyr Asn Gly Thr Gly
            340                 345                 350

Pro Leu Ser Arg Thr Ser Val Glu Ser Ala Lys Glu Leu Asp Gly Tyr
            355                 360                 365

Ser Ala Ser Trp Val Val Pro Phe Gly Ala Arg Ala Tyr Phe Glu Thr
            370                 375                 380

Met Gln Cys Lys Ser Glu Lys Glu Pro Leu Val Arg Ala Leu Ile Asn
385                 390                 395                 400

Asp Arg Val Val Pro Leu His Gly Cys Asp Val Asp Lys Leu Gly Arg
            405                 410                 415

Cys Lys Leu Asn Asp Phe Val Lys Gly Leu Ser Trp Ala Arg Ser Gly
            420                 425                 430

Gly Asn Trp Gly Glu Cys Phe Ser
            435                 440

<210> SEQ ID NO 8
<211> LENGTH: 440
<212> TYPE: PRT
<213> ORGANISM: Aspergillus fumigatus 58128

<400> SEQUENCE: 8

Gly Ser Lys Ser Cys Asp Thr Val Asp Leu Gly Tyr Gln Cys Ser Pro
1               5                   10                  15

Ala Thr Ser His Leu Trp Gly Gln Tyr Ser Pro Phe Phe Ser Leu Glu
            20                  25                  30

Asp Glu Leu Ser Val Ser Ser Lys Leu Pro Lys Asp Cys Arg Ile Thr
            35                  40                  45

Leu Val Gln Val Leu Ser Arg His Gly Ala Arg Tyr Pro Thr Ser Ser
    50                  55                  60

Lys Ser Lys Lys Tyr Lys Lys Leu Val Thr Ala Ile Gln Ala Asn Ala
65                  70                  75                  80

Thr Asp Phe Lys Gly Lys Phe Ala Phe Leu Lys Thr Tyr Asn Tyr Thr
            85                  90                  95

Leu Gly Ala Asp Asp Leu Thr Pro Phe Gly Glu Gln Gln Leu Val Asn
            100                 105                 110

Ser Gly Ile Lys Phe Tyr Gln Arg Tyr Lys Ala Leu Ala Arg Ser Val
            115                 120                 125

Val Pro Phe Ile Arg Ala Ser Gly Ser Asp Arg Val Ile Ala Ser Gly
            130                 135                 140

Glu Lys Phe Ile Glu Gly Phe Gln Gln Ala Lys Leu Ala Asp Pro Gly
145                 150                 155                 160

Ala Thr Asn Arg Ala Ala Pro Ala Ile Ser Val Ile Ile Pro Glu Ser
            165                 170                 175
```

```
Glu Thr Phe Asn Asn Thr Leu Asp His Gly Val Cys Thr Lys Phe Glu
            180                 185                 190

Ala Ser Gln Leu Gly Asp Glu Val Ala Ala Asn Phe Thr Ala Leu Phe
        195                 200                 205

Ala Pro Asp Ile Arg Ala Arg Ala Glu Lys His Leu Pro Gly Val Thr
    210                 215                 220

Leu Thr Asp Glu Asp Val Val Ser Leu Met Asp Met Cys Ser Phe Asp
225                 230                 235                 240

Thr Val Ala Arg Thr Ser Asp Ala Ser Gln Leu Ser Pro Phe Cys Gln
                245                 250                 255

Leu Phe Thr His Asn Glu Trp Lys Lys Tyr Asn Tyr Leu Gln Ser Leu
            260                 265                 270

Gly Lys Tyr Tyr Gly Tyr Gly Ala Gly Asn Pro Leu Gly Pro Ala Gln
        275                 280                 285

Gly Ile Gly Phe Thr Asn Glu Leu Ile Ala Arg Leu Thr Arg Ser Pro
    290                 295                 300

Val Gln Asp His Thr Ser Thr Asn Ser Thr Leu Val Ser Asn Pro Ala
305                 310                 315                 320

Thr Phe Pro Leu Asn Ala Thr Met Tyr Val Asp Phe Ser His Asp Asn
                325                 330                 335

Ser Met Val Ser Ile Phe Phe Ala Leu Gly Leu Tyr Asn Gly Thr Glu
            340                 345                 350

Pro Leu Ser Arg Thr Ser Val Glu Ser Ala Lys Glu Leu Asp Gly Tyr
        355                 360                 365

Ser Ala Ser Trp Val Val Pro Phe Gly Ala Arg Ala Tyr Phe Glu Thr
    370                 375                 380

Met Gln Cys Lys Ser Glu Lys Glu Ser Leu Val Arg Ala Leu Ile Asn
385                 390                 395                 400

Asp Arg Val Val Pro Leu His Gly Cys Asp Val Asp Lys Leu Gly Arg
                405                 410                 415

Cys Lys Leu Asn Asp Phe Val Lys Gly Leu Ser Trp Ala Arg Ser Gly
            420                 425                 430

Gly Asn Trp Gly Glu Cys Phe Ser
        435                 440

<210> SEQ ID NO 9
<211> LENGTH: 440
<212> TYPE: PRT
<213> ORGANISM: Aspergillus fumigatus 26906

<400> SEQUENCE: 9

Gly Ser Lys Ser Cys Asp Thr Val Asp Leu Gly Tyr Gln Cys Ser Pro
1               5                   10                  15

Ala Thr Ser His Leu Trp Gly Gln Tyr Ser Pro Phe Ser Leu Glu
            20                  25                  30

Asp Glu Leu Ser Val Ser Ser Lys Leu Pro Lys Asp Cys Arg Ile Thr
        35                  40                  45

Leu Val Gln Val Leu Ser Arg His Gly Ala Arg Tyr Pro Thr Ser Ser
    50                  55                  60

Lys Ser Lys Lys Tyr Lys Lys Leu Val Thr Ala Ile Gln Ala Asn Ala
65                  70                  75                  80

Thr Asp Phe Lys Gly Lys Phe Ala Phe Leu Lys Thr Tyr Asn Tyr Thr
                85                  90                  95

Leu Gly Ala Asp Asp Leu Thr Ala Phe Gly Glu Gln Gln Leu Val Asn
```

```
                    100                 105                 110
Ser Gly Ile Lys Phe Tyr Gln Arg Tyr Lys Ala Leu Ala Arg Ser Val
                115                 120                 125

Val Pro Phe Ile Arg Ala Ser Gly Ser Asp Arg Val Ile Ala Ser Gly
130                 135                 140

Glu Lys Phe Ile Glu Gly Phe Gln Gln Ala Lys Leu Ala Asp Pro Gly
145                 150                 155                 160

Ala Thr Asn Arg Ala Ala Pro Ala Ile Ser Val Ile Pro Glu Ser
                165                 170                 175

Glu Thr Phe Asn Asn Thr Leu Asp His Gly Val Cys Thr Lys Phe Glu
                180                 185                 190

Ala Ser Gln Leu Gly Asp Glu Val Ala Ala Asn Phe Thr Ala Leu Phe
                195                 200                 205

Ala Pro Asp Ile Arg Ala Arg Ala Lys Lys His Leu Pro Gly Val Thr
                210                 215                 220

Leu Thr Asp Glu Asp Val Val Ser Leu Met Asp Met Cys Ser Phe Asp
225                 230                 235                 240

Thr Val Ala Arg Thr Ser Asp Ala Ser Gln Leu Ser Pro Phe Cys Gln
                245                 250                 255

Leu Phe Thr His Asn Glu Trp Lys Lys Tyr Asn Tyr Leu Gln Ser Leu
                260                 265                 270

Gly Lys Tyr Tyr Gly Tyr Gly Ala Gly Asn Pro Leu Gly Pro Ala Gln
                275                 280                 285

Gly Ile Gly Phe Thr Asn Glu Leu Ile Ala Arg Leu Thr Arg Ser Pro
                290                 295                 300

Val Gln Asp His Thr Ser Thr Asn Ser Thr Leu Val Ser Asn Pro Ala
305                 310                 315                 320

Thr Phe Pro Leu Asn Ala Thr Met Tyr Val Asp Phe Ser His Asp Asn
                325                 330                 335

Ser Met Val Ser Ile Phe Phe Ala Leu Gly Leu Tyr Asn Gly Thr Glu
                340                 345                 350

Pro Leu Ser Arg Thr Ser Val Glu Ser Ala Lys Glu Leu Asp Gly Tyr
                355                 360                 365

Ser Ala Ser Trp Val Val Pro Phe Gly Ala Arg Ala Tyr Phe Glu Thr
370                 375                 380

Met Gln Cys Lys Ser Glu Lys Glu Pro Leu Val Arg Ala Leu Ile Asn
385                 390                 395                 400

Asp Arg Val Val Pro Leu His Gly Cys Asp Val Asp Lys Leu Gly Arg
                405                 410                 415

Cys Lys Leu Asn Asp Phe Val Lys Gly Leu Ser Trp Ala Arg Ser Gly
                420                 425                 430

Gly Asn Trp Gly Glu Cys Phe Ser
                435                 440

<210> SEQ ID NO 10
<211> LENGTH: 440
<212> TYPE: PRT
<213> ORGANISM: Aspergillus fumigatus 32239

<400> SEQUENCE: 10

Gly Ser Lys Ala Cys Asp Thr Val Glu Leu Gly Tyr Gln Cys Ser Pro
1               5                   10                  15

Gly Thr Ser His Leu Trp Gly Gln Tyr Ser Pro Phe Phe Ser Leu Glu
                20                  25                  30
```

-continued

```
Asp Glu Leu Ser Val Ser Ser Asp Leu Pro Lys Asp Cys Arg Val Thr
        35                  40                  45

Phe Val Gln Val Leu Ser Arg His Gly Ala Arg Tyr Pro Thr Ala Ser
        50                  55                  60

Lys Ser Lys Lys Tyr Lys Lys Leu Val Thr Ala Ile Gln Lys Asn Ala
 65              70                  75                  80

Thr Glu Phe Lys Gly Lys Phe Ala Phe Leu Glu Thr Tyr Asn Tyr Thr
                85                  90                  95

Leu Gly Ala Asp Asp Leu Thr Pro Phe Gly Glu Gln Gln Met Val Asn
            100                 105                 110

Ser Gly Ile Lys Phe Tyr Gln Lys Tyr Lys Ala Leu Ala Gly Ser Val
            115                 120                 125

Val Pro Phe Ile Arg Ser Ser Gly Ser Asp Arg Val Ile Ala Ser Gly
        130                 135                 140

Glu Lys Phe Ile Glu Gly Phe Gln Gln Ala Asn Val Ala Asp Pro Gly
145             150                 155                 160

Ala Thr Asn Arg Ala Ala Pro Val Ile Ser Val Ile Pro Glu Ser
            165                 170                 175

Glu Thr Tyr Asn Asn Thr Leu Asp His Ser Val Cys Thr Asn Phe Glu
            180                 185                 190

Ala Ser Glu Leu Gly Asp Glu Val Glu Ala Asn Phe Thr Ala Leu Phe
        195                 200                 205

Ala Pro Ala Ile Arg Ala Arg Ile Glu Lys His Leu Pro Gly Val Gln
    210                 215                 220

Leu Thr Asp Asp Val Val Ser Leu Met Asp Met Cys Ser Phe Asp
225                 230                 235                 240

Thr Val Ala Arg Thr Ala Asp Ala Ser Glu Leu Ser Pro Phe Cys Ala
                245                 250                 255

Ile Phe Thr His Asn Glu Trp Lys Lys Tyr Asp Tyr Leu Gln Ser Leu
            260                 265                 270

Gly Lys Tyr Tyr Gly Tyr Gly Ala Gly Asn Pro Leu Gly Pro Ala Gln
        275                 280                 285

Gly Ile Gly Phe Thr Asn Glu Leu Ile Ala Arg Leu Thr Asn Ser Pro
    290                 295                 300

Val Gln Asp His Thr Ser Thr Asn Ser Thr Leu Asp Ser Asp Pro Ala
305             310                 315                 320

Thr Phe Pro Leu Asn Ala Thr Ile Tyr Val Asp Phe Ser His Asp Asn
                325                 330                 335

Gly Met Ile Pro Ile Phe Phe Ala Met Gly Leu Tyr Asn Gly Thr Glu
            340                 345                 350

Pro Leu Ser Gln Thr Ser Glu Glu Ser Thr Lys Glu Ser Asn Gly Tyr
        355                 360                 365

Ser Ala Ser Trp Ala Val Pro Phe Gly Ala Arg Ala Tyr Phe Glu Thr
    370                 375                 380

Met Gln Cys Lys Ser Glu Lys Glu Pro Leu Val Arg Ala Leu Ile Asn
385             390                 395                 400

Asp Arg Val Val Pro Leu His Gly Cys Ala Val Asp Lys Leu Gly Arg
                405                 410                 415

Cys Lys Leu Lys Asp Phe Val Lys Gly Leu Ser Trp Ala Arg Ser Gly
            420                 425                 430

Gly Asn Ser Glu Gln Ser Phe Ser
            435                 440
```

```
<210> SEQ ID NO 11
<211> LENGTH: 439
<212> TYPE: PRT
<213> ORGANISM: Emericella nidulans

<400> SEQUENCE: 11

Gln Asn His Ser Cys Asn Thr Ala Asp Gly Gly Tyr Gln Cys Phe Pro
1               5                   10                  15

Asn Val Ser His Val Trp Gly Gln Tyr Ser Pro Tyr Phe Ser Ile Glu
            20                  25                  30

Gln Glu Ser Ala Ile Ser Glu Asp Val Pro His Gly Cys Glu Val Thr
        35                  40                  45

Phe Val Gln Val Leu Ser Arg His Gly Ala Arg Tyr Pro Thr Glu Ser
    50                  55                  60

Lys Ser Lys Ala Tyr Ser Gly Leu Ile Glu Ala Ile Gln Lys Asn Ala
65                  70                  75                  80

Thr Ser Phe Trp Gly Gln Tyr Ala Phe Leu Glu Ser Tyr Asn Tyr Thr
                85                  90                  95

Leu Gly Ala Asp Asp Leu Thr Ile Phe Gly Glu Asn Gln Met Val Asp
            100                 105                 110

Ser Gly Ala Lys Phe Tyr Arg Arg Tyr Lys Asn Leu Ala Arg Lys Asn
        115                 120                 125

Thr Pro Phe Ile Arg Ala Ser Gly Ser Asp Arg Val Val Ala Ser Ala
    130                 135                 140

Glu Lys Phe Ile Asn Gly Phe Arg Lys Ala Gln Leu His Asp His Gly
145                 150                 155                 160

Ser Gly Gln Ala Thr Pro Val Val Asn Val Ile Ile Pro Glu Ile Asp
                165                 170                 175

Gly Phe Asn Asn Thr Leu Asp His Ser Thr Cys Val Ser Phe Glu Asn
            180                 185                 190

Asp Glu Arg Ala Asp Glu Ile Glu Ala Asn Phe Thr Ala Ile Met Gly
        195                 200                 205

Pro Pro Ile Arg Lys Arg Leu Glu Asn Asp Leu Pro Gly Ile Lys Leu
    210                 215                 220

Thr Asn Glu Asn Val Ile Tyr Leu Met Asp Met Cys Ser Phe Asp Thr
225                 230                 235                 240

Met Ala Arg Thr Ala His Gly Thr Glu Leu Ser Pro Phe Cys Ala Ile
                245                 250                 255

Phe Thr Glu Lys Glu Trp Leu Gln Tyr Asp Tyr Leu Gln Ser Leu Ser
            260                 265                 270

Lys Tyr Tyr Gly Tyr Gly Ala Gly Ser Pro Leu Gly Pro Ala Gln Gly
        275                 280                 285

Ile Gly Phe Thr Asn Glu Leu Ile Ala Arg Leu Thr Gln Ser Pro Val
    290                 295                 300

Gln Asp Asn Thr Ser Thr Asn His Thr Leu Asp Ser Asn Pro Ala Thr
305                 310                 315                 320

Phe Pro Leu Asp Arg Lys Leu Tyr Ala Asp Phe Ser His Asp Asn Ser
                325                 330                 335

Met Ile Ser Ile Phe Phe Ala Met Gly Leu Tyr Asn Gly Thr Gln Pro
            340                 345                 350

Leu Ser Met Asp Ser Val Glu Ser Ile Gln Glu Met Asp Gly Tyr Ala
        355                 360                 365

Ala Ser Trp Thr Val Pro Phe Gly Ala Arg Ala Tyr Phe Glu Leu Met
    370                 375                 380
```

```
Gln Cys Glu Lys Lys Glu Pro Leu Val Arg Val Leu Asn Asp Arg
385                 390                 395                 400

Val Val Pro Leu His Gly Cys Ala Val Asp Lys Phe Gly Arg Cys Thr
            405                 410                 415

Leu Asp Asp Trp Val Glu Gly Leu Asn Phe Ala Arg Ser Gly Gly Asn
                420                 425                 430

Trp Lys Thr Cys Phe Thr Leu
            435

<210> SEQ ID NO 12
<211> LENGTH: 443
<212> TYPE: PRT
<213> ORGANISM: Talaromyces Thermophilus

<400> SEQUENCE: 12

Asp Ser His Ser Cys Asn Thr Val Glu Gly Gly Tyr Gln Cys Arg Pro
1               5                   10                  15

Glu Ile Ser His Ser Trp Gly Gln Tyr Ser Pro Phe Phe Ser Leu Ala
            20                  25                  30

Asp Gln Ser Glu Ile Ser Pro Asp Val Pro Gln Asn Cys Lys Ile Thr
        35                  40                  45

Phe Val Gln Leu Leu Ser Arg His Gly Ala Arg Tyr Pro Thr Ser Ser
    50                  55                  60

Lys Thr Glu Leu Tyr Ser Gln Leu Ile Ser Arg Ile Gln Lys Thr Ala
65                  70                  75                  80

Thr Ala Tyr Lys Gly Tyr Tyr Ala Phe Leu Lys Asp Tyr Arg Tyr Gln
                85                  90                  95

Leu Gly Ala Asn Asp Leu Thr Pro Phe Gly Glu Asn Gln Met Ile Gln
            100                 105                 110

Leu Gly Ile Lys Phe Tyr Asn His Tyr Lys Ser Leu Ala Arg Asn Ala
        115                 120                 125

Val Pro Phe Val Arg Cys Ser Gly Ser Asp Arg Val Ile Ala Ser Gly
    130                 135                 140

Arg Leu Phe Ile Glu Gly Phe Gln Ser Ala Lys Val Leu Asp Pro His
145                 150                 155                 160

Ser Asp Lys His Asp Ala Pro Pro Thr Ile Asn Val Ile Ile Glu Glu
                165                 170                 175

Gly Pro Ser Tyr Asn Asn Thr Leu Asp Thr Gly Ser Cys Pro Val Phe
            180                 185                 190

Glu Asp Ser Ser Gly Gly His Asp Ala Gln Glu Lys Phe Ala Lys Gln
        195                 200                 205

Phe Ala Pro Ala Ile Leu Glu Lys Ile Lys Asp His Leu Pro Gly Val
    210                 215                 220

Asp Leu Ala Val Ser Asp Val Pro Tyr Leu Met Asp Leu Cys Pro Phe
225                 230                 235                 240

Glu Thr Leu Ala Arg Asn His Thr Asp Thr Leu Ser Pro Phe Cys Ala
                245                 250                 255

Leu Ser Thr Gln Glu Glu Trp Gln Ala Tyr Asp Tyr Gln Ser Leu
            260                 265                 270

Gly Lys Tyr Tyr Gly Asn Gly Gly Asn Pro Leu Gly Pro Ala Gln
        275                 280                 285

Gly Val Gly Phe Val Asn Glu Leu Ile Ala Arg Met Thr His Ser Pro
    290                 295                 300

Val Gln Asp Tyr Thr Thr Val Asn His Thr Leu Asp Ser Asn Pro Ala
305                 310                 315                 320
```

-continued

```
Thr Phe Pro Leu Asn Ala Thr Leu Tyr Ala Asp Phe Ser His Asp Asn
            325                 330                 335

Thr Met Thr Ser Ile Phe Ala Ala Leu Gly Leu Tyr Asn Gly Thr Ala
            340                 345                 350

Lys Leu Ser Thr Thr Glu Ile Lys Ser Ile Glu Glu Thr Asp Gly Tyr
            355                 360                 365

Ser Ala Ala Trp Thr Val Pro Phe Gly Gly Arg Ala Tyr Ile Glu Met
    370                 375                 380

Met Gln Cys Asp Asp Ser Asp Glu Pro Val Val Arg Val Leu Val Asn
385                 390                 395                 400

Asp Arg Val Val Pro Leu His Gly Cys Glu Val Asp Ser Leu Gly Arg
                405                 410                 415

Cys Lys Arg Asp Asp Phe Val Arg Gly Leu Ser Phe Ala Arg Gln Gly
                420                 425                 430

Gly Asn Trp Glu Gly Cys Tyr Ala Ala Ser Glu
            435                 440

<210> SEQ ID NO 13
<211> LENGTH: 466
<212> TYPE: PRT
<213> ORGANISM: Myceliophthora thermophila

<400> SEQUENCE: 13

Glu Ser Arg Pro Cys Asp Thr Pro Asp Leu Gly Phe Gln Cys Gly Thr
1               5                   10                  15

Ala Ile Ser His Phe Trp Gly Gln Tyr Ser Pro Tyr Phe Ser Val Pro
            20                  25                  30

Ser Glu Leu Asp Ala Ser Ile Pro Asp Asp Cys Glu Val Thr Phe Ala
        35                  40                  45

Gln Val Leu Ser Arg His Gly Ala Arg Ala Pro Thr Leu Lys Arg Ala
    50                  55                  60

Ala Ser Tyr Val Asp Leu Ile Asp Arg Ile His His Gly Ala Ile Ser
65                  70                  75                  80

Tyr Gly Pro Gly Tyr Glu Phe Leu Arg Thr Tyr Asp Tyr Thr Leu Gly
                85                  90                  95

Ala Asp Glu Leu Thr Arg Thr Gly Gln Gln Gln Met Val Asn Ser Gly
            100                 105                 110

Ile Lys Phe Tyr Arg Arg Tyr Arg Ala Leu Ala Arg Lys Ser Ile Pro
        115                 120                 125

Phe Val Arg Thr Ala Gly Gln Asp Arg Val Val His Ser Ala Glu Asn
    130                 135                 140

Phe Thr Gln Gly Phe His Ser Ala Leu Leu Ala Asp Arg Gly Ser Thr
145                 150                 155                 160

Val Arg Pro Thr Leu Pro Tyr Asp Met Val Val Ile Pro Glu Thr Ala
                165                 170                 175

Gly Ala Asn Asn Thr Leu His Asn Asp Leu Cys Thr Ala Phe Glu Glu
            180                 185                 190

Gly Pro Tyr Ser Thr Ile Gly Asp Asp Ala Gln Asp Thr Tyr Leu Ser
        195                 200                 205

Thr Phe Ala Gly Pro Ile Thr Ala Arg Val Asn Ala Asn Leu Pro Gly
    210                 215                 220

Ala Asn Leu Thr Asp Ala Asp Thr Val Ala Leu Met Asp Leu Cys Pro
225                 230                 235                 240

Phe Glu Thr Val Ala Ser Ser Ser Ser Asp Pro Ala Thr Ala Asp Ala
```

```
                    245                 250                 255
Gly Gly Gly Asn Gly Arg Pro Leu Ser Pro Phe Cys Arg Leu Phe Ser
            260                 265                 270

Glu Ser Glu Trp Arg Ala Tyr Asp Tyr Leu Gln Ser Val Gly Lys Trp
        275                 280                 285

Tyr Gly Tyr Gly Pro Gly Asn Pro Leu Gly Pro Thr Gln Gly Val Gly
    290                 295                 300

Phe Val Asn Glu Leu Leu Ala Arg Leu Ala Gly Val Pro Val Arg Asp
305                 310                 315                 320

Gly Thr Ser Thr Asn Arg Thr Leu Asp Gly Asp Pro Arg Thr Phe Pro
                325                 330                 335

Leu Gly Arg Pro Leu Tyr Ala Asp Phe Ser His Asp Asn Asp Met Met
            340                 345                 350

Gly Val Leu Gly Ala Leu Gly Ala Tyr Asp Gly Val Pro Pro Leu Asp
        355                 360                 365

Lys Thr Ala Arg Arg Asp Pro Glu Glu Leu Gly Gly Tyr Ala Ala Ser
    370                 375                 380

Trp Ala Val Pro Phe Ala Ala Arg Ile Tyr Val Glu Lys Met Arg Cys
385                 390                 395                 400

Ser Gly Gly Gly Gly Gly Gly Gly Glu Gly Arg Gln Glu Lys
                405                 410                 415

Asp Glu Glu Met Val Arg Val Leu Val Asn Asp Arg Val Met Thr Leu
            420                 425                 430

Lys Gly Cys Gly Ala Asp Glu Arg Gly Met Cys Thr Leu Glu Arg Phe
        435                 440                 445

Ile Glu Ser Met Ala Phe Ala Arg Gly Asn Gly Lys Trp Asp Leu Cys
    450                 455                 460

Phe Ala
465

<210> SEQ ID NO 14
<211> LENGTH: 441
<212> TYPE: PRT
<213> ORGANISM: Artificial Sequence
<220> FEATURE:
<223> OTHER INFORMATION: Synthetic

<400> SEQUENCE: 14

Asn Ser His Ser Cys Asp Thr Val Asp Gly Gly Tyr Gln Cys Phe Pro
1               5                   10                  15

Glu Ile Ser His Leu Trp Gly Gln Tyr Ser Pro Tyr Phe Ser Leu Glu
            20                  25                  30

Asp Glu Ser Ala Ile Ser Pro Asp Val Pro Asp Asp Cys Arg Val Thr
        35                  40                  45

Phe Val Gln Val Leu Ser Arg His Gly Ala Arg Tyr Pro Thr Ser Ser
    50                  55                  60

Lys Ser Lys Ala Tyr Ser Ala Leu Ile Glu Ala Ile Gln Lys Asn Ala
65                  70                  75                  80

Thr Ala Phe Lys Gly Lys Tyr Ala Phe Leu Lys Thr Tyr Asn Tyr Thr
                85                  90                  95

Leu Gly Ala Asp Asp Leu Thr Pro Phe Gly Glu Asn Gln Met Val Asn
            100                 105                 110

Ser Gly Ile Lys Phe Tyr Arg Arg Tyr Lys Ala Leu Ala Arg Lys Ile
        115                 120                 125

Val Pro Phe Ile Arg Ala Ser Gly Ser Asp Arg Val Ile Ala Ser Ala
```

-continued

```
                    130                 135                 140
Glu Lys Phe Ile Glu Gly Phe Gln Ser Ala Lys Leu Ala Asp Pro Gly
145                 150                 155                 160

Ser Gln Pro His Gln Ala Ser Pro Val Ile Asp Val Ile Pro Glu
                165                 170                 175

Gly Ser Gly Tyr Asn Asn Thr Leu Asp His Gly Thr Cys Thr Ala Phe
                180                 185                 190

Glu Asp Ser Glu Leu Gly Asp Val Glu Ala Asn Phe Thr Ala Leu
                195                 200                 205

Phe Ala Pro Ala Ile Arg Ala Arg Leu Glu Ala Asp Leu Pro Gly Val
210                 215                 220

Thr Leu Thr Asp Glu Asp Val Val Tyr Leu Met Asp Met Cys Pro Phe
225                 230                 235                 240

Glu Thr Val Ala Arg Thr Ser Asp Ala Thr Glu Leu Ser Pro Phe Cys
                245                 250                 255

Ala Leu Phe Thr His Asp Glu Trp Arg Gln Tyr Asp Tyr Leu Gln Ser
                260                 265                 270

Leu Gly Lys Tyr Tyr Gly Tyr Gly Ala Gly Asn Pro Leu Gly Pro Ala
                275                 280                 285

Gln Gly Val Gly Phe Ala Asn Glu Leu Ile Ala Arg Leu Thr Arg Ser
290                 295                 300

Pro Val Gln Asp His Thr Ser Thr Asn His Thr Leu Asp Ser Asn Pro
305                 310                 315                 320

Ala Thr Phe Pro Leu Asn Ala Thr Leu Tyr Ala Asp Phe Ser His Asp
                325                 330                 335

Asn Ser Met Ile Ser Ile Phe Phe Ala Leu Gly Leu Tyr Asn Gly Thr
                340                 345                 350

Ala Pro Leu Ser Thr Thr Ser Val Glu Ser Ile Glu Glu Thr Asp Gly
                355                 360                 365

Tyr Ser Ala Ser Trp Thr Val Pro Phe Gly Ala Arg Ala Tyr Val Glu
370                 375                 380

Met Met Gln Cys Gln Ala Glu Lys Glu Pro Leu Val Arg Val Leu Val
385                 390                 395                 400

Asn Asp Arg Val Val Pro Leu His Gly Cys Ala Val Asp Lys Leu Gly
                405                 410                 415

Arg Cys Lys Arg Asp Asp Phe Val Glu Gly Leu Ser Phe Ala Arg Ser
                420                 425                 430

Gly Gly Asn Trp Ala Glu Cys Phe Ala
                435                 440
```

<210> SEQ ID NO 15
<211> LENGTH: 1426
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (12)..(1412)
<220> FEATURE:
<221> NAME/KEY: sig_peptide
<222> LOCATION: (12)..(89)
<220> FEATURE:
<221> NAME/KEY: mat_peptide
<222> LOCATION: (90)..()

<400> SEQUENCE: 15
tatatgaatt c atg ggc gtg ttc gtc gtg cta ctg tcc att gcc acc ttg      50

```
            Met Gly Val Phe Val Val Leu Leu Ser Ile Ala Thr Leu
                -25             -20                 -15 ttc ggt tcc aca tcc ggt acc gcc ttg ggt cct cgt ggt aat tct cac     98
Phe Gly Ser Thr Ser Gly Thr Ala Leu Gly Pro Arg Gly Asn Ser His
            -10             -5                  -1  1 tct tgt gac act gtt gac ggt ggt tac caa tgt ttc cca gaa att tct    146
Ser Cys Asp Thr Val Asp Gly Gly Tyr Gln Cys Phe Pro Glu Ile Ser
 5                  10                  15 cac ttg tgg ggt caa tac tct cca tac ttc tct ttg gaa gac gaa tct    194
His Leu Trp Gly Gln Tyr Ser Pro Tyr Phe Ser Leu Glu Asp Glu Ser
 20                 25                  30                  35 gct att tct cca gac gtt cca gac gac tgt aga gtt act ttc gtt caa    242
Ala Ile Ser Pro Asp Val Pro Asp Asp Cys Arg Val Thr Phe Val Gln
                40                  45                  50 gtt ttg tct aga cac ggt gct aga tac cca act tct tct aag tct aag    290
Val Leu Ser Arg His Gly Ala Arg Tyr Pro Thr Ser Ser Lys Ser Lys
            55                  60                  65 gct tac tct gct ttg att gaa gct att caa aag aac gct act gct ttc    338
Ala Tyr Ser Ala Leu Ile Glu Ala Ile Gln Lys Asn Ala Thr Ala Phe
        70                  75                  80 aag ggt aag tac gct ttc ttg aag act tac aac tac act ttg ggt gct    386
Lys Gly Lys Tyr Ala Phe Leu Lys Thr Tyr Asn Tyr Thr Leu Gly Ala
    85                  90                  95 gac gac ttg act cca ttc ggt gaa aac caa atg gtt aac tct ggt att    434
Asp Asp Leu Thr Pro Phe Gly Glu Asn Gln Met Val Asn Ser Gly Ile
100                 105                 110                 115 aag ttc tac aga aga tac aag gct ttg gct aga aag att gtt cca ttc    482
Lys Phe Tyr Arg Arg Tyr Lys Ala Leu Ala Arg Lys Ile Val Pro Phe
                120                 125                 130 att aga gct tct ggt tct gac aga gtt att gct tct gct gaa aag ttc    530
Ile Arg Ala Ser Gly Ser Asp Arg Val Ile Ala Ser Ala Glu Lys Phe
            135                 140                 145 att gaa ggt ttc caa tct gct aag ttg gct gac cca ggt tct caa cca    578
Ile Glu Gly Phe Gln Ser Ala Lys Leu Ala Asp Pro Gly Ser Gln Pro
        150                 155                 160 cac caa gct tct cca gtt att gac gtt att att cca gaa gga tcc ggt    626
His Gln Ala Ser Pro Val Ile Asp Val Ile Ile Pro Glu Gly Ser Gly
    165                 170                 175 tac aac aac act ttg gac cac ggt act tgt act gct ttc gaa gac tct    674
Tyr Asn Asn Thr Leu Asp His Gly Thr Cys Thr Ala Phe Glu Asp Ser
180                 185                 190                 195 gaa ttg ggt gac gac gtt gaa gct aac ttc act gct ttg ttc gct cca    722
Glu Leu Gly Asp Asp Val Glu Ala Asn Phe Thr Ala Leu Phe Ala Pro
                200                 205                 210 gct att aga gct aga ttg gaa gct gac ttg cca ggt gtt act ttg act    770
Ala Ile Arg Ala Arg Leu Glu Ala Asp Leu Pro Gly Val Thr Leu Thr
            215                 220                 225 gac gaa gac gtt gtt tac ttg atg gac atg tgt cca ttc gaa act gtt    818
Asp Glu Asp Val Val Tyr Leu Met Asp Met Cys Pro Phe Glu Thr Val
        230                 235                 240 gct aga act tct gac gct act gaa ttg tct cca ttc tgt gct ttg ttc    866
Ala Arg Thr Ser Asp Ala Thr Glu Leu Ser Pro Phe Cys Ala Leu Phe
    245                 250                 255 act cac gac gaa tgg aga caa tac gac tac ttg caa tct ttg ggt aag    914
Thr His Asp Glu Trp Arg Gln Tyr Asp Tyr Leu Gln Ser Leu Gly Lys
260                 265                 270                 275 tac tac ggt tac ggt gct ggt aac cca ttg ggt cca gct caa ggt gtt    962
Tyr Tyr Gly Tyr Gly Ala Gly Asn Pro Leu Gly Pro Ala Gln Gly Val
                280                 285                 290
```

-continued

```
ggt ttc gct aac gaa ttg att gct aga ttg act aga tct cca gtt caa      1010
Gly Phe Ala Asn Glu Leu Ile Ala Arg Leu Thr Arg Ser Pro Val Gln
            295                 300                 305 gac cac act tct act aac cac act ttg gac tct aac cca gct act ttc      1058
Asp His Thr Ser Thr Asn His Thr Leu Asp Ser Asn Pro Ala Thr Phe
        310                 315                 320 cca ttg aac gct act ttg tac gct gac ttc tct cac gac aac tct atg      1106
Pro Leu Asn Ala Thr Leu Tyr Ala Asp Phe Ser His Asp Asn Ser Met
    325                 330                 335 att tct att ttc ttc gct ttg ggt ttg tac aac ggt act gct cca ttg      1154
Ile Ser Ile Phe Phe Ala Leu Gly Leu Tyr Asn Gly Thr Ala Pro Leu
340                 345                 350                 355 tct act act tct gtt gaa tct att gaa gaa act gac ggt tac tct gct      1202
Ser Thr Thr Ser Val Glu Ser Ile Glu Glu Thr Asp Gly Tyr Ser Ala
                360                 365                 370 tct tgg act gtt cca ttc ggt gct aga gct tac gtt gaa atg atg caa      1250
Ser Trp Thr Val Pro Phe Gly Ala Arg Ala Tyr Val Glu Met Met Gln
            375                 380                 385 tgt caa gct gaa aag gaa cca ttg gtt aga gtt ttg gtt aac gac aga      1298
Cys Gln Ala Glu Lys Glu Pro Leu Val Arg Val Leu Val Asn Asp Arg
        390                 395                 400 gtt gtt cca ttg cac ggt tgt gct gtt gac aag ttg ggt aga tgt aag      1346
Val Val Pro Leu His Gly Cys Ala Val Asp Lys Leu Gly Arg Cys Lys
    405                 410                 415 aga gac gac ttc gtt gaa ggt ttg tct ttc gct aga tct ggt ggt aac      1394
Arg Asp Asp Phe Val Glu Gly Leu Ser Phe Ala Arg Ser Gly Gly Asn
420                 425                 430                 435 tgg gct gaa tgt ttc gct taagaattca tata                              1426
Trp Ala Glu Cys Phe Ala
                440
```

<210> SEQ ID NO 16
<211> LENGTH: 467
<212> TYPE: PRT
<213> ORGANISM: Artificial Sequence
<220> FEATURE:
<223> OTHER INFORMATION: Synthetic

<400> SEQUENCE: 16

```
Met Gly Val Phe Val Val Leu Leu Ser Ile Ala Thr Leu Phe Gly Ser
    -25                 -20                 -15

Thr Ser Gly Thr Ala Leu Gly Pro Arg Gly Asn Ser His Ser Cys Asp
-10                  -5                  -1   1                 5

Thr Val Asp Gly Gly Tyr Gln Cys Phe Pro Glu Ile Ser His Leu Trp
                10                  15                  20

Gly Gln Tyr Ser Pro Tyr Phe Ser Leu Glu Asp Glu Ser Ala Ile Ser
            25                  30                  35

Pro Asp Val Pro Asp Asp Cys Arg Val Thr Phe Val Gln Val Leu Ser
        40                  45                  50

Arg His Gly Ala Arg Tyr Pro Thr Ser Ser Lys Ser Lys Ala Tyr Ser
55                  60                  65                  70

Ala Leu Ile Glu Ala Ile Gln Lys Asn Ala Thr Ala Phe Lys Gly Lys
                75                  80                  85

Tyr Ala Phe Leu Lys Thr Tyr Asn Tyr Thr Leu Gly Ala Asp Asp Leu
            90                  95                  100

Thr Pro Phe Gly Glu Asn Gln Met Val Asn Ser Gly Ile Lys Phe Tyr
        105                 110                 115

Arg Arg Tyr Lys Ala Leu Ala Arg Lys Ile Val Pro Phe Ile Arg Ala
    120                 125                 130
```

```
Ser Gly Ser Asp Arg Val Ile Ala Ser Ala Glu Lys Phe Ile Glu Gly
135                 140                 145                 150

Phe Gln Ser Ala Lys Leu Ala Asp Pro Gly Ser Gln Pro His Gln Ala
            155                 160                 165

Ser Pro Val Ile Asp Val Ile Pro Glu Gly Ser Gly Tyr Asn Asn
            170                 175                 180

Thr Leu Asp His Gly Thr Cys Thr Ala Phe Glu Asp Ser Glu Leu Gly
            185                 190                 195

Asp Asp Val Glu Ala Asn Phe Thr Ala Leu Phe Ala Pro Ala Ile Arg
200                 205                 210

Ala Arg Leu Glu Ala Asp Leu Pro Gly Val Thr Leu Thr Asp Glu Asp
215                 220                 225                 230

Val Val Tyr Leu Met Asp Met Cys Pro Phe Glu Thr Val Ala Arg Thr
            235                 240                 245

Ser Asp Ala Thr Glu Leu Ser Pro Phe Cys Ala Leu Phe Thr His Asp
            250                 255                 260

Glu Trp Arg Gln Tyr Asp Tyr Leu Gln Ser Leu Gly Lys Tyr Tyr Gly
            265                 270                 275

Tyr Gly Ala Gly Asn Pro Leu Gly Pro Ala Gln Gly Val Gly Phe Ala
280                 285                 290

Asn Glu Leu Ile Ala Arg Leu Thr Arg Ser Pro Val Gln Asp His Thr
295                 300                 305                 310

Ser Thr Asn His Thr Leu Asp Ser Asn Pro Ala Thr Phe Pro Leu Asn
            315                 320                 325

Ala Thr Leu Tyr Ala Asp Phe Ser His Asp Asn Ser Met Ile Ser Ile
            330                 335                 340

Phe Phe Ala Leu Gly Leu Tyr Asn Gly Thr Ala Pro Leu Ser Thr Thr
            345                 350                 355

Ser Val Glu Ser Ile Glu Glu Thr Asp Gly Tyr Ser Ala Ser Trp Thr
            360                 365                 370

Val Pro Phe Gly Ala Arg Ala Tyr Val Glu Met Met Gln Cys Gln Ala
375                 380                 385                 390

Glu Lys Glu Pro Leu Val Arg Val Leu Val Asn Asp Arg Val Val Pro
            395                 400                 405

Leu His Gly Cys Ala Val Asp Lys Leu Gly Arg Cys Lys Arg Asp Asp
            410                 415                 420

Phe Val Glu Gly Leu Ser Phe Ala Arg Ser Gly Gly Asn Trp Ala Glu
            425                 430                 435

Cys Phe Ala
    440

<210> SEQ ID NO 17
<211> LENGTH: 422
<212> TYPE: PRT
<213> ORGANISM: Paxillus involutus phyA1

<400> SEQUENCE: 17

Ser Val Pro Lys Asn Thr Ala Pro Thr Phe Pro Ile Pro Glu Ser Glu
1               5                   10                  15

Gln Arg Asn Trp Ser Pro Tyr Ser Pro Tyr Phe Pro Leu Ala Glu Tyr
            20                  25                  30

Lys Ala Pro Pro Ala Gly Cys Gln Ile Asn Gln Val Asn Ile Ile Gln
            35                  40                  45

Arg His Gly Ala Arg Phe Pro Thr Ser Gly Ala Thr Thr Arg Ile Lys
```

```
                50                  55                  60
Ala Gly Leu Thr Lys Leu Gln Gly Val Gln Asn Phe Thr Asp Ala Lys
 65                  70                  75                  80

Phe Asn Phe Ile Lys Ser Phe Lys Tyr Asp Leu Gly Asn Ser Asp Leu
                 85                  90                  95

Val Pro Phe Gly Ala Ala Gln Ser Phe Asp Ala Gly Gln Glu Ala Phe
                100                 105                 110

Ala Arg Tyr Ser Lys Leu Val Ser Lys Asn Asn Leu Pro Phe Ile Arg
                115                 120                 125

Ala Asp Gly Ser Asp Arg Val Asp Ser Ala Thr Asn Trp Thr Ala
130                 135                 140

Gly Phe Ala Ser Ala Ser His Asn Thr Val Gln Pro Lys Leu Asn Leu
145                 150                 155                 160

Ile Leu Pro Gln Thr Gly Asn Asp Thr Leu Glu Asp Asn Met Cys Pro
                165                 170                 175

Ala Ala Gly Asp Ser Asp Pro Gln Val Asn Ala Trp Leu Ala Val Ala
                180                 185                 190

Phe Pro Ser Ile Thr Ala Arg Leu Asn Ala Ala Pro Ser Val Asn
                195                 200                 205

Leu Thr Asp Thr Asp Ala Phe Asn Leu Val Ser Leu Cys Ala Phe Leu
210                 215                 220

Thr Val Ser Lys Glu Lys Ser Asp Phe Cys Thr Leu Phe Glu Gly
225                 230                 235                 240

Ile Pro Gly Ser Phe Glu Ala Phe Ala Tyr Gly Gly Asp Leu Asp Lys
                245                 250                 255

Phe Tyr Gly Thr Gly Tyr Gly Gln Glu Leu Gly Pro Val Gln Gly Val
                260                 265                 270

Gly Tyr Val Asn Glu Leu Ile Ala Arg Leu Thr Asn Ser Ala Val Arg
                275                 280                 285

Asp Asn Thr Gln Thr Asn Arg Thr Leu Asp Ala Ser Pro Val Thr Phe
290                 295                 300

Pro Leu Asn Lys Thr Phe Tyr Ala Asp Phe Ser His Asp Asn Leu Met
305                 310                 315                 320

Val Ala Val Phe Ser Ala Met Gly Leu Phe Arg Gln Pro Ala Pro Leu
                325                 330                 335

Ser Thr Ser Val Pro Asn Pro Trp Arg Thr Trp Arg Thr Ser Ser Leu
                340                 345                 350

Val Pro Phe Ser Gly Arg Met Val Val Glu Arg Leu Ser Cys Phe Gly
                355                 360                 365

Thr Thr Lys Val Arg Val Leu Val Gln Asp Gln Val Gln Pro Leu Glu
                370                 375                 380

Phe Cys Gly Gly Asp Arg Asn Gly Leu Cys Thr Leu Ala Lys Phe Val
385                 390                 395                 400

Glu Ser Gln Thr Phe Ala Arg Ser Asp Gly Ala Gly Asp Phe Glu Lys
                405                 410                 415

Cys Phe Ala Thr Ser Ala
                420

<210> SEQ ID NO 18
<211> LENGTH: 422
<212> TYPE: PRT
<213> ORGANISM: Paxillus involutus phyA2

<400> SEQUENCE: 18
```

```
Ser Val Pro Arg Asn Ile Ala Pro Lys Phe Ser Ile Pro Glu Ser Glu
1               5                   10                  15

Gln Arg Asn Trp Ser Pro Tyr Ser Pro Tyr Phe Pro Leu Ala Glu Tyr
            20                  25                  30

Lys Ala Pro Pro Ala Gly Cys Glu Ile Asn Gln Val Asn Ile Ile Gln
        35                  40                  45

Arg His Gly Ala Arg Phe Pro Thr Ser Gly Ala Ala Thr Arg Ile Lys
    50                  55                  60

Ala Gly Leu Ser Lys Leu Gln Ser Val Gln Asn Phe Thr Asp Pro Lys
65                  70                  75                  80

Phe Asp Phe Ile Lys Ser Phe Thr Tyr Asp Leu Gly Thr Ser Asp Leu
                85                  90                  95

Val Pro Phe Gly Ala Ala Gln Ser Phe Asp Ala Gly Leu Glu Val Phe
                100                 105                 110

Ala Arg Tyr Ser Lys Leu Val Ser Ser Asp Asn Leu Pro Phe Ile Arg
            115                 120                 125

Ser Asp Gly Ser Asp Arg Val Val Asp Thr Ala Thr Asn Trp Thr Ala
    130                 135                 140

Gly Phe Ala Ser Ala Ser Arg Asn Ala Ile Gln Pro Lys Leu Asp Leu
145                 150                 155                 160

Ile Leu Pro Gln Thr Gly Asn Asp Thr Leu Glu Asp Asn Met Cys Pro
                165                 170                 175

Ala Ala Gly Glu Ser Asp Pro Gln Val Asp Ala Trp Leu Ala Ser Ala
            180                 185                 190

Phe Pro Ser Val Thr Ala Gln Leu Asn Ala Ala Pro Gly Ala Asn
                195                 200                 205

Leu Thr Asp Ala Asp Ala Phe Asn Leu Val Ser Leu Cys Pro Phe Met
    210                 215                 220

Thr Val Ser Lys Glu Gln Lys Ser Asp Phe Cys Thr Leu Phe Glu Gly
225                 230                 235                 240

Ile Pro Gly Ser Phe Glu Ala Phe Ala Tyr Ala Gly Asp Leu Asp Lys
                245                 250                 255

Phe Tyr Gly Thr Gly Tyr Gly Gln Ala Leu Gly Pro Val Gln Gly Val
                260                 265                 270

Gly Tyr Ile Asn Glu Leu Leu Ala Arg Leu Thr Asn Ser Ala Val Asn
                275                 280                 285

Asp Asn Thr Gln Thr Asn Arg Thr Leu Asp Ala Ala Pro Asp Thr Phe
    290                 295                 300

Pro Leu Asn Lys Thr Met Tyr Ala Asp Phe Ser His Asp Asn Leu Met
305                 310                 315                 320

Val Ala Val Phe Ser Ala Met Gly Leu Phe Arg Gln Ser Ala Pro Leu
                325                 330                 335

Ser Thr Ser Thr Pro Asp Pro Asn Arg Thr Trp Leu Thr Ser Ser Val
                340                 345                 350

Val Pro Phe Ser Ala Arg Met Ala Val Glu Arg Leu Ser Cys Ala Gly
                355                 360                 365

Thr Thr Lys Val Arg Val Leu Val Gln Asp Gln Val Gln Pro Leu Glu
    370                 375                 380

Phe Cys Gly Gly Asp Gln Asp Gly Leu Cys Ala Leu Asp Lys Phe Val
385                 390                 395                 400

Glu Ser Gln Ala Tyr Ala Arg Ser Gly Gly Ala Gly Asp Phe Glu Lys
                405                 410                 415

Cys Leu Ala Thr Thr Val
```

-continued

420

<210> SEQ ID NO 19
<211> LENGTH: 420
<212> TYPE: PRT
<213> ORGANISM: Trametes Pubescens

<400> SEQUENCE: 19

His Ile Pro Leu Arg Asp Thr Ser Ala Cys Leu Asp Val Thr Arg Asp
1               5                   10                  15

Val Gln Gln Ser Trp Ser Met Tyr Ser Pro Tyr Phe Pro Ala Ala Thr
            20                  25                  30

Tyr Val Ala Pro Pro Ala Ser Cys Gln Ile Asn Gln Val His Ile Ile
        35                  40                  45

Gln Arg His Gly Ala Arg Phe Pro Thr Ser Gly Ala Ala Lys Arg Ile
    50                  55                  60

Gln Thr Ala Val Ala Lys Leu Lys Ala Ala Ser Asn Tyr Thr Asp Pro
65                  70                  75                  80

Leu Leu Ala Phe Val Thr Asn Tyr Thr Tyr Ser Leu Gly Gln Asp Ser
                85                  90                  95

Leu Val Glu Leu Gly Ala Thr Gln Ser Ser Glu Ala Gly Gln Glu Ala
            100                 105                 110

Phe Thr Arg Tyr Ser Ser Leu Val Ser Ala Asp Glu Leu Pro Phe Val
        115                 120                 125

Arg Ala Ser Gly Ser Asp Arg Val Val Ala Thr Ala Asn Asn Trp Thr
    130                 135                 140

Ala Gly Phe Ala Leu Ala Ser Ser Asn Ser Ile Thr Pro Val Leu Ser
145                 150                 155                 160

Val Ile Ile Ser Glu Ala Gly Asn Asp Thr Leu Asp Asp Asn Met Cys
                165                 170                 175

Pro Ala Ala Gly Asp Ser Asp Pro Gln Val Asn Gln Trp Leu Ala Gln
            180                 185                 190

Phe Ala Pro Pro Met Thr Ala Arg Leu Asn Ala Gly Ala Pro Gly Ala
        195                 200                 205

Asn Leu Thr Asp Thr Asp Thr Tyr Asn Leu Leu Thr Leu Cys Pro Phe
    210                 215                 220

Glu Thr Val Ala Thr Glu Arg Arg Ser Glu Phe Cys Asp Ile Tyr Glu
225                 230                 235                 240

Glu Leu Gln Ala Glu Asp Ala Phe Ala Tyr Asn Ala Asp Leu Asp Lys
                245                 250                 255

Phe Tyr Gly Thr Gly Tyr Gly Gln Pro Leu Gly Pro Val Gln Gly Val
            260                 265                 270

Gly Tyr Ile Asn Glu Leu Ile Ala Arg Leu Thr Ala Gln Asn Val Ser
        275                 280                 285

Asp His Thr Gln Thr Asn Ser Thr Leu Asp Ser Ser Pro Glu Thr Phe
    290                 295                 300

Pro Leu Asn Arg Thr Leu Tyr Ala Asp Phe Ser His Asp Asn Gln Met
305                 310                 315                 320

Val Ala Ile Phe Ser Ala Met Gly Leu Phe Asn Gln Ser Ala Pro Leu
                325                 330                 335

Asp Pro Thr Thr Pro Asp Pro Ala Arg Thr Phe Leu Val Lys Lys Ile
            340                 345                 350

Val Pro Phe Ser Ala Arg Met Val Val Glu Arg Leu Asp Cys Gly Gly
        355                 360                 365

```
Ala Gln Ser Val Arg Leu Leu Val Asn Asp Ala Val Gln Pro Leu Ala
        370                 375                 380

Phe Cys Gly Ala Asp Thr Ser Gly Val Cys Thr Leu Asp Ala Phe Val
385                 390                 395                 400

Glu Ser Gln Ala Tyr Ala Arg Asn Asp Gly Glu Gly Asp Phe Glu Lys
                405                 410                 415

Cys Phe Ala Thr
            420

<210> SEQ ID NO 20
<211> LENGTH: 435
<212> TYPE: PRT
<213> ORGANISM: Agrocybe peidades

<400> SEQUENCE: 20

Gly Gly Val Val Gln Ala Thr Phe Val Gln Pro Phe Phe Pro Pro Gln
1               5                   10                  15

Ile Gln Asp Ser Trp Ala Ala Tyr Thr Pro Tyr Tyr Pro Val Gln Ala
            20                  25                  30

Tyr Thr Pro Pro Lys Asp Cys Lys Ile Thr Gln Val Asn Ile Ile
        35                  40                  45

Gln Arg His Gly Ala Arg Phe Pro Thr Ser Gly Ala Gly Thr Arg Ile
50                  55                  60

Gln Ala Ala Val Lys Lys Leu Gln Ser Ala Lys Thr Tyr Thr Asp Pro
65                  70                  75                  80

Arg Leu Asp Phe Leu Thr Asn Tyr Thr Tyr Thr Leu Gly His Asp Asp
                85                  90                  95

Leu Val Pro Phe Gly Ala Leu Gln Ser Ser Gln Ala Gly Glu Glu Thr
            100                 105                 110

Phe Gln Arg Tyr Ser Phe Leu Val Ser Lys Glu Asn Leu Pro Phe Val
        115                 120                 125

Arg Ala Ser Ser Ser Asn Arg Val Val Asp Ser Ala Thr Asn Trp Thr
130                 135                 140

Glu Gly Phe Ser Ala Ala Ser His His Val Leu Asn Pro Ile Leu Phe
145                 150                 155                 160

Val Ile Leu Ser Glu Ser Leu Asn Asp Thr Leu Asp Asp Ala Met Cys
                165                 170                 175

Pro Asn Ala Gly Ser Ser Asp Pro Gln Thr Gly Ile Trp Thr Ser Ile
            180                 185                 190

Tyr Gly Thr Pro Ile Ala Asn Arg Leu Asn Gln Gln Ala Pro Gly Ala
        195                 200                 205

Asn Ile Thr Ala Ala Asp Val Ser Asn Leu Ile Pro Leu Cys Ala Phe
210                 215                 220

Glu Thr Ile Val Lys Glu Thr Pro Ser Pro Phe Cys Asn Leu Phe Thr
225                 230                 235                 240

Pro Glu Glu Phe Ala Gln Phe Glu Tyr Phe Gly Asp Leu Asp Lys Phe
                245                 250                 255

Tyr Gly Thr Gly Tyr Gly Gln Pro Leu Gly Pro Val Gln Gly Val Gly
            260                 265                 270

Tyr Ile Asn Glu Leu Leu Ala Arg Leu Thr Glu Met Pro Val Arg Asp
        275                 280                 285

Asn Thr Gln Thr Asn Arg Thr Leu Asp Ser Ser Pro Leu Thr Phe Pro
        290                 295                 300

Leu Asp Arg Ser Ile Tyr Ala Asp Leu Ser His Asp Asn Gln Met Ile
305                 310                 315                 320
```

```
Ala Ile Phe Ser Ala Met Gly Leu Phe Asn Gln Ser Ser Pro Leu Asp
            325                 330                 335

Pro Ser Phe Pro Asn Pro Lys Arg Thr Trp Val Thr Ser Arg Leu Thr
            340                 345                 350

Pro Phe Ser Ala Arg Met Val Thr Glu Arg Leu Leu Cys Gln Arg Asp
            355                 360                 365

Gly Thr Gly Ser Gly Gly Pro Ser Arg Ile Met Arg Asn Gly Asn Val
            370                 375                 380

Gln Thr Phe Val Arg Ile Leu Val Asn Asp Ala Leu Gln Pro Leu Lys
385                 390                 395                 400

Phe Cys Gly Gly Asp Met Asp Ser Leu Cys Thr Leu Glu Ala Phe Val
            405                 410                 415

Glu Ser Gln Lys Tyr Ala Arg Glu Asp Gly Gln Gly Asp Phe Glu Lys
            420                 425                 430

Cys Phe Asp
        435

<210> SEQ ID NO 21
<211> LENGTH: 419
<212> TYPE: PRT
<213> ORGANISM: Peniophora lycii

<400> SEQUENCE: 21

Ser Thr Gln Phe Ser Phe Val Ala Ala Gln Leu Pro Ile Pro Ala Gln
1                 5                  10                  15

Asn Thr Ser Asn Trp Gly Pro Tyr Asp Pro Phe Phe Pro Val Glu Pro
            20                  25                  30

Tyr Ala Ala Pro Pro Glu Gly Cys Thr Val Thr Gln Val Asn Leu Ile
            35                  40                  45

Gln Arg His Gly Ala Arg Trp Pro Thr Ser Gly Ala Arg Ser Arg Gln
        50                  55                  60

Val Ala Ala Val Ala Lys Ile Gln Met Ala Arg Pro Phe Thr Asp Pro
65                  70                  75                  80

Lys Tyr Glu Phe Leu Asn Asp Phe Val Tyr Lys Phe Gly Val Ala Asp
                85                  90                  95

Leu Leu Pro Phe Gly Ala Asn Gln Ser His Gln Thr Gly Thr Asp Met
            100                 105                 110

Tyr Thr Arg Tyr Ser Thr Leu Phe Glu Gly Gly Asp Val Pro Phe Val
            115                 120                 125

Arg Ala Ala Gly Asp Gln Arg Val Val Asp Ser Ser Thr Asn Trp Thr
        130                 135                 140

Ala Gly Phe Gly Asp Ala Ser Gly Glu Thr Val Leu Pro Thr Leu Gln
145                 150                 155                 160

Val Val Leu Gln Glu Glu Gly Asn Cys Thr Leu Cys Asn Asn Met Cys
                165                 170                 175

Pro Asn Glu Val Asp Gly Asp Glu Ser Thr Thr Trp Leu Gly Val Phe
            180                 185                 190

Ala Pro Asn Ile Thr Ala Arg Leu Asn Ala Ala Pro Ser Ala Asn
            195                 200                 205

Leu Ser Asp Ser Asp Ala Leu Thr Leu Met Asp Met Cys Pro Phe Asp
        210                 215                 220

Thr Leu Ser Ser Gly Asn Ala Ser Pro Phe Cys Asp Leu Phe Thr Ala
225                 230                 235                 240

Glu Glu Tyr Val Ser Tyr Glu Tyr Tyr Asp Leu Asp Lys Tyr Tyr
```

```
                        245                 250                 255
Gly Thr Gly Pro Gly Asn Ala Leu Gly Pro Val Gln Gly Val Gly Tyr
                260                 265                 270

Val Asn Glu Leu Leu Ala Arg Leu Thr Gly Gln Ala Val Arg Asp Glu
            275                 280                 285

Thr Gln Thr Asn Arg Thr Leu Asp Ser Asp Pro Ala Thr Phe Pro Leu
        290                 295                 300

Asn Arg Thr Phe Tyr Ala Asp Phe Ser His Asp Asn Thr Met Val Pro
305                 310                 315                 320

Ile Phe Ala Ala Leu Gly Leu Phe Asn Ala Thr Ala Leu Asp Pro Leu
                325                 330                 335

Lys Pro Asp Glu Asn Arg Leu Trp Val Asp Ser Lys Leu Val Pro Phe
            340                 345                 350

Ser Gly His Met Thr Val Glu Lys Leu Ala Cys Ser Gly Lys Glu Ala
        355                 360                 365

Val Arg Val Leu Val Asn Asp Ala Val Gln Pro Leu Glu Phe Cys Gly
    370                 375                 380

Gly Val Asp Gly Val Cys Glu Leu Ser Ala Phe Val Glu Ser Gln Thr
385                 390                 395                 400

Tyr Ala Arg Glu Asn Gly Gln Gly Asp Phe Ala Lys Cys Gly Phe Val
                405                 410                 415

Pro Ser Glu

<210> SEQ ID NO 22
<211> LENGTH: 369
<212> TYPE: PRT
<213> ORGANISM: Artificial Sequence
<220> FEATURE:
<223> OTHER INFORMATION: Synthetic

<400> SEQUENCE: 22

Ser Pro Arg Thr Ala Ala Gln Leu Pro Ile Pro Gln Gln Trp Ser Pro
1               5                   10                  15

Tyr Ser Pro Tyr Phe Pro Val Ala Tyr Ala Pro Ala Gly Cys Gln
            20                  25                  30

Ile Gln Val Asn Ile Ile Gln Arg His Gly Ala Arg Phe Pro Thr Ser
        35                  40                  45

Gly Ala Ala Thr Arg Ile Gln Ala Ala Val Ala Lys Leu Gln Ser Ala
    50                  55                  60

Thr Asp Pro Lys Leu Asp Phe Leu Asn Thr Tyr Leu Gly Asp Asp Leu
65                  70                  75                  80

Val Pro Phe Gly Ala Gln Ser Ser Gln Ala Gly Gln Glu Ala Phe Thr
                85                  90                  95

Arg Tyr Ser Leu Val Ser Asp Asn Leu Pro Phe Val Arg Ala Ser Gly
            100                 105                 110

Ser Asp Arg Val Val Asp Ser Ala Thr Asn Trp Thr Ala Gly Phe Ala
        115                 120                 125

Ala Ser Asn Thr Pro Leu Val Ile Leu Ser Glu Gly Asn Asp Thr Leu
    130                 135                 140

Asp Asp Asn Met Cys Pro Ala Gly Asp Ser Asp Pro Gln Asn Trp Leu
145                 150                 155                 160

Ala Val Phe Ala Pro Pro Ile Thr Ala Arg Leu Asn Ala Ala Pro
                165                 170                 175

Gly Ala Asn Leu Thr Asp Asp Ala Asn Leu Leu Cys Pro Phe Glu Thr
            180                 185                 190
```

```
Val Ser Glu Ser Phe Cys Asp Leu Phe Glu Pro Glu Phe Ala Phe
            195                 200                 205

Tyr Gly Asp Leu Asp Lys Phe Tyr Gly Thr Gly Tyr Gly Gln Pro Leu
            210                 215                 220

Gly Pro Val Gln Gly Val Gly Tyr Ile Asn Glu Leu Leu Ala Arg Leu
225                 230                 235                 240

Thr Gln Ala Val Arg Asp Asn Thr Gln Thr Asn Arg Thr Leu Asp Ser
                245                 250                 255

Ser Pro Thr Phe Pro Leu Asn Arg Thr Phe Tyr Ala Asp Phe Ser His
            260                 265                 270

Asp Asn Gln Met Val Ala Ile Phe Ser Ala Met Gly Leu Phe Asn Gln
            275                 280                 285

Ser Ala Pro Leu Asp Pro Ser Pro Asp Pro Asn Arg Thr Trp Val Thr
    290                 295                 300

Ser Lys Leu Val Pro Phe Ser Ala Arg Met Val Val Glu Arg Leu Cys
305                 310                 315                 320

Gly Thr Val Arg Val Leu Val Asn Asp Ala Val Gln Pro Leu Glu Phe
                325                 330                 335

Cys Gly Gly Asp Asp Gly Cys Thr Leu Asp Ala Phe Val Glu Ser Gln
            340                 345                 350

Tyr Ala Arg Glu Asp Gly Gln Gly Asp Phe Glu Lys Cys Phe Ala Thr
            355                 360                 365

Pro

<210> SEQ ID NO 23
<211> LENGTH: 440
<212> TYPE: PRT
<213> ORGANISM: Thermomyces lanuginosus

<400> SEQUENCE: 23

Asn Val Asp Ile Ala Arg His Trp Gly Gln Tyr Ser Pro Phe Phe Ser
1               5                   10                  15

Leu Ala Glu Val Ser Glu Ile Ser Pro Ala Val Pro Lys Gly Cys Arg
                20                  25                  30

Val Glu Phe Val Gln Val Leu Ser Arg His Gly Ala Arg Tyr Pro Thr
            35                  40                  45

Ala His Lys Ser Glu Val Tyr Ala Glu Leu Leu Gln Arg Ile Gln Asp
    50                  55                  60

Thr Ala Thr Glu Phe Lys Gly Asp Phe Ala Phe Leu Arg Asp Tyr Ala
65                  70                  75                  80

Tyr His Leu Gly Ala Asp Asn Leu Thr Arg Phe Gly Glu Glu Gln Met
                85                  90                  95

Met Glu Ser Gly Arg Gln Phe Tyr His Arg Tyr Arg Glu Gln Ala Arg
            100                 105                 110

Glu Ile Val Pro Phe Val Arg Ala Ala Gly Ser Ala Arg Val Ile Ala
            115                 120                 125

Ser Ala Glu Phe Phe Asn Arg Gly Phe Gln Asp Ala Lys Asp Arg Asp
    130                 135                 140

Pro Arg Ser Asn Lys Asp Gln Ala Glu Pro Val Ile Asn Val Ile Ile
145                 150                 155                 160

Ser Glu Glu Thr Gly Ser Asn Asn Thr Leu Asp Gly Leu Thr Cys Pro
                165                 170                 175

Ala Ala Glu Glu Ala Pro Asp Pro Thr Gln Pro Ala Glu Phe Leu Gln
            180                 185                 190
```

-continued

```
Val Phe Gly Pro Arg Val Leu Lys Lys Ile Thr Lys His Met Pro Gly
            195                 200                 205
Val Asn Leu Thr Leu Glu Asp Val Pro Leu Phe Met Asp Leu Cys Pro
            210                 215                 220
Phe Asp Thr Val Gly Ser Asp Pro Val Leu Phe Pro Arg Gln Leu Ser
225                 230                 235                 240
Pro Phe Cys His Leu Phe Thr Ala Asp Asp Trp Met Ala Tyr Asp Tyr
            245                 250                 255
Tyr Tyr Thr Leu Asp Lys Tyr Tyr Ser His Gly Gly Gly Ser Ala Phe
            260                 265                 270
Gly Pro Ser Arg Gly Val Gly Phe Val Asn Glu Leu Ile Ala Arg Met
            275                 280                 285
Thr Gly Asn Leu Pro Val Lys Asp His Thr Thr Val Asn His Thr Leu
            290                 295                 300
Asp Asp Asn Pro Glu Thr Phe Pro Leu Asp Ala Val Leu Tyr Ala Asp
305                 310                 315                 320
Phe Ser His Asp Asn Thr Met Thr Gly Ile Phe Ser Ala Met Gly Leu
            325                 330                 335
Tyr Asn Gly Thr Lys Pro Leu Ser Thr Ser Lys Ile Gln Pro Pro Thr
            340                 345                 350
Gly Ala Ala Ala Asp Gly Tyr Ala Ala Ser Trp Thr Val Pro Phe Ala
            355                 360                 365
Ala Arg Ala Tyr Val Glu Leu Leu Arg Cys Glu Thr Glu Thr Ser Ser
            370                 375                 380
Glu Glu Glu Glu Glu Gly Glu Asp Glu Pro Phe Val Arg Val Leu Val
385                 390                 395                 400
Asn Asp Arg Val Val Pro Leu His Gly Cys Arg Val Asp Arg Trp Gly
            405                 410                 415
Arg Cys Arg Arg Asp Glu Trp Ile Lys Gly Leu Thr Phe Ala Arg Gln
            420                 425                 430
Gly Gly His Trp Asp Arg Cys Phe
            435                 440

<210> SEQ ID NO 24
<211> LENGTH: 441
<212> TYPE: PRT
<213> ORGANISM: Artificial Sequence
<220> FEATURE:
<223> OTHER INFORMATION: Synthetic

<400> SEQUENCE: 24

Asn Ser His Ser Cys Asp Thr Val Asp Gly Gly Tyr Gln Cys Phe Pro
1               5                   10                  15
Glu Ile Ser His Leu Trp Gly Gln Tyr Ser Pro Phe Phe Ser Leu Ala
            20                  25                  30
Asp Glu Ser Ala Ile Ser Pro Asp Val Pro Lys Gly Cys Arg Val Thr
            35                  40                  45
Phe Val Gln Val Leu Ser Arg His Gly Ala Arg Tyr Pro Thr Ser Ser
        50                  55                  60
Lys Ser Lys Lys Tyr Ser Ala Leu Ile Glu Ala Ile Gln Lys Asn Ala
65                  70                  75                  80
Thr Ala Phe Lys Gly Lys Tyr Ala Phe Leu Lys Thr Tyr Asn Tyr Thr
            85                  90                  95
Leu Gly Ala Asp Asp Leu Thr Pro Phe Gly Glu Gln Gln Met Val Asn
            100                 105                 110
```

```
Ser Gly Ile Lys Phe Tyr Arg Arg Tyr Lys Ala Leu Ala Arg Lys Ile
        115                 120                 125

Val Pro Phe Val Arg Ala Ser Gly Ser Asp Arg Val Ile Ala Ser Ala
130                 135                 140

Glu Lys Phe Ile Glu Gly Phe Gln Ser Ala Lys Leu Ala Asp Pro Gly
145                 150                 155                 160

Ala Asn Pro His Gln Ala Ser Pro Val Ile Asn Val Ile Pro Glu
                165                 170                 175

Gly Ala Gly Tyr Asn Asn Thr Leu Asp His Gly Leu Cys Thr Ala Phe
            180                 185                 190

Glu Glu Ser Glu Leu Gly Asp Asp Val Glu Ala Asn Phe Thr Ala Val
            195                 200                 205

Phe Ala Pro Pro Ile Arg Ala Arg Leu Glu Ala His Leu Pro Gly Val
        210                 215                 220

Asn Leu Thr Asp Glu Asp Val Val Asn Leu Met Asp Met Cys Pro Phe
225                 230                 235                 240

Asp Thr Val Ala Arg Thr Ser Asp Ala Thr Gln Leu Ser Pro Phe Cys
                245                 250                 255

Asp Leu Phe Thr His Asp Glu Trp Ile Gln Tyr Asp Tyr Leu Gln Ser
            260                 265                 270

Leu Gly Lys Tyr Tyr Gly Tyr Gly Ala Gly Asn Pro Leu Gly Pro Ala
        275                 280                 285

Gln Gly Val Gly Phe Val Asn Glu Leu Ile Ala Arg Leu Thr His Ser
        290                 295                 300

Pro Val Gln Asp His Thr Ser Thr Asn His Thr Leu Asp Ser Asn Pro
305                 310                 315                 320

Ala Thr Phe Pro Leu Asn Ala Thr Leu Tyr Ala Asp Phe Ser His Asp
                325                 330                 335

Asn Thr Met Val Ser Ile Phe Ala Leu Gly Leu Tyr Asn Gly Thr
            340                 345                 350

Lys Pro Leu Ser Thr Thr Ser Val Glu Ser Ile Glu Glu Thr Asp Gly
        355                 360                 365

Tyr Ala Ala Ser Trp Thr Val Pro Phe Ala Ala Arg Ala Tyr Val Glu
370                 375                 380

Met Met Gln Cys Glu Ala Glu Lys Glu Pro Leu Val Arg Val Leu Val
385                 390                 395                 400

Asn Asp Arg Val Val Pro Leu His Gly Cys Val Asp Lys Leu Gly
                405                 410                 415

Arg Cys Lys Arg Asp Asp Phe Val Glu Gly Leu Ser Phe Ala Arg Ser
                420                 425                 430

Gly Gly Asn Trp Glu Glu Cys Phe Ala
        435                 440

<210> SEQ ID NO 25
<211> LENGTH: 1426
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (12)..(1412)
<220> FEATURE:
<221> NAME/KEY: sig_peptide
<222> LOCATION: (12)..(89)
<220> FEATURE:
<221> NAME/KEY: mat_peptide
```

<222> LOCATION: (90)..()

<400> SEQUENCE: 25

```
tatatgaatt c atg ggc gtg ttc gtc gtg cta ctg tcc att gcc acc ttg        50
           Met Gly Val Phe Val Val Leu Leu Ser Ile Ala Thr Leu
           -25             -20                 -15 ttc ggt tcc aca tcc ggt acc gcc ttg ggt cct cgt ggt aat tct cac         98
Phe Gly Ser Thr Ser Gly Thr Ala Leu Gly Pro Arg Gly Asn Ser His
        -10             -5              -1  1 tct tgt gac act gtt gac ggt ggt tac caa tgt ttc cca gaa att tct        146
Ser Cys Asp Thr Val Asp Gly Gly Tyr Gln Cys Phe Pro Glu Ile Ser
    5               10              15 cac ttg tgg ggt caa tac tct cca ttc ttc tct ttg gct gac gaa tct        194
His Leu Trp Gly Gln Tyr Ser Pro Phe Phe Ser Leu Ala Asp Glu Ser
20              25              30              35 gct att tct cca gac gtt cca aag ggt tgt aga gtt act ttc gtt caa        242
Ala Ile Ser Pro Asp Val Pro Lys Gly Cys Arg Val Thr Phe Val Gln
            40              45              50 gtt ttg tct aga cac ggt gct aga tac cca act tct tct aag tct aag        290
Val Leu Ser Arg His Gly Ala Arg Tyr Pro Thr Ser Ser Lys Ser Lys
        55              60              65 aag tac tct gct ttg att gaa gct att caa aag aac gct act gct ttc        338
Lys Tyr Ser Ala Leu Ile Glu Ala Ile Gln Lys Asn Ala Thr Ala Phe
    70              75              80 aag ggt aag tac gct ttc ttg aag act tac aac tac act ttg ggt gct        386
Lys Gly Lys Tyr Ala Phe Leu Lys Thr Tyr Asn Tyr Thr Leu Gly Ala
85              90              95 gac gac ttg act cca ttc ggt gaa caa caa atg gtt aac tct ggt att        434
Asp Asp Leu Thr Pro Phe Gly Glu Gln Gln Met Val Asn Ser Gly Ile
100             105             110             115 aag ttc tac aga aga tac aag gct ttg gct aga aag att gtt cca ttc        482
Lys Phe Tyr Arg Arg Tyr Lys Ala Leu Ala Arg Lys Ile Val Pro Phe
            120             125             130 gtt aga gct tct ggt tct gac aga gtt att gct tct gct gaa aag ttc        530
Val Arg Ala Ser Gly Ser Asp Arg Val Ile Ala Ser Ala Glu Lys Phe
        135             140             145 att gaa ggt ttc caa tct gct aag ttg gct gac cca ggt gct aac cca        578
Ile Glu Gly Phe Gln Ser Ala Lys Leu Ala Asp Pro Gly Ala Asn Pro
    150             155             160 cac caa gct tct cca gtt att aac gtt att att cca gaa ggt gct ggt        626
His Gln Ala Ser Pro Val Ile Asn Val Ile Ile Pro Glu Gly Ala Gly
165             170             175 tac aac aac act ttg gac cac ggt ttg tgt act gct ttc gaa gaa tct        674
Tyr Asn Asn Thr Leu Asp His Gly Leu Cys Thr Ala Phe Glu Glu Ser
180             185             190             195 gaa ttg ggt gac gac gtt gaa gct aac ttc act gct gtt ttc gct cca        722
Glu Leu Gly Asp Asp Val Glu Ala Asn Phe Thr Ala Val Phe Ala Pro
            200             205             210 cct att aga gct aga ttg gaa gct cac ttg cca ggt gtt aac ttg act        770
Pro Ile Arg Ala Arg Leu Glu Ala His Leu Pro Gly Val Asn Leu Thr
        215             220             225 gac gaa gac gtt gtt aac ttg atg gac atg tgt cca ttc gac act gtt        818
Asp Glu Asp Val Val Asn Leu Met Asp Met Cys Pro Phe Asp Thr Val
    230             235             240 gct aga act tct gac gct act caa ttg tct cca ttc tgt gac ttg ttc        866
Ala Arg Thr Ser Asp Ala Thr Gln Leu Ser Pro Phe Cys Asp Leu Phe
245             250             255 act cac gac gaa tgg att caa tac gac tac ttg caa tct ttg ggt aag        914
Thr His Asp Glu Trp Ile Gln Tyr Asp Tyr Leu Gln Ser Leu Gly Lys
260             265             270             275
```

```
tac tac ggt tac ggt gct ggt aac cca ttg ggt cca gct caa ggt gtt        962
Tyr Tyr Gly Tyr Gly Ala Gly Asn Pro Leu Gly Pro Ala Gln Gly Val
            280                 285                 290 ggt ttc gtt aac gaa ttg att gct aga ttg act cac tct cca gtt caa       1010
Gly Phe Val Asn Glu Leu Ile Ala Arg Leu Thr His Ser Pro Val Gln
                295                 300                 305 gac cac act tct act aac cac act ttg gac tct aac cca gct act ttc       1058
Asp His Thr Ser Thr Asn His Thr Leu Asp Ser Asn Pro Ala Thr Phe
            310                 315                 320 cca ttg aac gct act ttg tac gct gac ttc tct cac gac aac act atg       1106
Pro Leu Asn Ala Thr Leu Tyr Ala Asp Phe Ser His Asp Asn Thr Met
        325                 330                 335 gtt tct att ttc ttc gct ttg ggt ttg tac aac ggt act aag cca ttg       1154
Val Ser Ile Phe Phe Ala Leu Gly Leu Tyr Asn Gly Thr Lys Pro Leu
340                 345                 350                 355 tct act act tct gtt gaa tct att gaa gaa act gac ggt tac gct gct       1202
Ser Thr Thr Ser Val Glu Ser Ile Glu Glu Thr Asp Gly Tyr Ala Ala
                360                 365                 370 tct tgg act gtt cca ttc gct gct aga gct tac gtt gaa atg atg caa       1250
Ser Trp Thr Val Pro Phe Ala Ala Arg Ala Tyr Val Glu Met Met Gln
            375                 380                 385 tgt gaa gct gaa aag gaa cca ttg gtt aga gtt ttg gtt aac gac aga       1298
Cys Glu Ala Glu Lys Glu Pro Leu Val Arg Val Leu Val Asn Asp Arg
        390                 395                 400 gtt gtt cca ttg cac ggt tgt ggt gtt gac aag ttg ggt aga tgt aag       1346
Val Val Pro Leu His Gly Cys Gly Val Asp Lys Leu Gly Arg Cys Lys
    405                 410                 415 aga gac gac ttc gtt gaa ggt ttg tct ttc gct aga tct ggt ggt aac       1394
Arg Asp Asp Phe Val Glu Gly Leu Ser Phe Ala Arg Ser Gly Gly Asn
420                 425                 430                 435 tgg gaa gaa tgt ttc gct taagaattca tata                               1426
Trp Glu Glu Cys Phe Ala
                440

<210> SEQ ID NO 26
<211> LENGTH: 467
<212> TYPE: PRT
<213> ORGANISM: Artificial Sequence
<220> FEATURE:
<223> OTHER INFORMATION: Synthetic

<400> SEQUENCE: 26

Met Gly Val Phe Val Leu Leu Ser Ile Ala Thr Leu Phe Gly Ser
        -25                 -20                 -15

Thr Ser Thr Ala Leu Gly Pro Arg Gly Asn Ser His Ser Cys Asp
-10                  -5              -1   1               5

Thr Val Asp Gly Gly Tyr Gln Cys Phe Pro Glu Ile Ser His Leu Trp
            10                  15                  20

Gly Gln Tyr Ser Pro Phe Phe Ser Leu Ala Asp Glu Ser Ala Ile Ser
        25                  30                  35

Pro Asp Val Pro Lys Gly Cys Arg Val Thr Phe Val Gln Val Leu Ser
        40                  45                  50

Arg His Gly Ala Arg Tyr Pro Thr Ser Ser Lys Ser Lys Tyr Ser
55                  60                  65                  70

Ala Leu Ile Glu Ala Ile Gln Lys Asn Ala Thr Ala Phe Lys Gly Lys
            75                  80                  85

Tyr Ala Phe Leu Lys Thr Tyr Asn Tyr Thr Leu Gly Ala Asp Asp Leu
        90                  95                  100
```

```
Thr Pro Phe Gly Glu Gln Gln Met Val Asn Ser Gly Ile Lys Phe Tyr
        105                 110                 115

Arg Arg Tyr Lys Ala Leu Ala Arg Lys Ile Val Pro Phe Val Arg Ala
120                 125                 130

Ser Gly Ser Asp Arg Val Ile Ala Ser Ala Glu Lys Phe Ile Glu Gly
135                 140                 145                 150

Phe Gln Ser Ala Lys Leu Ala Asp Pro Gly Ala Asn Pro His Gln Ala
                155                 160                 165

Ser Pro Val Ile Asn Val Ile Pro Glu Gly Ala Gly Tyr Asn Asn
                170                 175                 180

Thr Leu Asp His Gly Leu Cys Thr Ala Phe Glu Glu Ser Glu Leu Gly
                185                 190                 195

Asp Asp Val Glu Ala Asn Phe Thr Ala Val Phe Ala Pro Pro Ile Arg
200                 205                 210

Ala Arg Leu Glu Ala His Leu Pro Gly Val Asn Leu Thr Asp Glu Asp
215                 220                 225                 230

Val Val Asn Leu Met Asp Met Cys Pro Phe Asp Thr Val Ala Arg Thr
                235                 240                 245

Ser Asp Ala Thr Gln Leu Ser Pro Phe Cys Asp Leu Phe Thr His Asp
                250                 255                 260

Glu Trp Ile Gln Tyr Asp Tyr Leu Gln Ser Leu Gly Lys Tyr Tyr Gly
            265                 270                 275

Tyr Gly Ala Gly Asn Pro Leu Gly Pro Ala Gln Gly Val Gly Phe Val
                280                 285                 290

Asn Glu Leu Ile Ala Arg Leu Thr His Ser Pro Val Gln Asp His Thr
295                 300                 305                 310

Ser Thr Asn His Thr Leu Asp Ser Asn Pro Ala Thr Phe Pro Leu Asn
                315                 320                 325

Ala Thr Leu Tyr Ala Asp Phe Ser His Asp Asn Thr Met Val Ser Ile
                330                 335                 340

Phe Phe Ala Leu Gly Leu Tyr Asn Gly Thr Lys Pro Leu Ser Thr Thr
                345                 350                 355

Ser Val Glu Ser Ile Glu Glu Thr Asp Gly Tyr Ala Ala Ser Trp Thr
360                 365                 370

Val Pro Phe Ala Ala Arg Ala Tyr Val Glu Met Met Gln Cys Glu Ala
375                 380                 385                 390

Glu Lys Glu Pro Leu Val Arg Val Leu Val Asn Asp Arg Val Val Pro
                395                 400                 405

Leu His Gly Cys Gly Val Asp Lys Leu Gly Arg Cys Lys Arg Asp Asp
                410                 415                 420

Phe Val Glu Gly Leu Ser Phe Ala Arg Ser Gly Gly Asn Trp Glu Glu
                425                 430                 435

Cys Phe Ala
    440

<210> SEQ ID NO 27
<211> LENGTH: 437
<212> TYPE: PRT
<213> ORGANISM: Artificial Sequence
<220> FEATURE:
<223> OTHER INFORMATION: Synthetic

<400> SEQUENCE: 27

Asn Ser His Ser Cys Asp Thr Val Asp Gly Tyr Gln Cys Pro Glu Ile
1               5                   10                  15
```

-continued

```
Ser His Leu Trp Gly Gln Tyr Ser Pro Phe Ser Leu Ala Asp Glu
         20                  25                  30

Ser Ala Ile Ser Pro Asp Val Pro Lys Gly Cys Arg Val Thr Phe Val
             35                  40                  45

Gln Val Leu Ser Arg His Gly Ala Arg Tyr Pro Thr Ser Ser Lys Ser
 50                      55                  60

Lys Lys Tyr Ser Ala Leu Ile Glu Arg Ile Gln Lys Asn Ala Thr Phe
 65                  70                  75                  80

Lys Gly Lys Tyr Ala Phe Leu Lys Thr Tyr Asn Tyr Thr Leu Gly Ala
                 85                  90                  95

Asp Asp Leu Thr Pro Phe Gly Glu Asn Gln Met Val Asn Ser Gly Ile
             100                 105                 110

Lys Phe Tyr Arg Arg Tyr Lys Ala Leu Ala Arg Asn Ile Val Pro Phe
             115                 120                 125

Val Arg Ala Ser Gly Ser Asp Arg Val Ile Ala Ser Ala Glu Lys Phe
         130                 135                 140

Ile Glu Gly Phe Gln Ser Ala Lys Leu Ala Asp Pro Ala His Gln Ala
145                 150                 155                 160

Ser Pro Val Ile Asn Val Ile Ile Pro Glu Gly Ser Gly Tyr Asn Asn
                 165                 170                 175

Thr Leu Asp His Gly Leu Cys Thr Ala Phe Glu Asp Ser Thr Leu Gly
             180                 185                 190

Asp Asp Ala Glu Ala Asn Phe Thr Ala Val Phe Ala Pro Pro Ile Arg
         195                 200                 205

Ala Arg Leu Glu Ala Leu Pro Gly Val Asn Leu Thr Asp Glu Asp Val
     210                 215                 220

Val Asn Leu Met Asp Met Cys Pro Phe Asp Thr Val Ala Arg Thr Ser
225                 230                 235                 240

Asp Ala Thr Gln Leu Ser Pro Phe Cys Asp Leu Phe Thr Ala Asp Glu
                 245                 250                 255

Trp Gln Tyr Asp Tyr Leu Gln Ser Leu Lys Tyr Tyr Gly Tyr Gly Ala
             260                 265                 270

Gly Asn Pro Leu Gly Pro Ala Gln Gly Val Gly Phe Asn Glu Leu Ile
         275                 280                 285

Ala Arg Leu Thr His Ser Pro Val Gln Asp His Thr Ser Thr Asn His
     290                 295                 300

Thr Leu Asp Ser Asn Pro Ala Thr Phe Pro Leu Asn Ala Thr Leu Tyr
305                 310                 315                 320

Ala Asp Phe Ser His Asp Asn Thr Met Val Ser Ile Phe Ala Leu
                 325                 330                 335

Gly Leu Tyr Asn Gly Thr Lys Pro Leu Ser Thr Thr Ser Val Glu Ser
             340                 345                 350

Ile Glu Thr Asp Gly Tyr Ala Ala Ser Trp Thr Val Pro Phe Ala Ala
         355                 360                 365

Arg Ala Tyr Val Glu Met Met Gln Cys Glu Ala Gly Gly Gly Gly
     370                 375                 380

Glu Gly Glu Lys Glu Pro Leu Val Arg Val Leu Val Asn Asp Arg Val
385                 390                 395                 400

Val Pro Leu His Gly Cys Gly Val Asp Lys Leu Gly Arg Cys Lys Leu
                 405                 410                 415

Asp Asp Phe Val Glu Gly Leu Ser Phe Ala Arg Ser Gly Gly Asn Trp
             420                 425                 430

Ala Glu Cys Phe Ala
```

<210> SEQ ID NO 28
<211> LENGTH: 1404
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1401)
<220> FEATURE:
<221> NAME/KEY: sig_peptide
<222> LOCATION: (1)..(78)
<220> FEATURE:
<221> NAME/KEY: mat_peptide
<222> LOCATION: (79)..()

<400> SEQUENCE: 28

| | | | | | | | | | | | | | | | | |
|---|---|---|---|---|---|---|---|---|---|---|---|---|---|---|---|---|
| atg | ggc | gtg | ttc | gtc | gtg | cta | ctg | tcc | att | gcc | acc | ttg | ttc | ggt | tcc | 48 |
| Met | Gly | Val | Phe | Val | Val | Leu | Leu | Ser | Ile | Ala | Thr | Leu | Phe | Gly | Ser | |
| | -25 | | | | -20 | | | | | -15 | | | | | | |
| aca | tcc | ggt | acc | gcc | ttg | ggt | cct | cgt | ggt | aat | tct | cac | tct | tgt | gac | 96 |
| Thr | Ser | Gly | Thr | Ala | Leu | Gly | Pro | Arg | Gly | Asn | Ser | His | Ser | Cys | Asp | |
| -10 | | | | | -5 | | | | | -1 | 1 | | | | 5 | |
| act | gtt | gac | ggt | ggt | tac | caa | tgt | ttc | cca | gaa | att | tct | cac | ttg | tgg | 144 |
| Thr | Val | Asp | Gly | Gly | Tyr | Gln | Cys | Phe | Pro | Glu | Ile | Ser | His | Leu | Trp | |
| | | | 10 | | | | | 15 | | | | | 20 | | | |
| ggt | acc | tac | tct | cca | tac | ttc | tct | ttg | gca | gac | gaa | tct | gct | att | tct | 192 |
| Gly | Thr | Tyr | Ser | Pro | Tyr | Phe | Ser | Leu | Ala | Asp | Glu | Ser | Ala | Ile | Ser | |
| | | 25 | | | | | 30 | | | | | 35 | | | | |
| cca | gac | gtt | cca | gac | gac | tgt | aga | gtt | act | ttc | gtt | caa | gtt | ttg | tct | 240 |
| Pro | Asp | Val | Pro | Asp | Asp | Cys | Arg | Val | Thr | Phe | Val | Gln | Val | Leu | Ser | |
| | 40 | | | | | 45 | | | | | 50 | | | | | |
| aga | cac | ggt | gct | aga | tac | cca | act | tct | tct | gcg | tct | aag | gct | tac | tct | 288 |
| Arg | His | Gly | Ala | Arg | Tyr | Pro | Thr | Ser | Ser | Ala | Ser | Lys | Ala | Tyr | Ser | |
| 55 | | | | | 60 | | | | | 65 | | | | | 70 | |
| gct | ttg | att | gaa | gct | att | caa | aag | aac | gct | act | gct | ttc | aag | ggt | aag | 336 |
| Ala | Leu | Ile | Glu | Ala | Ile | Gln | Lys | Asn | Ala | Thr | Ala | Phe | Lys | Gly | Lys | |
| | | | 75 | | | | | 80 | | | | | 85 | | | |
| tac | gct | ttc | ttg | aag | act | tac | aac | tac | act | ttg | ggt | gct | gac | gac | ttg | 384 |
| Tyr | Ala | Phe | Leu | Lys | Thr | Tyr | Asn | Tyr | Thr | Leu | Gly | Ala | Asp | Asp | Leu | |
| | | 90 | | | | | 95 | | | | | 100 | | | | |
| act | cca | ttc | ggt | gaa | aac | caa | atg | gtt | aac | tct | ggt | att | aag | ttc | tac | 432 |
| Thr | Pro | Phe | Gly | Glu | Asn | Gln | Met | Val | Asn | Ser | Gly | Ile | Lys | Phe | Tyr | |
| | 105 | | | | | 110 | | | | | 115 | | | | | |
| aga | aga | tac | aag | gct | ttg | gct | aga | aag | att | gtt | cca | ttc | att | aga | gct | 480 |
| Arg | Arg | Tyr | Lys | Ala | Leu | Ala | Arg | Lys | Ile | Val | Pro | Phe | Ile | Arg | Ala | |
| 120 | | | | | 125 | | | | | 130 | | | | | | |
| tct | ggt | tct | gac | aga | gtt | att | gct | tct | gct | gaa | aag | ttc | att | gaa | ggt | 528 |
| Ser | Gly | Ser | Asp | Arg | Val | Ile | Ala | Ser | Ala | Glu | Lys | Phe | Ile | Glu | Gly | |
| 135 | | | | 140 | | | | | 145 | | | | | 150 | | |
| ttc | caa | tct | gct | aag | ttg | gct | gac | cca | ggt | tct | caa | cca | cac | caa | gct | 576 |
| Phe | Gln | Ser | Ala | Lys | Leu | Ala | Asp | Pro | Gly | Ser | Gln | Pro | His | Gln | Ala | |
| | | | 155 | | | | | 160 | | | | | 165 | | | |
| tct | cca | gtt | att | aac | gtg | atc | att | cca | gaa | gga | tcc | ggt | tac | aac | aac | 624 |
| Ser | Pro | Val | Ile | Asn | Val | Ile | Ile | Pro | Glu | Gly | Ser | Gly | Tyr | Asn | Asn | |
| | | 170 | | | | | 175 | | | | | 180 | | | | |
| act | ttg | gac | cac | ggt | act | tgt | act | gct | ttc | gaa | gac | tct | gaa | tta | ggt | 672 |
| Thr | Leu | Asp | His | Gly | Thr | Cys | Thr | Ala | Phe | Glu | Asp | Ser | Glu | Leu | Gly | |
| | 185 | | | | | 190 | | | | | 195 | | | | | |
| gac | gac | gtt | gaa | gct | aac | ttc | act | gct | ttg | ttc | gct | cca | gct | att | aga | 720 |
| Asp | Asp | Val | Glu | Ala | Asn | Phe | Thr | Ala | Leu | Phe | Ala | Pro | Ala | Ile | Arg | |

-continued

| | |
|---|---|
| gct aga ttg gaa gct gac ttg cca ggt gtt act ttg act gac gaa gac<br>Ala Arg Leu Glu Ala Asp Leu Pro Gly Val Thr Leu Thr Asp Glu Asp<br>215                    220                    225                    230 | 768 |
| gtt gtt tac ttg atg gac atg tgt cca ttc gac act gtc gct aga act<br>Val Val Tyr Leu Met Asp Met Cys Pro Phe Asp Thr Val Ala Arg Thr<br>                    235                    240                    245 | 816 |
| tct gac gct act gaa ttg tct cca ttc tgt gct ttg ttc act cac gac<br>Ser Asp Ala Thr Glu Leu Ser Pro Phe Cys Ala Leu Phe Thr His Asp<br>            250                    255                    260 | 864 |
| gaa tgg atc caa tac gac tac ttg caa agc ttg ggt aag tac tac ggt<br>Glu Trp Ile Gln Tyr Asp Tyr Leu Gln Ser Leu Gly Lys Tyr Tyr Gly<br>      265                    270                    275 | 912 |
| tac ggt gct ggt aac cca ttg ggt cca gct caa ggt gtt ggt ttc gct<br>Tyr Gly Ala Gly Asn Pro Leu Gly Pro Ala Gln Gly Val Gly Phe Ala<br>280                    285                    290 | 960 |
| aac gaa ttg att gct aga ttg act cac tct cca gtt caa gac cac act<br>Asn Glu Leu Ile Ala Arg Leu Thr His Ser Pro Val Gln Asp His Thr<br>295                    300                    305                    310 | 1008 |
| tct act aac cac act ttg gac tct aac cca gct act ttc cca ttg aac<br>Ser Thr Asn His Thr Leu Asp Ser Asn Pro Ala Thr Phe Pro Leu Asn<br>                315                    320                    325 | 1056 |
| gct act ttg tac gct gac ttc tct cac gac aac act atg ata tct att<br>Ala Thr Leu Tyr Ala Asp Phe Ser His Asp Asn Thr Met Ile Ser Ile<br>            330                    335                    340 | 1104 |
| ttc ttc gct ttg ggt ttg tac aac ggt acc aag cca ttg tct act act<br>Phe Phe Ala Leu Gly Leu Tyr Asn Gly Thr Lys Pro Leu Ser Thr Thr<br>      345                    350                    355 | 1152 |
| tct gtt gaa tct att gaa gaa act gac ggt tac tct gct tct tgg act<br>Ser Val Glu Ser Ile Glu Glu Thr Asp Gly Tyr Ser Ala Ser Trp Thr<br>360                    365                    370 | 1200 |
| gtt cca ttc gct gct aga gct tac gtt gaa atg atg caa tgt caa gct<br>Val Pro Phe Ala Ala Arg Ala Tyr Val Glu Met Met Gln Cys Gln Ala<br>375                    380                    385                    390 | 1248 |
| gaa aag gaa cca ttg gtt aga gtt ttg gtt aac gac aga gtt gtt cca<br>Glu Lys Glu Pro Leu Val Arg Val Leu Val Asn Asp Arg Val Val Pro<br>                395                    400                    405 | 1296 |
| ttg cac ggt tgt gct gtt gac aag ttg ggt aga tgt aag aga gac gac<br>Leu His Gly Cys Ala Val Asp Lys Leu Gly Arg Cys Lys Arg Asp Asp<br>            410                    415                    420 | 1344 |
| ttc gtt gaa ggt ttg tct ttc gct aga tct ggt ggt aac tgg gct gaa<br>Phe Val Glu Gly Leu Ser Phe Ala Arg Ser Gly Gly Asn Trp Ala Glu<br>      425                    430                    435 | 1392 |
| tgt ttc gct taa<br>Cys Phe Ala<br>      440 | 1404 |

<210> SEQ ID NO 29
<211> LENGTH: 467
<212> TYPE: PRT
<213> ORGANISM: Artificial Sequence
<220> FEATURE:
<223> OTHER INFORMATION: Synthetic

<400> SEQUENCE: 29

Met Gly Val Phe Val Val Leu Leu Ser Ile Ala Thr Leu Phe Gly Ser
      -25                    -20                    -15

Thr Ser Gly Thr Ala Leu Gly Pro Arg Gly Asn Ser His Ser Cys Asp
-10                    -5                    -1 1                    5

Thr Val Asp Gly Gly Tyr Gln Cys Phe Pro Glu Ile Ser His Leu Trp

-continued

```
                10                  15                  20
Gly Thr Tyr Ser Pro Tyr Phe Ser Leu Ala Asp Glu Ser Ala Ile Ser
            25                  30                  35

Pro Asp Val Pro Asp Cys Arg Val Thr Phe Val Gln Val Leu Ser
 40                  45                  50

Arg His Gly Ala Arg Tyr Pro Thr Ser Ser Ala Ser Lys Ala Tyr Ser
 55                  60                  65                  70

Ala Leu Ile Glu Ala Ile Gln Lys Asn Ala Thr Ala Phe Lys Gly Lys
                75                  80                  85

Tyr Ala Phe Leu Lys Thr Tyr Asn Tyr Thr Leu Gly Ala Asp Asp Leu
                90                  95                 100

Thr Pro Phe Gly Glu Asn Gln Met Val Asn Ser Gly Ile Lys Phe Tyr
               105                 110                 115

Arg Arg Tyr Lys Ala Leu Ala Arg Lys Ile Val Pro Phe Ile Arg Ala
    120                 125                 130

Ser Gly Ser Asp Arg Val Ile Ala Ser Ala Glu Lys Phe Ile Glu Gly
135                 140                 145                 150

Phe Gln Ser Ala Lys Leu Ala Asp Pro Gly Ser Gln Pro His Gln Ala
                155                 160                 165

Ser Pro Val Ile Asn Val Ile Ile Pro Glu Gly Ser Gly Tyr Asn Asn
                170                 175                 180

Thr Leu Asp His Gly Thr Cys Thr Ala Phe Glu Asp Ser Glu Leu Gly
                185                 190                 195

Asp Asp Val Glu Ala Asn Phe Thr Ala Leu Phe Ala Pro Ala Ile Arg
    200                 205                 210

Ala Arg Leu Glu Ala Asp Leu Pro Gly Val Thr Leu Thr Asp Glu Asp
215                 220                 225                 230

Val Val Tyr Leu Met Asp Met Cys Pro Phe Asp Thr Val Ala Arg Thr
                235                 240                 245

Ser Asp Ala Thr Glu Leu Ser Pro Phe Cys Ala Leu Phe Thr His Asp
                250                 255                 260

Glu Trp Ile Gln Tyr Asp Tyr Leu Gln Ser Leu Gly Lys Tyr Tyr Gly
                265                 270                 275

Tyr Gly Ala Gly Asn Pro Leu Gly Pro Ala Gln Gly Val Gly Phe Ala
    280                 285                 290

Asn Glu Leu Ile Ala Arg Leu Thr His Ser Pro Val Gln Asp His Thr
295                 300                 305                 310

Ser Thr Asn His Thr Leu Asp Ser Asn Pro Ala Thr Phe Pro Leu Asn
                315                 320                 325

Ala Thr Leu Tyr Ala Asp Phe Ser His Asp Asn Thr Met Ile Ser Ile
                330                 335                 340

Phe Phe Ala Leu Gly Leu Tyr Asn Gly Thr Lys Pro Leu Ser Thr Thr
                345                 350                 355

Ser Val Glu Ser Ile Glu Glu Thr Asp Gly Tyr Ser Ala Ser Trp Thr
    360                 365                 370

Val Pro Phe Ala Ala Arg Ala Tyr Val Glu Met Met Gln Cys Gln Ala
375                 380                 385                 390

Glu Lys Glu Pro Leu Val Arg Val Leu Asn Asp Arg Val Val Pro
                395                 400                 405

Leu His Gly Cys Ala Val Asp Lys Leu Gly Arg Cys Lys Arg Asp Asp
                410                 415                 420

Phe Val Glu Gly Leu Ser Phe Ala Arg Ser Gly Gly Asn Trp Ala Glu
                425                 430                 435
```

Cys Phe Ala
    440

<210> SEQ ID NO 30
<211> LENGTH: 1404
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1401)
<220> FEATURE:
<221> NAME/KEY: sig_peptide
<222> LOCATION: (1)..(78)
<220> FEATURE:
<221> NAME/KEY: mat_peptide
<222> LOCATION: (79)..()

<400> SEQUENCE: 30

```
atg ggc gtg ttc gtc gtg cta ctg tcc att gcc acc ttg ttc ggt tcc      48
Met Gly Val Phe Val Val Leu Leu Ser Ile Ala Thr Leu Phe Gly Ser
    -25                 -20                 -15 aca tcc ggt acc gcc ttg ggt cct cgt ggt aac tct cac tct tgt gac      96
Thr Ser Gly Thr Ala Leu Gly Pro Arg Gly Asn Ser His Ser Cys Asp
-10                  -5                  -1   1               5 act gtt gac ggt ggt tac caa tgt ttc cca gaa att tct cac ttg tgg     144
Thr Val Asp Gly Gly Tyr Gln Cys Phe Pro Glu Ile Ser His Leu Trp
                10                  15                  20 ggt aca tac tct cca ttc ttc tct ttg gct gac gaa tct gct att tct     192
Gly Thr Tyr Ser Pro Phe Phe Ser Leu Ala Asp Glu Ser Ala Ile Ser
            25                  30                  35 cca gac gtt cca aag ggt tgt aga gtt act ttc gtt caa gtt ttg tct     240
Pro Asp Val Pro Lys Gly Cys Arg Val Thr Phe Val Gln Val Leu Ser
    40                  45                  50 aga cac ggt gct aga tac cca act tct tct gcg tct aag gcg tac tct     288
Arg His Gly Ala Arg Tyr Pro Thr Ser Ser Ala Ser Lys Ala Tyr Ser
55                  60                  65                  70 gct ttg att gaa gct att caa aag aac gct act gct ttc aag ggt aag     336
Ala Leu Ile Glu Ala Ile Gln Lys Asn Ala Thr Ala Phe Lys Gly Lys
                75                  80                  85 tac gct ttc ttg aag act tac aac tac act ttg ggt gct gac gac ttg     384
Tyr Ala Phe Leu Lys Thr Tyr Asn Tyr Thr Leu Gly Ala Asp Asp Leu
            90                  95                 100 act cca ttc ggt gaa caa caa atg gtt aac tct ggt att aag ttc tac     432
Thr Pro Phe Gly Glu Gln Gln Met Val Asn Ser Gly Ile Lys Phe Tyr
        105                 110                 115 aga aga tac aag gct ttg gct aga aag att gtt cca ttc att aga gct     480
Arg Arg Tyr Lys Ala Leu Ala Arg Lys Ile Val Pro Phe Ile Arg Ala
    120                 125                 130 tct ggt tct gac aga gtt att gct tct gct gaa aag ttc att gaa ggt     528
Ser Gly Ser Asp Arg Val Ile Ala Ser Ala Glu Lys Phe Ile Glu Gly
135                 140                 145                 150 ttc caa tct gct aag ttg gct gac cca ggt gct aac cca cac caa gct     576
Phe Gln Ser Ala Lys Leu Ala Asp Pro Gly Ala Asn Pro His Gln Ala
                155                 160                 165 tct cca gtt att aac gtt att att cca gaa ggt gct ggt tac aac aac     624
Ser Pro Val Ile Asn Val Ile Ile Pro Glu Gly Ala Gly Tyr Asn Asn
            170                 175                 180 act ttg gac cac ggt ttg tgt act gct ttc gaa gaa tct gaa ttg ggt     672
Thr Leu Asp His Gly Leu Cys Thr Ala Phe Glu Glu Ser Glu Leu Gly
        185                 190                 195
```

```
gac gac gtt gaa gct aac ttc act gct gtt ttc gct cca cca att aga     720
Asp Asp Val Glu Ala Asn Phe Thr Ala Val Phe Ala Pro Pro Ile Arg
    200                 205                 210 gct aga ttg gaa gct cac ttg cca ggt gtt aac ttg act gac gaa gac     768
Ala Arg Leu Glu Ala His Leu Pro Gly Val Asn Leu Thr Asp Glu Asp
215                 220                 225                 230 gtt gtt aac ttg atg gac atg tgt cca ttc gac act gtt gct aga act     816
Val Val Asn Leu Met Asp Met Cys Pro Phe Asp Thr Val Ala Arg Thr
                235                 240                 245 tct gac gct act caa ttg tct cca ttc tgt gac ttg ttc act cac gac     864
Ser Asp Ala Thr Gln Leu Ser Pro Phe Cys Asp Leu Phe Thr His Asp
        250                 255                 260 gaa tgg att caa tac gac tac ttg caa tct ttg ggt aag tac tac ggt     912
Glu Trp Ile Gln Tyr Asp Tyr Leu Gln Ser Leu Gly Lys Tyr Tyr Gly
            265                 270                 275 tac ggt gct ggt aac cca ttg ggt cca gct caa ggt gtt ggt ttc gtt     960
Tyr Gly Ala Gly Asn Pro Leu Gly Pro Ala Gln Gly Val Gly Phe Val
    280                 285                 290 aac gaa ttg att gct aga ttg act cac tct cca gtt caa gac cac act    1008
Asn Glu Leu Ile Ala Arg Leu Thr His Ser Pro Val Gln Asp His Thr
295                 300                 305                 310 tct act aac cac act ttg gac tct aac cca gct act ttc cca ttg aac    1056
Ser Thr Asn His Thr Leu Asp Ser Asn Pro Ala Thr Phe Pro Leu Asn
                315                 320                 325 gct act ttg tac gct gac ttc tct cac gac aac act atg gtt tct att    1104
Ala Thr Leu Tyr Ala Asp Phe Ser His Asp Asn Thr Met Val Ser Ile
        330                 335                 340 ttc ttc gct ttg ggt ttg tac aac ggt act aag cca ttg tct act act    1152
Phe Phe Ala Leu Gly Leu Tyr Asn Gly Thr Lys Pro Leu Ser Thr Thr
            345                 350                 355 tct gtt gaa tct att gaa gaa act gac ggt tac tct gct tct tgg act    1200
Ser Val Glu Ser Ile Glu Glu Thr Asp Gly Tyr Ser Ala Ser Trp Thr
    360                 365                 370 gtt cca ttc gct gct aga gct tac gtt gaa atg atg caa tgt gaa gct    1248
Val Pro Phe Ala Ala Arg Ala Tyr Val Glu Met Met Gln Cys Glu Ala
375                 380                 385                 390 gaa aag gaa cca ttg gtt aga gtt ttg gtt aac gac aga gtt gtt cca    1296
Glu Lys Glu Pro Leu Val Arg Val Leu Val Asn Asp Arg Val Val Pro
                395                 400                 405 ttg cac ggt tgt ggt gtt gac aag ttg ggt aga tgt aag aga gac gac    1344
Leu His Gly Cys Gly Val Asp Lys Leu Gly Arg Cys Lys Arg Asp Asp
        410                 415                 420 ttc gtt gaa ggt ttg tct ttc gct aga tct ggt ggt aac tgg gaa gaa    1392
Phe Val Glu Gly Leu Ser Phe Ala Arg Ser Gly Gly Asn Trp Glu Glu
            425                 430                 435 tgt ttc gct taa                                                    1404
Cys Phe Ala
    440

<210> SEQ ID NO 31
<211> LENGTH: 467
<212> TYPE: PRT
<213> ORGANISM: Artificial Sequence
<220> FEATURE:
<223> OTHER INFORMATION: Synthetic

<400> SEQUENCE: 31

Met Gly Val Phe Val Val Leu Leu Ser Ile Ala Thr Leu Phe Gly Ser
        -25                 -20                 -15

Thr Ser Gly Thr Ala Leu Gly Pro Arg Gly Asn Ser His Ser Cys Asp
-10                  -5              -1  1                   5
```

```
Thr Val Asp Gly Gly Tyr Gln Cys Phe Pro Glu Ile Ser His Leu Trp
             10                  15                  20

Gly Thr Tyr Ser Pro Phe Phe Ser Leu Ala Asp Glu Ser Ala Ile Ser
             25                  30                  35

Pro Asp Val Pro Lys Gly Cys Arg Val Thr Phe Val Gln Val Leu Ser
             40                  45                  50

Arg His Gly Ala Arg Tyr Pro Thr Ser Ser Ala Ser Lys Ala Tyr Ser
 55                  60                  65                  70

Ala Leu Ile Glu Ala Ile Gln Lys Asn Ala Thr Ala Phe Lys Gly Lys
                 75                  80                  85

Tyr Ala Phe Leu Lys Thr Tyr Asn Tyr Thr Leu Gly Ala Asp Asp Leu
             90                  95                 100

Thr Pro Phe Gly Glu Gln Gln Met Val Asn Ser Gly Ile Lys Phe Tyr
            105                 110                 115

Arg Arg Tyr Lys Ala Leu Ala Arg Lys Ile Val Pro Phe Ile Arg Ala
            120                 125                 130

Ser Gly Ser Asp Arg Val Ile Ala Ser Ala Glu Lys Phe Ile Glu Gly
135                 140                 145                 150

Phe Gln Ser Ala Lys Leu Ala Asp Pro Gly Ala Asn Pro His Gln Ala
                155                 160                 165

Ser Pro Val Ile Asn Val Ile Ile Pro Glu Gly Ala Gly Tyr Asn Asn
            170                 175                 180

Thr Leu Asp His Gly Leu Cys Thr Ala Phe Glu Ser Glu Leu Gly
            185                 190                 195

Asp Asp Val Glu Ala Asn Phe Thr Ala Val Phe Ala Pro Pro Ile Arg
            200                 205                 210

Ala Arg Leu Glu Ala His Leu Pro Gly Val Asn Leu Thr Asp Glu Asp
215                 220                 225                 230

Val Val Asn Leu Met Asp Met Cys Pro Phe Asp Thr Val Ala Arg Thr
                235                 240                 245

Ser Asp Ala Thr Gln Leu Ser Pro Phe Cys Asp Leu Phe Thr His Asp
                250                 255                 260

Glu Trp Ile Gln Tyr Asp Tyr Leu Gln Ser Leu Gly Lys Tyr Tyr Gly
            265                 270                 275

Tyr Gly Ala Gly Asn Pro Leu Gly Pro Ala Gln Gly Val Gly Phe Val
            280                 285                 290

Asn Glu Leu Ile Ala Arg Leu Thr His Ser Pro Val Gln Asp His Thr
295                 300                 305                 310

Ser Thr Asn His Thr Leu Asp Ser Asn Pro Ala Thr Phe Pro Leu Asn
                315                 320                 325

Ala Thr Leu Tyr Ala Asp Phe Ser His Asp Asn Thr Met Val Ser Ile
            330                 335                 340

Phe Phe Ala Leu Gly Leu Tyr Asn Gly Thr Lys Pro Leu Ser Thr Thr
            345                 350                 355

Ser Val Glu Ser Ile Glu Glu Thr Asp Gly Tyr Ser Ala Ser Trp Thr
            360                 365                 370

Val Pro Phe Ala Ala Arg Ala Tyr Val Glu Met Met Gln Cys Glu Ala
375                 380                 385                 390

Glu Lys Glu Pro Leu Val Arg Val Leu Val Asn Asp Arg Val Val Pro
                395                 400                 405

Leu His Gly Cys Gly Val Asp Lys Leu Gly Arg Cys Lys Arg Asp Asp
                410                 415                 420
```

```
Phe Val Glu Gly Leu Ser Phe Ala Arg Ser Gly Gly Asn Trp Glu Glu
        425                 430                 435
Cys Phe Ala
        440

<210> SEQ ID NO 32
<211> LENGTH: 1404
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1401)
<220> FEATURE:
<221> NAME/KEY: sig_peptide
<222> LOCATION: (1)..(78)
<220> FEATURE:
<221> NAME/KEY: mat_peptide
<222> LOCATION: (79)..()

<400> SEQUENCE: 32 atg ggg gtt ttc gtc gtt cta tta tct atc gcg act ctg ttc ggc agc      48
Met Gly Val Phe Val Val Leu Leu Ser Ile Ala Thr Leu Phe Gly Ser
    -25                 -20                 -15 aca tcg ggc act gcg ctg ggc ccc cgt gga aat cac tcc aag tcc tgc      96
Thr Ser Gly Thr Ala Leu Gly Pro Arg Gly Asn His Ser Lys Ser Cys
-10                  -5                  -1   1               5 gat acg gta gac cta ggg tac cag tgc tcc cct gcg act tct cat cta     144
Asp Thr Val Asp Leu Gly Tyr Gln Cys Ser Pro Ala Thr Ser His Leu
             10                  15                  20 tgg ggc acg tac tcg cca tac ttt tcg ctc gag gac gag ctg tcc gtg     192
Trp Gly Thr Tyr Ser Pro Tyr Phe Ser Leu Glu Asp Glu Leu Ser Val
         25                  30                  35 tcg agt aag ctt ccc aag gat tgc cgg atc acc ttg gta cag gtg cta     240
Ser Ser Lys Leu Pro Lys Asp Cys Arg Ile Thr Leu Val Gln Val Leu
     40                  45                  50 tcg cgc cat gga gcg cgg tac cca acc agc tcc aag agc aaa aag tat     288
Ser Arg His Gly Ala Arg Tyr Pro Thr Ser Ser Lys Ser Lys Lys Tyr
 55                  60                  65                  70 aag aag ctt att acg gcg atc cag gcc aat gcc acc gac ttc aag ggc     336
Lys Lys Leu Ile Thr Ala Ile Gln Ala Asn Ala Thr Asp Phe Lys Gly
                 75                  80                  85 aag tac gcc ttt ttg aag acg tac aac tat act ctg ggt gcg gat gac     384
Lys Tyr Ala Phe Leu Lys Thr Tyr Asn Tyr Thr Leu Gly Ala Asp Asp
             90                  95                 100 ctc act ccc ttt ggg gag cag cag ctg gtg aac tcg ggc atc aag ttc     432
Leu Thr Pro Phe Gly Glu Gln Gln Leu Val Asn Ser Gly Ile Lys Phe
        105                 110                 115 tac cag agg tac aag gct ctg gcg cgc agt gtg gtg ccg ttt att cgc     480
Tyr Gln Arg Tyr Lys Ala Leu Ala Arg Ser Val Val Pro Phe Ile Arg
    120                 125                 130 gcc tca ggc tcg gac cgg gtt att gct tcg gga gag aag ttc atc gag     528
Ala Ser Gly Ser Asp Arg Val Ile Ala Ser Gly Glu Lys Phe Ile Glu
135                 140                 145                 150 ggg ttc cag cag gcg aag ctg gct gat cct ggc gcg acg aac cgc gcc     576
Gly Phe Gln Gln Ala Lys Leu Ala Asp Pro Gly Ala Thr Asn Arg Ala
                155                 160                 165 gct ccg gcg att agt gtg att att ccg gag agc gag acg ttc aac aat     624
Ala Pro Ala Ile Ser Val Ile Ile Pro Glu Ser Glu Thr Phe Asn Asn
            170                 175                 180 acg ctg gac cac ggt gtg tgc acg aag ttt gag gcg agt cag ctg gga     672
Thr Leu Asp His Gly Val Cys Thr Lys Phe Glu Ala Ser Gln Leu Gly
```

|  |  |
|---|---|
| gat gag gtt gcg gcc aat ttc act gcg ctc ttt gca ccc gac atc cga<br>Asp Glu Val Ala Ala Asn Phe Thr Ala Leu Phe Ala Pro Asp Ile Arg<br>200                            205                       210 | 720 |
| gct cgc ctc gag aag cat ctt cct ggc gtg acg ctg aca gac gag gac<br>Ala Arg Leu Glu Lys His Leu Pro Gly Val Thr Leu Thr Asp Glu Asp<br>215                           220                       225                     230 | 768 |
| gtt gtc agt cta atg gac atg tgt ccg ttt gat acg gta gcg cgc acc<br>Val Val Ser Leu Met Asp Met Cys Pro Phe Asp Thr Val Ala Arg Thr<br>                     235                       240                     245 | 816 |
| agc gac gca agt cag ctg tca ccg ttc tgt caa ctc ttc act cac aat<br>Ser Asp Ala Ser Gln Leu Ser Pro Phe Cys Gln Leu Phe Thr His Asn<br>250                            255                       260 | 864 |
| gag tgg aag aag tac gac tac ctt cag tcc ttg ggc aag tac tac ggc<br>Glu Trp Lys Lys Tyr Asp Tyr Leu Gln Ser Leu Gly Lys Tyr Tyr Gly<br>       265                     270                     275 | 912 |
| tac ggc gca ggc aac cct ctg gga ccg gct cag ggg ata ggg ttc acc<br>Tyr Gly Ala Gly Asn Pro Leu Gly Pro Ala Gln Gly Ile Gly Phe Thr<br>280                            285                       290 | 960 |
| aac gag ctg att gcc cgg ttg acg cgt tcg cca gtg cag gac cac acc<br>Asn Glu Leu Ile Ala Arg Leu Thr Arg Ser Pro Val Gln Asp His Thr<br>295                         300                       305                     310 | 1008 |
| agc act aac tcg act cta gtc tcc aac ccg gcc acc ttc ccg ttg aac<br>Ser Thr Asn Ser Thr Leu Val Ser Asn Pro Ala Thr Phe Pro Leu Asn<br>                     315                       320                     325 | 1056 |
| gct acc atg tac gtc gac ttt tca cac gac aac agc atg gtt tcc atc<br>Ala Thr Met Tyr Val Asp Phe Ser His Asp Asn Ser Met Val Ser Ile<br>                     330                       335                     340 | 1104 |
| ttc ttt gca ttg ggc ctg tac aac ggc act gaa ccc ttg tcc cgg acc<br>Phe Phe Ala Leu Gly Leu Tyr Asn Gly Thr Glu Pro Leu Ser Arg Thr<br>               345                       350                     355 | 1152 |
| tcg gtg gaa agc gcc aag gaa ttg gat ggg tat tct gca tcc tgg gtg<br>Ser Val Glu Ser Ala Lys Glu Leu Asp Gly Tyr Ser Ala Ser Trp Val<br>360                            365                       370 | 1200 |
| gtg cct ttc ggc gcg cga gcc tac ttc gag acg atg caa tgc aag tcg<br>Val Pro Phe Gly Ala Arg Ala Tyr Phe Glu Thr Met Gln Cys Lys Ser<br>375                            380                       385                     390 | 1248 |
| gaa aag gag cct ctt gtt cgc gct ttg att aat gac cgg gtt gtg cca<br>Glu Lys Glu Pro Leu Val Arg Ala Leu Ile Asn Asp Arg Val Val Pro<br>                     395                       400                     405 | 1296 |
| ctg cat ggc tgc gat gtg gac aag ctg ggg cga tgc aag ctg aat gac<br>Leu His Gly Cys Asp Val Asp Lys Leu Gly Arg Cys Lys Leu Asn Asp<br>               410                       415                     420 | 1344 |
| ttt gtc aag gga ttg agt tgg gcc aga tct ggg ggc aac tgg gga gag<br>Phe Val Lys Gly Leu Ser Trp Ala Arg Ser Gly Gly Asn Trp Gly Glu<br>               425                       430                     435 | 1392 |
| tgc ttt agt tga<br>Cys Phe Ser<br>    440 | 1404 |

<210> SEQ ID NO 33
<211> LENGTH: 467
<212> TYPE: PRT
<213> ORGANISM: Artificial Sequence
<220> FEATURE:
<223> OTHER INFORMATION: Synthetic

<400> SEQUENCE: 33

Met Gly Val Phe Val Val Leu Leu Ser Ile Ala Thr Leu Phe Gly Ser
    -25                     -20                     -15

-continued

```
Thr Ser Gly Thr Ala Leu Gly Pro Arg Gly Asn His Ser Lys Ser Cys
-10              -5                  -1  1               5

Asp Thr Val Asp Leu Gly Tyr Gln Cys Ser Pro Ala Thr Ser His Leu
             10              15              20

Trp Gly Thr Tyr Ser Pro Tyr Phe Ser Leu Glu Asp Glu Leu Ser Val
         25              30              35

Ser Ser Lys Leu Pro Lys Asp Cys Arg Ile Thr Leu Val Gln Val Leu
     40              45              50

Ser Arg His Gly Ala Arg Tyr Pro Thr Ser Ser Lys Ser Lys Lys Tyr
55              60              65                      70

Lys Lys Leu Ile Thr Ala Ile Gln Ala Asn Ala Thr Asp Phe Lys Gly
             75              80              85

Lys Tyr Ala Phe Leu Lys Thr Tyr Asn Tyr Thr Leu Gly Ala Asp Asp
             90              95              100

Leu Thr Pro Phe Gly Glu Gln Gln Leu Val Asn Ser Gly Ile Lys Phe
             105             110             115

Tyr Gln Arg Tyr Lys Ala Leu Ala Arg Ser Val Val Pro Phe Ile Arg
    120             125             130

Ala Ser Gly Ser Asp Arg Val Ile Ala Ser Gly Lys Phe Ile Glu
135             140             145             150

Gly Phe Gln Gln Ala Lys Leu Ala Asp Pro Gly Ala Thr Asn Arg Ala
             155             160             165

Ala Pro Ala Ile Ser Val Ile Ile Pro Glu Ser Glu Thr Phe Asn Asn
             170             175             180

Thr Leu Asp His Gly Val Cys Thr Lys Phe Glu Ala Ser Gln Leu Gly
             185             190             195

Asp Glu Val Ala Ala Asn Phe Thr Ala Leu Phe Ala Pro Asp Ile Arg
    200             205             210

Ala Arg Leu Glu Lys His Leu Pro Gly Val Thr Leu Thr Asp Glu Asp
215             220             225             230

Val Val Ser Leu Met Asp Met Cys Pro Phe Asp Thr Val Ala Arg Thr
             235             240             245

Ser Asp Ala Ser Gln Leu Ser Pro Phe Cys Gln Leu Phe Thr His Asn
             250             255             260

Glu Trp Lys Lys Tyr Asp Tyr Leu Gln Ser Leu Gly Lys Tyr Tyr Gly
         265             270             275

Tyr Gly Ala Gly Asn Pro Leu Gly Pro Ala Gln Gly Ile Gly Phe Thr
         280             285             290

Asn Glu Leu Ile Ala Arg Leu Thr Arg Ser Pro Val Gln Asp His Thr
295             300             305             310

Ser Thr Asn Ser Thr Leu Val Ser Asn Pro Ala Thr Phe Pro Leu Asn
             315             320             325

Ala Thr Met Tyr Val Asp Phe Ser His Asp Asn Ser Met Val Ser Ile
             330             335             340

Phe Phe Ala Leu Gly Leu Tyr Asn Gly Thr Glu Pro Leu Ser Arg Thr
             345             350             355

Ser Val Glu Ser Ala Lys Glu Leu Asp Gly Tyr Ser Ala Ser Trp Val
    360             365             370

Val Pro Phe Gly Ala Arg Ala Tyr Phe Glu Thr Met Gln Cys Lys Ser
375             380             385             390

Glu Lys Glu Pro Leu Val Arg Ala Leu Ile Asn Asp Arg Val Val Pro
             395             400             405

Leu His Gly Cys Asp Val Asp Lys Leu Gly Arg Cys Lys Leu Asn Asp
```

```
                    410              415              420
Phe Val Lys Gly Leu Ser Trp Ala Arg Ser Gly Gly Asn Trp Gly Glu
        425              430              435

Cys Phe Ser
    440

<210> SEQ ID NO 34
<211> LENGTH: 1426
<212> TYPE: DNA
<213> ORGANISM: Artificial Sequence
<220> FEATURE:
<223> OTHER INFORMATION: synthetic
<220> FEATURE:
<221> NAME/KEY: CDS
<222> LOCATION: (12)..(1412)
<220> FEATURE:
<221> NAME/KEY: sig_peptide
<222> LOCATION: (12)..(89)
<220> FEATURE:
<221> NAME/KEY: mat_peptide
<222> LOCATION: (90)..()

<400> SEQUENCE: 34
tatatgaatt c atg ggc gtg ttc gtc gtg cta ctg tcc att gcc acc ttg      50
            Met Gly Val Phe Val Val Leu Leu Ser Ile Ala Thr Leu
                -25              -20              -15 ttc ggt tcc aca tcc ggt acc gcc ttg ggt cct cgt ggt aat tct cac      98
Phe Gly Ser Thr Ser Gly Thr Ala Leu Gly Pro Arg Gly Asn Ser His
            -10              -5               -1  1 tct tgt gac act gtt gac ggt ggt tac caa tgt ttc cca gaa att tct     146
Ser Cys Asp Thr Val Asp Gly Gly Tyr Gln Cys Phe Pro Glu Ile Ser
        5               10              15 cac ttg tgg ggt caa tac tct cca tac ttc tct ttg gaa gac gaa tct     194
His Leu Trp Gly Gln Tyr Ser Pro Tyr Phe Ser Leu Glu Asp Glu Ser
20              25              30              35 gct att tct cca gac gtt cca gac gac tgt aga gtt act ttc gtt caa     242
Ala Ile Ser Pro Asp Val Pro Asp Asp Cys Arg Val Thr Phe Val Gln
                40              45              50 gtt ttg tct aga cac ggt gct aga tac cca act gac tct aag ggt aag     290
Val Leu Ser Arg His Gly Ala Arg Tyr Pro Thr Asp Ser Lys Gly Lys
        55              60              65 aag tac tct gct ttg att gaa gct att caa aag aac gct act gct ttc     338
Lys Tyr Ser Ala Leu Ile Glu Ala Ile Gln Lys Asn Ala Thr Ala Phe
            70              75              80 aag ggt aag tac gct ttc ttg aag act tac aac tac act ttg ggt gct     386
Lys Gly Lys Tyr Ala Phe Leu Lys Thr Tyr Asn Tyr Thr Leu Gly Ala
85              90              95 gac gac ttg act cca ttc ggt gaa aac caa atg gtt aac tct ggt att     434
Asp Asp Leu Thr Pro Phe Gly Glu Asn Gln Met Val Asn Ser Gly Ile
100             105             110             115 aag ttc tac aga aga tac aag gct ttg gct aga aag att gtt cca ttc     482
Lys Phe Tyr Arg Arg Tyr Lys Ala Leu Ala Arg Lys Ile Val Pro Phe
                120             125             130 att aga gct tct ggt tct tct aga gtt att gct tct gct gaa aag ttc     530
Ile Arg Ala Ser Gly Ser Ser Arg Val Ile Ala Ser Ala Glu Lys Phe
            135             140             145 att gaa ggt ttc caa tct gct aag ttg gct gac cca ggt tct caa cca     578
Ile Glu Gly Phe Gln Ser Ala Lys Leu Ala Asp Pro Gly Ser Gln Pro
        150             155             160 cac caa gct tct cca gtt att gac gtt att att tct gac gct tct tct     626
His Gln Ala Ser Pro Val Ile Asp Val Ile Ile Ser Asp Ala Ser Ser
165             170             175
```

```
tac aac aac act ttg gac cca ggt act tgt act gct ttc gaa gac tct      674
Tyr Asn Asn Thr Leu Asp Pro Gly Thr Cys Thr Ala Phe Glu Asp Ser
180                 185                 190                 195 gaa ttg gct gac act gtt gaa gct aac ttc act gct ttg ttc gct cca      722
Glu Leu Ala Asp Thr Val Glu Ala Asn Phe Thr Ala Leu Phe Ala Pro
                200                 205                 210 gct att aga gct aga ttg gaa gct gac ttg cca ggt gtt act ttg act      770
Ala Ile Arg Ala Arg Leu Glu Ala Asp Leu Pro Gly Val Thr Leu Thr
            215                 220                 225 gac act gaa gtt act tac ttg atg gac atg tgt tct ttc gaa act gtt      818
Asp Thr Glu Val Thr Tyr Leu Met Asp Met Cys Ser Phe Glu Thr Val
        230                 235                 240 gct aga act tct gac gct act gaa ttg tct cca ttc tgt gct ttg ttc      866
Ala Arg Thr Ser Asp Ala Thr Glu Leu Ser Pro Phe Cys Ala Leu Phe
    245                 250                 255 act cac gac gaa tgg aga cac tac gac tac ttg caa tct ttg aag aag      914
Thr His Asp Glu Trp Arg His Tyr Asp Tyr Leu Gln Ser Leu Lys Lys
260                 265                 270                 275 tac tac ggt cac ggt gct ggt aac cca ttg ggt cca act caa ggt gtt      962
Tyr Tyr Gly His Gly Ala Gly Asn Pro Leu Gly Pro Thr Gln Gly Val
                280                 285                 290 ggt ttc gct aac gaa ttg att gct aga ttg act aga tct cca gtt caa     1010
Gly Phe Ala Asn Glu Leu Ile Ala Arg Leu Thr Arg Ser Pro Val Gln
            295                 300                 305 gac cac act tct act aac cac act ttg gac tct aac cca gct act ttc     1058
Asp His Thr Ser Thr Asn His Thr Leu Asp Ser Asn Pro Ala Thr Phe
        310                 315                 320 cca ttg aac gct act ttg tac gct gac ttc tct cac gac aac ggt att     1106
Pro Leu Asn Ala Thr Leu Tyr Ala Asp Phe Ser His Asp Asn Gly Ile
    325                 330                 335 att tct att ttc ttc gct ttg ggt ttg tac aac ggt act gct cca ttg     1154
Ile Ser Ile Phe Phe Ala Leu Gly Leu Tyr Asn Gly Thr Ala Pro Leu
340                 345                 350                 355 tct act act tct gtt gaa tct att gaa gaa act gac ggt tac tct tct     1202
Ser Thr Thr Ser Val Glu Ser Ile Glu Glu Thr Asp Gly Tyr Ser Ser
                360                 365                 370 gct tgg act gtt cca ttc gct tct aga gct tac gtt gaa atg atg caa     1250
Ala Trp Thr Val Pro Phe Ala Ser Arg Ala Tyr Val Glu Met Met Gln
            375                 380                 385 tgt caa gct gaa aag gaa cca ttg gtt aga gtt ttg gtt aac gac aga     1298
Cys Gln Ala Glu Lys Glu Pro Leu Val Arg Val Leu Val Asn Asp Arg
        390                 395                 400 gtt gtt cca ttg cac ggt tgt gct gtt gac aag ttg ggt aga tgt aag     1346
Val Val Pro Leu His Gly Cys Ala Val Asp Lys Leu Gly Arg Cys Lys
    405                 410                 415 aga gac gac ttc gtt gaa ggt ttg tct ttc gct aga tct ggt ggt aac     1394
Arg Asp Asp Phe Val Glu Gly Leu Ser Phe Ala Arg Ser Gly Gly Asn
420                 425                 430                 435 tgg gct gaa tgt ttc gct taagaattca tata                             1426
Trp Ala Glu Cys Phe Ala
                440

<210> SEQ ID NO 35
<211> LENGTH: 467
<212> TYPE: PRT
<213> ORGANISM: Artificial Sequence
<220> FEATURE:
<223> OTHER INFORMATION: synthetic

<400> SEQUENCE: 35

Met Gly Val Phe Val Val Leu Leu Ser Ile Ala Thr Leu Phe Gly Ser
```

```
        -25                  -20                 -15
Thr Ser Gly Thr Ala Leu Gly Pro Arg Gly Asn Ser His Ser Cys Asp
-10              -5              -1  1               5

Thr Val Asp Gly Gly Tyr Gln Cys Phe Pro Glu Ile Ser His Leu Trp
             10              15              20

Gly Gln Tyr Ser Pro Tyr Phe Ser Leu Glu Asp Glu Ser Ala Ile Ser
         25              30              35

Pro Asp Val Pro Asp Asp Cys Arg Val Thr Phe Val Gln Val Leu Ser
    40              45              50

Arg His Gly Ala Arg Tyr Pro Thr Asp Ser Lys Gly Lys Lys Tyr Ser
55              60              65              70

Ala Leu Ile Glu Ala Ile Gln Lys Asn Ala Thr Ala Phe Lys Gly Lys
             75              80              85

Tyr Ala Phe Leu Lys Thr Tyr Asn Tyr Thr Leu Gly Ala Asp Asp Leu
             90              95             100

Thr Pro Phe Gly Glu Asn Gln Met Val Asn Ser Gly Ile Lys Phe Tyr
            105             110             115

Arg Arg Tyr Lys Ala Leu Ala Arg Lys Ile Val Pro Phe Ile Arg Ala
        120             125             130

Ser Gly Ser Ser Arg Val Ile Ala Ser Glu Lys Phe Ile Glu Gly
135             140             145             150

Phe Gln Ser Ala Lys Leu Ala Asp Pro Gly Ser Gln Pro His Gln Ala
            155             160             165

Ser Pro Val Ile Asp Val Ile Ser Asp Ala Ser Ser Tyr Asn Asn
            170             175             180

Thr Leu Asp Pro Gly Thr Cys Thr Ala Phe Glu Asp Ser Glu Leu Ala
        185             190             195

Asp Thr Val Glu Ala Asn Phe Thr Ala Leu Phe Ala Pro Ala Ile Arg
    200             205             210

Ala Arg Leu Glu Ala Asp Leu Pro Gly Val Thr Leu Thr Asp Thr Glu
215             220             225             230

Val Thr Tyr Leu Met Asp Met Cys Ser Phe Glu Thr Val Ala Arg Thr
            235             240             245

Ser Asp Ala Thr Glu Leu Ser Pro Phe Cys Ala Leu Phe Thr His Asp
            250             255             260

Glu Trp Arg His Tyr Asp Tyr Leu Gln Ser Leu Lys Lys Tyr Tyr Gly
            265             270             275

His Gly Ala Gly Asn Pro Leu Gly Pro Thr Gln Gly Val Gly Phe Ala
            280             285             290

Asn Glu Leu Ile Ala Arg Leu Thr Arg Ser Pro Val Gln Asp His Thr
295             300             305             310

Ser Thr Asn His Thr Leu Asp Ser Asn Pro Ala Thr Phe Pro Leu Asn
            315             320             325

Ala Thr Leu Tyr Ala Asp Phe Ser His Asp Asn Gly Ile Ile Ser Ile
            330             335             340

Phe Phe Ala Leu Gly Leu Tyr Asn Gly Thr Ala Pro Leu Ser Thr Thr
            345             350             355

Ser Val Glu Ser Ile Glu Glu Thr Asp Gly Tyr Ser Ser Ala Trp Thr
            360             365             370

Val Pro Phe Ala Ser Arg Ala Tyr Val Glu Met Met Gln Cys Gln Ala
375             380             385             390

Glu Lys Glu Pro Leu Val Arg Val Leu Val Asn Asp Arg Val Val Pro
            395             400             405
```

```
Leu His Gly Cys Ala Val Asp Lys Leu Gly Arg Cys Lys Arg Asp Asp
            410                 415                 420

Phe Val Glu Gly Leu Ser Phe Ala Arg Ser Gly Gly Asn Trp Ala Glu
            425                 430                 435

Cys Phe Ala
    440

<210> SEQ ID NO 36
<211> LENGTH: 467
<212> TYPE: PRT
<213> ORGANISM: Artificial Sequence
<220> FEATURE:
<223> OTHER INFORMATION: synthetic

<400> SEQUENCE: 36

Met Gly Val Phe Val Val Leu Leu Ser Ile Ala Thr Leu Phe Gly Ser
1               5                   10                  15

Thr Ser Gly Thr Ala Leu Gly Pro Arg Gly Asn Ser His Ser Cys Asp
            20                  25                  30

Thr Val Asp Gly Gly Tyr Gln Cys Phe Pro Glu Ile Ser Ser Asn Trp
        35                  40                  45

Ser Pro Tyr Ser Pro Tyr Phe Ser Leu Ala Asp Glu Ser Ala Ile Ser
    50                  55                  60

Pro Asp Val Pro Lys Gly Cys Arg Val Thr Phe Val Gln Val Leu Gln
65                  70                  75                  80

Arg His Gly Ala Arg Phe Pro Thr Ser Gly Ala Ala Thr Arg Ile Ser
                85                  90                  95

Ala Leu Ile Glu Ala Ile Gln Lys Asn Ala Thr Ala Phe Lys Gly Lys
            100                 105                 110

Tyr Ala Phe Leu Lys Thr Tyr Asn Tyr Thr Leu Gly Ala Asp Asp Leu
        115                 120                 125

Val Pro Phe Gly Ala Asn Gln Ser Ser Gln Ala Gly Ile Lys Phe Tyr
    130                 135                 140

Arg Arg Tyr Lys Ala Leu Ala Arg Lys Ile Val Pro Phe Ile Arg Ala
145                 150                 155                 160

Ser Gly Ser Asp Arg Val Ile Asp Ser Ala Thr Asn Trp Ile Glu Gly
                165                 170                 175

Phe Gln Ser Ala Lys Leu Ala Asp Pro Gly Ala Asn Pro His Gln Ala
            180                 185                 190

Ser Pro Val Ile Asn Val Ile Ile Pro Glu Gly Ala Gly Tyr Asn Asn
        195                 200                 205

Thr Leu Asp His Gly Leu Cys Thr Ala Phe Glu Glu Ser Glu Leu Gly
    210                 215                 220

Asp Asp Val Glu Ala Asn Phe Thr Ala Val Phe Ala Pro Pro Ile Arg
225                 230                 235                 240

Ala Arg Leu Glu Ala His Leu Pro Gly Val Asn Leu Thr Asp Glu Asp
                245                 250                 255

Val Val Asn Leu Met Asp Met Cys Pro Phe Asp Thr Val Ala Arg Thr
            260                 265                 270

Ser Asp Ala Thr Glu Leu Ser Pro Phe Cys Asp Leu Phe Thr His Asp
        275                 280                 285

Glu Trp Ile Gln Tyr Asp Tyr Leu Gly Asp Leu Asp Lys Tyr Tyr Gly
    290                 295                 300

Thr Gly Ala Gly Asn Pro Leu Gly Pro Ala Gln Gly Val Gly Phe Val
305                 310                 315                 320
```

```
Asn Glu Leu Ile Ala Arg Leu Thr His Ser Pro Val Gln Asp His Thr
                325                 330                 335

Ser Thr Asn His Thr Leu Asp Ser Asn Pro Ala Thr Phe Pro Leu Asn
        340                 345                 350

Ala Thr Leu Tyr Ala Asp Phe Ser His Asp Asn Thr Met Val Ala Ile
            355                 360                 365

Phe Phe Ala Leu Gly Leu Tyr Asn Gly Thr Lys Pro Leu Ser Thr Thr
    370                 375                 380

Ser Val Glu Ser Ile Glu Glu Thr Asp Gly Tyr Ser Ala Ser Trp Leu
385                 390                 395                 400

Val Pro Phe Ser Ala Arg Met Tyr Val Glu Met Met Gln Cys Glu Ala
                405                 410                 415

Glu Lys Glu Pro Leu Val Arg Val Leu Val Asn Asp Arg Val Val Pro
                420                 425                 430

Leu His Gly Cys Gly Val Asp Lys Leu Gly Arg Cys Lys Arg Asp Asp
            435                 440                 445

Phe Val Glu Gly Leu Ser Phe Ala Arg Ser Gly Gly Asn Trp Glu Glu
    450                 455                 460

Cys Phe Ala
465

<210> SEQ ID NO 37
<211> LENGTH: 26
<212> TYPE: DNA
<213> ORGANISM: Artificial Sequence
<220> FEATURE:
<223> OTHER INFORMATION: Primer

<400> SEQUENCE: 37
tatatgaatt catgggcgtg ttcgtc                                      26

<210> SEQ ID NO 38
<211> LENGTH: 22
<212> TYPE: DNA
<213> ORGANISM: Artificial Sequence
<220> FEATURE:
<223> OTHER INFORMATION: Primer

<400> SEQUENCE: 38
tgaaaagttc attgaaggtt tc                                          22

<210> SEQ ID NO 39
<211> LENGTH: 22
<212> TYPE: DNA
<213> ORGANISM: Artificial Sequence
<220> FEATURE:
<223> OTHER INFORMATION: Primer

<400> SEQUENCE: 39
tcttcgaaag cagtacacaa ac                                          22

<210> SEQ ID NO 40
<211> LENGTH: 22
<212> TYPE: DNA
<213> ORGANISM: Artificial Sequence
<220> FEATURE:
<223> OTHER INFORMATION: Primer

<400> SEQUENCE: 40
tatatgaatt cttaagcgaa ac                                          22
```

```
<210> SEQ ID NO 41
<211> LENGTH: 32
<212> TYPE: DNA
<213> ORGANISM: Artificial Sequence
<220> FEATURE:
<223> OTHER INFORMATION: Primer

<400> SEQUENCE: 41
cacttgtggg gtacctactc tccatacttc tc                         32

<210> SEQ ID NO 42
<211> LENGTH: 31
<212> TYPE: DNA
<213> ORGANISM: Artificial Sequence
<220> FEATURE:
<223> OTHER INFORMATION: Primer

<400> SEQUENCE: 42
ggtcaatact ctccattctt ctctttggaa g                          31

<210> SEQ ID NO 43
<211> LENGTH: 28
<212> TYPE: DNA
<213> ORGANISM: Artificial Sequence
<220> FEATURE:
<223> OTHER INFORMATION: Primer

<400> SEQUENCE: 43
catacttctc tttggcagac gaatctgc                              28

<210> SEQ ID NO 44
<211> LENGTH: 31
<212> TYPE: DNA
<213> ORGANISM: Artificial Sequence
<220> FEATURE:
<223> OTHER INFORMATION: Primer

<400> SEQUENCE: 44
ctccagacgt cccaaaggac tgtagagtta c                          31

<210> SEQ ID NO 45
<211> LENGTH: 31
<212> TYPE: DNA
<213> ORGANISM: Artificial Sequence
<220> FEATURE:
<223> OTHER INFORMATION: Primer

<400> SEQUENCE: 45
ctccagacgt cccagacggc tgtagagtta c                          31

<210> SEQ ID NO 46
<211> LENGTH: 36
<212> TYPE: DNA
<213> ORGANISM: Artificial Sequence
<220> FEATURE:
<223> OTHER INFORMATION: Primer

<400> SEQUENCE: 46
gatacccaac ttcttctgcg tctaaggctt actctg                     36

<210> SEQ ID NO 47
<211> LENGTH: 29
<212> TYPE: DNA
<213> ORGANISM: Artificial Sequence
<220> FEATURE:
<223> OTHER INFORMATION: Primer
```

<400> SEQUENCE: 47
cttctaagtc taagaagtac tctgctttg                29

<210> SEQ ID NO 48
<211> LENGTH: 41
<212> TYPE: DNA
<213> ORGANISM: Artificial Sequence
<220> FEATURE:
<223> OTHER INFORMATION: Primer

<400> SEQUENCE: 48
gcttactctg ctttgattga acggattcaa aagaacgcta c                41

<210> SEQ ID NO 49
<211> LENGTH: 29
<212> TYPE: DNA
<213> ORGANISM: Artificial Sequence
<220> FEATURE:
<223> OTHER INFORMATION: Primer

<400> SEQUENCE: 49
ccattcggtg aacagcaaat ggttaactc                29

<210> SEQ ID NO 50
<211> LENGTH: 30
<212> TYPE: DNA
<213> ORGANISM: Artificial Sequence
<220> FEATURE:
<223> OTHER INFORMATION: Primer

<400> SEQUENCE: 50
gatacaaggc tctcgcgaga aacattgttc                30

<210> SEQ ID NO 51
<211> LENGTH: 30
<212> TYPE: DNA
<213> ORGANISM: Artificial Sequence
<220> FEATURE:
<223> OTHER INFORMATION: Primer

<400> SEQUENCE: 51
gattgttcca ttcgtgcgcg cttctggttc                30

<210> SEQ ID NO 52
<211> LENGTH: 31
<212> TYPE: DNA
<213> ORGANISM: Artificial Sequence
<220> FEATURE:
<223> OTHER INFORMATION: Primer

<400> SEQUENCE: 52
ctccagttat taacgtgatc attccagaag g                31

<210> SEQ ID NO 53
<211> LENGTH: 30
<212> TYPE: DNA
<213> ORGANISM: Artificial Sequence
<220> FEATURE:
<223> OTHER INFORMATION: Primer

<400> SEQUENCE: 53
ggctgaccca ggggcccaac cacaccaagc                30

<210> SEQ ID NO 54

```
<211> LENGTH: 32
<212> TYPE: DNA
<213> ORGANISM: Artificial Sequence
<220> FEATURE:
<223> OTHER INFORMATION: Primer

<400> SEQUENCE: 54
cactttggac catggtcttt gtactgcttt cg                              32

<210> SEQ ID NO 55
<211> LENGTH: 34
<212> TYPE: DNA
<213> ORGANISM: Artificial Sequence
<220> FEATURE:
<223> OTHER INFORMATION: Primer

<400> SEQUENCE: 55
gctttcgaag actctaccct aggtgacgac gttg                            34

<210> SEQ ID NO 56
<211> LENGTH: 26
<212> TYPE: DNA
<213> ORGANISM: Artificial Sequence
<220> FEATURE:
<223> OTHER INFORMATION: Primer

<400> SEQUENCE: 56
ggtgacgacg ctgaagctaa cttcac                                     26

<210> SEQ ID NO 57
<211> LENGTH: 27
<212> TYPE: DNA
<213> ORGANISM: Artificial Sequence
<220> FEATURE:
<223> OTHER INFORMATION: Primer

<400> SEQUENCE: 57
ctaacttcac cgcggtgttc gctccag                                    27

<210> SEQ ID NO 58
<211> LENGTH: 34
<212> TYPE: DNA
<213> ORGANISM: Artificial Sequence
<220> FEATURE:
<223> OTHER INFORMATION: Primer

<400> SEQUENCE: 58
gctttgttcg ctccacctat tagagctaga ttgg                            34

<210> SEQ ID NO 59
<211> LENGTH: 26
<212> TYPE: DNA
<213> ORGANISM: Artificial Sequence
<220> FEATURE:
<223> OTHER INFORMATION: Primer

<400> SEQUENCE: 59
gccaggtgtt aacttgactg acgaag                                     26

<210> SEQ ID NO 60
<211> LENGTH: 27
<212> TYPE: DNA
<213> ORGANISM: Artificial Sequence
<220> FEATURE:
<223> OTHER INFORMATION: Primer

<400> SEQUENCE: 60
```

-continued gacgaagacg tcgttaactt gatggac                                27

<210> SEQ ID NO 61
<211> LENGTH: 28
<212> TYPE: DNA
<213> ORGANISM: Artificial Sequence
<220> FEATURE:
<223> OTHER INFORMATION: Primer

<400> SEQUENCE: 61
gtccattcga cactgtcgct agaacttc                               28

<210> SEQ ID NO 62
<211> LENGTH: 26
<212> TYPE: DNA
<213> ORGANISM: Artificial Sequence
<220> FEATURE:
<223> OTHER INFORMATION: Primer

<400> SEQUENCE: 62
ctgacgctac tcagctgtct ccattc                                 26

<210> SEQ ID NO 63
<211> LENGTH: 28
<212> TYPE: DNA
<213> ORGANISM: Artificial Sequence
<220> FEATURE:
<223> OTHER INFORMATION: Primer

<400> SEQUENCE: 63
gtctccattc tgtgatttgt tcactcac                               28

<210> SEQ ID NO 64
<211> LENGTH: 26
<212> TYPE: DNA
<213> ORGANISM: Artificial Sequence
<220> FEATURE:
<223> OTHER INFORMATION: Primer

<400> SEQUENCE: 64
gctttgttca ccgcggacga atggag                                 26

<210> SEQ ID NO 65
<211> LENGTH: 27
<212> TYPE: DNA
<213> ORGANISM: Primer

<400> SEQUENCE: 65
cacgacgaat ggatccaata cgactac                                27

<210> SEQ ID NO 66
<211> LENGTH: 27
<212> TYPE: DNA
<213> ORGANISM: Artificial Sequence
<220> FEATURE:
<223> OTHER INFORMATION: Primer

<400> SEQUENCE: 66
gacgaatgga gagcgtacga ctacttg                                27

<210> SEQ ID NO 67
<211> LENGTH: 29
<212> TYPE: DNA
<213> ORGANISM: Artificial Sequence
<220> FEATURE:

<223> OTHER INFORMATION: Primer

<400> SEQUENCE: 67
ggtgttggtt tcgttaacga attgattgc                                29

<210> SEQ ID NO 68
<211> LENGTH: 28
<212> TYPE: DNA
<213> ORGANISM: Artificial Sequence
<220> FEATURE:
<223> OTHER INFORMATION: Primer

<400> SEQUENCE: 68
gctagattga ctcactctcc agttcaag                                 28

<210> SEQ ID NO 69
<211> LENGTH: 32
<212> TYPE: DNA
<213> ORGANISM: Artificial Sequence
<220> FEATURE:
<223> OTHER INFORMATION: Primer

<400> SEQUENCE: 69
ctcacgacaa cactatgata tctattttct tc                            32

<210> SEQ ID NO 70
<211> LENGTH: 30
<212> TYPE: DNA
<213> ORGANISM: Artificial Sequence
<220> FEATURE:
<223> OTHER INFORMATION: Primer

<400> SEQUENCE: 70
cgacaactcc atggtttcta ttttcttcgc                               30

<210> SEQ ID NO 71
<211> LENGTH: 27
<212> TYPE: DNA
<213> ORGANISM: Artificial Sequence
<220> FEATURE:
<223> OTHER INFORMATION: Primer

<400> SEQUENCE: 71
gtacaacggt accaagccat tgtctac                                  27

<210> SEQ ID NO 72
<211> LENGTH: 25
<212> TYPE: DNA
<213> ORGANISM: Artificial Sequence
<220> FEATURE:
<223> OTHER INFORMATION: Primer

<400> SEQUENCE: 72
ctgacggtta cgctgcttct tggac                                    25

<210> SEQ ID NO 73
<211> LENGTH: 26
<212> TYPE: DNA
<213> ORGANISM: Artificial Sequence
<220> FEATURE:
<223> OTHER INFORMATION: Primer

<400> SEQUENCE: 73
ctgttccatt cgctgctaga gcttac                                   26

<210> SEQ ID NO 74
<211> LENGTH: 27
<212> TYPE: DNA
<213> ORGANISM: Artificial Sequence
<220> FEATURE:
<223> OTHER INFORMATION: Primer

<400> SEQUENCE: 74
gatgcaatgt gaagctgaaa aggaacc                              27

<210> SEQ ID NO 75
<211> LENGTH: 26
<212> TYPE: DNA
<213> ORGANISM: Artificial Sequence
<220> FEATURE:
<223> OTHER INFORMATION: Primer

<400> SEQUENCE: 75
cacggttgtg gtgtcgacaa gttggg                               26

<210> SEQ ID NO 76
<211> LENGTH: 30
<212> TYPE: DNA
<213> ORGANISM: Artificial Sequence
<220> FEATURE:
<223> OTHER INFORMATION: Primer

<400> SEQUENCE: 76
gatctggtgg caattgggag gaatgtttcg                           30

<210> SEQ ID NO 77
<211> LENGTH: 28
<212> TYPE: DNA
<213> ORGANISM: Artificial Sequence
<220> FEATURE:
<223> OTHER INFORMATION: Primer

<400> SEQUENCE: 77
cacgtactcg ccatactttt cgctcgag                             28

<210> SEQ ID NO 78
<211> LENGTH: 33
<212> TYPE: DNA
<213> ORGANISM: Artificial Sequence
<220> FEATURE:
<223> OTHER INFORMATION: Primer

<400> SEQUENCE: 78
ccatactttt cgctcgcgga cgagctgtcc gtg                       33

<210> SEQ ID NO 79
<211> LENGTH: 31
<212> TYPE: DNA
<213> ORGANISM: Artificial Sequence
<220> FEATURE:
<223> OTHER INFORMATION: Primer

<400> SEQUENCE: 79
gtataagaag cttattacgg cgatccaggc c                         31

<210> SEQ ID NO 80
<211> LENGTH: 31
<212> TYPE: DNA
<213> ORGANISM: Artificial Sequence
<220> FEATURE:
<223> OTHER INFORMATION: Primer

<400> SEQUENCE: 80
cttcaagggc aagtacgcct ttttgaagac g                                    31

<210> SEQ ID NO 81
<211> LENGTH: 29
<212> TYPE: DNA
<213> ORGANISM: Artificial Sequence
<220> FEATURE:
<223> OTHER INFORMATION: Primer

<400> SEQUENCE: 81
catccgagct cgcctcgaga agcatcttc                                       29

<210> SEQ ID NO 82
<211> LENGTH: 29
<212> TYPE: DNA
<213> ORGANISM: Artificial Sequence
<220> FEATURE:
<223> OTHER INFORMATION: Primer

<400> SEQUENCE: 82
ctaatggatg tgtccgtttg atacggtag                                       29

<210> SEQ ID NO 83
<211> LENGTH: 27
<212> TYPE: DNA
<213> ORGANISM: Artificial Sequence
<220> FEATURE:
<223> OTHER INFORMATION: Primer

<400> SEQUENCE: 83
gtggaagaag tacgactacc ttcagtc                                         27

<210> SEQ ID NO 84
<211> LENGTH: 28
<212> TYPE: DNA
<213> ORGANISM: Artificial Sequence
<220> FEATURE:
<223> OTHER INFORMATION: Primer

<400> SEQUENCE: 84
gcccggttga cgcattcgcc agtgcagg                                        28

<210> SEQ ID NO 85
<211> LENGTH: 29
<212> TYPE: DNA
<213> ORGANISM: Artificial Sequence
<220> FEATURE:
<223> OTHER INFORMATION: Primer

<400> SEQUENCE: 85
cacacgacaa caccatggtt tccatcttc                                       29

<210> SEQ ID NO 86
<211> LENGTH: 30
<212> TYPE: DNA
<213> ORGANISM: Artificial Sequence
<220> FEATURE:
<223> OTHER INFORMATION: Primer

<400> SEQUENCE: 86
gtggtgcctt tcgccgcgcg agcctacttc                                      30

<210> SEQ ID NO 87
<211> LENGTH: 33

-continued

```
<212> TYPE: DNA
<213> ORGANISM: Artificial Sequence
<220> FEATURE:
<223> OTHER INFORMATION: Primer

<400> SEQUENCE: 87
tatatcatga gcgtgttcgt cgtgctactg ttc                              33

<210> SEQ ID NO 88
<211> LENGTH: 33
<212> TYPE: DNA
<213> ORGANISM: Artificial Sequence
<220> FEATURE:
<223> OTHER INFORMATION: Primer

<400> SEQUENCE: 88
acccgactta caaagcgaat tctatagata tat                              33

<210> SEQ ID NO 89
<211> LENGTH: 33
<212> TYPE: DNA
<213> ORGANISM: Artificial Sequence
<220> FEATURE:
<223> OTHER INFORMATION: Primer

<400> SEQUENCE: 89
acccttctta caaagcgaat tctatagata tat                              33

<210> SEQ ID NO 90
<211> LENGTH: 1404
<212> TYPE: DNA
<213> ORGANISM: Artificial Sequence
<220> FEATURE:
<223> OTHER INFORMATION: Primer
<220> FEATURE:
<221> NAME/KEY: CDS
<222> LOCATION: (1)..(1401)
<220> FEATURE:
<221> NAME/KEY: sig_peptide
<222> LOCATION: (1)..(69)
<220> FEATURE:
<221> NAME/KEY: mat_peptide
<222> LOCATION: (70)..()

<400> SEQUENCE: 90
```

| | | | | | | | | | | | | | | | | |
|---|---|---|---|---|---|---|---|---|---|---|---|---|---|---|---|---|
| atg | ggc | gtg | ttc | gtc | gtg | cta | ctg | tcc | att | gcc | acc | ttg | ttc | ggt | tcc | 48 |
| Met | Gly | Val | Phe | Val | Val | Leu | Leu | Ser | Ile | Ala | Thr | Leu | Phe | Gly | Ser | |
| | | | -20 | | | | -15 | | | | | -10 | | | | |
| aca | tcc | ggt | acc | gcc | ttg | ggt | cct | cgt | ggt | aat | tct | cac | tct | tgt | gac | 96 |
| Thr | Ser | Gly | Thr | Ala | Leu | Gly | Pro | Arg | Gly | Asn | Ser | His | Ser | Cys | Asp | |
| | | -5 | | | | -1 | 1 | | | | 5 | | | | | |
| act | gtt | gac | ggt | ggt | tac | caa | tgt | ttc | cca | gaa | att | tct | cac | ttg | tgg | 144 |
| Thr | Val | Asp | Gly | Gly | Tyr | Gln | Cys | Phe | Pro | Glu | Ile | Ser | His | Leu | Trp | |
| 10 | | | | 15 | | | | | 20 | | | | | 25 | | |
| ggt | acc | tac | tct | cca | tac | ttc | tct | ttg | gca | gac | gaa | tct | gct | att | tct | 192 |
| Gly | Thr | Tyr | Ser | Pro | Tyr | Phe | Ser | Leu | Ala | Asp | Glu | Ser | Ala | Ile | Ser | |
| | | | 30 | | | | 35 | | | | 40 | | | | | |
| cca | gac | gtc | cca | aag | gac | tgt | aga | gtt | act | ttc | gtt | caa | gtt | ttg | tct | 240 |
| Pro | Asp | Val | Pro | Lys | Asp | Cys | Arg | Val | Thr | Phe | Val | Gln | Val | Leu | Ser | |
| | | | 45 | | | | 50 | | | | 55 | | | | | |
| aga | cac | ggt | gct | aga | tac | cca | act | tct | tct | aag | tct | aag | gct | tac | tct | 288 |
| Arg | His | Gly | Ala | Arg | Tyr | Pro | Thr | Ser | Ser | Lys | Ser | Lys | Ala | Tyr | Ser | |
| | | 60 | | | | 65 | | | | | 70 | | | | | |
| gct | ttg | att | gaa | gct | att | caa | aag | aac | gct | act | gct | ttc | aag | ggt | aag | 336 |
| Ala | Leu | Ile | Glu | Ala | Ile | Gln | Lys | Asn | Ala | Thr | Ala | Phe | Lys | Gly | Lys | |
| | 75 | | | | 80 | | | | 85 | | | | | | | |

```
tac gct ttc ttg aag act tac aac tac act ttg ggt gct gac gac ttg      384
Tyr Ala Phe Leu Lys Thr Tyr Asn Tyr Thr Leu Gly Ala Asp Asp Leu
 90              95                 100                 105 act cca ttc ggt gaa aac caa atg gtt aac tct ggt att aag ttc tac      432
Thr Pro Phe Gly Glu Asn Gln Met Val Asn Ser Gly Ile Lys Phe Tyr
                 110                 115                 120 aga aga tac aag gct ttg gct aga aag att gtt cca ttc att aga gct      480
Arg Arg Tyr Lys Ala Leu Ala Arg Lys Ile Val Pro Phe Ile Arg Ala
             125                 130                 135 tct ggt tct gac aga gtt att gct tct gct gaa aag ttc att gaa ggt      528
Ser Gly Ser Asp Arg Val Ile Ala Ser Ala Glu Lys Phe Ile Glu Gly
             140                 145                 150 ttc caa tct gct aag ttg gct gac cca ggt tct caa cca cac caa gct      576
Phe Gln Ser Ala Lys Leu Ala Asp Pro Gly Ser Gln Pro His Gln Ala
155                 160                 165 tct cca gtt att aac gtg atc att cca gaa gga tcc ggt tac aac aac      624
Ser Pro Val Ile Asn Val Ile Ile Pro Glu Gly Ser Gly Tyr Asn Asn
170                 175                 180                 185 act ttg gac cat ggt ctt tgt act gct ttc gaa gac tct acc cta ggt      672
Thr Leu Asp His Gly Leu Cys Thr Ala Phe Glu Asp Ser Thr Leu Gly
                 190                 195                 200 gac gac gtt gaa gct aac ttc act gct ttg ttc gct cca gct att aga      720
Asp Asp Val Glu Ala Asn Phe Thr Ala Leu Phe Ala Pro Ala Ile Arg
                 205                 210                 215 gct aga ttg gaa gct gac ttg cca ggt gtt act ttg act gac gaa gac      768
Ala Arg Leu Glu Ala Asp Leu Pro Gly Val Thr Leu Thr Asp Glu Asp
             220                 225                 230 gtt gtt tac ttg atg gac atg tgt cca ttc gac act gtc gct aga act      816
Val Val Tyr Leu Met Asp Met Cys Pro Phe Asp Thr Val Ala Arg Thr
             235                 240                 245 tct gac gct act gaa ttg tct cca ttc tgt gct ttg ttc act cac gac      864
Ser Asp Ala Thr Glu Leu Ser Pro Phe Cys Ala Leu Phe Thr His Asp
250                 255                 260                 265 gaa tgg atc caa tac gac tac ttg caa agc ttg ggt aag tac tac ggt      912
Glu Trp Ile Gln Tyr Asp Tyr Leu Gln Ser Leu Gly Lys Tyr Tyr Gly
                 270                 275                 280 tac ggt gct ggt aac cca ttg ggt cca gct caa ggt gtt ggt ttc gct      960
Tyr Gly Ala Gly Asn Pro Leu Gly Pro Ala Gln Gly Val Gly Phe Ala
             285                 290                 295 aac gaa ttg att gct aga ttg act cac tct cca gtt caa gac cac act     1008
Asn Glu Leu Ile Ala Arg Leu Thr His Ser Pro Val Gln Asp His Thr
             300                 305                 310 tct act aac cac act ttg gac tct aac cca gct act ttc cca ttg aac     1056
Ser Thr Asn His Thr Leu Asp Ser Asn Pro Ala Thr Phe Pro Leu Asn
315                 320                 325 gct act ttg tac gct gac ttc tct cac gac aac act atg ata tct att     1104
Ala Thr Leu Tyr Ala Asp Phe Ser His Asp Asn Thr Met Ile Ser Ile
330                 335                 340                 345 ttc ttc gct ttg ggt ttg tac aac ggt acc aag cca ttg tct act act     1152
Phe Phe Ala Leu Gly Leu Tyr Asn Gly Thr Lys Pro Leu Ser Thr Thr
                 350                 355                 360 tct gtt gaa tct att gaa gaa act gac ggt tac tct gct tct tgg act     1200
Ser Val Glu Ser Ile Glu Glu Thr Asp Gly Tyr Ser Ala Ser Trp Thr
             365                 370                 375 gtt cca ttc gct gct aga gct tac gtt gaa atg atg caa tgt caa gct     1248
Val Pro Phe Ala Ala Arg Ala Tyr Val Glu Met Met Gln Cys Gln Ala
             380                 385                 390 gaa aag gaa cca ttg gtt aga gtt ttg gtt aac gac aga gtt gtt cca     1296
Glu Lys Glu Pro Leu Val Arg Val Leu Val Asn Asp Arg Val Val Pro
```

-continued

```
           395                 400                 405
ttg cac ggt tgt gct gtt gac aag ttg ggt aga tgt aag aga gac gac      1344
Leu His Gly Cys Ala Val Asp Lys Leu Gly Arg Cys Lys Arg Asp Asp
410                 415                 420                 425 ttc gtt gaa ggt ttg tct ttc gct aga tct ggt ggt aac tgg gct gaa      1392
Phe Val Glu Gly Leu Ser Phe Ala Arg Ser Gly Gly Asn Trp Ala Glu
                    430                 435                 440 tgt ttc gct taa                                                       1404
Cys Phe Ala <210> SEQ ID NO 91
<211> LENGTH: 467
<212> TYPE: PRT
<213> ORGANISM: Artificial Sequence
<220> FEATURE:
<223> OTHER INFORMATION: Primer

<400> SEQUENCE: 91

Met Gly Val Phe Val Val Leu Leu Ser Ile Ala Thr Leu Phe Gly Ser
            -20                 -15                 -10

Thr Ser Gly Thr Ala Leu Gly Pro Arg Gly Asn Ser His Ser Cys Asp
        -5                  -1   1               5

Thr Val Asp Gly Gly Tyr Gln Cys Phe Pro Glu Ile Ser His Leu Trp
 10                  15                  20                  25

Gly Thr Tyr Ser Pro Tyr Phe Ser Leu Ala Asp Glu Ser Ala Ile Ser
                 30                  35                  40

Pro Asp Val Pro Lys Asp Cys Arg Val Thr Phe Val Gln Val Leu Ser
                 45                  50                  55

Arg His Gly Ala Arg Tyr Pro Thr Ser Ser Lys Ser Lys Ala Tyr Ser
             60                  65                  70

Ala Leu Ile Glu Ala Ile Gln Lys Asn Ala Thr Ala Phe Lys Gly Lys
 75                  80                  85

Tyr Ala Phe Leu Lys Thr Tyr Asn Tyr Thr Leu Gly Ala Asp Asp Leu
 90                  95                 100                 105

Thr Pro Phe Gly Glu Asn Gln Met Val Asn Ser Gly Ile Lys Phe Tyr
                110                 115                 120

Arg Arg Tyr Lys Ala Leu Ala Arg Lys Ile Val Pro Phe Ile Arg Ala
             125                 130                 135

Ser Gly Ser Asp Arg Val Ile Ala Ser Ala Glu Lys Phe Ile Glu Gly
         140                 145                 150

Phe Gln Ser Ala Lys Leu Ala Asp Pro Gly Ser Gln Pro His Gln Ala
155                 160                 165

Ser Pro Val Ile Asn Val Ile Ile Pro Glu Gly Ser Gly Tyr Asn Asn
170                 175                 180                 185

Thr Leu Asp His Gly Leu Cys Thr Ala Phe Glu Asp Ser Thr Leu Gly
             190                 195                 200

Asp Asp Val Glu Ala Asn Phe Thr Ala Leu Phe Ala Pro Ala Ile Arg
         205                 210                 215

Ala Arg Leu Glu Ala Asp Leu Pro Gly Val Thr Leu Thr Asp Glu Asp
     220                 225                 230

Val Val Tyr Leu Met Asp Met Cys Pro Phe Asp Thr Val Ala Arg Thr
 235                 240                 245

Ser Asp Ala Thr Glu Leu Ser Pro Phe Cys Ala Leu Phe Thr His Asp
250                 255                 260                 265

Glu Trp Ile Gln Tyr Asp Tyr Leu Gln Ser Leu Gly Lys Tyr Tyr Gly
             270                 275                 280
```

```
            Tyr Gly Ala Gly Asn Pro Leu Gly Pro Ala Gln Gly Val Gly Phe Ala
                    285                 290                 295

Asn Glu Leu Ile Ala Arg Leu Thr His Ser Pro Val Gln Asp His Thr
                    300                 305                 310

Ser Thr Asn His Thr Leu Asp Ser Asn Pro Ala Thr Phe Pro Leu Asn
                    315                 320                 325

Ala Thr Leu Tyr Ala Asp Phe Ser His Asp Asn Thr Met Ile Ser Ile
            330                 335                 340                 345

Phe Phe Ala Leu Gly Leu Tyr Asn Gly Thr Lys Pro Leu Ser Thr Thr
                            350                 355                 360

Ser Val Glu Ser Ile Glu Glu Thr Asp Gly Tyr Ser Ala Ser Trp Thr
                        365                 370                 375

Val Pro Phe Ala Ala Arg Ala Tyr Val Glu Met Met Gln Cys Gln Ala
                    380                 385                 390

Glu Lys Glu Pro Leu Val Arg Val Leu Val Asn Asp Arg Val Val Pro
                395                 400                 405

Leu His Gly Cys Ala Val Asp Lys Leu Gly Arg Cys Lys Arg Asp Asp
            410                 415                 420                 425

Phe Val Glu Gly Leu Ser Phe Ala Arg Ser Gly Gly Asn Trp Ala Glu
                            430                 435                 440

Cys Phe Ala

<210> SEQ ID NO 92
<211> LENGTH: 1404
<212> TYPE: DNA
<213> ORGANISM: Artificial Sequence
<220> FEATURE:
<223> OTHER INFORMATION: Synthetic
<220> FEATURE:
<221> NAME/KEY: sig_peptide
<222> LOCATION: (1)..(69)
<220> FEATURE:
<221> NAME/KEY: CDS
<222> LOCATION: (1)..(1401)
<220> FEATURE:
<221> NAME/KEY: mat_peptide
<222> LOCATION: (70)..()

<400> SEQUENCE: 92 atg ggc gtg ttc gtc gtg cta ctg tcc att gcc acc ttg ttc ggt tcc        48
Met Gly Val Phe Val Val Leu Leu Ser Ile Ala Thr Leu Phe Gly Ser
            -20                 -15                 -10 aca tcc ggt acc gcc ttg ggt cct cgt ggt aat tct cac tct tgt gac        96
Thr Ser Gly Thr Ala Leu Gly Pro Arg Gly Asn Ser His Ser Cys Asp
        -5                  -1   1                   5 act gtt gac ggt ggt tac caa tgt ttc cca gaa att tct cac ttg tgg       144
Thr Val Asp Gly Gly Tyr Gln Cys Phe Pro Glu Ile Ser His Leu Trp
 10                  15                  20                  25 ggt acc tac tct cca tac ttc tct ttg gca gac gaa tct gct att tct       192
Gly Thr Tyr Ser Pro Tyr Phe Ser Leu Ala Asp Glu Ser Ala Ile Ser
                 30                  35                  40 cca gac gtc cca aag gac tgt aga gtt act ttc gtt caa gtt ttg tct       240
Pro Asp Val Pro Lys Asp Cys Arg Val Thr Phe Val Gln Val Leu Ser
             45                  50                  55 aga cac ggt gct aga tac cca act tct tct gcg tct aag gct tac tct       288
Arg His Gly Ala Arg Tyr Pro Thr Ser Ser Ala Ser Lys Ala Tyr Ser
         60                  65                  70 gct ttg att gaa gct att caa aag aac gct act gct ttc aag ggt aag       336
Ala Leu Ile Glu Ala Ile Gln Lys Asn Ala Thr Ala Phe Lys Gly Lys
     75                  80                  85
```

-continued

| | |
|---|---|
| tac gct ttc ttg aag act tac aac tac act ttg ggt gct gac gac ttg<br>Tyr Ala Phe Leu Lys Thr Tyr Asn Tyr Thr Leu Gly Ala Asp Asp Leu<br>90                95                  100              105 | 384 |
| act cca ttc ggt gaa aac caa atg gtt aac tct ggt att aag ttc tac<br>Thr Pro Phe Gly Glu Asn Gln Met Val Asn Ser Gly Ile Lys Phe Tyr<br>              110                  115                120 | 432 |
| aga aga tac aag gct ttg gct aga aag att gtt cca ttc att aga gct<br>Arg Arg Tyr Lys Ala Leu Ala Arg Lys Ile Val Pro Phe Ile Arg Ala<br>            125                  130                135 | 480 |
| tct ggt tct gac aga gtt att gct tct gct gaa aag ttc att gaa ggt<br>Ser Gly Ser Asp Arg Val Ile Ala Ser Ala Glu Lys Phe Ile Glu Gly<br>140                  145                  150 | 528 |
| ttc caa tct gct aag ttg gct gac cca ggt tct caa cca cac caa gct<br>Phe Gln Ser Ala Lys Leu Ala Asp Pro Gly Ser Gln Pro His Gln Ala<br>     155                  160                165 | 576 |
| tct cca gtt att aac gtg atc att cca gaa gga tcc ggt tac aac aac<br>Ser Pro Val Ile Asn Val Ile Ile Pro Glu Gly Ser Gly Tyr Asn Asn<br>170                  175                  180              185 | 624 |
| act ttg gac cat ggt ctt tgt act gct ttc gaa gac tct acc cta ggt<br>Thr Leu Asp His Gly Leu Cys Thr Ala Phe Glu Asp Ser Thr Leu Gly<br>                190                  195              200 | 672 |
| gac gac gtt gaa gct aac ttc act gct ttg ttc gct cca gct att aga<br>Asp Asp Val Glu Ala Asn Phe Thr Ala Leu Phe Ala Pro Ala Ile Arg<br>            205                  210                215 | 720 |
| gct aga ttg gaa gct gac ttg cca ggt gtt act ttg act gac gaa gac<br>Ala Arg Leu Glu Ala Asp Leu Pro Gly Val Thr Leu Thr Asp Glu Asp<br>220                  225                  230 | 768 |
| gtt gtt tac ttg atg gac atg tgt cca ttc gac act gtc gct aga act<br>Val Val Tyr Leu Met Asp Met Cys Pro Phe Asp Thr Val Ala Arg Thr<br>     235                  240                245 | 816 |
| tct gac gct act gaa ttg tct cca ttc tgt gct ttg ttc act cac gac<br>Ser Asp Ala Thr Glu Leu Ser Pro Phe Cys Ala Leu Phe Thr His Asp<br>250                  255                  260              265 | 864 |
| gaa tgg atc caa tac gac tac ttg caa agc ttg ggt aag tac tac ggt<br>Glu Trp Ile Gln Tyr Asp Tyr Leu Gln Ser Leu Gly Lys Tyr Tyr Gly<br>            270                  275                280 | 912 |
| tac ggt gct ggt aac cca ttg ggt cca gct caa ggt gtt ggt ttc gct<br>Tyr Gly Ala Gly Asn Pro Leu Gly Pro Ala Gln Gly Val Gly Phe Ala<br>                285                  290              295 | 960 |
| aac gaa ttg att gct aga ttg act cac tct cca gtt caa gac cac act<br>Asn Glu Leu Ile Ala Arg Leu Thr His Ser Pro Val Gln Asp His Thr<br>300                  305                  310 | 1008 |
| tct act aac cac act ttg gac tct aac cca gct act ttc cca ttg aac<br>Ser Thr Asn His Thr Leu Asp Ser Asn Pro Ala Thr Phe Pro Leu Asn<br>     315                  320                325 | 1056 |
| gct act ttg tac gct gac ttc tct cac gac aac act atg ata tct att<br>Ala Thr Leu Tyr Ala Asp Phe Ser His Asp Asn Thr Met Ile Ser Ile<br>330                  335                  340              345 | 1104 |
| ttc ttc gct ttg ggt ttg tac aac ggt acc aag cca ttg tct act act<br>Phe Phe Ala Leu Gly Leu Tyr Asn Gly Thr Lys Pro Leu Ser Thr Thr<br>            350                  355                360 | 1152 |
| tct gtt gaa tct att gaa gaa act gac ggt tac tct gct tct tgg act<br>Ser Val Glu Ser Ile Glu Glu Thr Asp Gly Tyr Ser Ala Ser Trp Thr<br>                365                  370              375 | 1200 |
| gtt cca ttc gct gct aga gct tac gtt gaa atg atg caa tgt caa gct<br>Val Pro Phe Ala Ala Arg Ala Tyr Val Glu Met Met Gln Cys Gln Ala<br>                380                  385              390 | 1248 |
| gaa aag gaa cca ttg gtt aga gtt ttg gtt aac gac aga gtt gtt cca<br>Glu Lys Glu Pro Leu Val Arg Val Leu Val Asn Asp Arg Val Val Pro | 1296 |

```
                                395                 400                 405
    ttg cac ggt tgt gct gtt gac aag ttg ggt aga tgt aag aga gac gac    1344
    Leu His Gly Cys Ala Val Asp Lys Leu Gly Arg Cys Lys Arg Asp Asp
    410                 415                 420                 425 ttc gtt gaa ggt ttg tct ttc gct aga tct ggt ggt aac tgg gct gaa    1392
    Phe Val Glu Gly Leu Ser Phe Ala Arg Ser Gly Gly Asn Trp Ala Glu
                        430                 435                 440 tgt ttc gct taa                                                    1404
    Cys Phe Ala
```

<210> SEQ ID NO 93
<211> LENGTH: 467
<212> TYPE: PRT
<213> ORGANISM: Artificial Sequence
<220> FEATURE:
<223> OTHER INFORMATION: Synthetic

<400> SEQUENCE: 93

```
Met Gly Val Phe Val Val Leu Leu Ser Ile Ala Thr Leu Phe Gly Ser
            -20                 -15                 -10

Thr Ser Gly Thr Ala Leu Gly Pro Arg Gly Asn Ser His Ser Cys Asp
        -5              -1   1               5

Thr Val Asp Gly Gly Tyr Gln Cys Phe Pro Glu Ile Ser His Leu Trp
 10                  15                  20                  25

Gly Thr Tyr Ser Pro Tyr Phe Ser Leu Ala Asp Glu Ser Ala Ile Ser
                 30                  35                  40

Pro Asp Val Pro Lys Asp Cys Arg Val Thr Phe Val Gln Val Leu Ser
                 45                  50                  55

Arg His Gly Ala Arg Tyr Pro Thr Ser Ser Ala Ser Lys Ala Tyr Ser
                 60                  65                  70

Ala Leu Ile Glu Ala Ile Gln Lys Asn Ala Thr Ala Phe Lys Gly Lys
 75                  80                  85

Tyr Ala Phe Leu Lys Thr Tyr Asn Tyr Thr Leu Gly Ala Asp Asp Leu
 90                  95                 100                 105

Thr Pro Phe Gly Glu Asn Gln Met Val Asn Ser Gly Ile Lys Phe Tyr
                110                 115                 120

Arg Arg Tyr Lys Ala Leu Ala Arg Lys Ile Val Pro Phe Ile Arg Ala
                125                 130                 135

Ser Gly Ser Asp Arg Val Ile Ala Ser Ala Glu Lys Phe Ile Glu Gly
            140                 145                 150

Phe Gln Ser Ala Lys Leu Ala Asp Pro Gly Ser Gln Pro His Gln Ala
    155                 160                 165

Ser Pro Val Ile Asn Val Ile Ile Pro Glu Gly Ser Gly Tyr Asn Asn
170                 175                 180                 185

Thr Leu Asp His Gly Leu Cys Thr Ala Phe Glu Asp Ser Thr Leu Gly
                190                 195                 200

Asp Asp Val Glu Ala Asn Phe Thr Ala Leu Phe Ala Pro Ala Ile Arg
            205                 210                 215

Ala Arg Leu Glu Ala Asp Leu Pro Gly Val Thr Leu Thr Asp Glu Asp
            220                 225                 230

Val Val Tyr Leu Met Asp Met Cys Pro Phe Asp Thr Val Ala Arg Thr
        235                 240                 245

Ser Asp Ala Thr Glu Leu Ser Pro Phe Cys Ala Leu Phe Thr His Asp
250                 255                 260                 265

Glu Trp Ile Gln Tyr Asp Tyr Leu Gln Ser Leu Gly Lys Tyr Tyr Gly
                270                 275                 280
```

```
                Tyr Gly Ala Gly Asn Pro Leu Gly Pro Ala Gln Gly Val Gly Phe Ala
                            285                 290                 295

Asn Glu Leu Ile Ala Arg Leu Thr His Ser Pro Val Gln Asp His Thr
                            300                 305                 310

Ser Thr Asn His Thr Leu Asp Ser Asn Pro Ala Thr Phe Pro Leu Asn
                            315                 320                 325

Ala Thr Leu Tyr Ala Asp Phe Ser His Asp Asn Thr Met Ile Ser Ile
                330                 335                 340                 345

Phe Phe Ala Leu Gly Leu Tyr Asn Gly Thr Lys Pro Leu Ser Thr Thr
                            350                 355                 360

Ser Val Glu Ser Ile Glu Glu Thr Asp Gly Tyr Ser Ala Ser Trp Thr
                            365                 370                 375

Val Pro Phe Ala Ala Arg Ala Tyr Val Glu Met Met Gln Cys Gln Ala
                            380                 385                 390

Glu Lys Glu Pro Leu Val Arg Val Leu Val Asn Asp Arg Val Val Pro
                            395                 400                 405

Leu His Gly Cys Ala Val Asp Lys Leu Gly Arg Cys Lys Arg Asp Asp
                410                 415                 420                 425

Phe Val Glu Gly Leu Ser Phe Ala Arg Ser Gly Gly Asn Trp Ala Glu
                            430                 435                 440

Cys Phe Ala

<210> SEQ ID NO 94
<211> LENGTH: 1404
<212> TYPE: DNA
<213> ORGANISM: Artificial Sequence
<220> FEATURE:
<223> OTHER INFORMATION: Synthetic
<220> FEATURE:
<221> NAME/KEY: sig_peptide
<222> LOCATION: (1)..(69)
<220> FEATURE:
<221> NAME/KEY: CDS
<222> LOCATION: (1)..(1401)
<220> FEATURE:
<221> NAME/KEY: mat_peptide
<222> LOCATION: (70)..()

<400> SEQUENCE: 94 atg ggc gtg ttc gtc gtg cta ctg tcc att gcc acc ttg ttc ggt tcc      48
Met Gly Val Phe Val Val Leu Leu Ser Ile Ala Thr Leu Phe Gly Ser
            -20                 -15                 -10 aca tcc ggt acc gcc ttg ggt cct cgt ggt aat tct cac tct tgt gac      96
Thr Ser Gly Thr Ala Leu Gly Pro Arg Gly Asn Ser His Ser Cys Asp
        -5                  -1   1                   5 act gtt gac ggt ggt tac caa tgt ttc cca gaa att tct cac ttg tgg     144
Thr Val Asp Gly Gly Tyr Gln Cys Phe Pro Glu Ile Ser His Leu Trp
 10                  15                  20                  25 ggt aca tac tct cca ttc ttc tct ttg gct gac gaa tct gct att tct     192
Gly Thr Tyr Ser Pro Phe Phe Ser Leu Ala Asp Glu Ser Ala Ile Ser
                 30                  35                  40 cca gac gtt cca aag ggt tgt aga gtt act ttc gtt caa gtt ttg tct     240
Pro Asp Val Pro Lys Gly Cys Arg Val Thr Phe Val Gln Val Leu Ser
             45                  50                  55 aga cac ggt gct aga tac cca act tct tct aag tct aag gct tac tct     288
Arg His Gly Ala Arg Tyr Pro Thr Ser Ser Lys Ser Lys Ala Tyr Ser
         60                  65                  70 gct ttg att gaa gct att caa aag aac gct act gct ttc aag ggt aag     336
Ala Leu Ile Glu Ala Ile Gln Lys Asn Ala Thr Ala Phe Lys Gly Lys
     75                  80                  85
```

```
tac gct ttc ttg aag act tac aat tac act ttg ggt gct gac gac ttg    384
Tyr Ala Phe Leu Lys Thr Tyr Asn Tyr Thr Leu Gly Ala Asp Asp Leu
 90              95                 100                 105 act cca ttc ggt gaa caa caa atg gtt aac tct ggt att aag ttc tac    432
Thr Pro Phe Gly Glu Gln Gln Met Val Asn Ser Gly Ile Lys Phe Tyr
                    110                 115                 120 aga aga tac aag gct ttg gct aga aag att gtt cca ttc att aga gct    480
Arg Arg Tyr Lys Ala Leu Ala Arg Lys Ile Val Pro Phe Ile Arg Ala
                125                 130                 135 tct ggt tct gac aga gtt att gct tct gcc gaa aag ttc att gaa ggt    528
Ser Gly Ser Asp Arg Val Ile Ala Ser Ala Glu Lys Phe Ile Glu Gly
                140                 145                 150 ttc caa tct gct aag ttg gct gac cca ggt gct aac cca cac caa gct    576
Phe Gln Ser Ala Lys Leu Ala Asp Pro Gly Ala Asn Pro His Gln Ala
155                 160                 165 tct cca gtt att aac gtt att att cca gaa ggt gct ggt tac aac aac    624
Ser Pro Val Ile Asn Val Ile Ile Pro Glu Gly Ala Gly Tyr Asn Asn
170                 175                 180                 185 act ttg gac cac ggt ttg tgt act gct ttc gaa gaa tct acc cta ggt    672
Thr Leu Asp His Gly Leu Cys Thr Ala Phe Glu Glu Ser Thr Leu Gly
                190                 195                 200 gac gac gtt gaa gct aac ttc act gct gtt ttc gct cca cca att aga    720
Asp Asp Val Glu Ala Asn Phe Thr Ala Val Phe Ala Pro Pro Ile Arg
                205                 210                 215 gct aga ttg gaa gct cac ttg cca ggt gtt aac ttg act gac gaa gac    768
Ala Arg Leu Glu Ala His Leu Pro Gly Val Asn Leu Thr Asp Glu Asp
                220                 225                 230 gtt gtt aac ttg atg gac atg tgt cca ttc gac act gtt gct aga act    816
Val Val Asn Leu Met Asp Met Cys Pro Phe Asp Thr Val Ala Arg Thr
                235                 240                 245 tct gac gct act caa ttg tct cca ttc tgt gac ttg ttc act cac gac    864
Ser Asp Ala Thr Gln Leu Ser Pro Phe Cys Asp Leu Phe Thr His Asp
250                 255                 260                 265 gaa tgg att caa tac gac tac ttg caa tct ttg ggt aag tac tac ggt    912
Glu Trp Ile Gln Tyr Asp Tyr Leu Gln Ser Leu Gly Lys Tyr Tyr Gly
                270                 275                 280 tac ggt gct ggt aac cca ttg ggt cca gct caa ggt gtt ggt ttc gtt    960
Tyr Gly Ala Gly Asn Pro Leu Gly Pro Ala Gln Gly Val Gly Phe Val
                285                 290                 295 aac gaa ttg att gct aga ttg act cac tct cca gtt caa gac cac act   1008
Asn Glu Leu Ile Ala Arg Leu Thr His Ser Pro Val Gln Asp His Thr
                300                 305                 310 tct act aac cac act ttg gac tct aac cca gct act ttc cca ttg aac   1056
Ser Thr Asn His Thr Leu Asp Ser Asn Pro Ala Thr Phe Pro Leu Asn
315                 320                 325 gct act ttg tac gct gac ttc tct cac gac aac act atg gtt tct att   1104
Ala Thr Leu Tyr Ala Asp Phe Ser His Asp Asn Thr Met Val Ser Ile
330                 335                 340                 345 ttc ttc gct ttg ggt ttg tac aac ggt act aag cca ttg tct act act   1152
Phe Phe Ala Leu Gly Leu Tyr Asn Gly Thr Lys Pro Leu Ser Thr Thr
                350                 355                 360 tct gtt gaa tct att gaa gaa act gac ggt tac tct gct tct tgg act   1200
Ser Val Glu Ser Ile Glu Glu Thr Asp Gly Tyr Ser Ala Ser Trp Thr
                365                 370                 375 gtt cca ttc gct gct aga gct tac gtt gaa atg atg caa tgt gaa gct   1248
Val Pro Phe Ala Ala Arg Ala Tyr Val Glu Met Met Gln Cys Glu Ala
                380                 385                 390 gaa aag gaa cca ttg gtt aga gtt ttg gtt aac gac aga gtt gtt cca   1296
Glu Lys Glu Pro Leu Val Arg Val Leu Val Asn Asp Arg Val Val Pro
```

```
                395                 400                 405
ttg cac ggt tgt gct gtt gac aag ttg ggt aga tgt aag aga gac gac    1344
Leu His Gly Cys Ala Val Asp Lys Leu Gly Arg Cys Lys Arg Asp Asp
410                 415                 420                 425 ttc gtt gaa ggt ttg tct ttc gct aga tct ggt ggt aac tgg gaa gaa    1392
Phe Val Glu Gly Leu Ser Phe Ala Arg Ser Gly Gly Asn Trp Glu Glu
                    430                 435                 440 tgt ttc gct taa                                                    1404
Cys Phe Ala <210> SEQ ID NO 95
<211> LENGTH: 467
<212> TYPE: PRT
<213> ORGANISM: Artificial Sequence
<220> FEATURE:
<223> OTHER INFORMATION: Synthetic

<400> SEQUENCE: 95

Met Gly Val Phe Val Val Leu Leu Ser Ile Ala Thr Leu Phe Gly Ser
            -20                 -15                 -10

Thr Ser Gly Thr Ala Leu Gly Pro Arg Gly Asn Ser His Ser Cys Asp
         -5              -1   1               5

Thr Val Asp Gly Gly Tyr Gln Cys Phe Pro Glu Ile Ser His Leu Trp
 10                  15                  20                  25

Gly Thr Tyr Ser Pro Phe Phe Ser Leu Ala Asp Glu Ser Ala Ile Ser
                 30                  35                  40

Pro Asp Val Pro Lys Gly Cys Arg Val Thr Phe Val Gln Val Leu Ser
                 45                  50                  55

Arg His Gly Ala Arg Tyr Pro Thr Ser Ser Lys Ser Lys Ala Tyr Ser
             60                  65                  70

Ala Leu Ile Glu Ala Ile Gln Lys Asn Ala Thr Ala Phe Lys Gly Lys
 75                  80                  85

Tyr Ala Phe Leu Lys Thr Tyr Asn Tyr Thr Leu Gly Ala Asp Asp Leu
 90                  95                 100                 105

Thr Pro Phe Gly Glu Gln Gln Met Val Asn Ser Gly Ile Lys Phe Tyr
                110                 115                 120

Arg Arg Tyr Lys Ala Leu Ala Arg Lys Ile Val Pro Phe Ile Arg Ala
                125                 130                 135

Ser Gly Ser Asp Arg Val Ile Ala Ser Ala Glu Lys Phe Ile Glu Gly
            140                 145                 150

Phe Gln Ser Ala Lys Leu Ala Asp Pro Gly Ala Asn Pro His Gln Ala
155                 160                 165

Ser Pro Val Ile Asn Val Ile Ile Pro Glu Gly Ala Gly Tyr Asn Asn
170                 175                 180                 185

Thr Leu Asp His Gly Leu Cys Thr Ala Phe Glu Glu Ser Thr Leu Gly
                190                 195                 200

Asp Asp Val Glu Ala Asn Phe Thr Ala Val Phe Ala Pro Pro Ile Arg
                205                 210                 215

Ala Arg Leu Glu Ala His Leu Pro Gly Val Asn Leu Thr Asp Glu Asp
                220                 225                 230

Val Val Asn Leu Met Asp Met Cys Pro Phe Asp Thr Val Ala Arg Thr
            235                 240                 245

Ser Asp Ala Thr Gln Leu Ser Pro Phe Cys Asp Leu Phe Thr His Asp
250                 255                 260                 265

Glu Trp Ile Gln Tyr Asp Tyr Leu Gln Ser Leu Gly Lys Tyr Tyr Gly
                270                 275                 280
```

```
Tyr Gly Ala Gly Asn Pro Leu Gly Pro Ala Gln Gly Val Gly Phe Val
            285                 290                 295

Asn Glu Leu Ile Ala Arg Leu Thr His Ser Pro Val Gln Asp His Thr
        300                 305                 310

Ser Thr Asn His Thr Leu Asp Ser Asn Pro Ala Thr Phe Pro Leu Asn
        315                 320                 325

Ala Thr Leu Tyr Ala Asp Phe Ser His Asp Asn Thr Met Val Ser Ile
330                 335                 340                 345

Phe Phe Ala Leu Gly Leu Tyr Asn Gly Thr Lys Pro Leu Ser Thr Thr
                350                 355                 360

Ser Val Glu Ser Ile Glu Glu Thr Asp Gly Tyr Ser Ala Ser Trp Thr
            365                 370                 375

Val Pro Phe Ala Ala Arg Ala Tyr Val Glu Met Met Gln Cys Glu Ala
            380                 385                 390

Glu Lys Glu Pro Leu Val Arg Val Leu Val Asn Asp Arg Val Val Pro
        395                 400                 405

Leu His Gly Cys Ala Val Asp Lys Leu Gly Arg Cys Lys Arg Asp Asp
410                 415                 420                 425

Phe Val Glu Gly Leu Ser Phe Ala Arg Ser Gly Gly Asn Trp Glu Glu
                430                 435                 440

Cys Phe Ala
```

<210> SEQ ID NO 96
<211> LENGTH: 1404
<212> TYPE: DNA
<213> ORGANISM: Artificial Sequence
<220> FEATURE:
<223> OTHER INFORMATION: Synthetic
<220> FEATURE:
<221> NAME/KEY: sig_peptide
<222> LOCATION: (1)..(69)
<220> FEATURE:
<221> NAME/KEY: CDS
<222> LOCATION: (1)..(1401)
<220> FEATURE:
<221> NAME/KEY: mat_peptide
<222> LOCATION: (70)..()

<400> SEQUENCE: 96

```
atg ggc gtg ttc gtc gtg cta ctg tcc att gcc acc ttg ttc ggt tcc      48
Met Gly Val Phe Val Val Leu Leu Ser Ile Ala Thr Leu Phe Gly Ser
        -20                 -15                 -10 aca tcc ggt acc gcc ttg ggt cct cgt ggt aat tct cac tct tgt gac      96
Thr Ser Gly Thr Ala Leu Gly Pro Arg Gly Asn Ser His Ser Cys Asp
    -5                  -1   1               5 act gtt gac ggt ggt tac caa tgt ttc cca gaa att tct cac ttg tgg     144
Thr Val Asp Gly Gly Tyr Gln Cys Phe Pro Glu Ile Ser His Leu Trp
10                  15                  20                  25 ggt aca tac tct cca ttc ttc tct ttg gct gac gaa tct gct att tct     192
Gly Thr Tyr Ser Pro Phe Phe Ser Leu Ala Asp Glu Ser Ala Ile Ser
                30                  35                  40 cca gac gtt cca aag ggt tgt aga gtt act ttc gtt caa gtt ttg tct     240
Pro Asp Val Pro Lys Gly Cys Arg Val Thr Phe Val Gln Val Leu Ser
            45                  50                  55 aga cac ggt gct aga tac cca act tct tct gcg tct aag gct tac tct     288
Arg His Gly Ala Arg Tyr Pro Thr Ser Ser Ala Ser Lys Ala Tyr Ser
        60                  65                  70 gct ttg att gaa gct att caa aag aac gct act gct ttc aag ggt aag     336
Ala Leu Ile Glu Ala Ile Gln Lys Asn Ala Thr Ala Phe Lys Gly Lys
75                  80                  85
```

```
tac gct ttc ttg aag act tac aat tac act ttg ggt gct gac gac ttg    384
Tyr Ala Phe Leu Lys Thr Tyr Asn Tyr Thr Leu Gly Ala Asp Asp Leu
 90              95                 100                 105 act cca ttc ggt gaa caa caa atg gtt aac tct ggt att aag ttc tac    432
Thr Pro Phe Gly Glu Gln Gln Met Val Asn Ser Gly Ile Lys Phe Tyr
                 110                 115                 120 aga aga tac aag gct ttg gct aga aag att gtt cca ttc att aga gct    480
Arg Arg Tyr Lys Ala Leu Ala Arg Lys Ile Val Pro Phe Ile Arg Ala
             125                 130                 135 tct ggt tct gac aga gtt att gct tct gcc gaa aag ttc att gaa ggt    528
Ser Gly Ser Asp Arg Val Ile Ala Ser Ala Glu Lys Phe Ile Glu Gly
         140                 145                 150 ttc caa tct gct aag ttg gct gac cca ggt gct aac cca cac caa gct    576
Phe Gln Ser Ala Lys Leu Ala Asp Pro Gly Ala Asn Pro His Gln Ala
 155                 160                 165 tct cca gtt att aac gtt att att cca gaa ggt gct ggt tac aac aac    624
Ser Pro Val Ile Asn Val Ile Ile Pro Glu Gly Ala Gly Tyr Asn Asn
170                 175                 180                 185 act ttg gac cac ggt ttg tgt act gct ttc gaa gaa tct acc cta ggt    672
Thr Leu Asp His Gly Leu Cys Thr Ala Phe Glu Glu Ser Thr Leu Gly
                 190                 195                 200 gac gac gtt gaa gct aac ttc act gct gtt ttc gct cca cca att aga    720
Asp Asp Val Glu Ala Asn Phe Thr Ala Val Phe Ala Pro Pro Ile Arg
             205                 210                 215 gct aga ttg gaa gct cac ttg cca ggt gtt aac ttg act gac gaa gac    768
Ala Arg Leu Glu Ala His Leu Pro Gly Val Asn Leu Thr Asp Glu Asp
         220                 225                 230 gtt gtt aac ttg atg gac atg tgt cca ttc gac act gtt gct aga act    816
Val Val Asn Leu Met Asp Met Cys Pro Phe Asp Thr Val Ala Arg Thr
 235                 240                 245 tct gac gct act caa ttg tct cca ttc tgt gac ttg ttc act cac gac    864
Ser Asp Ala Thr Gln Leu Ser Pro Phe Cys Asp Leu Phe Thr His Asp
250                 255                 260                 265 gaa tgg att caa tac gac tac ttg caa tct ttg ggt aag tac tac ggt    912
Glu Trp Ile Gln Tyr Asp Tyr Leu Gln Ser Leu Gly Lys Tyr Tyr Gly
                 270                 275                 280 tac ggt gct ggt aac cca ttg ggt cca gct caa ggt gtt ggt ttc gtt    960
Tyr Gly Ala Gly Asn Pro Leu Gly Pro Ala Gln Gly Val Gly Phe Val
             285                 290                 295 aac gaa ttg att gct aga ttg act cac tct cca gtt caa gac cac act   1008
Asn Glu Leu Ile Ala Arg Leu Thr His Ser Pro Val Gln Asp His Thr
         300                 305                 310 tct act aac cac act ttg gac tct aac cca gct act ttc cca ttg aac   1056
Ser Thr Asn His Thr Leu Asp Ser Asn Pro Ala Thr Phe Pro Leu Asn
 315                 320                 325 gct act ttg tac gct gac ttc tct cac gac aac act atg gtt tct att   1104
Ala Thr Leu Tyr Ala Asp Phe Ser His Asp Asn Thr Met Val Ser Ile
330                 335                 340                 345 ttc ttc gct ttg ggt ttg tac aac ggt act aag cca ttg tct act act   1152
Phe Phe Ala Leu Gly Leu Tyr Asn Gly Thr Lys Pro Leu Ser Thr Thr
                 350                 355                 360 tct gtt gaa tct att gaa gaa act gac ggt tac tct gct tct tgg act   1200
Ser Val Glu Ser Ile Glu Glu Thr Asp Gly Tyr Ser Ala Ser Trp Thr
             365                 370                 375 gtt cca ttc gct gct aga gct tac gtt gaa atg atg caa tgt gaa gct   1248
Val Pro Phe Ala Ala Arg Ala Tyr Val Glu Met Met Gln Cys Glu Ala
         380                 385                 390 gaa aag gaa cca ttg gtt aga gtt ttg gtt aac gac aga gtt gtt cca   1296
Glu Lys Glu Pro Leu Val Arg Val Leu Val Asn Asp Arg Val Val Pro
```

```
      395                 400                 405
ttg cac ggt tgt gct gtt gac aag ttg ggt aga tgt aag aga gac gac    1344
Leu His Gly Cys Ala Val Asp Lys Leu Gly Arg Cys Lys Arg Asp Asp
410                 415                 420                 425 ttc gtt gaa ggt ttg tct ttc gct aga tct ggt ggt aac tgg gaa gaa    1392
Phe Val Glu Gly Leu Ser Phe Ala Arg Ser Gly Gly Asn Trp Glu Glu
                430                 435                 440 tgt ttc gct taa                                                    1404
Cys Phe Ala <210> SEQ ID NO 97
<211> LENGTH: 467
<212> TYPE: PRT
<213> ORGANISM: Artificial Sequence
<220> FEATURE:
<223> OTHER INFORMATION: Synthetic

<400> SEQUENCE: 97

Met Gly Val Phe Val Val Leu Leu Ser Ile Ala Thr Leu Phe Gly Ser
            -20                 -15                 -10

Thr Ser Gly Thr Ala Leu Gly Pro Arg Gly Asn Ser His Ser Cys Asp
        -5                  -1  1               5

Thr Val Asp Gly Gly Tyr Gln Cys Phe Pro Glu Ile Ser His Leu Trp
 10                  15                  20                  25

Gly Thr Tyr Ser Pro Phe Phe Ser Leu Ala Asp Glu Ser Ala Ile Ser
                 30                  35                  40

Pro Asp Val Pro Lys Gly Cys Arg Val Thr Phe Val Gln Val Leu Ser
                 45                  50                  55

Arg His Gly Ala Arg Tyr Pro Thr Ser Ser Ala Ser Lys Ala Tyr Ser
             60                  65                  70

Ala Leu Ile Glu Ala Ile Gln Lys Asn Ala Thr Ala Phe Lys Gly Lys
 75                  80                  85

Tyr Ala Phe Leu Lys Thr Tyr Asn Tyr Thr Leu Gly Ala Asp Asp Leu
 90                  95                 100                 105

Thr Pro Phe Gly Glu Gln Gln Met Val Asn Ser Gly Ile Lys Phe Tyr
                110                 115                 120

Arg Arg Tyr Lys Ala Leu Ala Arg Lys Ile Val Pro Phe Ile Arg Ala
             125                 130                 135

Ser Gly Ser Asp Arg Val Ile Ala Ser Ala Glu Lys Phe Ile Glu Gly
         140                 145                 150

Phe Gln Ser Ala Lys Leu Ala Asp Pro Gly Ala Asn Pro His Gln Ala
 155                 160                 165

Ser Pro Val Ile Asn Val Ile Ile Pro Glu Gly Ala Gly Tyr Asn Asn
170                 175                 180                 185

Thr Leu Asp His Gly Leu Cys Thr Ala Phe Glu Glu Ser Thr Leu Gly
                190                 195                 200

Asp Asp Val Glu Ala Asn Phe Thr Ala Val Phe Ala Pro Pro Ile Arg
             205                 210                 215

Ala Arg Leu Glu Ala His Leu Pro Gly Val Asn Leu Thr Asp Glu Asp
         220                 225                 230

Val Val Asn Leu Met Asp Met Cys Pro Phe Asp Thr Val Ala Arg Thr
 235                 240                 245

Ser Asp Ala Thr Gln Leu Ser Pro Phe Cys Asp Leu Phe Thr His Asp
250                 255                 260                 265

Glu Trp Ile Gln Tyr Asp Tyr Leu Gln Ser Leu Gly Lys Tyr Tyr Gly
                270                 275                 280
```

-continued

```
Tyr Gly Ala Gly Asn Pro Leu Gly Pro Ala Gln Gly Val Gly Phe Val
            285                 290                 295
Asn Glu Leu Ile Ala Arg Leu Thr His Ser Pro Val Gln Asp His Thr
        300                 305                 310
Ser Thr Asn His Thr Leu Asp Ser Asn Pro Ala Thr Phe Pro Leu Asn
    315                 320                 325
Ala Thr Leu Tyr Ala Asp Phe Ser His Asp Asn Thr Met Val Ser Ile
330                 335                 340                 345
Phe Phe Ala Leu Gly Leu Tyr Asn Gly Thr Lys Pro Leu Ser Thr Thr
                350                 355                 360
Ser Val Glu Ser Ile Glu Glu Thr Asp Gly Tyr Ser Ala Ser Trp Thr
            365                 370                 375
Val Pro Phe Ala Ala Arg Ala Tyr Val Glu Met Met Gln Cys Glu Ala
        380                 385                 390
Glu Lys Glu Pro Leu Val Arg Val Leu Val Asn Asp Arg Val Val Pro
395                 400                 405
Leu His Gly Cys Ala Val Asp Lys Leu Gly Arg Cys Lys Arg Asp Asp
410                 415                 420                 425
Phe Val Glu Gly Leu Ser Phe Ala Arg Ser Gly Gly Asn Trp Glu Glu
                430                 435                 440
Cys Phe Ala

<210> SEQ ID NO 98
<211> LENGTH: 441
<212> TYPE: PRT
<213> ORGANISM: Artificial Sequence
<220> FEATURE:
<223> OTHER INFORMATION: synthetic

<400> SEQUENCE: 98

Asn Ser His Ser Cys Asp Thr Val Asp Gly Gly Tyr Gln Cys Phe Pro
1               5                   10                  15
Glu Ile Ser His Leu Trp Gly Gln Tyr Ser Pro Tyr Phe Ser Leu Glu
            20                  25                  30
Asp Glu Ser Ala Ile Ser Pro Asp Val Pro Asp Asp Cys Arg Val Thr
        35                  40                  45
Phe Val Gln Val Leu Ser Arg His Gly Ala Arg Tyr Pro Thr Ser Ser
    50                  55                  60
Lys Ser Lys Ala Tyr Ser Ala Leu Ile Glu Ala Ile Gln Lys Asn Ala
65                  70                  75                  80
Thr Ala Phe Lys Gly Lys Tyr Ala Phe Leu Lys Thr Tyr Asn Tyr Thr
                85                  90                  95
Leu Gly Ala Asp Asp Leu Thr Pro Phe Gly Glu Asn Gln Met Val Asn
            100                 105                 110
Ser Gly Ile Lys Phe Tyr Arg Arg Tyr Lys Ala Leu Ala Arg Lys Ile
        115                 120                 125
Val Pro Phe Ile Arg Ala Ser Gly Ser Asp Arg Val Ile Ala Ser Ala
    130                 135                 140
Glu Lys Phe Ile Glu Gly Phe Gln Ser Ala Lys Leu Ala Asp Pro Gly
145                 150                 155                 160
Ser Gln Pro His Gln Ala Ser Pro Val Ile Asp Val Ile Ile Pro Glu
                165                 170                 175
Gly Ser Gly Tyr Asn Asn Thr Leu Asp His Gly Thr Cys Thr Ala Phe
            180                 185                 190
```

-continued

```
Glu Asp Ser Glu Leu Gly Asp Asp Val Glu Ala Asn Phe Thr Ala Leu
            195                 200                 205

Phe Ala Pro Ala Ile Arg Ala Arg Leu Glu Ala Asp Leu Pro Gly Val
            210                 215                 220

Thr Leu Thr Asp Glu Asp Val Val Tyr Leu Met Asp Met Cys Pro Phe
225                 230                 235                 240

Glu Thr Val Ala Arg Thr Ser Asp Ala Thr Glu Leu Ser Pro Phe Cys
                245                 250                 255

Ala Leu Phe Thr His Asp Glu Trp Arg Gln Tyr Asp Tyr Leu Gln Ser
                260                 265                 270

Leu Gly Lys Tyr Tyr Gly Tyr Gly Ala Gly Asn Pro Leu Gly Pro Ala
            275                 280                 285

Gln Gly Val Gly Phe Ala Asn Glu Leu Ile Ala Arg Leu Thr Arg Ser
            290                 295                 300

Pro Val Gln Asp His Thr Ser Thr Asn His Thr Leu Asp Ser Asn Pro
305                 310                 315                 320

Ala Thr Phe Pro Leu Asn Ala Thr Leu Tyr Ala Asp Phe Ser His Asp
                325                 330                 335

Asn Ser Met Ile Ser Ile Phe Phe Ala Leu Gly Leu Tyr Asn Gly Thr
                340                 345                 350

Ala Pro Leu Ser Thr Thr Ser Val Glu Ser Ile Glu Glu Thr Asp Gly
            355                 360                 365

Tyr Ser Ala Ser Trp Thr Val Pro Phe Gly Ala Arg Ala Tyr Val Glu
            370                 375                 380

Met Met Gln Cys Gln Ala Glu Lys Glu Pro Leu Val Arg Val Leu Val
385                 390                 395                 400

Asn Asp Arg Val Val Pro Leu His Gly Cys Ala Val Asp Lys Leu Gly
                405                 410                 415

Arg Cys Lys Arg Asp Asp Phe Val Glu Gly Leu Ser Phe Ala Arg Ser
                420                 425                 430

Gly Gly Asn Trp Ala Glu Cys Phe Ala
            435                 440
```